(12) United States Patent
Quattropani et al.

(10) Patent No.: US 8,815,919 B2
(45) Date of Patent: *Aug. 26, 2014

(54) OXADIAZOLE DERIVATIVES

(75) Inventors: Anna Quattropani, Geneva (CH); Cyril Montagne, Saint-Genis-Pouilly (FR); Wolfgang Sauer, Chambésy (CH); Stefano Crosignani, St. Genis-Pouilly (FR); Agnès Bombrun, Chambesy (CH)

(73) Assignee: Merck Serono SA, Coinsins, Vaud (CH)

( * ) Notice: Subject to any disclaimer, the term of this patent is extended or adjusted under 35 U.S.C. 154(b) by 2 days.

This patent is subject to a terminal disclaimer.

(21) Appl. No.: 13/260,779

(22) PCT Filed: Mar. 29, 2010

(86) PCT No.: PCT/EP2010/054100
§ 371 (c)(1),
(2), (4) Date: Sep. 28, 2011

(87) PCT Pub. No.: WO2010/115751
PCT Pub. Date: Oct. 14, 2010

(65) Prior Publication Data
US 2012/0022109 A1    Jan. 26, 2012

Related U.S. Application Data

(60) Provisional application No. 61/169,773, filed on Apr. 16, 2009.

(30) Foreign Application Priority Data

Apr. 3, 2009  (EP) .................................. 09157301

(51) Int. Cl.
| A61K 31/4245 | (2006.01) |
| A61K 31/197 | (2006.01) |
| C07D 271/06 | (2006.01) |

(52) U.S. Cl.
CPC ............ *A61K 31/4245* (2013.01); *A61K 31/197* (2013.01); *C07D 271/06* (2013.01)
USPC ............ 514/364; 514/561; 514/570; 548/131; 562/405

(58) Field of Classification Search
CPC ........................ A61K 31/4245; C07D 271/06
USPC ............ 514/364, 561, 570; 548/131; 562/405
See application file for complete search history.

(56) References Cited

U.S. PATENT DOCUMENTS

| 8,202,865 B2 * | 6/2012 | Quattropani et al. ...... 514/236.2 |
| 2008/0200535 A1 | 8/2008 | Ohmori et al. |
| 2012/0022109 A1 * | 1/2012 | Quattropani et al. ......... 514/326 |

FOREIGN PATENT DOCUMENTS

| WO | WO 2005/058848 | 6/2005 |
| WO | WO 2006/131336 | 12/2006 |
| WO | WO 2009043889 A2 * | 4/2009 |

OTHER PUBLICATIONS

Written Opinion in International Application No. PCT/EP2010/054100, Oct. 4, 2010, pp. 1-8.

* cited by examiner

*Primary Examiner* — Yong Chu
(74) *Attorney, Agent, or Firm* — Saliwanchik, Lloyd & Eisenschenk

(57) ABSTRACT

The invention relates to oxadiazole compounds of formula I. The compounds are useful e.g. in the treatment of autoimmune disorders, such as multiple sclerosis.

5 Claims, No Drawings

OXADIAZOLE DERIVATIVES

CROSS-REFERENCE TO RELATED APPLICATIONS

This application is the U.S. national stage application of International Patent Application No. PCT/EP2010/054100, filed Mar. 29, 2010, which claims the benefit of U.S. Provisional Patent Application No. 61/169,773, filed Apr. 16, 2009.

The present invention relates to oxadiazoles, their use as medicaments and their use for treating multiple sclerosis and other diseases.

In particular, the invention relates to compounds of formula (I):

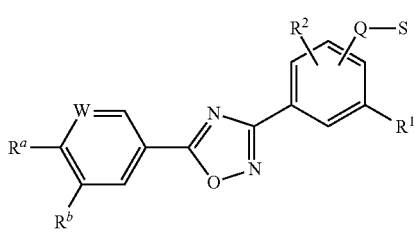

Wherein
$R^1$, $R^2$ denote H, Hal, $CF_3$, $OCF_3$, CN, or $NO_2$, OH, A, OA,
S is NHCOMe, $COOR^3$, $SO_2A$, $CONA_2$
Q denotes $(CH_2)_mX(CH_2)_{m*}$ or, if S denotes NHCOMe, $SO_2A$, Q also denotes a single bond,
X is —$NR^3$—, —COO—
W denotes CH or N,
$R^a$ is Ar or Het,
$R^b$ is $CH_3$, $CH_2CH_3$, $OR^3$, Hal, $OCF_3$, $(CH_2)_nOH$, $(CH_2)_nOA$, $(CH_2)_nN(R^3)_2$, CN, $NO_2$, $N(R^3)_2$, $(CH_2)_nSO_2N(R^3)_2$, $SO_2N(R^3)_2$, $(CH_2)_nNR^3SO_2A$, $(CH_2)_nSO_2A$, $(CH_2)_nN(SO_2A)_2$, $NR^3CON(R^3)_2$ or $NR^3COA$, $NR^3SO_2N(R^3)_2$, or when Q denotes $(CH_2)_mX(CH_2)_{m*}$ with X being —COO— or —$NR^3$— wherein $R^3$ is H, $R^b$ also denotes $CF_3$.
A is branched or linear alkyl having 1 to 12 C-atoms, wherein one or more, preferably 1 to 7 H-atoms may be replaced by Hal, $OR^3$, $COOR^3$, CN, $N(R^3)_2$ and wherein one or more, preferably 1 to 7 non-adjacent $CH_2$-groups may be replaced by O, —$NR^3CO$—, —CO— or S and/or by —CH=CH— or —C≡C-groups or cycloalkylene groups having 3 to 7 carbon atoms, or denotes cycloalkyl or cycloalkylalkylene having 3-7 ring C atoms,
Hal is F, Cl, Br or I,
Ar denotes a monocyclic or bicyclic, saturated, unsaturated or aromatic carbocyclic ring having 6 to 14 carbon atoms, which may be monosubstituted, disubstituted or trisubstituted by Hal, $CH_3$, —$CH_2CH_3OR^3$, $N(R^3)_2$, $NO_2$, CN, $COOR^3$, $OCF_3$, $CON(R^3)_2$, $NR^3COA$, $NR^3CON(R^3)_2$, $NR^3SO_2A$, $COR^3$, $SO_2N(R^3)_2$, SOA or $SO_2A$, phenyl, pyridyl —$[C(R^3)_2]_n$—$COOR^3$ and/or —$O[C(R^3)_2]_n$—CON$(R^3)_2$, such that at least one atom adjacent to the atom linking the group Ar to the rest of the molecule bears one of said substituents.
Het denotes a monocyclic or bicyclic, unsaturated or aromatic heterocyclic ring having 1 to 4 N, O and/or S atoms which may be monosubstituted, disubstituted or trisubstituted by Hal, —$CH_3$, —$CH_2CH_3$, —[C$(R^3)_2]_n$—Ar, —[C$(R^3)_2]_n$-cycloalkyl, $OR^3$, $OCF_3$, $N(R^3)_2$, $NR^3CON(R^3)_2$, $NO_2$, CN, —[C$(R^3)_2]_n$—$COOR^3$, —[C$(R^3)_2]_n$—CON$(R^3)_2$, $NR^3COA$, $NR^3SO_2A$, $COR^3$, $SO_2N(R^3)_2$, SOA, phenyl, pyridyl and/or $SO_2A$, such that at least one atom adjacent to the atom linking the group Het to the rest of the molecule bears one of said substituents,
$R^3$ is H or A; 2 geminal groups $R^3$ together may form a ring with the atom they are attached to,
n is 0, 1, 2, 3, 4, 5, 6, 7 or 8,
and
m, m* are independently from each other 1, 2, 3, 4, 5, 6, 7 or 8,
with the proviso that the following compounds are not included:

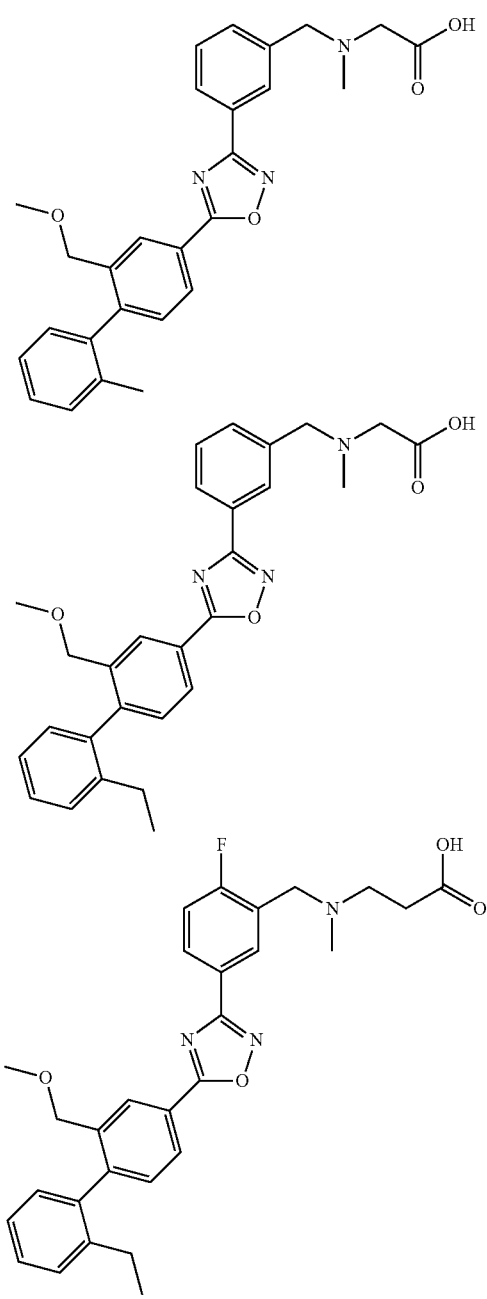

3
-continued
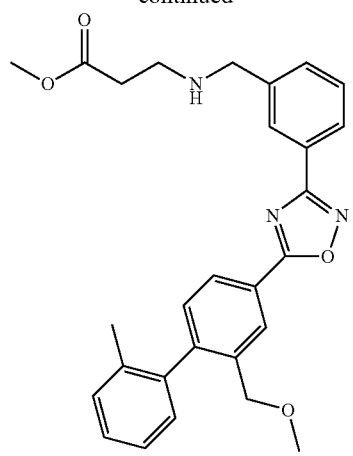
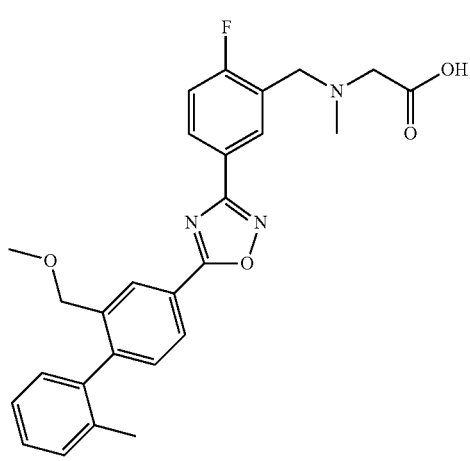
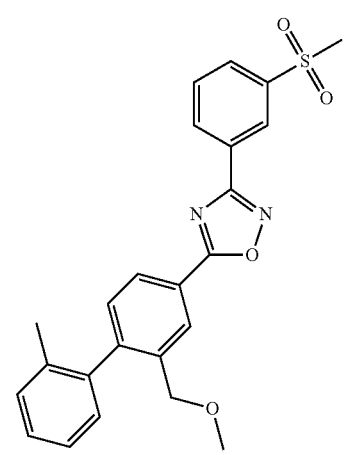
4
-continued
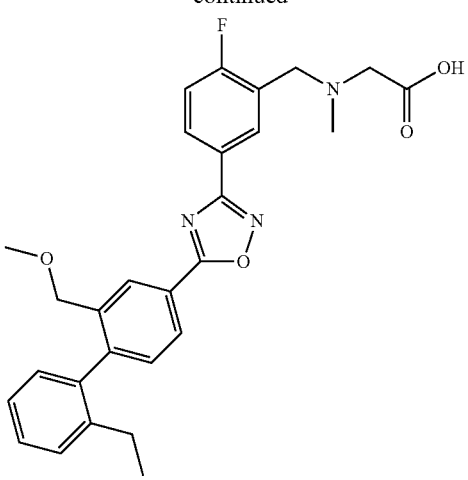
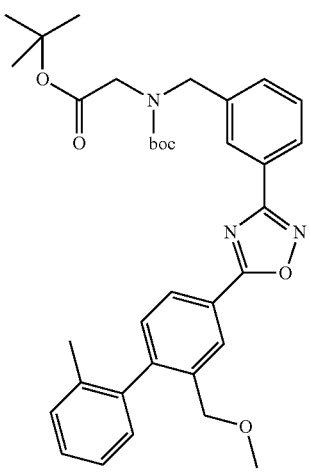

-continued

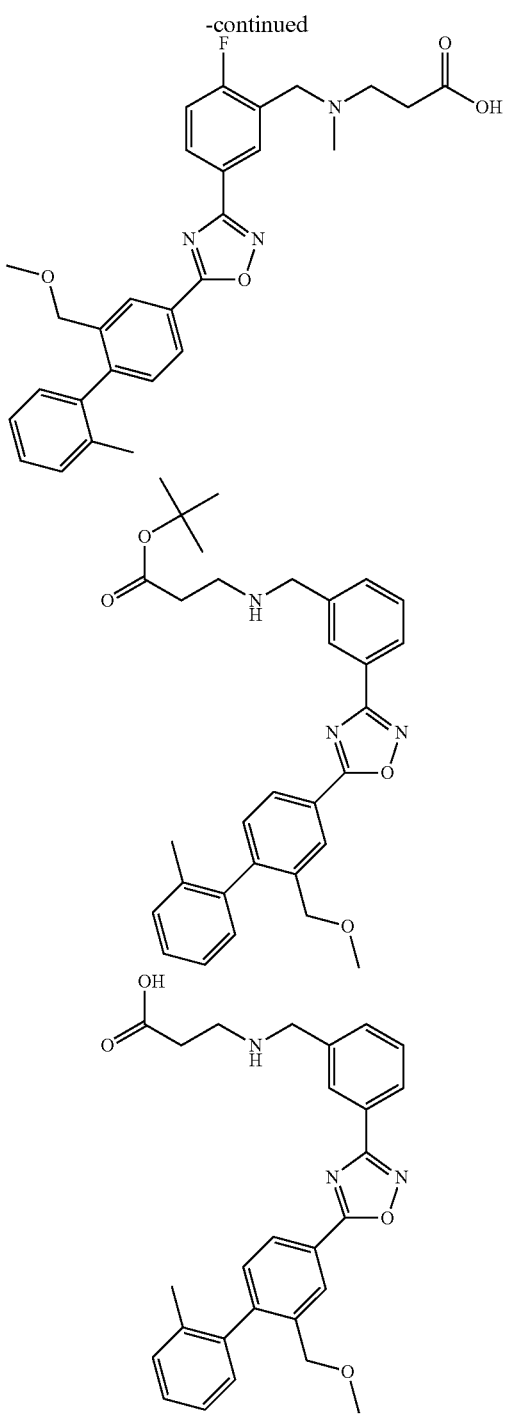

In another specific embodiment, the definitions of the substituents of Formula (I) are the following:
R$^1$, R$^2$ independently from one another denote H, Hal, CF$_3$, OCF$_3$, CN, or NO$_2$, OH, A, OA.
S is OR$^3$ or COOR$^3$,
Q denotes (CH$_2$)$_m$X(CH$_2$)$_{m^*}$,
X is —NA—,
W denotes CH,
R$^a$ is Ar,
R$^b$ is CH$_3$, Hal, OCH$_3$, OCH$_2$CH$_3$, OCF$_3$, (CH$_2$)$_n$OH, CH(CH$_3$)OCH$_3$, (CH$_2$)$_n$N(R$^3$)$_2$, CN, NO$_2$, N(R$^3$)$_2$, (CH$_2$)$_n$SO$_2$N(R$^3$)$_2$, SO$_2$N(R$^3$)$_2$, (CH$_2$)$_n$NR$^3$SO$_2$A, (CH$_2$)$_n$SO$_2$A, (CH$_2$)$_n$N(SO$_2$A)$_2$, NR$^3$CON(R$^3$)$_2$ or NR$^3$COA, NR$^3$SO$_2$N(R$^3$)$_2$,
or if R$^1$ is Hal, CF$_3$, OCF$_3$, CN, NO$_2$, OH, A, OA,
or if R$^2$ is Br, Cl, I, CF$_3$, OCF$_3$, CN, NO$_2$, OH, A, OA,
or if R$^a$ denotes a monocyclic or bicyclic aromatic carbocyclic ring having 6 to 14 carbon atoms, which is disubstituted or trisubstituted by CHF$_2$, Hal, OR$^3$, N(R$^3$)$_2$, NO$_2$, CN, OCF$_3$, CH$_3$, CH$_2$CH$_3$
or if m is 2 to 8,
then R$^b$ also denotes (CH$_2$)$_n$OA or A.
A denotes a linear or branched alkyl having 1 to 6 C-atoms, preferably 1 to 3 carbon atoms, wherein one H-atom may be replaced by Hal, OH, COOR$^3$, CN, N(R$^3$)$_2$ and wherein one CH$_2$-group may be replaced by O, —NR$^3$—, —NR$^3$CO—, —CO— or S and/or by —CH=CH— or —C≡C-groups,
Ar denotes a monocyclic or bicyclic aromatic carbocyclic ring having 6 to 14 carbon atoms, which is monosubstituted, disubstituted or trisubstituted by CHF$_2$, Hal, OR$^3$, N(R$^3$)$_2$, NO$_2$, CN, OCF$_3$,
or if R$^b$ is Hal, OCH$_3$, OCH$_2$CH$_3$, OCF$_3$, (CH$_2$)$_n$OH, (CH$_2$)$_n$N(R$^3$)$_2$, CN, NO$_2$, N(R$^3$)$_2$, (CH$_2$)$_n$SO$_2$N(R$^3$)$_2$, SO$_2$N(R$^3$)$_2$, (CH$_2$)$_n$NR$^3$SO$_2$A, (CH$_2$)$_n$SO$_2$A, (CH$_2$)$_n$N(SO$_2$A)$_2$, NR$^3$CON(R$^3$)$_2$, NR$^3$COA, NR$^3$SO$_2$N(R$^3$)$_2$,
or if R$^2$ is Br, Cl, I, CF$_3$, OCF$_3$, CN, or NO$_2$, OH, A, OA,
or if R$^1$ is Hal, CF$_3$, OCF$_3$, CN, or NO$_2$, OH, A, OA,
Ar may also be substituted by A,
such that at least one atom adjacent to the atom linking the group Ar to the rest of the molecule bears one of said substituents,
R$^3$ is H or A
n is 0, 1, 2, 3, 4, 5, 6, 7 or 8,
and
m and m* independently from one another denote 1, 2, 3, 4, 5, 6, 7 or 8
and pharmaceutically acceptable derivatives, solvates, tautomers, salts and stereoisomers thereof, including mixtures thereof in all ratios.

In another specific embodiment, the definitions of the substituents in Formula (I) are the following:
R$^1$, R$^2$ independently from one another denote H, Hal, CF$_3$, OCF$_3$, CN, or NO$_2$, OH, A, OA.
S is OR$^3$ or COOR$^3$,
Q denotes (CH$_2$)$_m$X(CH$_2$)$_{m^*}$,
X is —NA—,
W denotes CH,
R$^a$ is Ar,
R$^b$ is CH$_3$, Hal, OCF$_3$, CN, NO$_2$, N(R$^3$)$_2$,
A denotes a linear or branched alkyl having 1 to 6 C-atoms, preferably 1 to 3 carbon atoms, wherein one H-atom may be replaced by Hal, OH, COOR$^3$, CN, N(R$^3$)$_2$ and wherein one CH$_2$-group may be replaced by O, —NR$^3$—, —NR$^3$CO—, —CO— or S and/or by —CH=CH— or —C≡C-groups,
Ar denotes a monocyclic or bicyclic aromatic carbocyclic ring having 6 to 14 carbon atoms, which is monosubstituted, disubstituted or trisubstituted by A, CHF$_2$, Hal, OR$^3$, N(R$^3$)$_2$, NO$_2$, CN, OCF$_3$,
such that at least one atom adjacent to the atom linking the group Ar to the rest of the molecule bears one of said substituents,
R$^3$ is H or A
n is 0, 1, 2, 3, 4, 5, 6, 7 or 8,
and
m and m* are independently from each other 1, 2, 3, 4, 5, 6, 7 or 8

In a specific embodiment, the definitions of the substitutents of Formula (I) are the following:

$R^1$, $R^2$ denote H, Hal, $CF_3$, $OCF_3$, CN, or $NO_2$, OH, A, OA,

S is NHCOMe, $OR^3$, $COOR^3$, $SO_2A$, CONHA, $CONA_2$ or Z

Q denotes $X(CH_2)_m$, $(CH_2)_mX(CH_2)_m$ or, if S denotes NHCOMe, $SO_2A$, CONHA or Z, Q also denotes a single bond X is —O—, —$NR^3$—, —COO— or —$CONR^3$—

W denotes CH or N, $R^a$ is Ar or Het, $R^b$ is, A, Hal, $OCF_3$, $(CH_2)_nOH$, $(CH_2)_nOA$, $(CH_2)_nN(R^3)_2$, CN, $NO_2$, $N(R^3)_2$, $(CH_2)_nSO_2N(R^3)_2$, $SO_2N(R^3)_2$, $(CH_2)_nNR^3SO_2A$, $(CH_2)_nSO_2A$, $(CH_2)_nN(SO_2A)_2$, $NR^3CON(R^3)_2$ or $NR^3COA$, $NR^3SO_2N(R^3)_2$, or if $R^1$ or $R^2$ is Hal, or if S is $COOR^3$, or if $R^a$ is Het or substituted Ar, also $CF_3$, $OR^3$.

A is branched or linear alkyl having 1 to 12 C-atoms, wherein one or more, preferably 1 to 7 H-atoms may be replaced by Hal, $OR^3$, $COOR^3$, CN, $N(R^3)$, and wherein one or more, preferably 1 to 7 non-adjacent $CH_2$-groups may be replaced by O, —$NR^3$—, —$NR^3CO$—, —CO— or S and/or by —CH=CH— or —C≡C-groups or cycloalkylene groups having 3 to 7 carbon atoms, or denotes cycloalkyl or cycloalkylalkylene having 3-7 ring C atoms, Z is branched or linear alkyl chain having 1 to 12 C-atoms, wherein one or more, preferably 1 to 7 H-atoms are replaced by $OR^3$, $COOR^3$, $CON(R^3)_2$, CN, $SO_2A$, $N(R^3)_2$ and/or wherein one or more, preferably 1 to 7 non-adjacent $CH_2$-groups are replaced by —O—, —COO—, —$NR^3$—, —$NR^3CO$—, —NBoc-, —CO— or —S—, —$SO_2$— and/or by —CH=CH— or —C≡C— groups or cycloalkylene groups having 3 to 7 carbon atoms, or denotes cycloalkyl or cycloalkylalkylene having 3-7 ring C atoms, Hal is F, Cl, Br or I, Ar denotes a monocyclic or bicyclic, saturated, unsaturated or aromatic carbocyclic ring having 6 to 14 carbon atoms, which may be monosubstituted, disubstituted or trisubstituted by Hal, A, $OR^3$, $N(R^3)_2$, $NO_2$, CN, $COOR^3$, $CF_3$, $OCF_3$, $CON(R^3)_2$, $NR^3COA$, $NR^3CON(R^3)_2$, $NR^3SO_2A$, $COR^3$, $SO_2N(R^3)_2$, SOA or $SO_2A$, phenyl, pyridyl —$[C(R^3)_2]_n$—$COOR^3$ and/or —O$[C(R^3)_2]_n$—$CON(R^3)_2$, such that at least one atom adjacent to the atom linking the group Ar to the rest of the molecule bears one of said substituents.

Het denotes a monocyclic or bicyclic, saturated, unsaturated or aromatic heterocyclic ring having 1 to 4 N, O and/or S atoms which may be monosubstituted, disubstituted or trisubstituted by Hal, A, —$[C(R^3)_2]n$-Ar, —$[C(R^3)_2]_n$-cycloalkyl, $OR^3$, $CF_3$, $OCF_3$, $N(R^3)_2$, $NR^3CON(R^3)_2$, $NO_2$, CN, —$[C(R^3)_2]_n$—$COOR^3$, —$[C(R^3)_2]_n$—$CON(R^3)_2$, $NR^3COA$, $NR^3SO_2A$, $COR^3$, $SO_2N(R^3)_2$, SOA, phenyl, pyridyl and/or $SO_2A$, such that at least one atom adjacent to the atom linking the group Het to the rest of the molecule bears one of said substituents.

$R^3$ is H or A; 2 geminal groups $R^3$ together may form a ring with the atom they are attached to.

n is 0, 1, 2, 3, 4, 5, 6, 7 or 8, and m is 1, 2, 3, 4, 5, 6, 7 or 8 and pharmaceutically acceptable derivatives, solvates, tautomers, salts and stereoisomers thereof, including mixtures thereof in all ratios.

In another specific embodiment, the definitions of the substituents in Formula (I) are the following:

$R^1$, $R^2$ independently from one another denote H, Hal, $CF_3$, $OCF_3$, CN, or $NO_2$, OH, A, OA.

S is $OR^3$ or $COOR^3$,

Q denotes $(CH_2)_mX(CH_2)_m$,

X is —NA-,

W denotes CH, $R^a$ is Ar, $R^b$ is $CH_3$, Hal, $OCF_3$, $(CH_2)_nOH$, $CH(CH_3)OCH_3$, $(CH_2)_nN(R^3)_2$, CN, $NO_2$, $N(R^3)_2$, $(CH_2)_nSO_2N(R^3)_2$, $SO_2N(R^3)_2$, $(CH_2)_nNR^3SO_2A$, $(CH_2)_nSO_2A$, $(CH_2)_nN(SO_2A)_2$, $NR^3CON(R^3)_2$ or $NR^3COA$, $NR^3SO_2N(R^3)_2$, A denotes a linear or branched alkyl having 1 to 6 C-atoms, preferably 1 to 3 carbon atoms, wherein one H-atom may be replaced by Hal, OH, $COOR^3$, CN, $N(R^3)_2$ and wherein one $CH_2$-group may be replaced by O, —$NR^3$—, —$NR^3CO$—, —CO— or S and/or by —CH=CH— or —C≡C-groups, Ar denotes a monocyclic or bicyclic aromatic carbocyclic ring having 6 to 14 carbon atoms, which is monosubstituted, disubstituted or trisubstituted by A, $CHF_2$, Hal, $OR^3$, $N(R^3)_2$, $NO_2$, CN, $OCF_3$, such that at least one atom adjacent to the atom linking the group Ar to the rest of the molecule bears one of said substituents, $R^3$ is H or A n is 0, 1, 2, 3, 4, 5, 6, 7 or 8, and m is 1, 2, 3, 4, 5, 6, 7 or 8

In another embodiment, the present invention provides compounds of formula (AB)

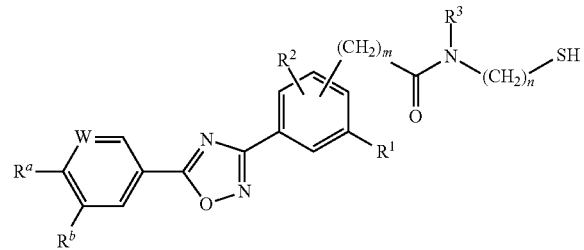

Wherein W, $R^a$, $R^b$, $R^1$, $R^2$, $R^3$, S, m and n are as above defined and pharmaceutically acceptable derivatives, solvates, tautomers, salts and stereoisomers thereof, including mixtures thereof in all ratios.

In another embodiment, the present invention provides compounds of Formula (AC)

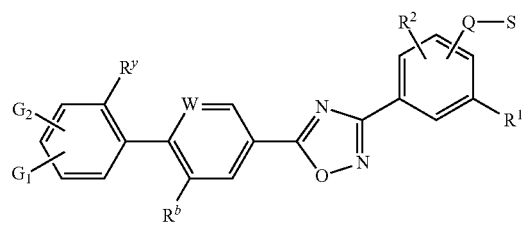

Wherein $R^y$ is $CH_3$, $CH_2CH_3$, F, Br, Cl, preferably F, $CH_3$, $G_1$, $G_2$ independently from one another denote H, Hal, or $CH_3$, preferably H.

And wherein $R^b$, W, $R^1$, $R^2$, Q and S are as above defined.

In a very preferred embodiment, the present invention provides compounds of Formula (AE)

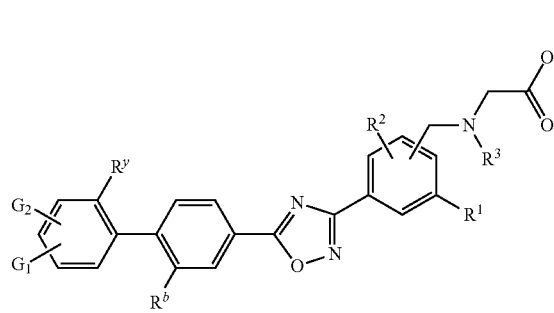

Wherein $G_1$, $G_2$, $R^y$, $R^b$, $R^1$, $R^2$, $R^3$ are as defined above. Preferably $G^1$, $G^2$ are H.

The compounds of formula (I) are preferably binding on receptors for sphingosine 1-phosphate (S1P). S1P is a bioactive sphingolipid metabolite that is secreted by hematopoietic cells and stored and released from activated platelets. It acts as an agonist on a family of G protein-coupled receptors (GPCR). Five sphingosine 1-phosphate receptors have been identified ($S1P_1$, $S1P_2$, $S1P_3$, $S1P_4$, and $S1P_5$, also known as endothelial differentiation genes, which are Edg1, Edg5, Edg3, Edg6 and Edg8 respectively), that have widespread cellular and tissue distribution and are well conserved in human and rodent species.

S1P is involved in a number of cellular functions such as survival, proliferation and immunological responses. The compounds of the present invention are preferably acting as $S1P_1$/Edg1 receptor agonists and thus have immunosuppressive activities by modulating leukocyte trafficking, sequestering lymphocytes in secondary lymphoid tissues, and interfering with cell-cell interactions required for an efficient immune response. The invention is also directed to pharmaceutical compositions containing such compounds and methods of treatment or prevention.

FTY720 or fingolimod, a non selective $S1P_1$ agonist, exerts immunosuppressive activity and shows therapeutic effects in the treatment of relapsing-remitting multiple sclerosis. Numerous publications have been already published using this compound: Cyster J G Annu Rev Immunol 23:127-59, 2005, Rosen H Nat Rev Immunol 5:560-570, 2005, Rosen H Trends Immunol 28:102-107, 2007, Yopp A C Clin Transplant 20:788-795, 2006, Kappos L N Engl J Med 355:1124-1140, 2006, Massberg S N Engl J Med 355:1088-1089, 2006.

Immunosuppressive agents are further useful in a wide variety of autoimmune and chronic inflammatory diseases, including systemic lupus erythematosus, chronic rheumatoid arthritis, type I diabetes mellitus, inflammatory bowel diseases, biliary cirrhosis, uveitis and other disorders such as Crohn's diseases, ulcerative colitis, bullous pemphigoid, sarcoidosis, psoriasis, autoimmune myositis, Wegener's granulomatosis, ichthyosis, Graves' ophthalmopathy, atopic dermatitis and asthma. They are also useful as part of chemotherapeutic regimens for the treatment of cancers, lymphomas and leukemias.

Patent application WO2006/131336 describes oxadiazoles derivatives containing a biphenyl ring. Further oxadiazole derivatives containing a phenyl group substituted with a cycloalkyl group are known from Bioorg Med. Chem. Lett. 16 (2006) 3679-3683.

Oxadiazole derivatives are described in the patent application EP07117921.2.

It has been found that the compounds of the present invention are selective $S1P_1$ agonists with improved pharmacological and/or other properties.

The present invention uses compounds of Formula (I) and pharmaceutically usable derivatives, salts, tautomers, solvates and stereoisomers thereof, including mixtures thereof in all ratios, for the preparation of a medicament for the treatment and/or prophylaxis of diseases in which the inhibition, activation, regulation, and/or modulation of $S1P_1$ receptor signal transduction plays a role.

Thus, the present invention preferably comprises compounds which are agonists of the $S1P_1$/Edg1 receptor, especially having selectivity over the $51P_3$/Edg3 receptor. An $S1P_1$/Edg1 receptor selective agonist has advantages over current therapies and extends the therapeutic window of lymphocyte sequestration agents, allowing better tolerability with higher dosing and thus improving efficacy.

The invention further relates to the manufacture of a medicament for the improvement of vascular function, either alone or in combination with other active compounds or therapies.

The oxadiazole compounds according to formula (I) may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The following abbreviations refer respectively to the definitions below: aq (aqueous), h (hour), g (gram), L (liter), mg (milligram), MHz (Megahertz), μM (micromolar) min. (minute), mm (millimeter), mmol (millimole), mM (millimolar), m.p. (melting point), eq (equivalent), mL (milliliter), μL (microliter), ACN (acetonitrile), BINAP (2,2'-bis(disphenylphosphino)-1,1'-binaphthalene, BOC (tert-butoxy-carbonyl), CBZ (carbobenzoxy), CDCl3 (deuterated chloroform), CD3OD (deuterated methanol), CH3CN (acetonitrile), c-hex (cHex), DCC (dicyclohexyl carbodiimide), DCM (DCM), dppf (1,1'-bis(diphenylphosphino)ferrocene), DIC (diisopropyl carbodiimide), DIEA (diisopropylethylamine), DMF (dimethylformamide), DMSO (dimethylsulfoxide), DMSO-d6 (deuterated dimethylsulfoxide), EDC (1-(3-dimethyl-amino-propyl)-3-ethylcarbodiimide), ESI (Electro-spray ionization), EtOAc (EtOAc), Et2O (diethyl ether), EtOH (ethanol), FMOC (fluorenylmethyloxycarbonyl), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), K2CO3 (potassium carbonate), LC (Liquid Chromatography), MD Autoprep (Mass directed Autoprep), MeOH (methanol), MgSO4 (magnesium sulfate), MS (mass spectrometry), MTBE (Methyl tert-butyl ether), Mtr. (4-Methoxy-2,3,6-trimethylbenzensulfonyl), MW (microwave), NBS (N-bromo succinimide), NaHCO3 (sodium bicarbonate), NaBH4 (sodium borohydride), NMM (N-methyl morpholine), NMR (Nuclear Magnetic Resonance), POA (phenoxyacetate), Py (pyridine), PyBOP® (benzotriazole-1-yl-oxy-tris-pyrrolidino-phosphonium hexafluorophosphate), RT (RT), Rt (retention time), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (THF), TLC (Thin Layer Chromatography), UV (Ultraviolet).

Depending on the nature of $R^1$, $R^2$, $R^a$, $R^b$, W, Q, and S, different synthetic strategies may be selected for the synthesis of compounds of formula (I). In the process illustrated in the following schemes $R^1$, $R^2$, $R^a$, $R^b$, W, Q, and S, are as above-defined in the description.

In general, the oxadiazole compounds according to formula (I) of this invention may be prepared from readily available starting materials. If such starting materials are not commercially available they may be prepared by standard synthetic techniques. The following general methods and procedures described hereinafter in the examples may be employed to prepare compounds of formula (I). Reaction conditions depicted in the following schemes, such as temperatures, solvent, or co-reagents, are given as examples only and are not restrictive.

Compounds of Formula (I) and related formulae, wherein $R^a$, $R^b$, $R^1$, $R^2$, Q and S are defined as above, can be converted to alternative compounds of Formula (I) and related formulae, $R^a$, $R^b$, $R^1$, $R^2$, Q and S are defined as above, employing suitable interconversion techniques well known by a person skilled in the art.

Generally, compounds of formula (I'), wherein $R^1$, $R^2$, $R^a$, $R^b$, W and Q are defined as above, can be prepared by hydrolysis of the ester derivatives of formula (I''), wherein $R^3$ is as above defined and more preferably $R^3$ is a methyl or tertbutyl group, using conditions well known to those skilled in the art, such as a metal hydroxide, e.g. lithium hydroxide, sodium hydroxide or potassium hydroxide, in a suitable solvent such as THF, methanol, ethanol or water or mixtures thereof, or using an acid, e.g. HCl or TFA, in a suitable solvent such as dioxane, DCM, at a temperature between about 20° C. to about 50° C., preferably at RT, for a few hours, e.g. one hour to 24 h (Scheme 1).

Scheme 1

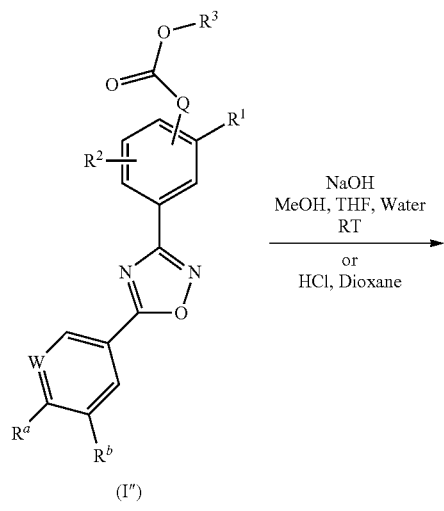

(I'')

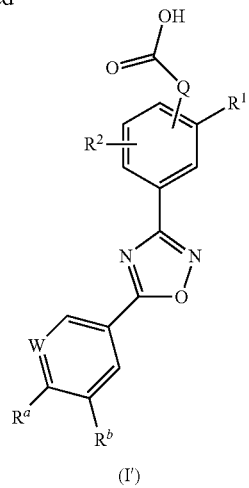

(I')

The method for preparing ester derivatives of Formula (I'') selected below:

Tert-butyl N-(3-{5-[2'-ethyl-2-(methoxymethyl)biphenyl-4-yl]-1,2,4-oxadiazol-3-yl}benzyl)-N-methyl-beta-alaninate Tert-butyl N-(3-{5-[3-(methoxymethyl)-4-(2-methylpiperidin-1-yl)phenyl]-1,2,4-oxadiazol-3-yl}benzyl)-N-methyl-beta-alaninate Ethyl N-(2-fluoro-4-{5-[3-(methoxymethyl)-4-(2-methyl piperidin-1-yl)phenyl]-1,2,4-oxadiazol-3-yl}benzoyl)-beta-alaninate Tert-butyl [(3-{5-[3-(methoxymethyl)-4-(2-methylpiperidin-1-yl)phenyl]-1,2,4-oxadiazol-3-yl}benzyl)oxy]acetate Ethyl 4-(2,3-difluoro-5-{5-[2-(methoxymethyl)-2'-methylbiphenyl-4-yl]-1,2,4-oxadiazol-3-yl}phenoxy)butanoate Tert-butyl 3-[(3-{5-[2-(methoxymethyl)-2'-methylbiphenyl-4-yl]-1,2,4-oxadiazol-3-yl}benzyl)oxy]propanoate Tert-butyl 3-[(3-{5-[3-(methoxymethyl)-4-(2-methylpiperidin-1-yl)phenyl]-1,2,4-oxadiazol-3-yl}benzyl)oxy]propanoate Tert-butyl N-(3-{5-[2'-fluoro-2-(methoxymethyl)biphenyl-4-yl]-1,2,4-oxadiazol-3-yl}benzyl)-N-methylglycinate Tert-butyl N-(3-{5-[2'-chloro-2-(methoxymethyl)biphenyl-4-yl]-1,2,4-oxadiazol-3-yl}benzyl)-N-methylglycinate Tert-butyl 3-[(3-{5-[4-(2-methylpiperidin-1-yl)-3-(trifluoromethyl)phenyl]-1,2,4-oxadiazol-3-yl}benzyl)oxy]propanoate Tert-butyl N-methyl-N-(3-{5-[4-(2-methylpiperidin-1-yl)-3-(trifluoromethyl)phenyl]-1,2,4-oxadiazol-3-yl}benzyl)glycinate Tert-butyl N-methyl-N-(3-{5-[2'-methyl-2-(trifluoromethyl)biphenyl-4-yl]-1,2,4-oxadiazol-3-yl}benzyl)glycinate Methyl 2-chloro-4-{5-[2-(methoxymethyl)-2'-methylbiphenyl-4-yl]-1,2,4-oxadiazol-3-yl}benzoate Example 13 Step 1

Methyl N-(2-chloro-4-{5-[2-(methoxymethyl)-2'-methylbiphenyl-4-yl]-1,2,4-oxadiazol-3-yl}benzoyl)-beta-alaninate Ethyl N-(4-{5-[2'-ethyl-2-(methoxymethyl)biphenyl-4-yl]-1,2,4-oxadiazol-3-yl}-2-fluorobenzoyl)-beta-alaninate Tert-butyl N-(3-{5-[4-(2-ethylpiperidin-1-yl)-3-(methoxymethyl)phenyl]-1,2,4-oxadiazol-3-yl}benzyl)-N-methylglycinate Tert-butyl N-(tert-butoxycarbonyl)-N-(3-{5-[2'-ethyl-2-(methoxymethyl)biphenyl-4-yl]-1,2,4-oxadiazol-3-yl}benzyl)-beta-alaninate Tert-butyl N-(2-fluoro-5-{5-[3-(methoxymethyl)-4-(2-methylpiperidin-1-yl)phenyl]-1,2,4-oxadiazol-3-yl}benzyl)-N-methyl-beta-alaninate Tert-butyl N-(3-fluoro-5-{5-[2-(methoxymethyl)-2'-methylbiphenyl-4-yl]-1,2,4-oxadiazol-3-yl}benzyl)-N-methylglycinate Tert-butyl N-(3-fluoro-5-{5-[2-(methoxymethyl)-2'-methylbiphenyl-4-yl]-1,2,4-oxadiazol-3-yl}benzyl)-N-methyl-beta-alaninate Tert-butyl N-(3-{5-[3-(methoxymethyl)-4-(2-methylpyrrolidin-1-yl)phenyl]-1,2,4-oxadiazol-3-yl}benzyl)-N-methylglycinate Tert-butyl N-(3-{5-[3'-fluoro-2-(methoxymethyl)-2'-methylbiphenyl-4-yl]-1,2,4-oxadiazol-3-yl}benzyl)-N-methylglycinate Tert-butyl N-(3-{5-[4'-fluoro-2-(methoxymethyl)-2'-methylbiphenyl-4-yl]-1,2,4-oxadiazol-3-yl}benzyl)-N-methylglycinate Tert-butyl N-(3-{5-[5'-fluoro-2-(methoxymethyl)-2'-methylbiphenyl-4-yl]-1,2,4-oxadiazol-3-yl}benzyl)-N-methylglycinate Tert-butyl [(3-{5-[4-(2-methylpiperidin-1-yl)-3-(trifluoromethyl)phenyl]-1,2,4-oxadiazol-3-yl}benzyl)oxy]acetate Tert-butyl N-(3-{5-[3',4'-difluoro-2-(methoxymethyl)-2'-methylbiphenyl-4-yl]-1,2,4-oxadiazol-3-yl}benzyl)-N-methylglycinate Ethyl N-[(3-{5-[2-(methoxymethyl)-2'-methylbiphenyl-4-yl]-1,2,4-oxadiazol-3-yl}phenyl)acetyl]-beta-alaninate methyl N-[(3-{5-[2-(methoxymethyl)-2'-methylbiphenyl-4-yl]-1,2,4-oxadiazol-3-yl}phenyl)acetyl]-N-methylglycinate Tert-butyl N-methyl-N-(3-{5-[4-[(2R)-2-methylpiperidin-1-yl]-3-(trifluoromethyl)phenyl]-1,2,4-oxadiazol-3-yl}benzyl)glycinate Tert-butyl N-methyl-N-(3-{5-[4-[(2S)-2-methylpiperidin-1-yl]-3-(trifluoromethyl)phenyl]-1,2,4-oxadiazol-3-yl}benzyl)glycinate methyl 2,5-difluoro-4-{5-[2-(methoxymethyl)-2'-methylbiphenyl-4-yl]-1,2,4-oxadiazol-3-yl}benzoate Methyl N-(2,5-difluoro-4-{5-[2-(methoxymethyl)-2'-methylbiphenyl-4-yl]-1,2,4-oxadiazol-3-yl}benzoyl)-beta-alaninate Tert-butyl [(3-{5-[2'-methyl-2-(trifluoromethyl)biphenyl-4-yl]-1,2,4-oxadiazol-3-yl}benzyl)oxy]acetate Tert-butyl N-(3-{5-[2-(methoxymethyl)-2'-(trifluoromethyl)biphenyl-4-yl]-1,2,4-oxadiazol-3-yl}benzyl)-N-methylglycinate Tert-butyl N-(3-{5-[4'-fluoro-2-(methoxymethyl)-2'-(trifluoromethyl)biphenyl-4-yl]-1,2,4-oxadiazol-3-yl}benzyl)-N-methylglycinate Tert-butyl N-(4-{5-[2-(methoxymethyl)-2'-methylbiphenyl-4-yl]-1,2,4-oxadiazol-3-yl}benzyl)-N-methylglycinate Tert-butyl N-(2-fluoro-4-{5-[2-(methoxymethyl)-2'-methylbiphenyl-4-yl]-1,2,4-oxadiazol-3-yl}benzyl)-N-methylglycinate Tert-butyl N-(2-bromo-4-{5-[2-(methoxymethyl)-2'-methylbiphenyl-4-yl]-1,2,4-oxadiazol-3-yl}benzyl)-N-methylglycinate Tert-butyl N-(4-{5-[2'-fluoro-2-(methoxymethyl)biphenyl-4-yl]-1,2,4-oxadiazol-3-yl}benzyl)-N-methylglycinate Tert-butyl N-(2-fluoro-4-{5-[2'-fluoro-2-(methoxymethyl)biphenyl-4-yl]-1,2,4-oxadiazol-3-yl}benzyl)-N-methylglycinate Tert-butyl N-(3-fluoro-5-{5-[4-(2-methylpiperidin-1-yl)-3-(trifluoromethyl)phenyl]-1,2,4-oxadiazol-3-yl}benzyl)-N-methylglycinate Tert-butyl N-(3-fluoro-5-{5-[2'-fluoro-2-(methoxymethyl)biphenyl-4-yl]-1,2,4-oxadiazol-3-yl}benzyl)-N-methylglycinate tert-butyl N-isopropyl-N-(3-{5-[2-(methoxymethyl)-2'-methylbiphenyl-4-yl]-1,2,4-oxadiazol-3-yl}benzyl)glycinate Tert-butyl N-(tert-butoxycarbonyl)-N-(4-{5-[2-(methoxymethyl)-2'-methylbiphenyl-4-yl]-1,2,4-oxadiazol-3-yl}benzyl)glycinate Tert-butyl N-(tert-butoxycarbonyl)-N-(4-{5-[2'-fluoro-2-(methoxymethyl)biphenyl-4-yl]-1,2,4-oxadiazol-3-yl}benzyl)glycinate Tert-butyl N-ethyl-N-(3-{5-[2'-fluoro-2-(methoxymethyl)biphenyl-4-yl]-1,2,4-oxadiazol-3-yl}benzyl)-beta-alaninate Tert-butyl N-ethyl-N-(3-{5-[2-(methoxymethyl)-2'-methylbiphenyl-4-yl]-1,2,4-oxadiazol-3-yl}benzyl)-beta-alaninate Tert-butyl N-(3-fluoro-5-{5-[2'-methyl-2-(trifluoromethyl)biphenyl-4-yl]-1,2,4-oxadiazol-3-yl}benzyl)-N-methylglycinate Tert-butyl N-(3-{5-[2'-chloro-5'-fluoro-2-(methoxymethyl)biphenyl-4-yl]-1,2,4-oxadiazol-3-yl}benzyl)-N-methylglycinate Tert-butyl N-(2-hydroxyethyl)-N-(3-{5-[2-(methoxymethyl)-2'-methylbiphenyl-4-yl]-1,2,4-oxadiazol-3-yl}benzyl)-beta-alaninate Tert-butyl N-ethyl-N-(3-{5-[2'-methyl-2-(trifluoromethyl)biphenyl-4-yl]-1,2,4-oxadiazol-3-yl}benzyl)-beta-alaninate Tert-butyl N-(2-fluoro-4-{5-[2'-methyl-2-(trifluoromethyl)biphenyl-4-yl]-1,2,4-oxadiazol-3-yl}benzyl)-N-methylglycinate Tert-butyl N-(2-fluoro-4-{5-[2'-methyl-2-(trifluoromethyl)biphenyl-4-yl]-1,2,4-oxadiazol-3-yl}benzyl)-N-methyl-beta-alaninate Tert-butyl N-(2-fluoro-4-{5-[2-(methoxymethyl)-2'-methylbiphenyl-4-yl]-1,2,4-oxadiazol-3-yl}benzyl)-N-methyl-beta-alaninate Tert-butyl N-(4-{5-[2-(methoxymethyl)-2'-methylbiphenyl-4-yl]-1,2,4-oxadiazol-3-yl}benzyl)-N-methyl-beta-alaninate tert-butyl 2-((2-methoxy-4-(5-(2-(methoxymethyl)-2'-methylbiphenyl-4-yl)-1,2,4-oxadiazol-3-yl)benzyl)(methyl)amino)acetate Tert-butyl N-methyl-N-(4-{5-[2'-methyl-2-(trifluoromethyl)biphenyl-4-yl]-1,2,4-oxadiazol-3-yl}benzyl)glycinate Tert-butyl N-(tert-butoxycarbonyl)-N-(2-fluoro-4-{5-[2'-fluoro-2-(methoxymethyl)biphenyl-4-yl]-1,2,4-oxadiazol-3-yl}benzyl)glycinate Tert-butyl N-(tert-butoxycarbonyl)-N-(2-fluoro-4-{5-[2-(methoxymethyl)-2'-methylbiphenyl-4-yl]-1,2,4-oxadiazol-3-yl}benzyl)glycinate Tert-butyl N-(2-fluoro-4-{5-[4-(2-methylpiperidin-1-yl)-3-(trifluoromethyl)phenyl]-1,2,4-oxadiazol-3-yl}benzyl)-N-methylglycinate tert-butyl N-[2-(3-{5-[2-(methoxymethyl)-2'-methylbiphenyl-4-yl]-1,2,4-oxadiazol-3-yl}phenyl)ethyl]-N-methylglycinate Tert-butyl N-(3-fluoro-5-{5-[3'-fluoro-2-(methoxymethyl)-2'-methylbiphenyl-4-yl]-1,2,4-oxadiazol-3-yl}benzyl)-N-methylglycinate Tert-butyl N-(4-{5-[2'-fluoro-2-(trifluoromethyl)biphenyl-4-yl]-1,2,4-oxadiazol-3-yl}benzyl)-N-methylglycinate Tert-butyl N-(4-{5-[3'-fluoro-2-(methoxymethyl)-2'-methylbiphenyl-4-yl]-1,2,4-oxadiazol-3-yl}benzyl)-N-methylglycinate Tert-butyl N-(2-fluoro-4-{5-[3'-fluoro-2-(methoxymethyl)-2'-methylbiphenyl-4-yl]-1,2,4-oxadiazol-3-yl}benzyl)-N-methylglycinate Tert-butyl N-{4-[5-(2-ethoxy-2'-methylbiphenyl-4-yl)-1,2,4-oxadiazol-3-yl]-2-fluorobenzyl}-N-methylglycinate Tert-butyl N-(3-chloro-5-{5-[2-(methoxymethyl)-2'-methylbiphenyl-4-yl]-1,2,4-oxadiazol-3-yl}benzyl)-N-methylglycinate Tert-butyl N-(2-fluoro-4-{5-[2-(methoxymethyl)-2'-(trifluoromethyl)biphenyl-4-yl]-1,2,4-oxadiazol-3-yl}benzyl)-N-methylglycinate Tert-butyl N-(2-fluoro-3-{5-[2-(methoxymethyl)-2'-methylbiphenyl-4-yl]-1,2,4-oxadiazol-3-yl}benzyl)-N-methylglycinate Tert-butyl N-(4-{5-[2-(methoxymethyl)-2'-(trifluoromethyl)biphenyl-4-yl]-1,2,4-oxadiazol-3-yl}benzyl)-N-methylglycinate Tert-butyl N-(tert-oxycarbonyl)-N-(2-fluoro-4-{5-[2'-methyl-2-(trifluoromethyl)biphenyl-4-yl]-1,2,4-oxadiazol-3-yl}benzyl)glycinate Tert-butyl N-{4-[5-(2-ethoxy-2'-ethylbiphenyl-4-yl)-1,2,4-oxadiazol-3-yl]benzyl]-N-methylglycinate Tert-butyl N-methyl-N-(4-{5-[2-methyl-2'-(trifluoromethyl)biphenyl-4-yl]-1,2,4-oxadiazol-3-yl}benzyl)glycinate Tert-butyl N-isopropyl-N-(3-{5-[2'-methyl-2-(trifluoromethyl)biphenyl-4-yl]-1,2,4-oxadiazol-3-yl}benzyl)-beta-alaninate Tert-butyl N-(3-fluoro-5-{5-[2-methyl-2'-(trifluoromethyl)biphenyl-4-yl]-1,2,4-oxadiazol-3-yl}benzyl)-N-methylglycinate Tert-butyl N-isopropyl-N-(3-{5-[2-(methoxymethyl)-2'-methylbiphenyl-4-yl]-1,2,4-oxadiazol-3-yl}benzyl)-beta-alaninate Tert-butyl N-(4-{5-[2'-ethyl-2-(trifluoromethyl)biphenyl-4-yl]-1,2,4-oxadiazol-3-yl}benzyl)-N-methylglycinate Tert-butyl N-(4-{5-[2'-ethyl-2-(trifluoromethyl)biphenyl-4-yl]-1,2,4-oxadiazol-3-yl}-2-fluorobenzyl)-N-methylglycinate Tert-butyl N-(2-chloro-5-{5-[2'-methyl-2-(trifluoromethyl)biphenyl-4-yl]-1,2,4-oxadiazol-3-yl}benzyl)-N-methylglycinate Tert-butyl N-(2-fluoro-3-{5-[2'-methyl-2-(trifluoromethyl)biphenyl-4-yl]-1,2,4-oxadiazol-3-yl}benzyl)-N-methylglycinate Tert-butyl N-(2-fluoro-3-{5-[2-(methoxymethyl)-2'-(trifluoromethyl)biphenyl-4-yl]-1,2,4-oxadiazol-3-yl}benzyl)-N-methylglycinate Tert-butyl N-(4-{5-[2-ethoxy-2'-(trifluoromethyl)biphenyl-4-yl]-1,2,4-oxadiazol-3-yl}benzyl)-N-methylglycinate Tert-butyl 4-[methyl(4-{5-[2'-methyl-2-(trifluoromethyl)biphenyl-4-yl]-1,2,4-oxadiazol-3-yl}benzyl)amino]butanoate Tert-butyl N-(4-{5-[2'-chloro-2-(methoxymethyl)biphenyl-4-yl]-1,2,4-oxadiazol-3-yl}benzyl)-N-methylglycinate Tert-butyl N-(4-{5-[2'-chloro-2-(methoxymethyl)biphenyl-4-yl]-1,2,4-oxadiazol-3-yl}-2-fluorobenzyl)-N-methylglycinate Tert-butyl [(2-fluoro-4-{5-[2'-methyl-2-(trifluoromethyl)biphenyl-4-yl]-1,2,4-oxadiazol-3-yl}benzyl)oxy]acetate Tert-butyl N-(4-{5-[2'-chloro-3'-fluoro-2-(methoxymethyl)biphenyl-4-yl]-1,2,4-oxadiazol-3-yl}-2-fluorobenzyl)-N-methylglycinate Tert-butyl N-(4-{5-[2'-chloro-3'-fluoro-2-(methoxymethyl)biphenyl-4-yl]-1,2,4-oxadiazol-3-yl}benzyl)-N-methylglycinate tert-butyl N-(2-ethyl-4-{5-[2-(methoxymethyl)-2'-methylbiphenyl-4-yl]-1,2,4-oxadiazol-3-yl}phenyl)-N-methylglycinate Tert-butyl N-(3,4-difluoro-5-{5-[2-(methoxymethyl)-2'-methylbiphenyl-4-yl]-1,2,4-oxadiazol-3-yl}benzyl)-N-methylglycinate Tert-butyl N-(4-{5-[5'-fluoro-2-(methoxymethyl)-2'-methylbiphenyl-4-yl]-1,2,4-oxadiazol-3-yl}benzyl)-N-methylglycinate tert-butyl 2-((2-chloro-4-(5-(2-(methoxymethyl)-2'-methylbiphenyl-4-yl)-1,2,4-oxadiazol-3-yl)benzyl)(methyl)amino)acetate Tert-butyl N-{4-[5-(2,2'-dimethylbiphenyl-4-yl)-1,2,4-oxadiazol-3-yl]benzyl}-N-methylglycinate Tert-butyl N-{4-[5-(2,2'-dimethylbiphenyl-4-yl)-1,2,4-oxadiazol-3-yl]-2-fluorobenzyl}-N-methylglycinate Tert-butyl N-{3-[5-(2,2'-dimethylbiphenyl-4-yl)-1,2,4-oxadiazol-3-yl]benzyl}-N-methylglycinate Tert-butyl N-{3-[5-(2,2'-dimethylbiphenyl-4-yl)-1,2,4-oxadiazol-3-yl]-5-fluorobenzyl}-N-methylglycinate Tert-butyl N-(4-{5-[2-chloro-2'-(trifluoromethyl)biphenyl-4-yl]-1,2,4-oxadiazol-3-yl}-2-fluorobenzyl)-N-methylglycinate Tert-butyl N-(4-{5-[2-chloro-2'-(trifluoromethyl)biphenyl-4-yl]-1,2,4-oxadiazol-3-yl}benzyl)-N-methylglycinate Tert-butyl N-(3-{5-[2-chloro-2'-(trifluoromethyl)biphenyl-4-yl]-1,2,4-oxadiazol-3-yl}-5-fluorobenzyl)-N-methylglycinate Tert-butyl N-(4-{5-[2'-(difluoromethyl)-2-methylbiphenyl-4-yl]-1,2,4-oxadiazol-3-yl}benzyl)-N-methylglycinate Tert-butyl N-(2-methoxyethyl)-N-(4-{5-[2'-methyl-2-(trifluoromethyl)biphenyl-4-yl]-1,2,4-oxadiazol-3-yl}benzyl)glycinate Tert-butyl [(4-{5-[2'-methyl-2-(trifluoromethyl)biphenyl-4-yl]-1,2,4-oxadiazol-3-yl}benzyl)oxy]acetate Tert-butyl N-(4-{5-[2-(1-methoxyethyl)-2'-methylbiphenyl-4-yl]-1,2,4-oxadiazol-3-yl}benzyl)-N-methylglycinate Tert-butyl [(4-{5-[2-(1-methoxyethyl)-2'-methylbiphenyl-4-yl]-1,2,4-oxadiazol-3-yl}benzyl)oxy]acetate Tert-butyl 2-((3-chloro-4-(5-(2-(methoxymethyl)-2'-methylbiphenyl-4-yl)-1,2,4-oxadiazol-3-yl)benzyl)(methyl)amino)acetate Tert-butyl 2-((2,6-difluoro-4-(5-(2'-methyl-2-(trifluoromethyl)biphenyl-4-yl)-1,2,4-oxadiazol-3-yl)benzyl)(methyl)amino)acetate Tert-butyl N-(2-ethyl-4-{5-[2'-methyl-2-(trifluoromethyl)biphenyl-4-yl]-1,2,4-oxadiazol-3-yl}phenyl)-N-methylglycinate is more particularly described in the examples.

Alternatively, alcohol derivatives of Formula (I''') may be converted into the corresponding amine derivatives of Formula (I), wherein Q=$(CH_2)_m X(CH_2)_m$ with X=$-NR^3-$, and S, m, $R^1$, $R^2$, $R^3$, $R^a$ and $R^b$ are defined as above, as outlined in Scheme 1a. Compounds of Formula (I''') can be first be transformed into the corresponding mesyl or tosyl groups (I''''), which can then reacted with an amine $HN(R^3)(CH_2)_m S$, affording compounds of Formula (I) wherein Q-S=$(CH_2)_m N(R^3)(CH_2)_m S$ and S, m, $R^1$, $R^2$, $R^3$, $R^a$ and $R^b$ are defined as above (Scheme 1a). Alcohol (I''') can be oxidized into the corresponding aldehyde (I''''), using conditions well known to those skilled in the art, such as but not limited to Swern oxidation conditions, or the use of $MnO_2$ as oxidative agent for benzylic alcohols, as illustrated on Scheme 1a. Then a reductive amination of the compounds of Formula (I'''') with a suitable amine $HN(R^3)(CH_2)_m S$, affords compounds of Formula (I), wherein S, m, $R^1$, $R^2$, $R^3$, $R^a$ and $R^b$ are defined as above.

Scheme 1a

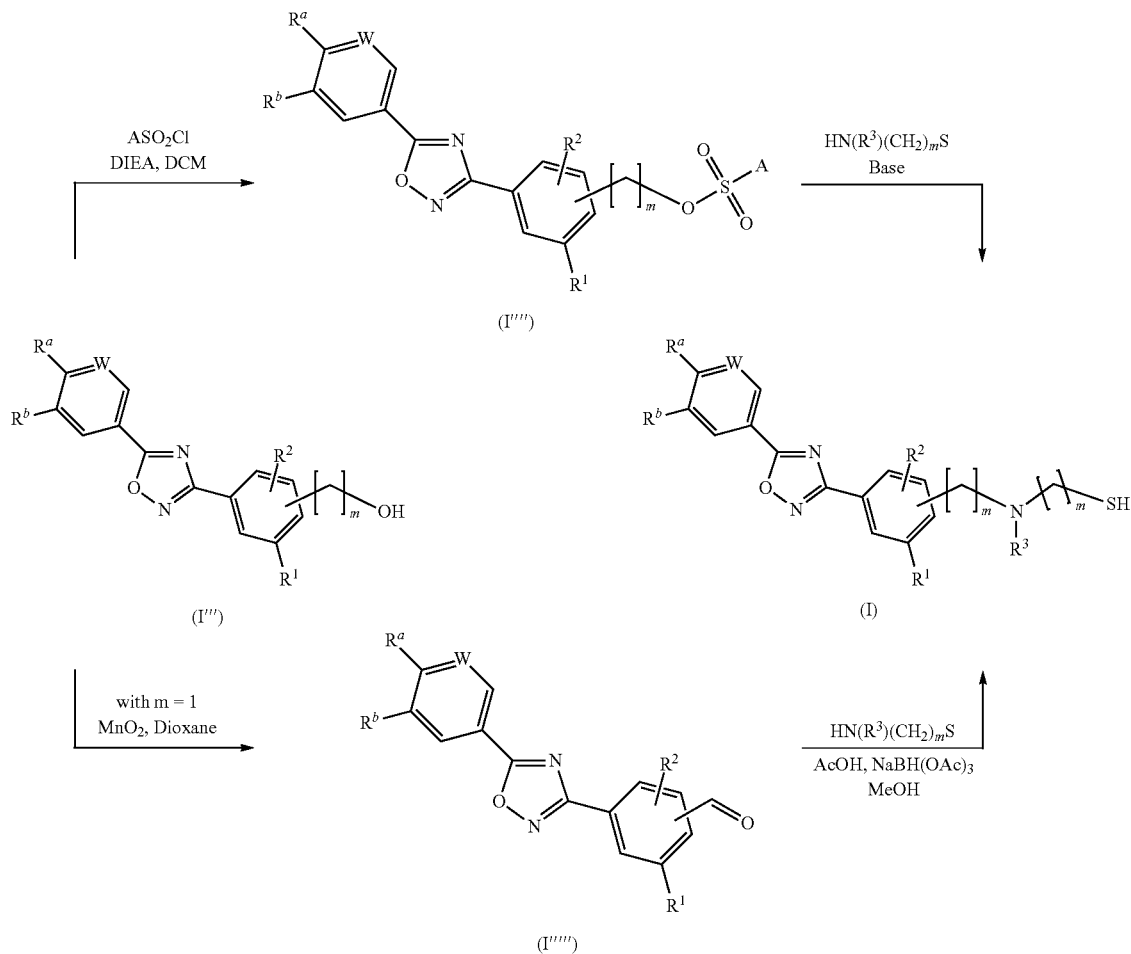

The method for preparing alcohol derivatives of Formula (I''') selected below:
(3-{5-[2-(methoxymethyl)-2'-methylbiphenyl-4-yl]-1,2,4-oxadiazol-3-yl}phenyl)methanol
2-(3-{5-[2-(methoxymethyl)-2'-methylbiphenyl-4-yl]-1,2,4-oxadiazol-3-yl}phenyl)ethanol
2-(4-(5-(2-(methoxymethyl)-2'-methylbiphenyl-4-yl)-1,2,4-oxadiazol-3-yl)phenyl)ethanol
(4-(5-(2-(methoxymethyl)-2'-methylbiphenyl-4-yl)-1,2,4-oxadiazol-3-yl)-3-methylphenyl)methanol
(4-(5-(2'-methyl-2-(trifluoromethyl)biphenyl-4-yl)-1,2,4-oxadiazol-3-yl)phenyl)methanol
(4-(5-(2-(methoxymethyl)-2'-methylbiphenyl-4-yl)-1,2,4-oxadiazol-3-yl)-2-methylphenyl)methanol
(3-fluoro-4-(5-(2-(methoxymethyl)-2'-methylbiphenyl-4-yl)-1,2,4-oxadiazol-3-yl)phenyl)methanol
(2,6-difluoro-4-(5-(2-(methoxymethyl)-2'-methylbiphenyl-4-yl)-1,2,4-oxadiazol-3-yl)phenyl)methanol
(2-methyl-4-(5-(2'-methyl-2-(trifluoromethyl)biphenyl-4-yl)-1,2,4-oxadiazol-3-yl)phenyl)methanol
is more particularly described in the examples.

The method for preparing aldehyde derivatives of Formula (I'''') selected below:
4-(5-(2-(methoxymethyl)-2'-methylbiphenyl-4-yl)-1,2,4-oxadiazol-3-yl)-3-methylbenzaldehyde
4-(5-(2'-methyl-2-(trifluoromethyl)biphenyl-4-yl)-1,2,4-oxadiazol-3-yl)benzaldehyde
4-(5-(2-(methoxymethyl)-2'-methylbiphenyl-4-yl)-1,2,4-oxadiazol-3-yl)-2-methylbenzaldehyde
is more particularly described in the examples.

The compounds of formula (I), wherein $R^1$, $R^2$, $R^a$, $R^b$, W, W, Q, and S are defined as above, can be obtained in a 2-step protocol as outlined in Scheme 2. The first step consists in the coupling of a carboxylic acid of formula (VII) with an amidoxime of formula (VI), wherein $R^1$, $R^2$, $R^a$, $R^b$, W, Q, and S are defined as above. General protocols for such coupling are given below in the examples, using conditions and methods well known to those skilled in the art to prepare an O-substituted amidoximes (V) from a carboxylic acid (VII) and an aryl amidoxime (VI), with standard coupling agents, such as but not limited to EDC, HATU, TBTU, in the presence or absence of bases such as TEA, DIEA, NMM in a suitable solvent such as DCM, ACN, THF or DMF, at a temperature rising from about 20° C. to about 50° C., preferably at RT, for a few hours, e.g. one hour to 24 h. Alternatively, a carboxylic acid derivative (e.g. acyl chloride VIIa) may be coupled with the amidoxime (VI), using conditions and methods well known to those skilled in the art, in the presence of bases such as TEA, DIEA, NMM in a suitable solvent such as DCM, THF or DMF, at a temperature rising from about 20° C. to about 50° C., preferably at RT, for a few hours, e.g. one hour to 24 h (Scheme 3). The second step consists of the cyclization and dehydration of the O-substituted amidoximes (V) to form oxadiazole (I). Conditions are given below in the examples, using methods well known to those skilled in the art to prepare oxadiazole, such as thermolysis at temperature rising from RT to about 150° C., typically 150° C., using possibly a microwave oven, for a time comprised between 15 minutes and 24 hours, preferably for 30 min, in a suitable solvent or mixture of solvents such as ACN, THF, Pyridine, DMF, in the presence or absence of a base such as DIEA, TEA, or tetrabutyl ammonium fluoride.

Scheme 3

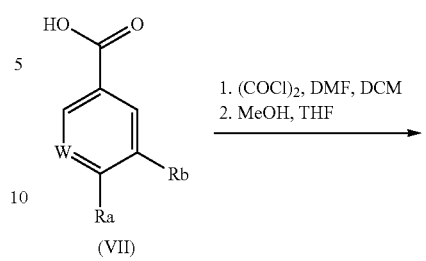

Scheme 2

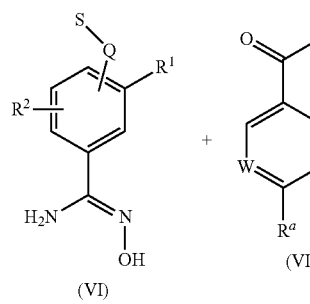

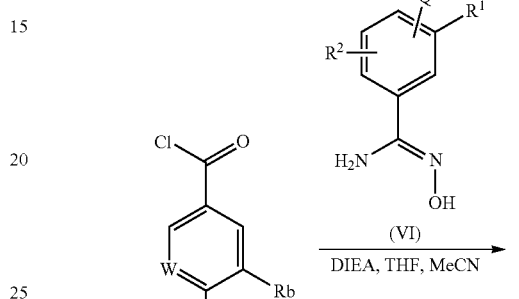

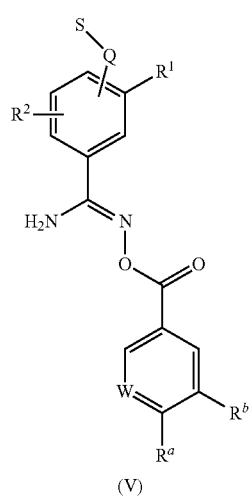

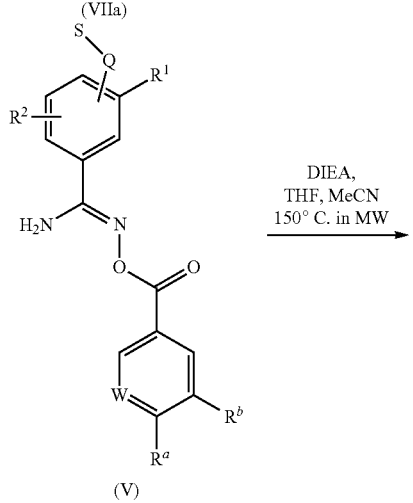

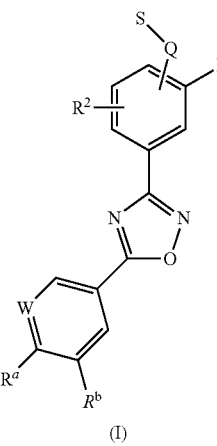

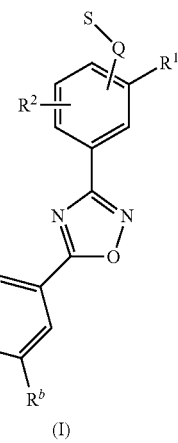

Compounds of formula (VII), wherein $R^a$, $R^b$ and W are defined as above, are either commercially available or may be prepared by standard synthetic techniques, as hereinafter described in the examples, for example by metal catalyzed coupling reaction or aromatic nucleophilic substitution on the corresponding halogenated benzoic acid or alkyl benzoate. Alternatively, compounds of formula (VII), wherein $R^a$, $R^b$ and W are defined as above, may be obtained by metal catalyzed cross-coupling reaction followed by hydrolysis of the resulting ester (XI), as shown in Scheme 4 below. More particularly, they may be obtained by Suzuki-Miyura coupling reaction between an alkyl benzoate (VIII), where $R^c$ may preferably be Br, I or a sulfonate ester such as triflate, and a boronic acid (Xa) or ester (Xb), using well known Suzuki-Miyura reaction conditions such as shown in Scheme 4 (Miyaura, N.; Suzuki, A. *Chem. Rev.* 1995, 95, 2457; Takavent or mixture of solvents such as THF, Toluene, Dioxane, MeOH, ACN, DMF, water. All the different combinations described above may be used. Alternatively, alkyl benzoate (IX) wherein $R^c$ is as above defined and boronic acid (Xc) or ester (Xd) may be coupled under the same palladium catalyzed procedure as described above. The resulting ester (XI) can then be hydrolyzed using conditions well known to those skilled in the art, such as but not limited to the use of a metal hydroxide, e.g. lithium hydroxide, sodium hydroxide or potassium hydroxide, in a suitable solvent such as THF, methanol, ethanol or water or mixtures thereof, at a temperature rising from about 20° C. to about 60° C., preferably at RT, for a few hours, e.g. one hour to 24 h.

Scheme 4

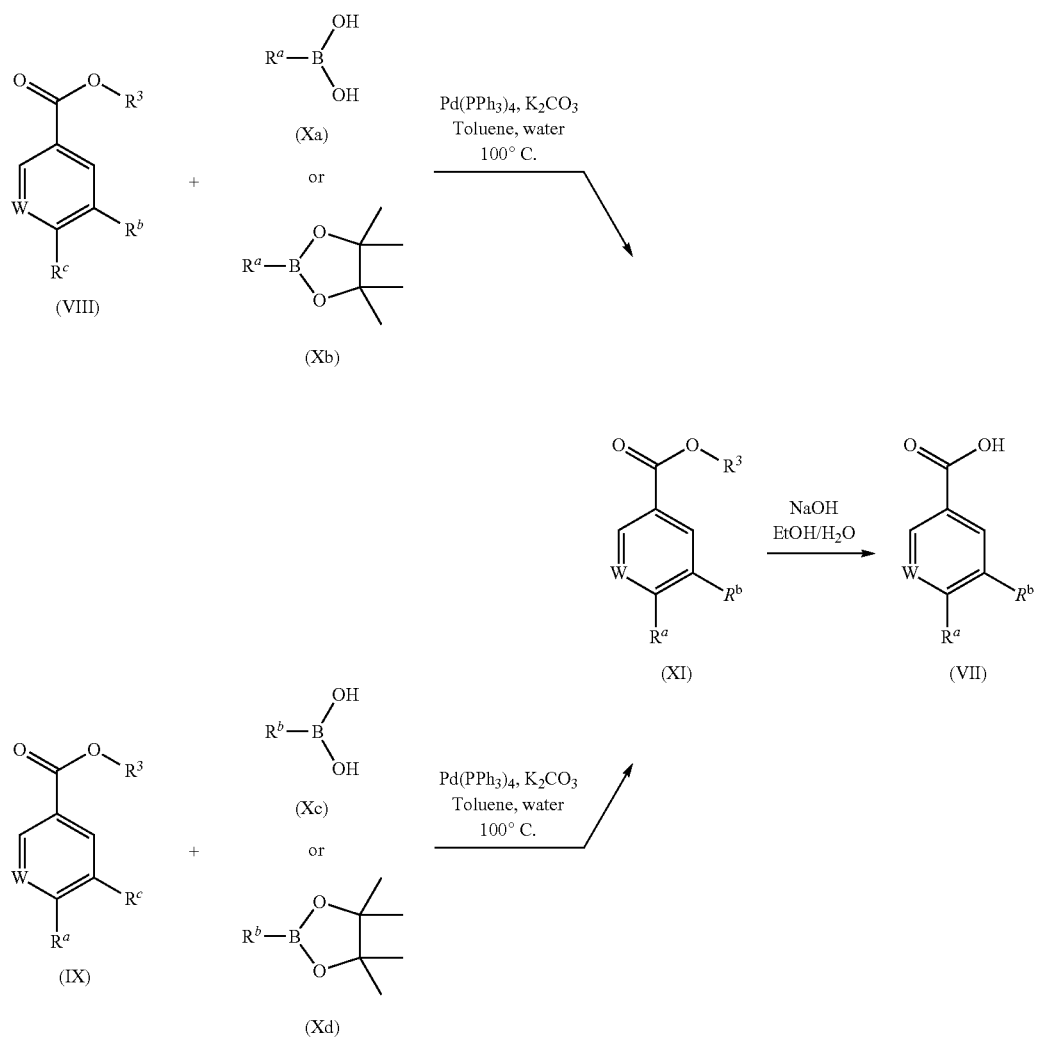

hiro I. and Toshiaki M., *Tetrahedron Lett.* 2005, 46, 3573-3577). In a typical procedure, alkyl benzoate (VIII) and boronic acid (Xa) or ester (Xb) are heated at various temperature by traditional thermic methods or using microwave technology in the presence of a base such as but not limited to a carbonate salt, e.g. $K_2CO_3$, $Na_2CO_3$, $Cs_2CO_3$, and a catalytic amount of palladium catalyst such as $Pd(PPh_3)_4$, $PdCl_2(PPh_3)_2$, $Pd(OAc)_2$, with the possible addition of phosphine ligands such as $PPh_3$, S-Phos, X-Phos in an appropriate sol- An alternative route for the preparation of compounds of formula (VII), wherein $R^a$, $R^b$ and W are defined as above, maybe via Suzuki-Miyura coupling reaction between an alkyl benzoate boronic acid or ester derivative of formula (XII) or (XIII), where $R^d$ is a boronic acid or tetramethyl-dioxaborolane, with an optionally substituted aryl, respectively (Xe) and (Xf), where $R^c$ is preferably Br, I or a sulfonate ester such as triflate, using well known Suzuki-Miyura reaction conditions such as shown in Scheme 5 below and described above.

The resulting ester can be hydrolyzed into compounds of formula (VII) under conditions described above and in the examples below.

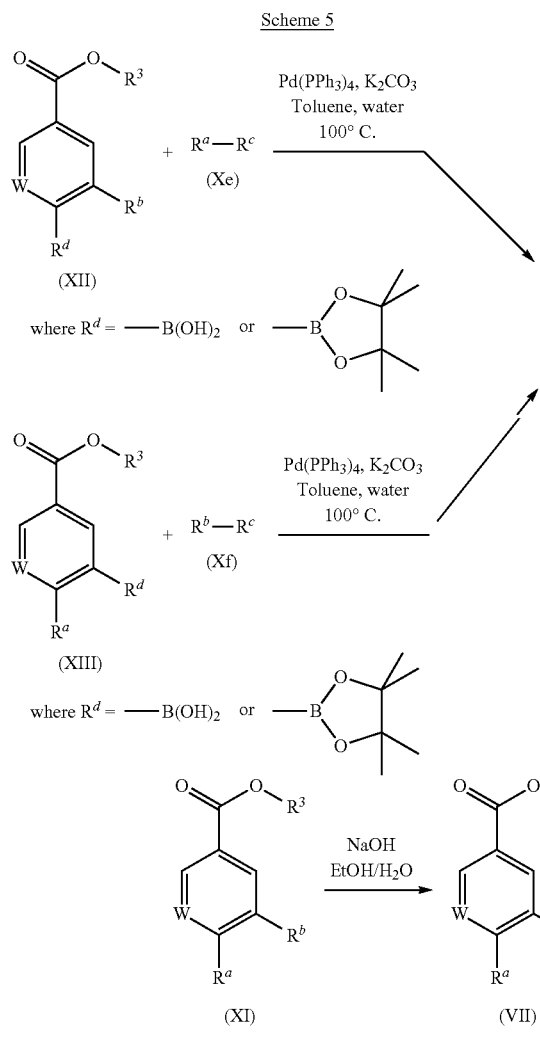

Scheme 5

An alternative route for the preparation of compounds of formula (VII), wherein $R^a$, $R^b$ and W are defined as above, may be the addition of an amino derivative $R^aH$ of formula (Xg) to an alkyl benzoate of formula (VIIIa) or a benzoic acid of formula (VIIIb), as outlined in Scheme 6, in the optional presence of a suitable base, such as TEA, DIEA, NMM in a solvent such as THF or DMF, at a temperature rising from about 20° C. to about 100° C., preferably at RT, for a few hours, e.g. one hour to 24 h. An amino derivative $R^aH$ of formula (Xg) can be also used neat, as solvent. Alternatively, compounds of formula (VII) may be obtained by addition of an amino derivative $R^bH$ of formula (Xh) to an alkyl benzoate (IXa) or a benzoic acid (IXb), as outlined in Scheme 6, under reaction conditions described above and in the examples below. In the cases where ester of formula (XI) is first obtained, it can be hydrolyzed into compounds of formula (VII) under conditions described above and in the examples below. Alternatively, an amino derivative of formula (Xg) and (Xh) can be added respectively to benzonitrile (XIVa) and (XIVb) under similar conditions as the one described above and in the examples below. The resulting benzonitrile of formula (XIV) can be hydrolyzed into the corresponding ester (XI), using conditions well known to those skilled in the art, such as but not limited to the use of an acid, e.g. HCl, in a suitable solvent such as THF, methanol or water or mixtures thereof, at a temperature rising from about 20° C. to about 100° C., preferably at 78° C., for 12 h to 48 h.

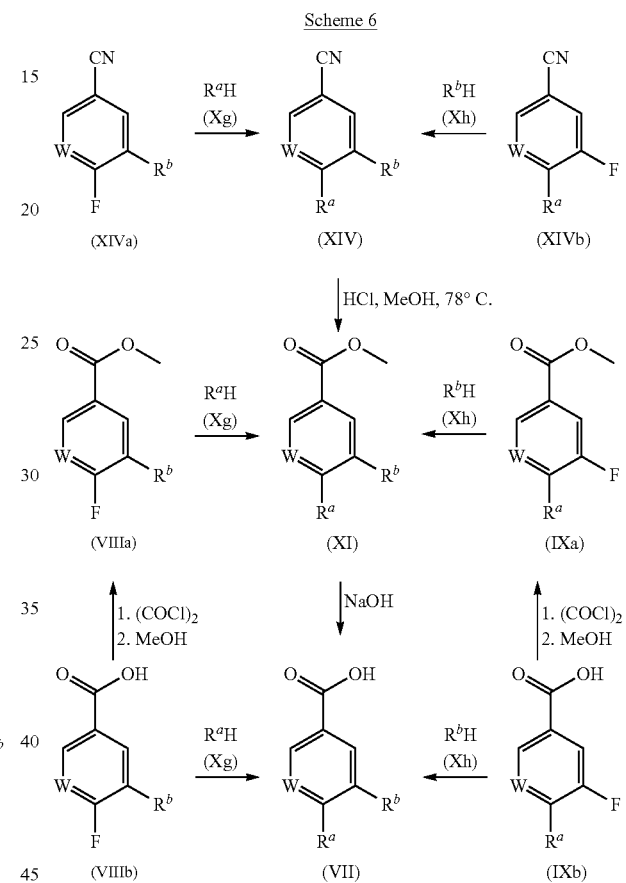

Scheme 6

Compounds of formula (VIIIa) and (IXa), wherein $R^a$, $R^b$ and W are defined as above, are either commercially available or may be prepared by standard synthetic techniques, as hereinafter described in the examples. Typically, they may be prepared by esterification of the corresponding benzoic acid, (VIIIb) and (IXb) respectively, such as but not limited to the formation of the corresponding acid chloride with oxalyl chloride, followed by the addition of the suitable alcohol, such as MeOH for methyl carboxylate, at temperatures ranging from about 0° C. to about 50° C., preferably at RT for a few hours, e.g. one hour to 24 hours.

Alternatively, compounds of formula (VII), wherein $R^a$, $R^b$ and W are defined as above, may be obtained by metal catalyzed cross-coupling reaction followed by hydrolysis of the resulting ester of formula (XI), as shown in Scheme 7 below. More particularly, they may be obtained by Buchwald-Hartwig cross-coupling reaction between an alkyl benzoate of formula (VIII) or (IX), where $R^c$ may preferably be Br, I or a sulfonate ester such as triflate, and an amino derivative, respectively (Xg) or (Xh), using well known Buchwald-Hartwig reaction conditions such as shown in Scheme 7 below (Muci, A. R.; Buchwald, S. L. *Top. Curr. Chem.* 2002, 219, 131-209; Jiang, L.; Buchwald, S. L. *Metal-Catalyzed Cross-Coupling Reactions* ($2^{nd}$ Edition) 2004, 2, 699-760). In a typical procedure, alkyl benzoate of formula (VIII) and (IX), and respectively amino derivatives (Xg) and (Xh) are heated at various temperature by traditional thermic methods or using microwave technology in presence of a base such as but not limited to a carbonate salt, e.g. $K_2CO_3$, $Na_2CO_3$, $Cs_2CO_3$, and a catalytic amount of palladium catalyst such as $Pd(PPh_3)_4$, $PdCl_2(PPh_3)_2$, $Pd(OAc)_2$, with the possible addition of phosphine ligands such as BINAP, X-phos, in an appropriate solvent or mixture of solvents such as THF, Toluene, Dioxane, MeOH, ACN, DMF, water. All the different combinations described above may be used. The resulting ester of formula (XI) can be then hydrolyzed using conditions well known to those skilled in the art, such as but not limited to the use of a metal hydroxide, e.g. lithium hydroxide, sodium hydroxide or potassium hydroxide, in a suitable solvent such as THF, methanol, ethanol or water or mixtures thereof, at a temperature rising from about 20° C. to about 60° C., preferably at RT, for a few hours, e.g. one hour to 24 h.

Scheme 7

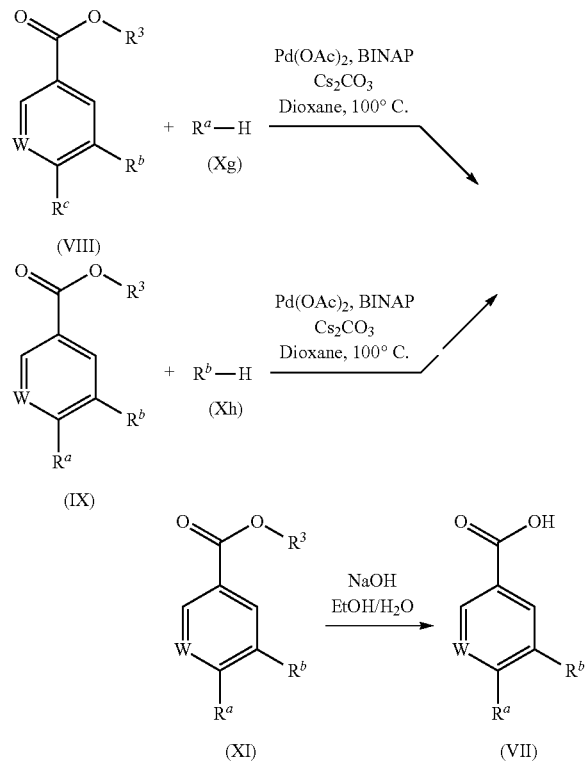

Alternatively, compounds of formula (VII) wherein W is as defined above and wherein $R^a$ or $R^b$ is OA can be prepared by adding alkyl bromide (Xi) or (Xj) to the corresponding intermediates of formula (VIIIp) or (IXc) respectively, in the presence of a base, e.g. $K_2CO_3$ in DMF at about 90° C. Such transformation can also be performed on compounds of formula (I), wherein $R^a$ or $R^b$ is OH, as it is described hereinafter in the examples.

Scheme 8

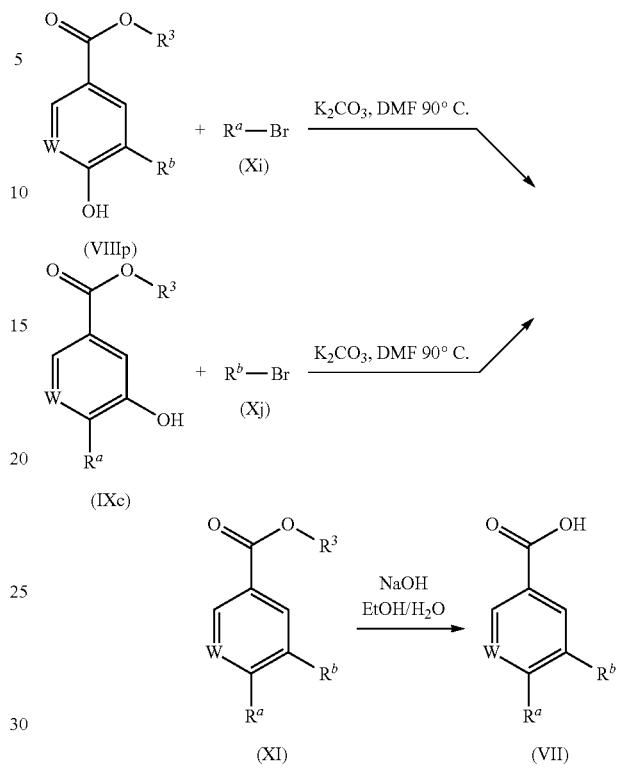

Compounds of formula (VIII) are either commercially available or may be prepared by standard synthetic techniques, as hereinafter described in the examples. Typically, when $R^b$ is $(CH_2)OH$, $(CH_2)OA$, $(CH_2)N(R^3)_2$ or $(CH_2)SO_2Me$, $R^c$ is F, Cl, Br, I or a sulfonate ester such as triflate and $R^3$ is as defined above, compounds of formula (VIII), respectively (VIIIf), (VIIIg), (VIIIh) and (VIIIj), may be prepared by bromination of the corresponding toluoyl derivative (VIIIc) followed by an $S_N2$ reaction on the benzyl bromine derivative (VIIId) with a suitable group, such as but not exclusively, an acetate salt, e.g. NaOAc in HOAc, an alcoholate salt, e.g. NaOA in the corresponding alcohol, THF or DMF, an alcohol, e.g. HOA, that can be used as solvent, an amine, e.g. $HN(R^3)_2$ or a thiolate salt, e.g. NaSA, in a suitable solvent, such as but not exclusively THF, MeCN, DMF, at a temperature ranging from RT to 130° C., with the possible use of the microwave (see Scheme 9). Hydrolysis of the acetate group on compounds of formula (VIIIe), using conditions well known to those skilled in the art, such as but not limited to sodium hydroxide in EtOH at about 60° C., afforded compounds of formula (VIIIf). Sulfide oxidation of compounds of formula (VIIIi), using conditions well known to those skilled in the art, such as but not limited to mCPBA, afforded compounds of formula (VIIIj). Compounds of formula (VIIIf), when $R^b$ is $(CH_2)OH$, can be further transformed into the corresponding alkyl sulfonate (VIIIk) that can be used as starting material for $S_N2$ reactions similarly to (VIIIb), as it illustrated on Scheme 9. Such diversification can also be performed at a later stage, on compounds of formula (I) wherein $R^b$ is $(CH_2)OH$, as described hereinafter in the examples.

Scheme 9

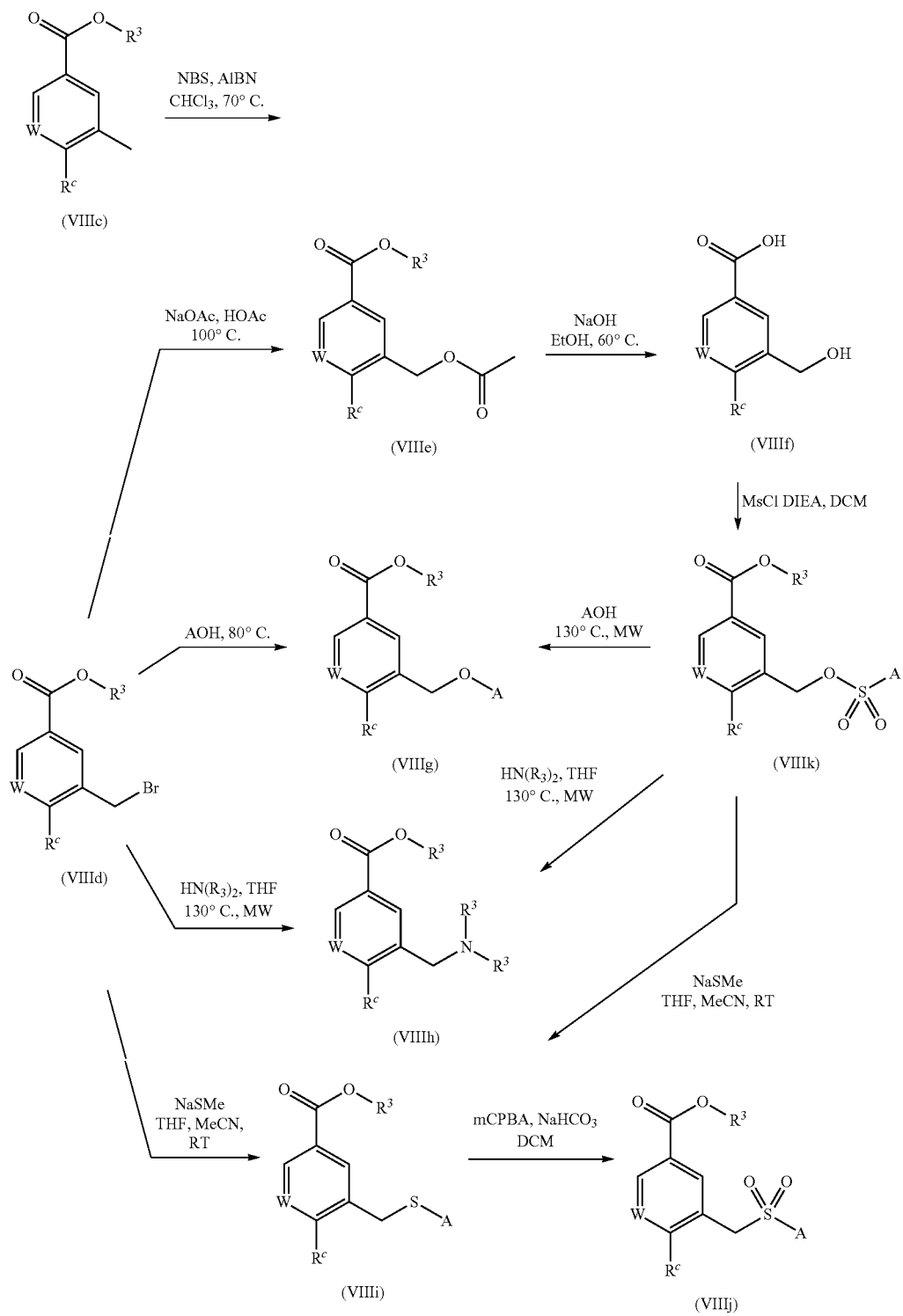

Alternatively, compounds of formula (VIIIf) can be prepared by double bromination of (VIIIc), followed by hydrolysis of (VIIIm), as it is described in Scheme 10. The reduction of the resulting benzaldehyde derivative of formula (VIIIn), with a suitable reducing agent, such as but not limited to NaBH$_4$, yields the benzylic alcohol of (VIIIf), compound (VIIIo). Transformation of compounds of formula (VIIIn) into compounds of formula (XIa) by metal catalyzed cross coupling reaction or S$_N$Ar reaction can be performed first. Then the reduction gives the corresponding alcohol of formula (XIa), as outlined in Scheme 10.

Scheme 10

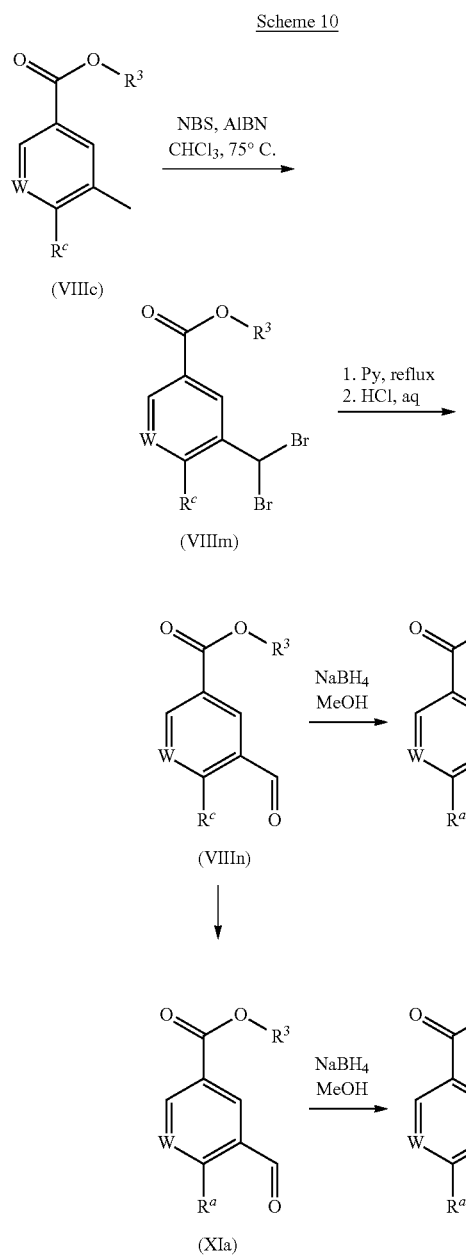

Scheme 11

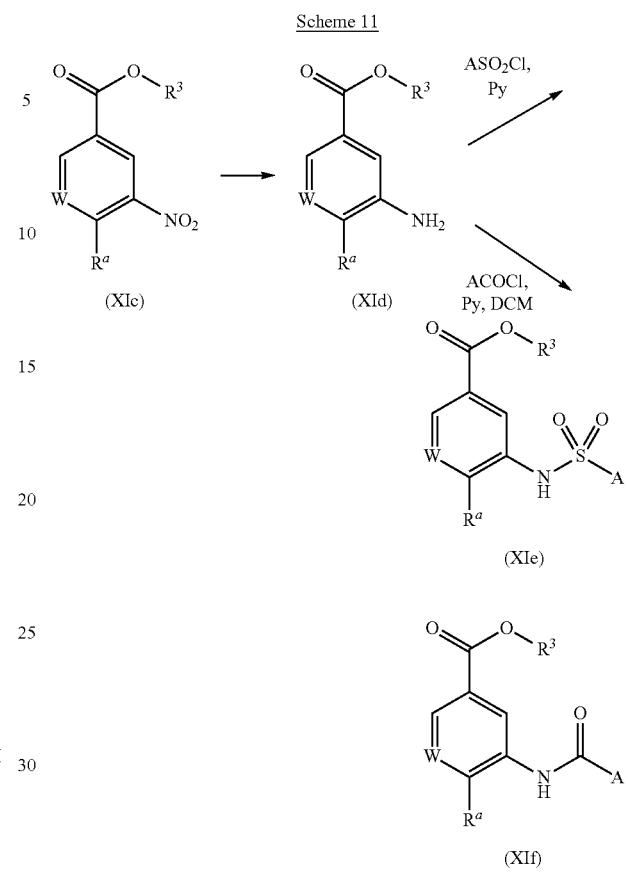

Compounds of formula (VIIb), where $R^b$ is $(CH_2)_3OA$, can be synthesized from compound (VIIIp) via the sequential Sonogashira and Suzuki-Miyura cross-coupling reactions, as it is outlined in Scheme 12. The resulting compounds of formula (VIIa) can be then reduced by standard techniques well known to those skilled in the art, such as but not limited to Pd/C in $H_2$ atmosphere, affording compounds of formula (VIIb).

Scheme 12

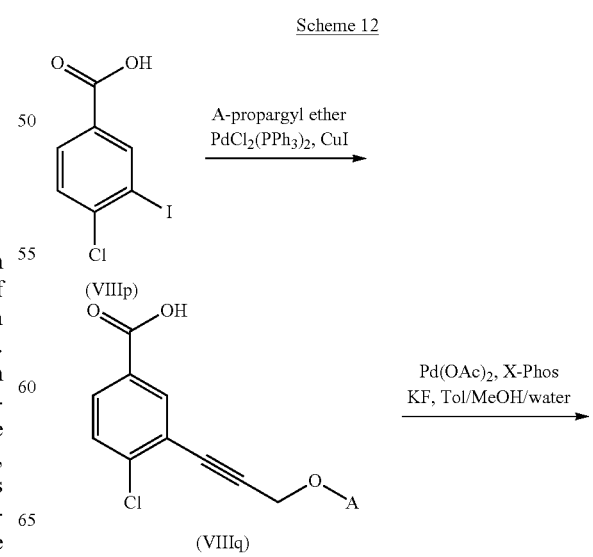

When $R^b$ is $(CH_2)_nNR^3SO_2A$ or $(CH_2)_nNR^3COA$, wherein n=0 and $R^a$, $R^3$ and W are defined as above, compounds of formula (XIe) or (XIf) respectively can be synthesized from compounds of formula (XIc), as it is outlined in Scheme 11. After reduction of nitro group, the resulting aniline (XId) can be transformed into a sulphonamide (XIe) with $ASO_2Cl$ addition or into an amide (XIf) with ACOCl addition, in the presence of a base, such as but not limited to TEA, DIEA, NMM, pyridine, in a solvent or a mixture of solvents such as DCM, DMF, Pyridine. Such diversification can also be performed on a later stage, on compounds of formula (I) where Rb is $NH_2$, as it is described hereinafter in the examples.

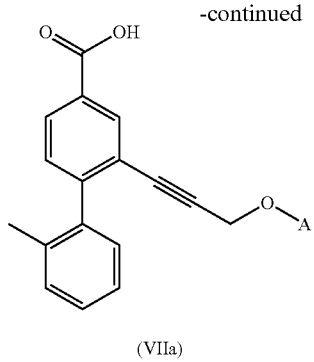

(VIIa)

H₂, 10% Pd/C
MeOH

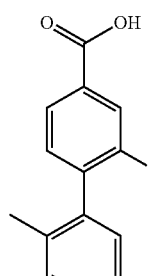

(VIIb)

Alternatively, compounds of formula (VII), wherein R$^a$, R$^b$ and W are defined as above, may be prepared from compounds of formula (XV) in a two steps process, as outlined in Scheme 13. The first step is a halogen-metal exchange with, typically but not exclusively, an alkyl lithium salt, such as nBuLi or tBuLi. The second step is the addition of CO2, at gas or solid state, as electrophile.

Scheme 13

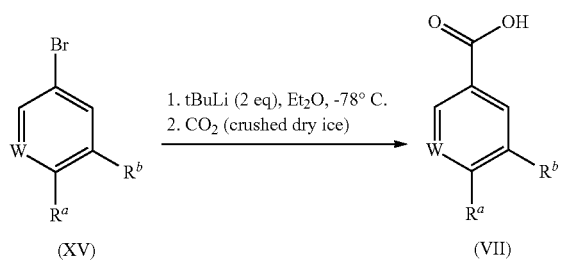

1. tBuLi (2 eq), Et₂O, -78° C.
2. CO₂ (crushed dry ice)

(XV)    (VII)

The method for preparing benzoic acids of Formula (VII) selected below:
3'-fluoro-2-(methoxymethyl)-2'-methylbiphenyl-4-carboxylic acid
3-(methoxymethyl)-4-(2-methylpiperidin-1-yl)benzoic acid
2-(methoxymethyl)-2'-methyl biphenyl-4-carboxylic acid
4-(2-methylpiperidin-1-yl)-3-(trifluoromethyl)benzoic acid
2'-methyl-2-(trifluoromethyl)biphenyl-4-carboxylic acid
2'-ethyl-2-(methoxymethyl)-1,1'-biphenyl-4-carboxylic acid
2-[(dimethylamino)methyl]-2'-methylbiphenyl-4-carboxylic acid
4-(2-ethylpiperidin-1-yl)-3-(methoxymethyl)benzoic acid,
4-[(2R)-2-methylpiperidin-1-yl]-3-(trifluoromethyl)benzoic acid
4-[(2S)-2-methylpiperidin-1-yl]-3-(trifluoromethyl)benzoic acid
2'-fluoro-2-(methoxymethyl)biphenyl-4-carboxylic acid
2'-chloro-2-(methoxymethyl)biphenyl-4-carboxylic acid
3-(methoxymethyl)-4-(2-methylpyrrolidin-1-yl)benzoic acid
2-(methoxymethyl)-2'-(trifluoromethyl)biphenyl-4-carboxylic acid
2-ethoxy-2'-methyl-1,1'-biphenyl-4-carboxylic acid
2-methyl-2'-(trifluoromethyl)biphenyl-4-carboxylic acid
2'-ethyl-2-(trifluoromethyl)biphenyl-4-carboxylic acid
2,2'-dimethyl-1,1'-biphenyl-4-carboxylic acid
2-chloro-2'-(trifluoromethyl)biphenyl-4-carboxylic acid
2'-(difluoromethyl)-2-methylbiphenyl-4-carboxylic acid
2'-fluoro-2-(trifluoromethyl)biphenyl-4-carboxylic acid
is more particularly described in the examples.

Compounds of formula (VI), wherein, R$^1$, R$^2$, Q and S are defined as above, can be prepared according to Scheme 14 by addition of hydroxylamine to the corresponding substituted benzonitrile of formula (XVI) in a solvent or a mixture of solvents, such as EtOH, water, at a temperature ranging from about 20° C. to about 50° C., preferably at RT, for a few hours, e.g. one hour to 24 h.

Scheme 14

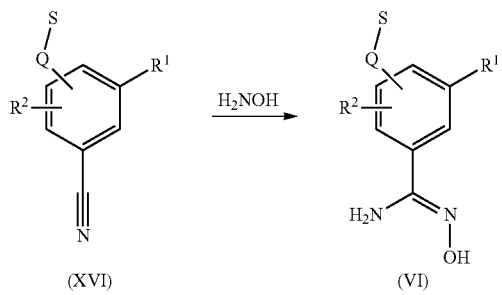

(XVI)    (VI)

The method for preparing amidoxime of Formula (VI) selected below:
ethyl N-{4-[amino(hydroxyimino)methyl]-2-fluorobenzoyl}-beta-alaninate
tert-butyl ({4-[amino(hydroxyimino)methyl]benzyl}oxy)acetate
tert-butyl 3-[{3-[amino(hydroxyimino)methyl]benzyl}(methyl)amino]propanoate
tert-yl ({3-[amino(hydroxyimino)methyl]benzyl}oxy)acetate
ethyl 4-{5-[amino(hydroxyimino)methyl]-2,3-difluoro phenoxy}butanoate
N'-hydroxy-3-(methylsulfonyl)benzenecarboximidamide
tert-butyl 3-({3-[amino(hydroxyimino)methyl]benzyl}oxy)propanoate
tert-butyl [{3-[amino(hydroxyimino)methyl]benzyl}(methyl)amino]acetate
tert-butyl N-{3-[amino(hydroxyimino)methyl]benzyl}-N-(tert-butoxycarbonyl)-beta-alaninate
tert-butyl N-{5-[amino(hydroxyimino)methyl]-2-fluorobenzyl}-N-methyl-beta-alaninate
tert-butyl N-{3-[amino(hydroxyimino)methyl]-5-fluorobenzyl}-N-methylglycinate
tert-butyl N-{3-[amino(hydroxyimino)methyl]-5-fluorobenzyl}-N-methyl-beta-alaninate 3-[(2,3-dihydroxypropyl)amino]-N'-hydroxybenzenecarboximidamide N'-hydroxy-4-(2-hydroxyethoxy)benzenecarboximidamide 4-(2-{[tert-butyl(dimethyl)silyl]oxy}ethoxy)-3-fluoro-N'-hydroxybenzenecarboximidamide 3-{[(2,3-dihydroxypropyl)(methyl)amino]methyl}-N'-hydroxybenzenecarboximidamide 3-{[bis(2-hydroxyethyl)amino]methyl}-N'-hydroxybenzenecarboximidamide tert-butyl N-{4-[amino(hydroxyimino)methyl]benzyl}-N-methylglycinate tert-butyl N-{4-[amino(hydroxyimino)methyl]-2-fluorobenzyl}-N-methylglycinate tert-butyl N-{4-[amino(hydroxyimino)methyl]-2-bromobenzyl}-N-methylglycinate methyl 4-[amino(hydroxyimino)methyl]-2-chlorobenzoate methyl 4-[amino(hydroxyimino)methyl]-2-fluorobenzoate tert-butyl N-{4-[amino(hydroxyimino)methyl]benzyl}-N-(tert-butoxycarbonyl)glycinate 3-{ethyl-[3-(n-hydroxycarbamimidoyl)-benzyl]-amino}-propionic acid tert-butyl ester tert-butyl N-{3-[amino(hydroxyimino)methyl]benzyl}-N-(2-hydroxyethyl)-beta-alaninate tert-butyl N-{-4-[amino(hydroxyimino)methyl]-2-fluorobenzyl}-N-methyl-beta-alaninate tert-butyl N-{4-[amino(hydroxyimino)methyl]benzyl}-N-methyl-beta-alaninate methyl 4-[amino(hydroxyimino)methyl]-2,5-difluorobenzoate tert-butyl N-{-4-[amino(hydroxyimino)methyl]-2-methoxybenzyl}-N-methylglycinate tert-butyl N-{-4-[amino(hydroxyimino)methyl]-2-fluorobenzyl}-N-(tert-butoxycarbonyl)glycinate tert-butyl N-{2-fluoro-3-[(hydroxyamino)(imino)methyl]benzyl}-N-methylglycinate 3-{[3-(N-Hydroxycarbamimidoyl)-benzyl]-isopropyl-amino}-propionic acid tert-butyl ester tert-butyl N-{4-[amino(hydroxyimino)methyl]-2-chlorobenzyl}-N-methylglycinate tert-butyl-4-[{-4-[amino(hydroxyimino)methyl]benzyl}(methyl)amino]butanoate tert-butyl 2-((3-chloro-4-(N'-hydroxycarbamimidoyl)benzyl)(methyl)amino)acetate N'-hydroxy-4-(hydroxymethyl)-3-methylbenzimidamide tert-butyl 2-((2-ethyl-4-(N'-hydroxycarbamimidoyl)benzyl)(methyl)amino)acetate N'-hydroxy-3-(hydroxymethyl)benzimidamide tert-butyl N-{4-[amino(hydroxyimino)methyl]benzyl}-N-(2-methoxyethyl)glycinate N'-hydroxy-4-(hydroxymethyl)benzenecarboximidamide tert-butyl 2-((3-chloro-4-(N'-hydroxycarbamimidoyl)benzyl)(methyl)amino)acetate:

tert-butyl 2-((2,6-difluoro-4-(N'-hydroxycarbamimidoyl)benzyl)(methyl)amino)acetate {3-[amino(hydroxyimino)methyl]phenyl}acetic acid is more particularly described in the examples.

Scheme 15

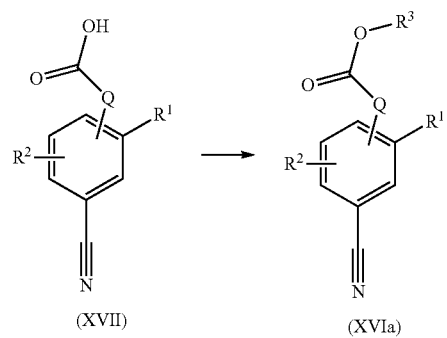

Compounds of formula (XVI), wherein $R^1$, $R^2$, Q and S are defined as above, are either commercially available or may be prepared by standard synthetic techniques well known to those skilled in the art. Typically, when S is $COOR^3$ as defined above, compounds of formula (XVIa) may be prepared by coupling the corresponding carboxylic acid of formula (XVII) to an alcohol, using conditions such as but not limited to the formation of the corresponding acid chloride of compounds of formula (XVII) with oxalyl chloride, followed by the addition of the suitable alcohol, such as MeOH at temperatures ranging from about 0° C. to about 50° C., preferably at RT for few hours, e.g. one hour to 24 hours, as it is outlined on Scheme 15. It may be also prepared with standard coupling agents, such as but not limited to EDC, HATU, TBTU, in the presence or absence of bases such as TEA, DIEA, NMM in the suitable alcohol, such as MeOH, at a temperature between about 20° C. to about 50° C., preferably at RT, for a few hours, e.g. one hour to 24 h.

Alternatively compounds of formula (XVIb) wherein $Q=(CH_2)_mX(CH_2)_m$, X=—O—, and $R^1$, $R^2$, m and S are defined as above, may be prepared from alcohol (XVIII), by addition of an electrophile, LG-$(CH_2)_m$S, where LG- is a leaving group, such as but not exclusively Br, I, OMs, in the presence of a base such as LiHMDS, NaH, NaOH, in a solvent or a mixture of solvent such as THF or Toluene-water in the presence of a phase transfer agent, such as but not limited to $(Bu_4N)HSO_4$ at temperatures ranging from RT to about 100° C., as it is outlined in Scheme 16. Alternatively, alcohol (XVIII) can be transformed into the corresponding mesyl or tosyl groups, which can then react with an alcohol (for X=—O—) or an amine (for X=—$NR^3$—), affording compounds of formula (XVIb) and (XVIc) respectively, wherein $Q=(CH_2)_mX(CH_2)_m$ and $R^1$, $R^2$, m and S are defined as above (Scheme 16). Alcohol (XVIII) can be oxidized into the corresponding aldehyde (XVIIIb), according to Scheme 16.

Then a reductive amination of the compounds of formula (XVIIIb) with a suitable amine, affords compounds of formula (XVIc), wherein $Q=(CH_2)_mX(CH_2)_m$ with X=—$NR^3$—, and $R^1$, $R^2$, m and S are defined as above, according to Scheme 16. The different transformations described in Scheme 16 may be performed on compounds of formula (I) with the suitable substitution pattern, as it is described in the examples.

Scheme 16

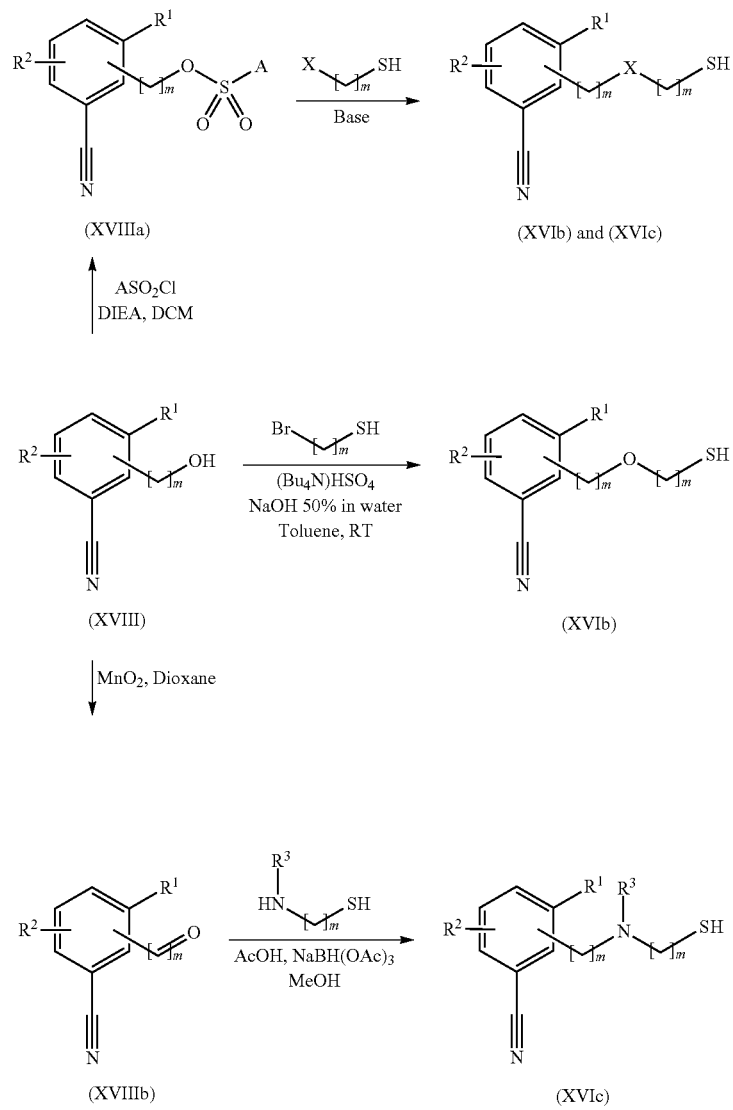

Alternatively, addition of an alcohol or an amine to benzyl bromide of formula (XVIIIc), as outlined in Scheme 17, in the presence of a base, such as but not limited to DIEA, TEA, $K_2CO_3$, $Cs_2CO_3$, in a suitable solvent such as MeCN, THF, DMF, yields compounds of formula (XVIb) and (XVIc), wherein Q=$(CH_2)X(CH_2)_m$, X=—O— or —$NR^3$— respectively, and $R^1$, $R^2$, m and S are defined as above.

Scheme 17

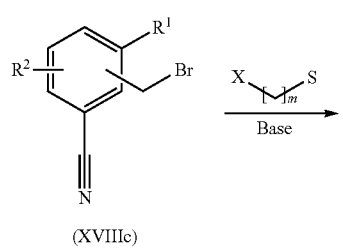

-continued

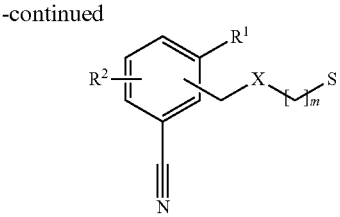

Phenol derivative of formula (XIX) may be transformed into compounds of formula (XVId) by Mitsunobu or alkylation reaction, using conditions known to the person skilled in the art and as described below in the examples. Typically, phenol alkylation with LG-$(CH_2)_m$S, where LG- is a leaving group, such as but not limited to Br, I, OMs, is performed in a solvent such as THF or DMF, in the presence of a base such as DIEA, TEA, $K_2CO_3$ or $Cs_2CO_3$, at temperature ranging from RT to about 100° C.

Scheme 18

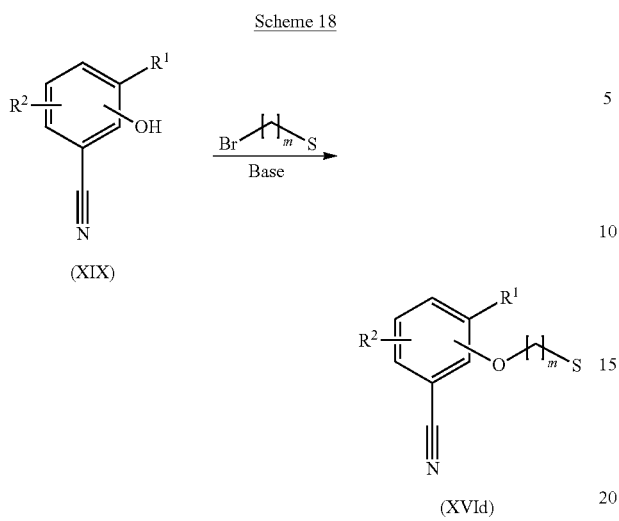

Alternatively, aniline derivative of formula (XX) may be transformed into compounds of formula (XVIe) by alkylation reaction, using conditions known to the person skilled in the art and as described below in Scheme 19 and in the examples. Typically, aniline alkylation with LG-$(CH_2)_m$S, where LG- is a leaving group, such as but not exclusively Br, I, OMs, is performed in a solvent such as THF or DMF, in the presence of a base such as DIEA, TEA, $K_2CO_3$ or $Cs_2CO_3$, at temperature ranging from RT to about 100° C.

Scheme 19

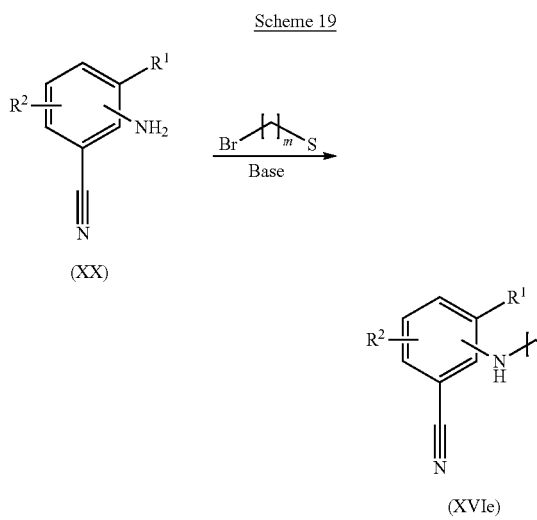

Alternatively, compounds of formula (XVI), wherein Q, S, $R^1$, and $R^2$ are defined as above, may be obtained from the corresponding aryl fluoride (XIII) by aromatic nucleophilic substitution with a cyanide salt, typically but not exclusively sodium cyanide in the presence of tetrabutylammonium bromide, in a solvent such as DMF and at a temperature ranging from about 20° C. to about 100° C., preferably at about 60° C., for few hours, e.g. 12 h, as it is described in Scheme 20, according to Jenkins, T. J. et al. *J. Med. Chem.* 2007, 50, 566.

Metal catalyzed cyanation of aryl bromide of formula (XIV) can be used as alternative strategy, as shown on Scheme 20. Addition of $Zn(CN)_2$ in the presence of a palladium catalyst, such as but not limited to $Pd_2(dba)_3$ or $Pd(PPh_3)_4$, with the optional addition of a ligand such as dppf (according to Maligres, P. E. et al *Tetrahedron Lett.* 1999, 40, 8193-8195), and zinc derivatives such as but not limited to Zn dust and $Zn(OAc)_2$ (according to Chidambaram, R. et al *Tetrahedron Lett.* 2004, 45, 1441-1444) in a solvent such as DMF and at temperature raising from RT to 150° C., typically 100° C., yields the formation of compounds of formula (XI). The cyanation of aryl bromide of formula (XIV) can be also performed in the absence of palladium, with the use of CuCN in DMF (according to Couture. C.; Paine, A. J. *Can. J. Chem.* 1985, 63, 111-120).

Cyanide group may be introduced by Sandmeyer reaction, starting from an aniline of formula (XXI), as outlined in Scheme 20. Its transformation into the corresponding diazonium salt can be achieved with sodium nitrite in the presence of a mineral acid, such as HCl in water. It can then further react with copper cyanide, prepared from a mixture of CuCN and KCN, in water at a temperature ranging from about 20° C. to about 100° C., affording compounds of formula (XI) (according to Barraclough, P. et al. *Arch. Pharm.* 1990, 323, 507-512). The starting anline derivatives of formula (XXI) are either commercially available or can be obtained by reduction of the corresponding nitro group by Pd/C catalyzed hydrogenation, as described hereafter in the examples.

Scheme 20

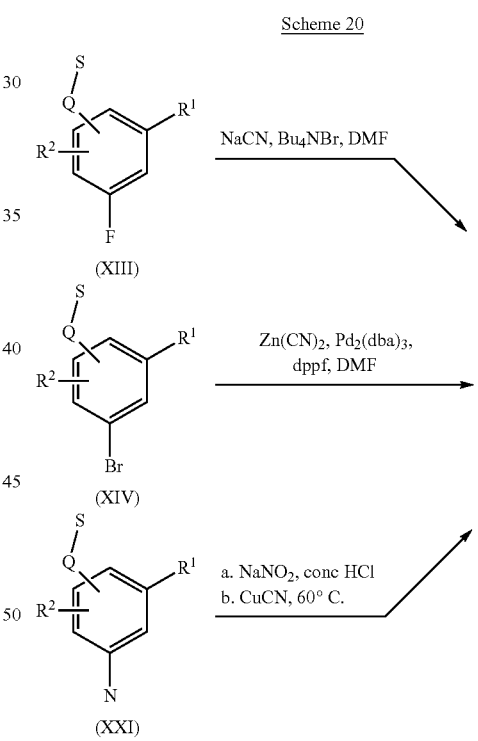

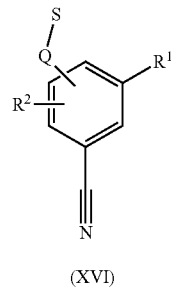

If the above set out general synthetic methods are not applicable to obtain the compounds of formula (I), suitable methods of preparation known by a person skilled in the art should be used.

The pharmaceutically acceptable cationic salts of compounds of the present invention are readily prepared by reacting the acid forms with an appropriate base, usually one equivalent, in a co-solvent. Typical bases are sodium hydroxide, sodium methoxide, sodium ethoxide, sodium hydride, potassium hydroxide, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of the cation (sodium ethylhexanoate, magnesium oleate), employing a solvent in which the desired cationic salt precipitates, or can be otherwise isolated by concentration and addition of a non-solvent.

According to a further general process, compounds of formula (I), and any subformulae can be converted to alternative compounds of formula (I) and any subformulae, employing suitable inter-conversion techniques well known by a person skilled in the art.

In general, the synthesis pathways for any individual compounds of formula (I) will depend on the specific substituents of each molecule and upon the ready availability of Intermediates necessary; again such factors being appreciated by those of ordinary skill in the art. For all the protection and de-protection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, $3^{rd}$ Edition 1999.

Compounds of this invention can be isolated in association with solvent molecules by crystallization from evaporation of an appropriate solvent. The pharmaceutically acceptable acid addition salts of the compounds of formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compounds of formula (I), which contain an acid center, with a suitable base. Both types of salts may be formed or interconverted using ion-exchange resin techniques.

Depending on the conditions used, the reaction times are generally between a few minutes and 14 days, and the reaction temperature is between about −30° C. and 140° C., normally between −10° C. and 90° C., in particular between about 0° C. and 70° C.

Compounds of the formula (I) can furthermore be obtained by liberating compounds of the formula (I) from one of their functional derivatives by treatment with a solvolysing or hydrogenolysing agent.

Preferred starting materials for the solvolysis or hydrogenolysis are those which conform to the formula (I), but contain corresponding protected amino and/or hydroxyl groups instead of one or more free amino and/or hydroxyl groups, preferably those which carry an amino-protecting group instead of an H atom bound to an N atom, in particular those which carry an R'—N group, in which R' denotes an amino-protecting group, instead of an HN group, and/or those which carry a hydroxyl-protecting group instead of the H atom of a hydroxyl group, for example those which conform to the formula (I), but carry a —COOR" group, in which R" denotes a hydroxylprotecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxy-carbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy-carbonyl, ethoxycarbonyl, 2,2,2-trichloroethoxycarbonyl, BOC (tert-butoxy-carbonyl) and 2-iodoethoxycarbonyl; aralkoxycarbonyl, such as CBZ ("carbo-benz-oxy"), 4-methoxybenzyloxycarbonyl and FMOC; and aryl-sulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitro-benzoyl, p-toluenesulfonyl, tert-butyl and acetyl, where benzyl and tert-butyl are particularly preferred.

The compounds of the formula (I) are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as THF or dioxane, amides, such as DMF, halogenated hydrocarbons, such as DCM, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (RT).

The BOC, OBut and Mtr groups can, for example, preferably be cleaved off using TFA in DCM or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, tri-fluoro-methylbenzene, chloroform or DCM; alcohols, such as methanol, ethanol, isopropanol, n-propanol, n-butanol or tert-butanol; ethers, such as diethyl ether, diisopropyl ether, tetrahydrofurane (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethyl-formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as EtOAc, or mixtures of the said solvents.

Esters can be saponified, for example, using LiOH, NaOH or KOH in water, water/THF, water/THF/ethanol or water/dioxane, at temperatures between 0 and 100° C. Furthermore, ester can be hydrolysed, for example, using acetic acid, TFA or HCL.

Free amino groups can furthermore be acylated in a conventional manner using an acid chloride or anhydride or alkylated using an unsubstituted or substituted alkyl halide or reacted with CH$_3$—C(=NH)—OEt, advantageously in an inert solvent, such as DCM or THF and/or in the presence of a base, such as triethylamine or pyridine, at temperatures between −60° C. and +30° C.

Therefore, the invention also relates to the preparation of the compounds of formula (I), and salts thereof, characterized in that a compounds of formula A:

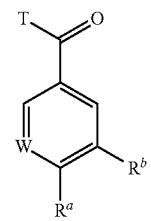

wherein W, $R^a$ and $R^b$ have the meanings given above, and T is OH, or a leaving group, such as Cl, Br, I, imidazolyl, pentafluorophenoxy or the product of the reaction of isobutyl chloroformate with formula A, wherein T is OH, is reacted with
a compounds of formula B:

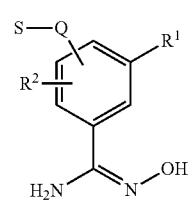

wherein $R^1$ and $R^2$ Q and S have the meanings given above preferably in the presence of a solvent and of a suitable base, such as an amine like TEA, DIEA or NMM, or in case T is OH, in the presence of a suitable condensation reagent, such as EDC, HATU, and the resulting product is cyclized, preferably in the presence of an amine, such as DIEA, TEA or tetrabatylaminonium fluoride
and optionally a base or acid of the formula I is converted into one of its salts.

Throughout the specification, the term leaving group preferably denotes Cl, Br, I or a reactively modified OH group, such as, for example, an activated ester, an imidazolide or alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolyl-sulfonyloxy). Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N-hydroxysuccinimide.

The formula (I) also encompasses the optically active forms (stereoisomers), the enantiomers, the racemates, the diastereomers and the hydrates and solvates of these compounds. The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds of the formula I and so-called prodrug compounds.

The term "prodrug derivatives" is taken to mean compounds of the formula I which have been modified with, for example, alkyl or acyl groups, sugars or oligopeptides and which are rapidly cleaved in the organism to form the active compounds.

These also include biodegradable polymer derivatives of the compounds according to the invention, as described, for example, in Int. J. Pharm. 115, 61-67 (1995).

The formula (I) also encompasses mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

In a preferred embodiment, the invention relates to compounds of Formula (I) wherein $R^1$, $R^2$, W, Q, S and $R^b$ are as defined above, and wherein $R^a$ is Ar or Het monosubstituted at the carbon adjacent to the carbon linked to the rest of the molecule.

In another preferred embodiment, the invention relates to compounds of Formula (I) wherein Q is on meta position with regards to the oxadiazole moiety.

Preferred embodiments of formula (I) are the compounds of formula IA, IB, IC and ID:

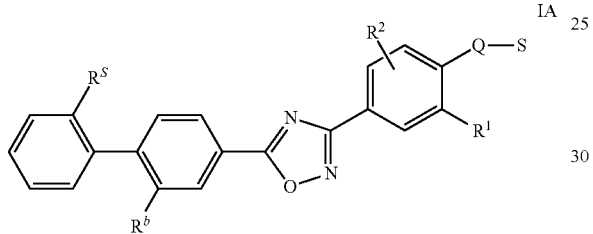
IA

Wherein $R^b$, $R^1$, $R^2$, Q and S are as above defined, and $R^s$ denotes Hal, $CH_3$, $CH_2CH_3$, $OR^3$, $N(R^3)_2$, $NO_2$, CN, $COOR^3$, $OCF_3$, $CON(R^3)_2$, $NR^3COA$, $NR^3CON(R^3)_2$, $NR^3SO_2A$, $COR^3$, $SO_2N(R^3)_2$, SOA or $SO_2A$,

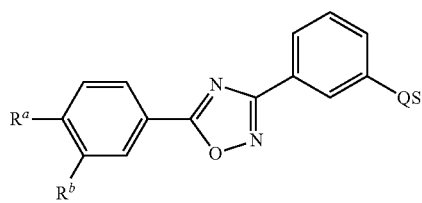
IB

Wherein $R^a$, $R^b$, Q, and S are as defined above.

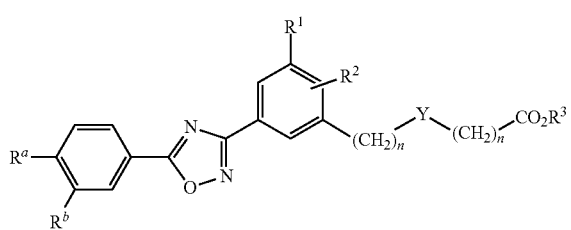
IC

Wherein $R^a$, $R^b$, $R^1$, $R^2$, $R^3$ and n are as defined above, Y denotes $NR^3$,

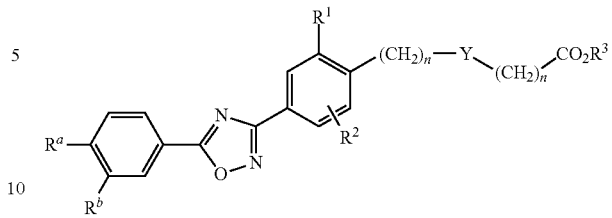
ID

Wherein $R^a$, $R^b$, $R^1$, $R^2$, $R^3$, and n are as defined above, Y denotes $NR^3$, Alternatively, Y can also be 0, $CONR^3$, Other preferred embodiments of Formula (I) are compounds of Formula (IE) to (IH)

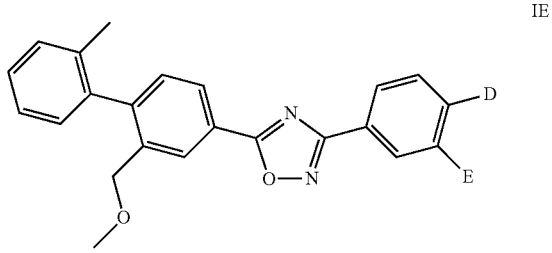
IE

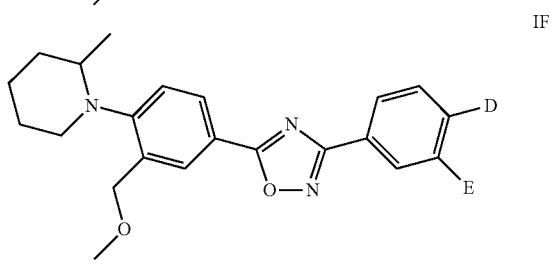
IF

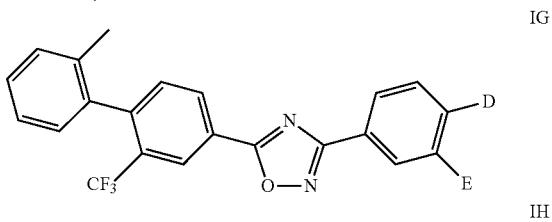
IG

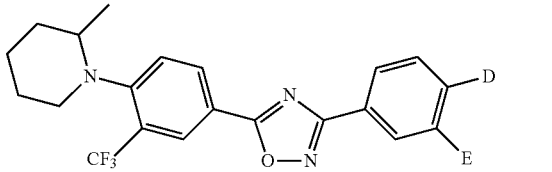
IH

Wherein
D denotes $R^2$ or Q-S, more preferably D is H, F, Cl, —$CO_2H$, —$SO_2CH_3$, $O(CH_2)_nCOOR^3$, —CO—NH—$(CH_2)_n$—$CO_2R^3$, —CO—$NR^3$-alkyl-$CO_2R^3$, —CO—$NR^3$—($C_3$-$C_6$cycloalkyl)-$CO_2R^3$, —$(CH_2)_nNR^3$—(alkyl)-$CO_2R^3$, —$NH(CH_2)_nCO_2R^3$, —$(CH_2)_n$—O—$(CH_2)_nCO_2R^3$, E denotes $R^1$, more preferably, E is H, F, Cl, —$CO_2H$, —$SO_2CH_3$, $O(CH_2)_nCOOR^3$, —CO—NH—$(CH_2)_n$—$CO_2R^3$, —CO—$NR^3$-alkyl-$CO_2R^3$, —CO—$NR^3$—

$(C_3\text{-}C_6\text{cycloalkyl})\text{-}CO_2R^3$, $-(CH_2)_nNR^3-$ (alkyl)-$CO_2R^3$, $-NH(CH_2)_nCO_2R^3$, $-(CH_2)_n-O-(CH_2)_nCO_2R^3$, Wherein $R^3$ and n are as above defined.

In another embodiment, the present invention provides compounds of Formula (IJ)

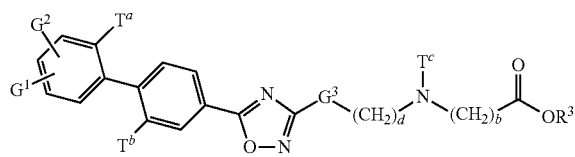

Wherein
$T^c$ is an alkyl having 1 to 6 carbon atoms, preferably a $CH_3$ group,
$T^b$ is $CH_3$, $CH_2CH_3$,
$T^a$ is $CH_3$, Hal, $CH_2CH_3$.
d is 1, 2 or 3, preferably 1 or 2,
b is 1, 2 or 3 preferably 1 or 2,
$G^1$ and $G^2$ are as above defined, preferably H,
$R^3$ is as above defined, preferably, H, $CH_3$ or $CH_2CH_3$,
$G^3$ is one of the following groups:

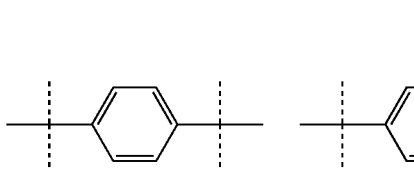

In another preferred embodiment, compounds of Formula (I) exhibit a selectivity on $S_1P_1$ receptor over $S_1P_3$ receptor of more than 20 fold, preferably more than 50 fold, more preferably more than 100 fold, even more preferably more than 1000 fold.

The preferred compounds of the present invention have a high oral bioavailability and/or a low clearance. More particularly, compounds of the present invention are characterized by a ratio Cl/F, wherein Cl is the clearance and F the bioavailability, of 0.5 or lower, more preferably lower than 0.4, and most preferably of 0.3 or lower.

In another preferred embodiment, compounds of the present invention have a Plasma Area Under Curve (AUC∞) of 80000 h*ng/ml or higher, more preferably higher than 100000 h*ng/ml.

In another preferred embodiment, compounds of the present invention exhibit a selectivity on $S_1P_1$ receptor over $S_1P_3$ receptor of more than 20 fold, preferably more than 50 fold, more preferably more than 100 fold, even more preferably more than 1000 fold and show a ratio Cl/F, wherein Cl is the clearance and F the bioavailability, of 0.5 or lower, more preferably lower than 0.4, and most preferably of 0.3 or lower.

In another preferred embodiment, compounds of the present invention exhibit a selectivity on $S_1P_1$ receptor over $S_1P_3$ receptor of more than 20 fold, preferably more than 50 fold, more preferably more than 100 fold, even more preferably more than 1000 fold and have a Plasma Area Under Curve (AUC) of 80000 h*ng/ml or higher, more preferably higher than 100000 h*ng/ml.

Preference is given to the compounds of the present invention selected from the following examples 1 to 151:

| Example Nb | structure |
|---|---|
| 1 | 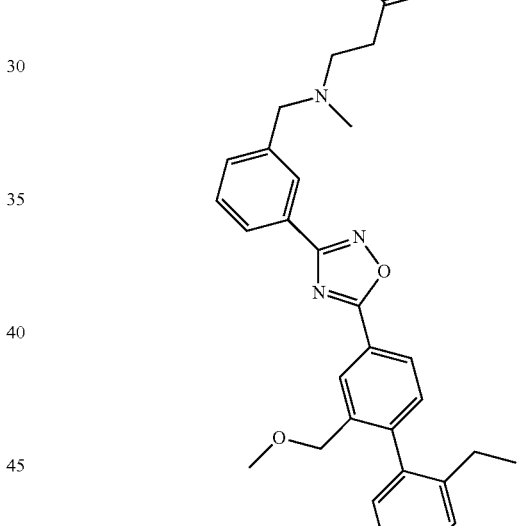 |
| 8 | 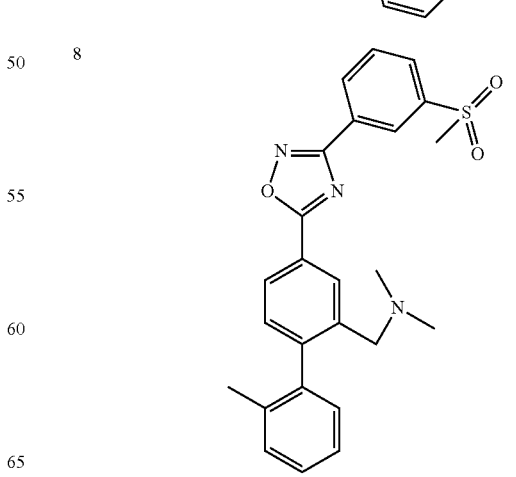 |

| Example Nb | structure |
|---|---|
| 10 | 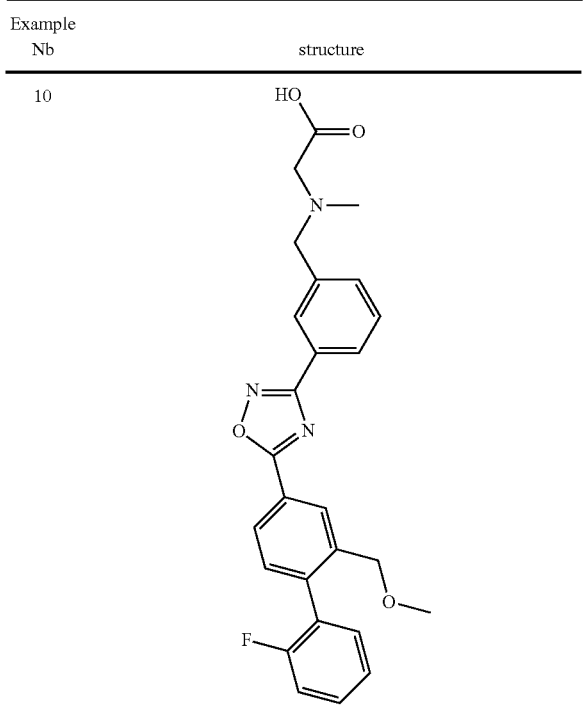 |
| 11 | 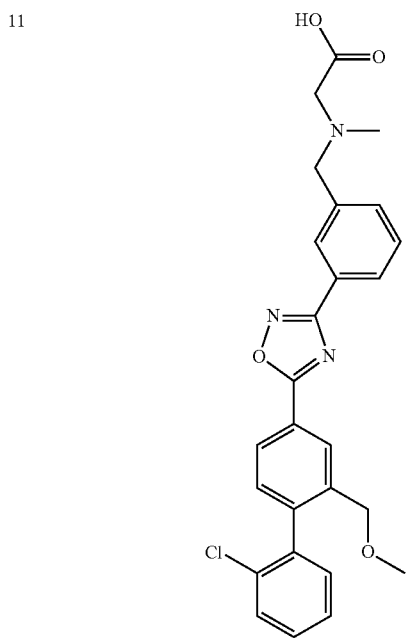 |
| Example Nb | structure |
|---|---|
| 18 | 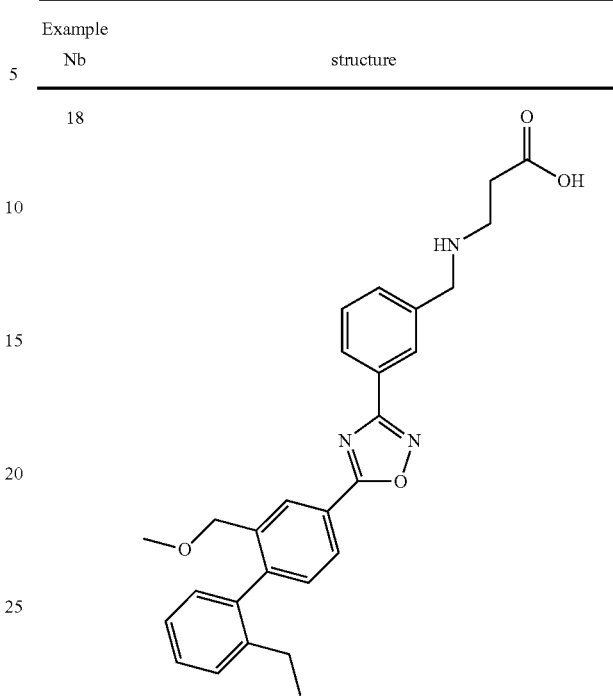 |
| 20 | 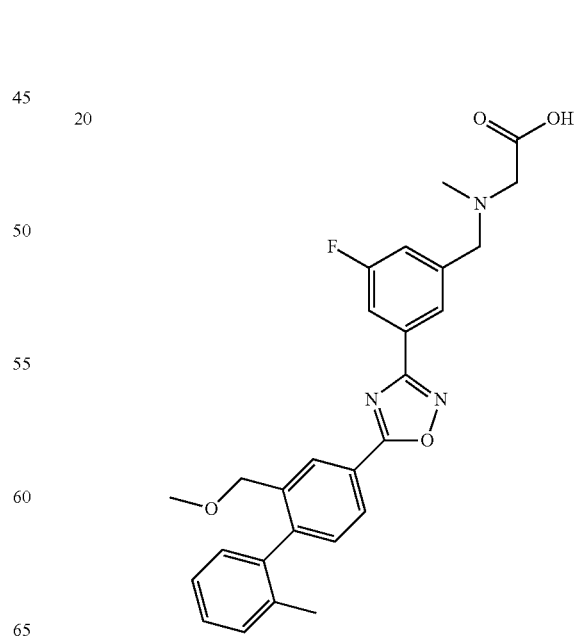 |

| Example Nb | structure |
|---|---|
| 21 | 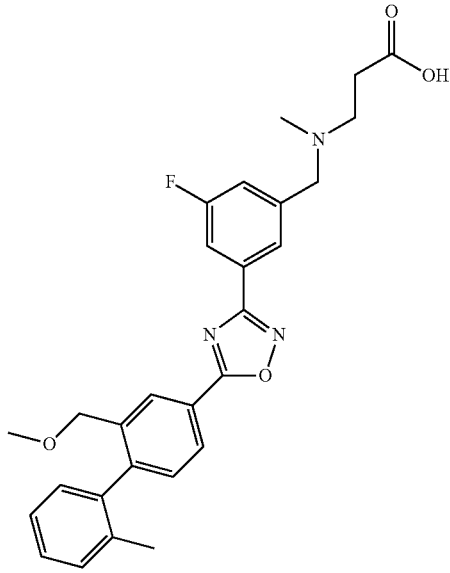 [SMILES: COCc1cc(-c2nc(-c3cc(F)cc(CN(C)CCC(=O)O)c3)no2)ccc1-c1ccccc1C] |
| 22 | 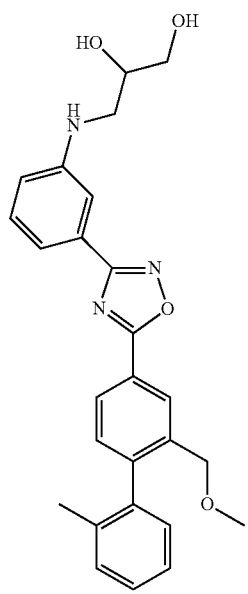 [SMILES: COCc1cc(-c2nc(-c3cccc(NCC(O)CO)c3)no2)ccc1-c1ccccc1C] |
| 30 | 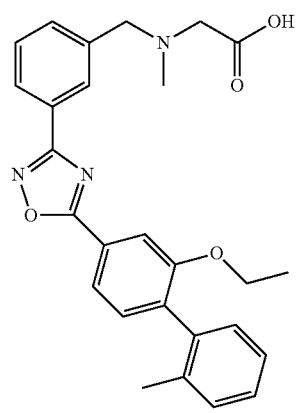 [SMILES: CCOc1cc(-c2nc(-c3cccc(CN(C)CC(=O)O)c3)no2)ccc1-c1ccccc1C] |
| Example Nb | structure |
|---|---|
| 35 | 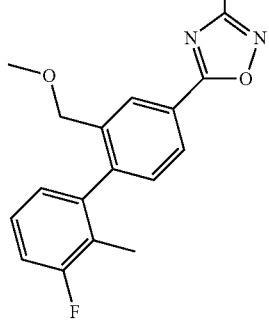 |
| 36 | 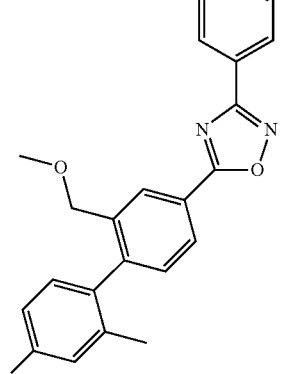 |
| 37 | 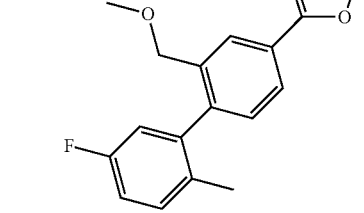 |

| Example Nb | structure |
|---|---|
| 42 | 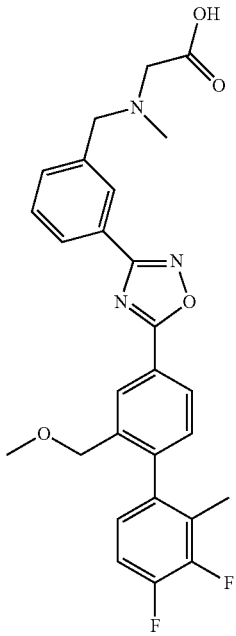 [SMILES: COCc1cc(-c2nc(-c3cccc(CN(C)CC(=O)O)c3)no2)ccc1-c1ccc(F)c(F)c1C] |
| 51 | 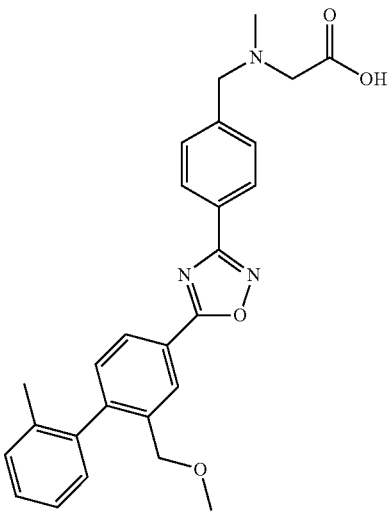 [SMILES: COCc1cc(-c2nc(-c3ccc(CN(C)CC(=O)O)cc3)no2)ccc1-c1ccccc1C] |
| Example Nb | structure |
|---|---|
| 52 | 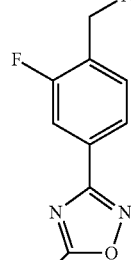 |
| 53 | 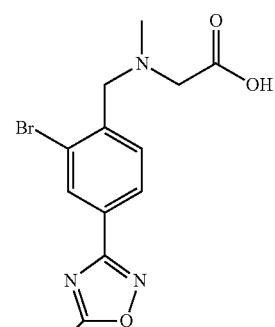 |
| 54 | 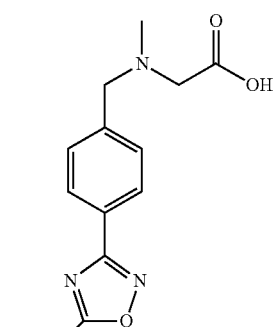 |

| Example Nb | structure |
|---|---|
| 55 | 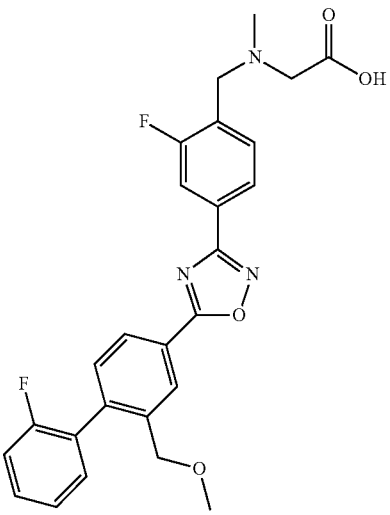 [SMILES: COCc1cc(-c2nc(-c3ccc(CN(C)CC(=O)O)c(F)c3)no2)ccc1-c1ccccc1F] |
| 57 | 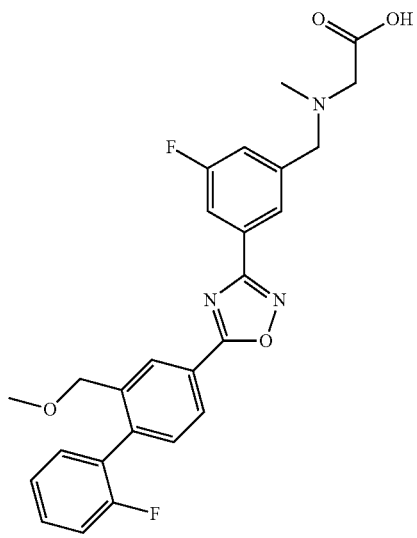 |
| 58 | 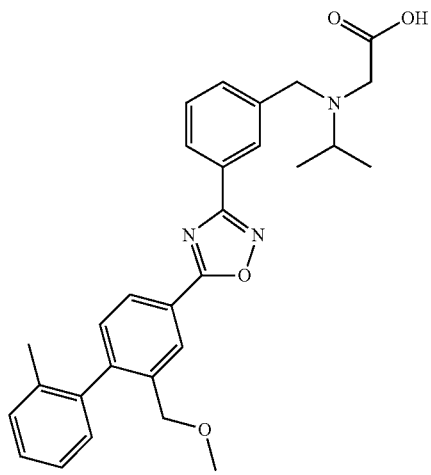 [SMILES: COCc1cc(-c2nc(-c3cccc(CN(CC(=O)O)C(C)C)c3)no2)ccc1-c1ccccc1C] |
| Example Nb | structure |
|---|---|
| 59 | 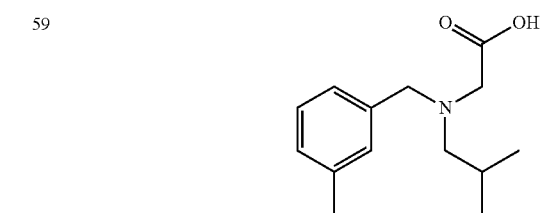 |
| 60 | 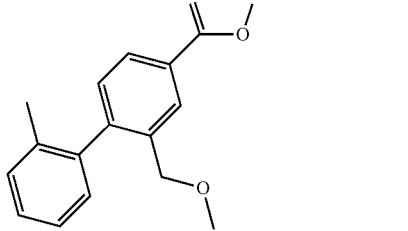 |
| 61 | |

-continued
| Example Nb | structure |
|---|---|
| 62 | 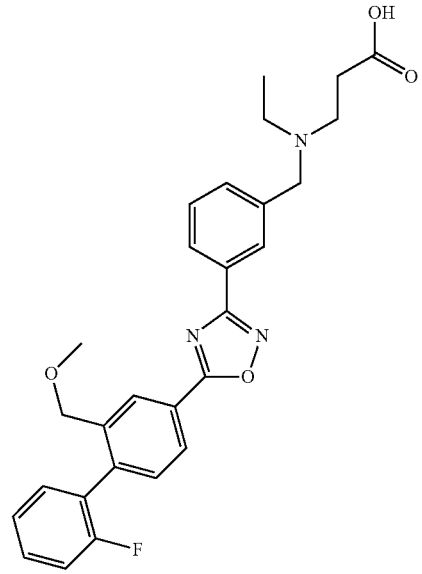 [SMILES: CCN(CCC(=O)O)Cc1cccc(-c2noc(-c3ccc(-c4ccccc4C)c(COC)c3)n2)c1] |
| 63 | 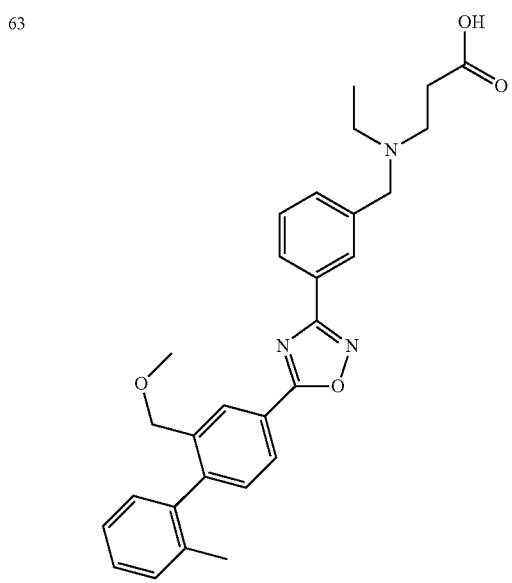 |
| 65 | 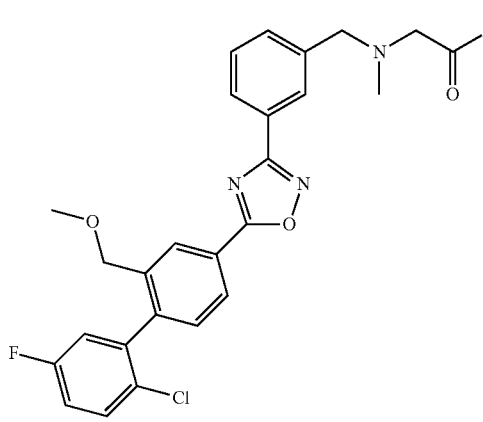 |
-continued
| Example Nb | structure |
|---|---|
| 66 | 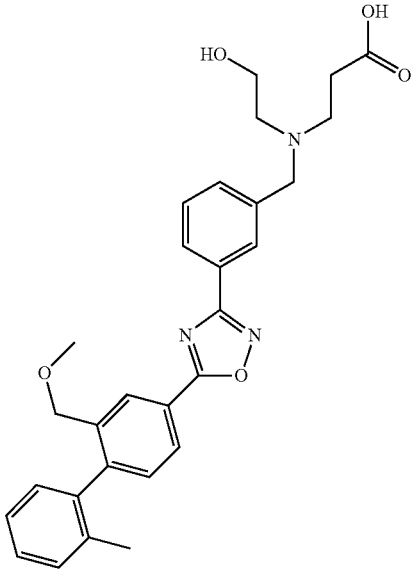 [SMILES: COCc1cc(-c2nc(-c3cccc(CN(CCO)CCC(=O)O)c3)no2)ccc1-c1ccccc1C] |
| 73 | 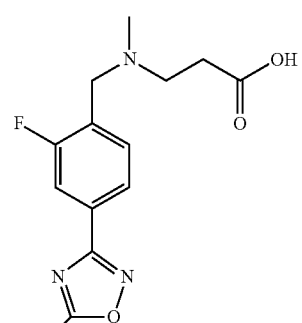 |
| 74 | 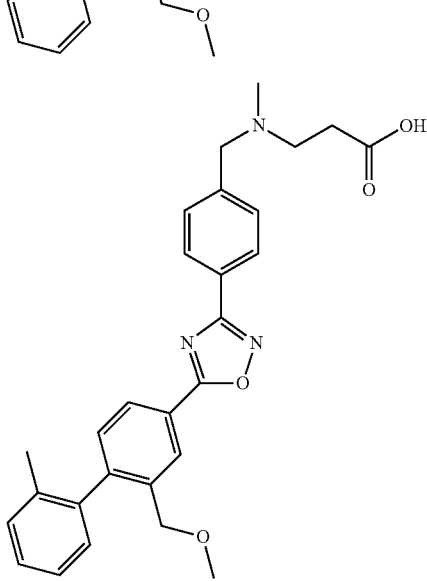 |

| Example Nb | structure |
|---|---|
| 75 | 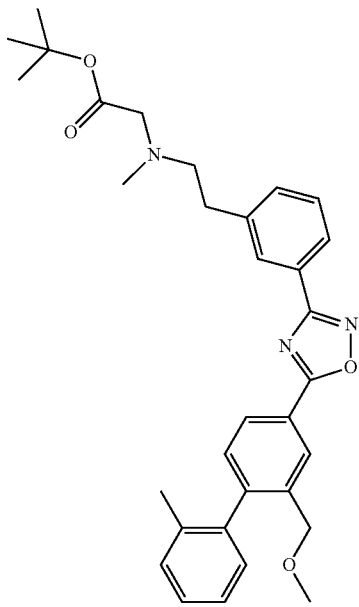 [SMILES: COCc1cc(-c2nc(-c3cccc(CCN(C)CC(=O)OC(C)(C)C)c3)no2)ccc1-c1ccccc1C] |
| 77 | 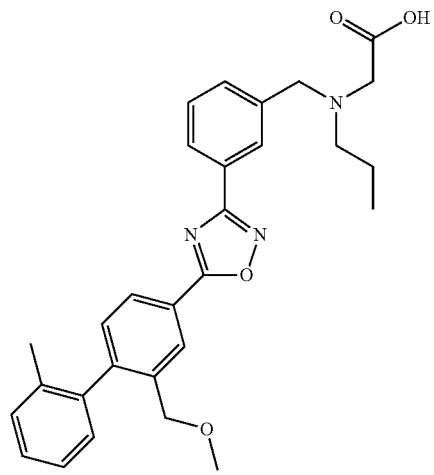 |
| 78 | 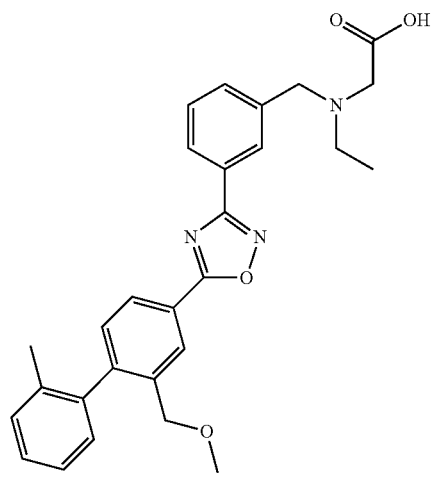 [SMILES: CCN(CC(=O)O)Cc1cccc(-c2noc(-c3ccc(-c4ccccc4C)c(COC)c3)n2)c1] |
| Example Nb | structure |
|---|---|
| 79 | 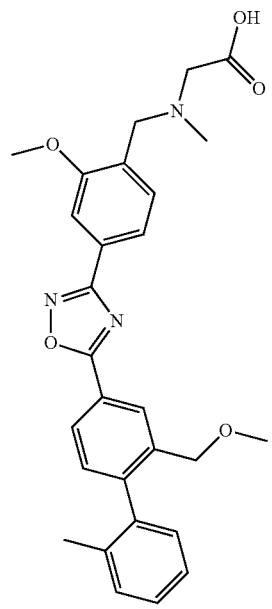 |
| 82 | 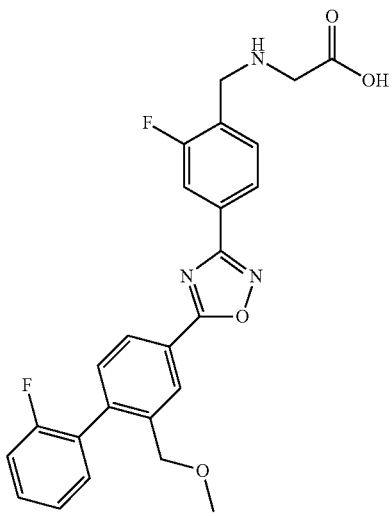 [SMILES: COCc1cc(-c2nc(-c3ccc(CNCC(=O)O)c(F)c3)no2)ccc1-c1ccccc1F] |

TABLE-continued
| Example Nb | structure |
|---|---|
| 83 | 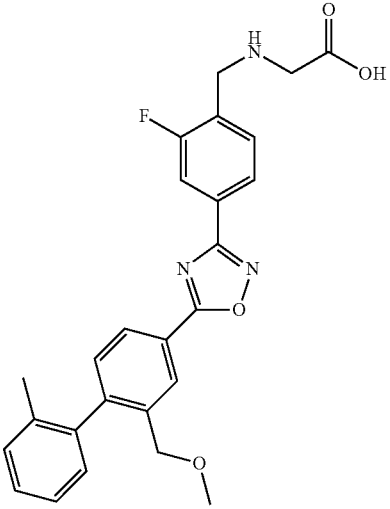 [SMILES: COCc1cc(-c2nc(-c3ccc(CNCC(=O)O)c(F)c3)no2)ccc1-c1ccccc1C] |
| 86 | 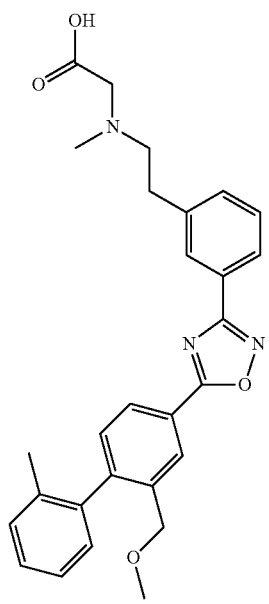 [SMILES: COCc1cc(-c2nc(-c3cccc(CCN(C)CC(=O)O)c3)no2)ccc1-c1ccccc1C] |
| 87 | 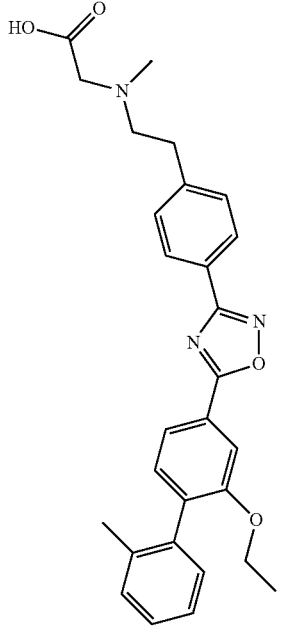 |
| 88 | 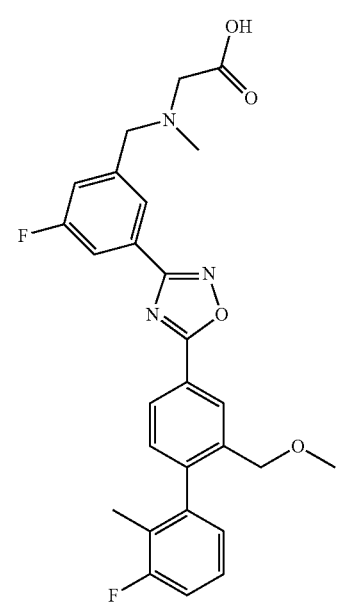 [SMILES: COCc1cc(-c2nc(-c3cc(F)cc(CN(C)CC(=O)O)c3)no2)ccc1-c1cccc(F)c1C] |

-continued
| Example Nb | structure |
|---|---|
| 90 | 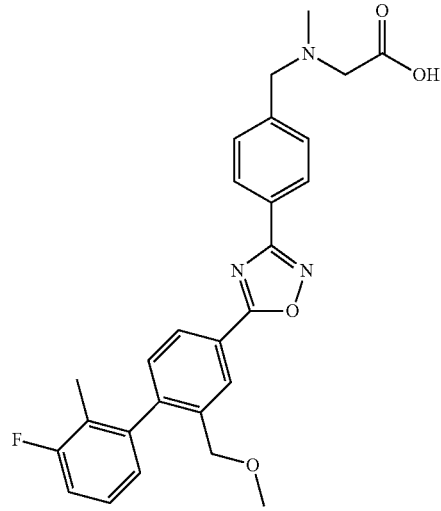 [SMILES: COCc1cc(-c2nc(-c3ccc(CN(C)CC(=O)O)cc3)no2)ccc1-c1cccc(F)c1C] |
| 91 | 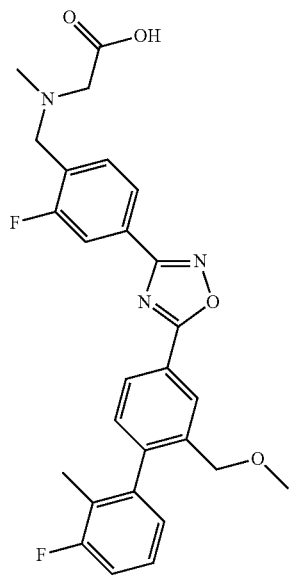 [SMILES: COCc1cc(-c2nc(-c3ccc(CN(C)CC(=O)O)c(F)c3)no2)ccc1-c1cccc(F)c1C] |
| 92 | 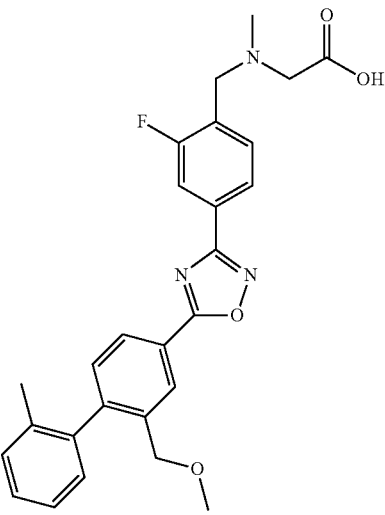 |
-continued
| Example Nb | structure |
|---|---|
| 93 | 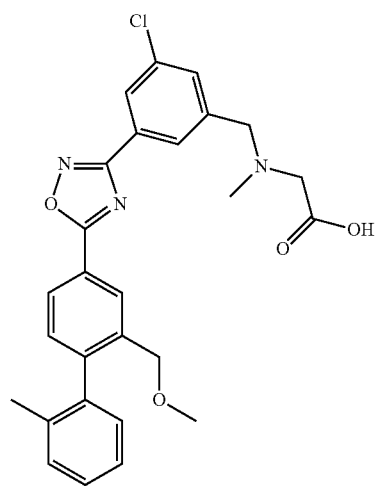 [SMILES: COCc1cc(-c2nc(-c3cc(Cl)cc(CN(C)CC(=O)O)c3)no2)ccc1-c1ccccc1C] |
| 102 | 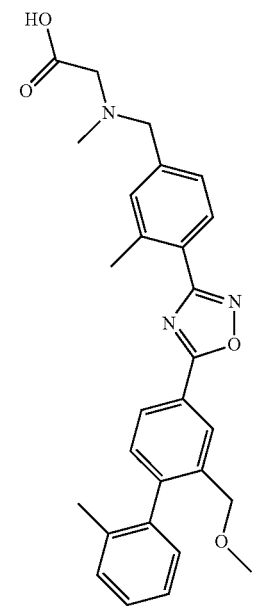 [SMILES: COCc1cc(-c2nc(-c3ccc(CN(C)CC(=O)O)cc3C)no2)ccc1-c1ccccc1C] |

63
-continued
| Example Nb | structure |
|---|---|
| 105 | 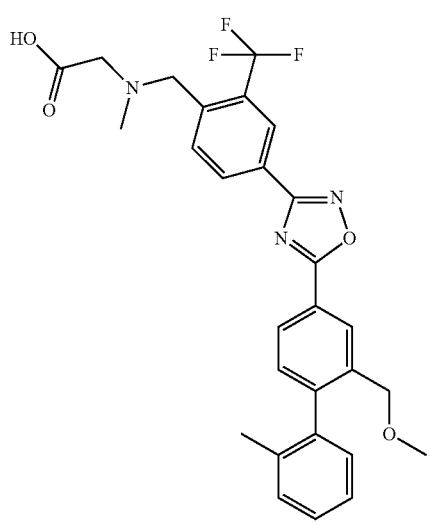 [SMILES: COCc1cc(-c2nc(-c3ccc(CN(C)CC(=O)O)c(C(F)(F)F)c3)no2)ccc1-c1ccccc1C] |
| 106 | 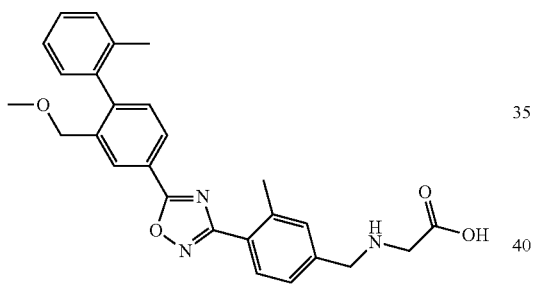 |
| 108 | 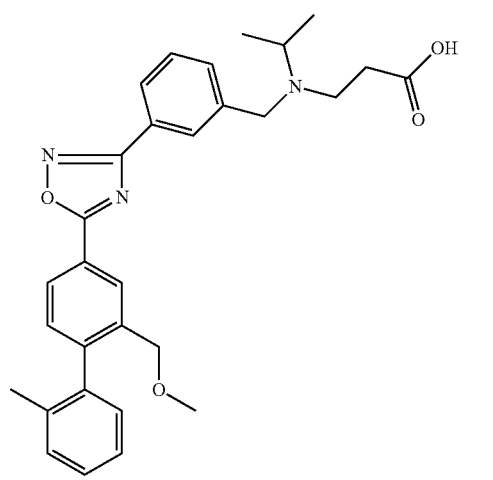 [SMILES: COCc1cc(-c2nc(-c3cccc(CN(CCC(=O)O)C(C)C)c3)no2)ccc1-c1ccccc1C] |
64
-continued
| Example Nb | structure |
|---|---|
| 118 | 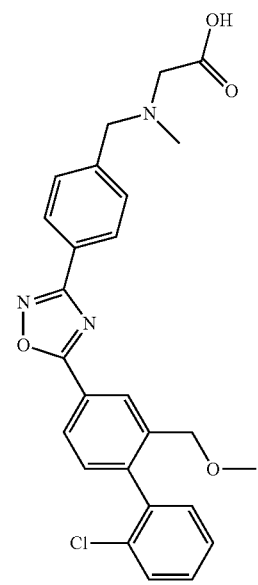 [SMILES: COCc1cc(-c2nc(-c3ccc(CN(C)CC(=O)O)cc3)no2)ccc1-c1ccccc1Cl] |
| 119 | 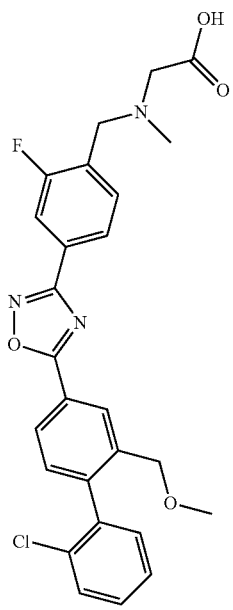 [SMILES: COCc1cc(-c2nc(-c3ccc(CN(C)CC(=O)O)c(F)c3)no2)ccc1-c1ccccc1Cl] |

-continued
| Example Nb | structure |
|---|---|
| 121 | 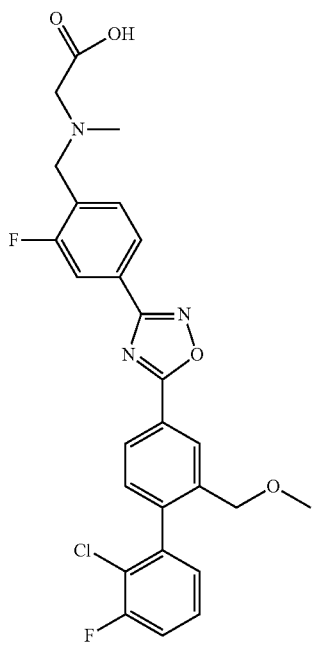 [SMILES: COCc1cc(-c2nc(-c3ccc(CN(C)CC(=O)O)c(F)c3)no2)ccc1-c1cccc(F)c1Cl] |
-continued
| Example Nb | structure |
|---|---|
| 124 | 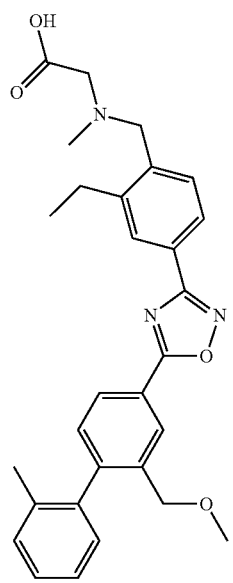 [SMILES: CCc1cc(-c2noc(-c3ccc(-c4ccccc4C)c(COC)c3)n2)ccc1CN(C)CC(=O)O] |
| 125 | 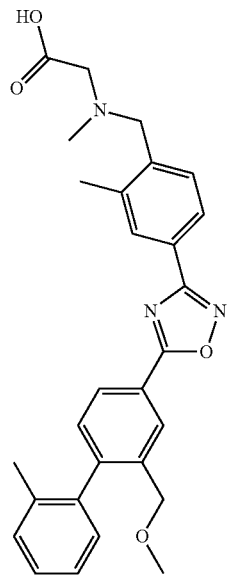 [SMILES: COCc1cc(-c2nc(-c3ccc(CN(C)CC(=O)O)c(C)c3)no2)ccc1-c1ccccc1C] |
122

-continued
| Example Nb | structure |
|---|---|
| 126 | 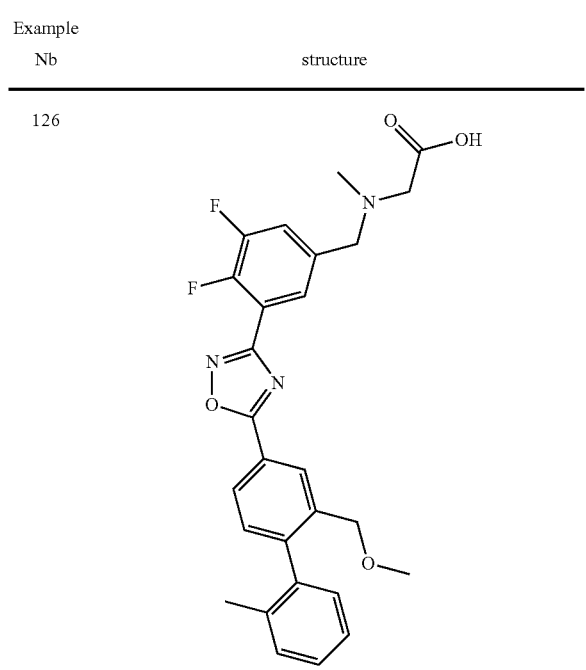 |
| 127 | 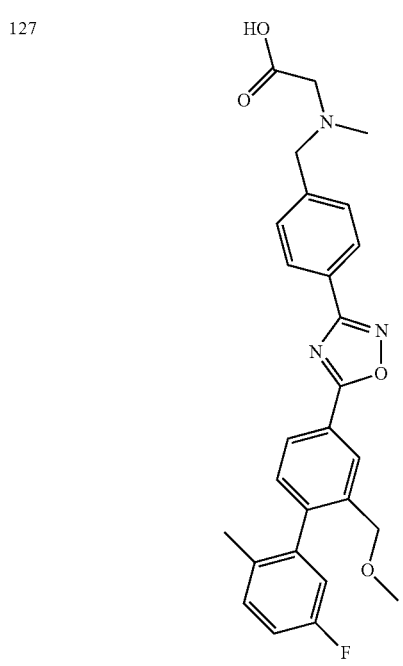 |
-continued
| Example Nb | structure |
|---|---|
| 128 | 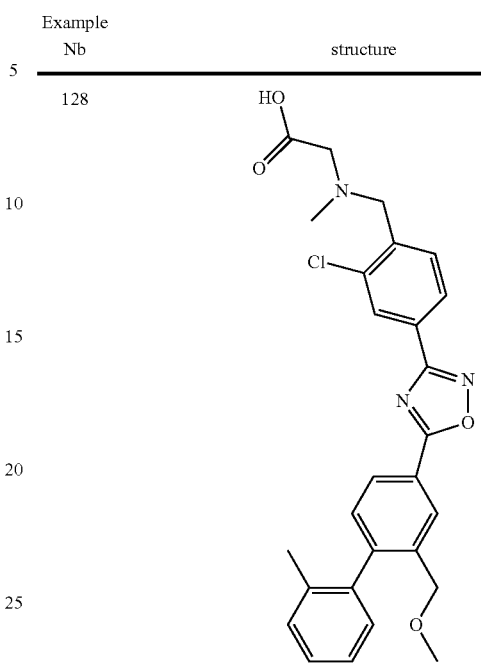 |
| 130 | 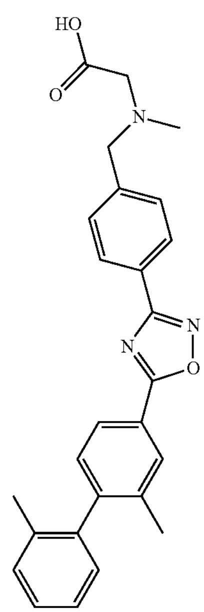 [SMILES: Cc1ccccc1-c1ccc(-c2nc(-c3ccc(CN(C)CC(=O)O)cc3)no2)cc1C] |

-continued
| Example Nb | structure |
|---|---|
| 131 | 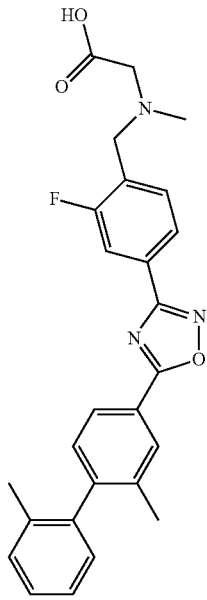 [SMILES: Cc1ccccc1-c1ccc(-c2nc(-c3ccc(CN(C)CC(=O)O)c(F)c3)no2)cc1C] |
| 132 | 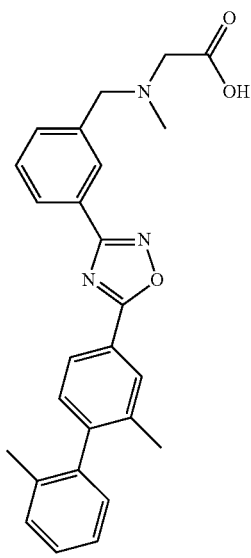 [SMILES: Cc1ccccc1-c1ccc(-c2nc(-c3cccc(CN(C)CC(=O)O)c3)no2)cc1C] |
-continued
| Example Nb | structure |
|---|---|
| 133 | 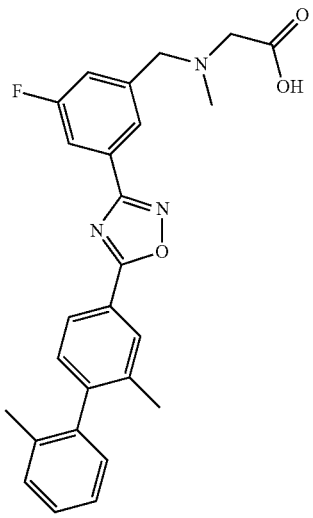 [SMILES: Cc1ccccc1-c1ccc(-c2nc(-c3cc(F)cc(CN(C)CC(=O)O)c3)no2)cc1C] |
| 137 | 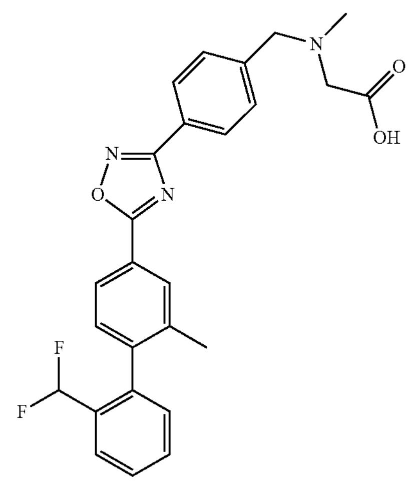 [SMILES: Cc1cc(-c2nc(-c3ccc(CN(C)CC(=O)O)cc3)no2)ccc1-c1ccccc1C(F)F] |
| 140 | 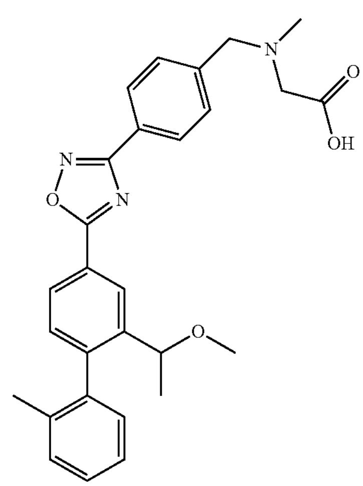 [SMILES: COC(C)c1cc(-c2nc(-c3ccc(CN(C)CC(=O)O)cc3)no2)ccc1-c1ccccc1C] |

TABLE-continued
| Example Nb | structure |
|---|---|
| 143 | 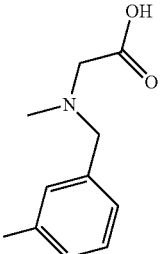 |
| 144 | 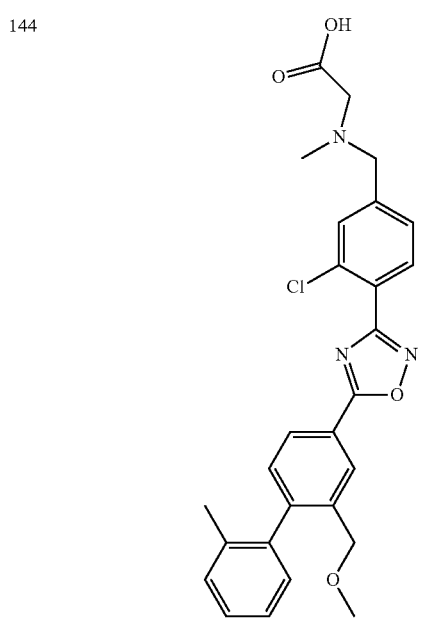 |
TABLE-continued
| Example Nb | structure |
|---|---|
| 146 | 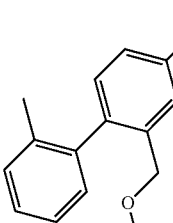 |
| 147 | 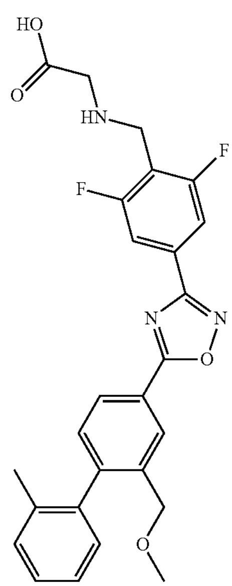 [SMILES: COCc1cc(-c2nc(-c3cc(F)c(CNCC(=O)O)c(F)c3)no2)ccc1-c1ccccc1C] |

-continued

| Example Nb | structure |
|---|---|
| 149 | 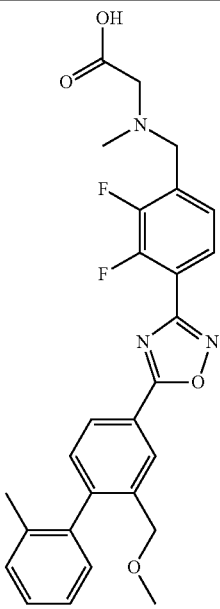 |
| 151 | 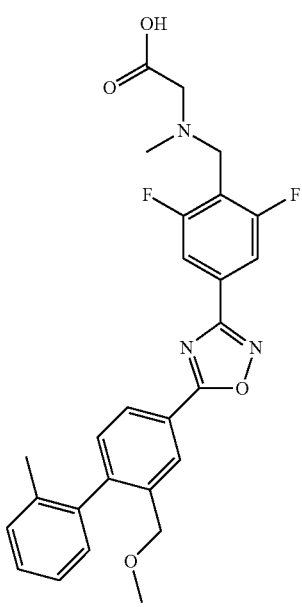 [SMILES: COCc1cc(-c2nc(-c3cc(F)c(CN(C)CC(=O)O)c(F)c3)no2)ccc1-c1ccccc1C] | and pharmaceutically usable derivatives, solvates, salts and stereoisomers thereof, including mixtures thereof in all ratios.

For all radicals and indices such as m which occur more than once within the same chemical structure, their meanings are independent of one another.

Above and below, the radicals or parameters $R^a$, $R^b$, $R^1$, $R^2$, $R^3$, W, Q, S, T, X, $X^1$, $X^2$, A, Ar, Het, m and n have the meaning indicated under the formula (I) and subformulae, unless expressly stated otherwise.

A denotes alkyl, is unbranched (linear) or branched, and has 1, 2, 3, 4, 5, 6, 7, 8, 9, 10, 11 or 12 carbon atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 carbon atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. A furthermore denotes $(CH_2)_nO(CH_2)_nOR^3$, $(CH_2)_nNR^3(CH_2)_2N(R^3)_2$, especially $(CH_2)_2O(CH_2)_2OR^3$ or $(CH_2)_2NH(CH_2)_2N(R^3)_2$.

Cycloalkyl is a cyclic alkyl containing 3 to 12 carbon atomes. Cycloalkyl preferably denotes cyclopropyl, cyclobutyl, cyclopentyl, cyclohexyl or cycloheptyl.

Cycloalkylalkylene is a cycloalkyl group bond to the rest of the molecule via a carbon chain and having 1, 2, 3, 4, 5, 6, 7, 8, 9, 10, 11, 12, 13, 14, 15, 16, 17, or 18 carbon atoms.

Cycloalkylalkylene preferably denotes cyclopropylmethylene, cyclobutylmethylene, cyclopentylmethylene, cyclohexylmethylene or cycloheptylmethylene.

Alkylene is a bivalent carbon chain having 1, 2, 3, 4, 5, 6, 7, 8, 9, 10, 11, or 12 carbon atoms. Alkylene is preferably methylene, ethylene, propylene, butylene, pentylene or hexylene, furthermore branched alkylene.

$R^a$ is preferably Ar, Het or OA especially Ar or Het.

Ar or Het is preferably substituted with methyl, trifluoromethyl methoxy or $NO_2$.

If Het denotes a N-Atom bearing saturated heterocycle, Het is preferably linked to the rest of the molecule via an N-Atom. The alpha position is next to this N-Atom.

$R^a$ very preferably denotes one of the following groups:

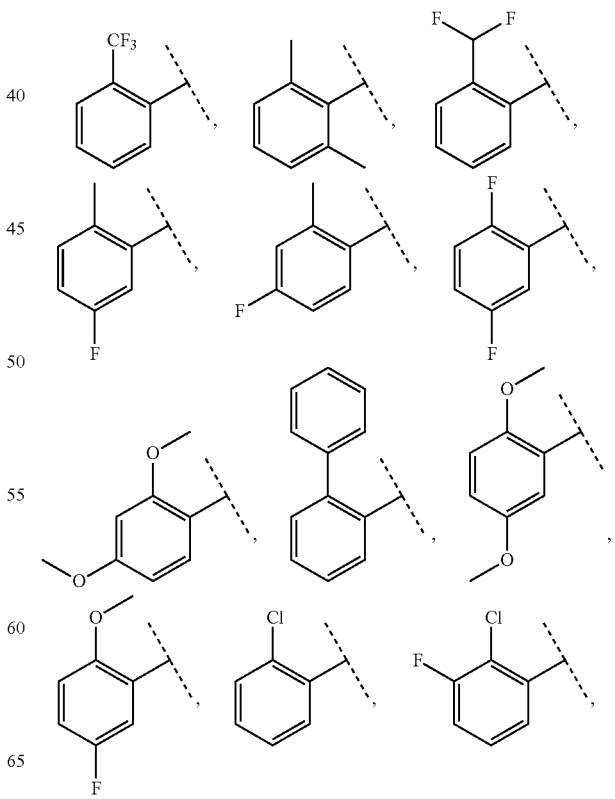

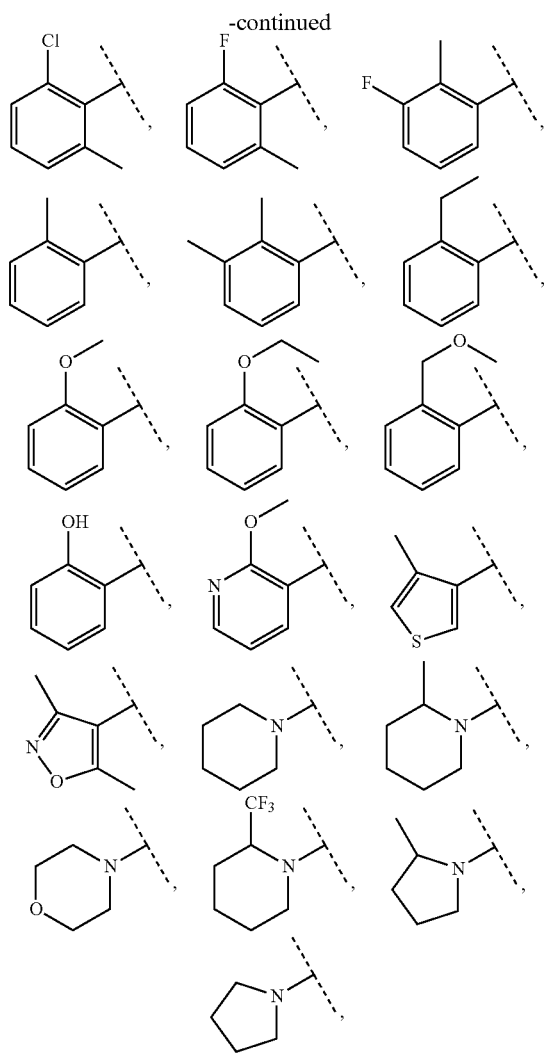

$R^b$ is preferably H, A, $OR^3$, $CF_3$, $NO_2$, $NH_3$, Hal, $CH_2OR^3$, $(CH_2)_mOA$, especially $CH_2OCH_3$, $CH_2NHSO_2A$, $NHSO_2A$, such as $NHSO_2CH_3$, $CH_2NHCOCH_3$, $CH_2N(CH_3)_2$, $CH_2NH_2$, $NHCONH_2$ or $CF_3$. Very preferably, $R^b$ is one of the following groups:

—$CH_3$, —OH, $NO_2$, —$CH_2OH$, —$CH_2OCH_3$, —$CH_2OC_2H_5$, —$CH_2OCH(CH_3)_2$, —$CH_2NHCH_3$, —$CH(CH_3)OCH_3$, —$CH_2N(CH_3)_2$, —$CH_2SO_2CH_3$, —$(CH_2)_3OCH_3$, —$OCH_3$, —$O(CH_2)_2OCH_3$, —$OCH_2CH(CH_3)_2$, —$CF_3$, CN, —$NHCOCH_3$, —$NHCOC_2H_5$, —$NHSO_2CH_3$, —$NHSO_2C_2H_5$, —$NHSO_2C_3H_7$, —$NHSO_2N(CH_3)_2$, Cl, $R^3$ preferably denotes H, ($C_1$-$C_6$ alkyl), ($C_1$-$C_6$ fluoroalkyl), more preferably, $R^3$ is H. 2 geminal groups $R^3$ linked to a N atom particularly denote

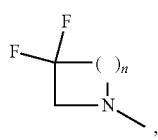

wherein n is 0, 1, 2 or 3.

Hal is preferably F, Cl or Br and especially F or Cl.

Preferably, at least one of $R^1$ and $R^2$ denotes F or Cl.

$R^1$ preferably denotes F or O-alkyl, especially F or $OCH_3$, $R^2$ is preferably H.

W preferably denotes CH.

Q is preferably in para-position, or in meta-position with respect to the oxadiazole moiety.

S is preferably $COOR_3$ and especially COOH.

The group Q-S is preferably selected from the following groups:

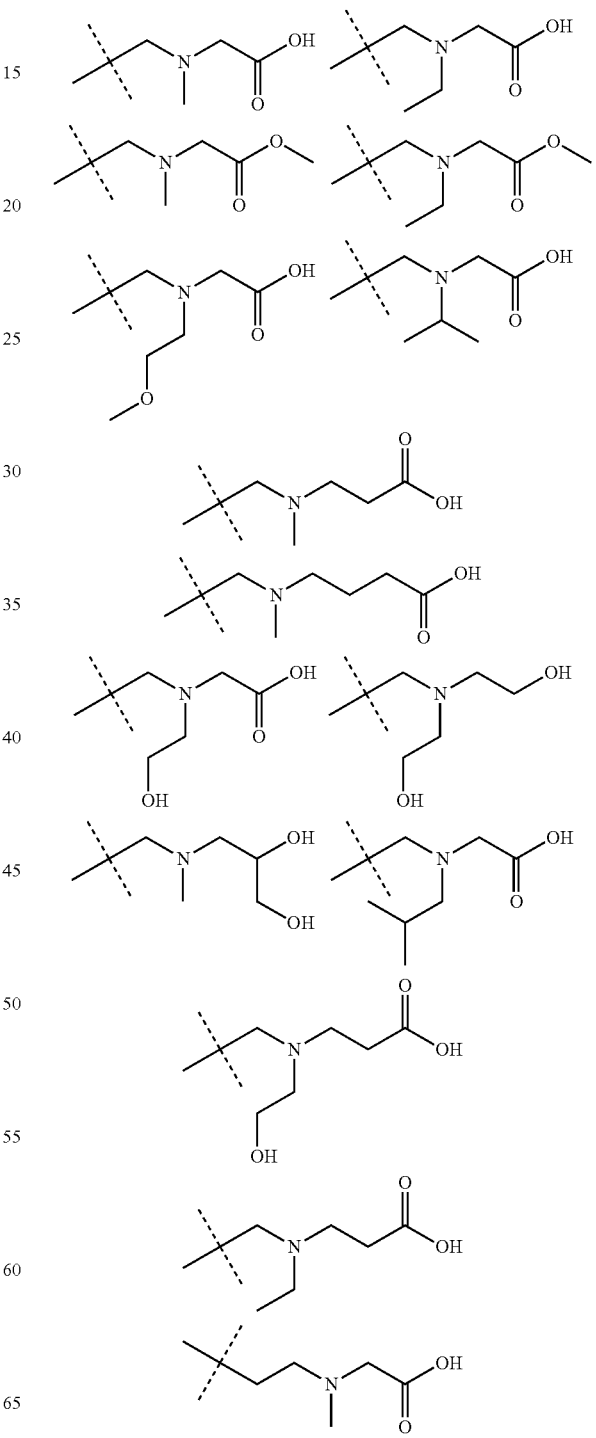

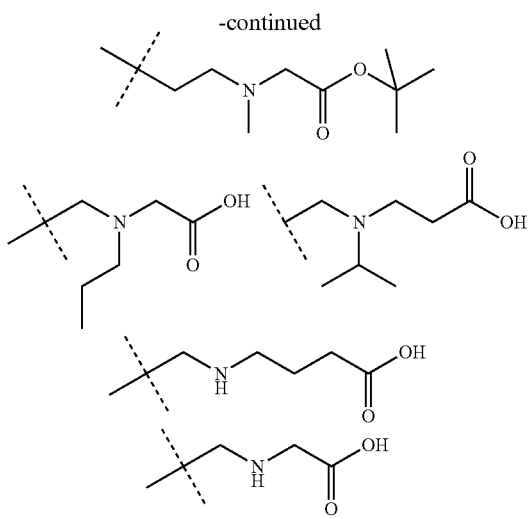

Alternatively, the group Q-S denotes —CONH(CH$_2$)$_n$COOH, —CH$_2$CONH(CH$_2$)$_n$COOH, CH$_2$CON(CH$_3$)(CH$_2$)$_n$COOH, —CH$_2$CONH(CH$_2$)$_n$NHCOCH$_3$, —CH$_2$NH(CH$_2$)$_n$COOH, —CH$_2$N(CH$_3$)(CH$_2$)$_n$COOH, —(CH$_2$)$_3$N(CH$_3$)(CH$_2$)$_n$COOtBu, —CH$_2$N(iPr)(CH$_2$)$_n$COOH, —CH$_2$N(iBu)(CH$_2$)$_n$COOH, —CH$_2$N(C$_2$H$_4$OH)(CH$_2$)$_n$COOH, —CH$_2$N(C$_2$H$_5$)(CH$_2$)$_n$COOH, —CH$_2$N(C$_3$H$_7$)(CH$_2$)$_n$COOH, —CH$_2$N(CH$_3$)(CH$_2$)CH(OH)CH$_2$OH, —CH$_2$N(C$_2$H$_4$OH)$_2$, —CH$_2$CONH(CH$_2$)$_n$N(CH$_3$)$_2$, —SO$_2$Me, —O(CH$_2$)$_n$COOH, —O(CH$_2$)$_n$OH, —CH$_2$—O—(CH$_2$)$_n$COOH, NHCH$_2$CH(OH)CH$_2$OH, CONHCH$_2$CH(OH)CH$_2$OH, —CONHCH$_2$CH(CH$_3$)COOEt, —CONHCH$_2$CH(CH$_3$)COOH, n is preferably 0, 1, 2, 3, 4 or 5 and more preferably 0, 1, 2, 3 or 4.

m is preferably 1, 2 or 3.

An aromatic carbocyclic ring preferably denotes phenyl, naphthyl or biphenyl.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o, m or p-amino-sulfanyl-phenyl, o-, m- or p-phenoxyphenyl, further preferably 2,3-, 2,4-, 2,5-, 2,6-, 3,4- or 3,5-dimethylphenyl, 2,3-, 2,4-, 2,5-, 2,6-, 3,4- or 3,5-di-fluorophenyl, 2,3-, 2,4-, 2,5-, 2,6-, 3,4- or 3,5-dichlorophenyl, 2,3-, 2,4-, 2,5-, 2,6-, 3,4- or 3,5-di-bromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chloro-phenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxy-phenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar preferably denotes, for example, phenyl which is unsubstituted or monosubstituted, disubstituted or trisubstituted by A, Hal, OR$^3$, CF$_3$, OCF$_3$, NO$_2$ and/or CN. If Ar is phenyl, it is preferably substituted in ortho-position to the C-atom linking Ar to the rest of the molecule. The ortho-position is also indicated by the figure "2" in chemical nomenclature. Ar is preferably substituted by, —CH$_3$, —(CH$_2$)$_n$OR$^3$, —(CH$_2$)$_n$NR$^3$SO$_2$A.

Ar particularly preferably denotes, for example, phenyl which is unsubstituted or monosubstituted or disubstituted preferably monosubstituted, by OCH$_3$, OH, CH$_3$, CF$_3$, such as, for example, 2'-methoxy-phenyl-, 2'-trifluoromethyl-phenyl- preferably, aryl bearing at least a 2' substituent, 2'-chlorophenyl, 2',6'-dimethyl-phenyl- or 2'-alkyl-phenyl-, preferably 2'-methyl-phenyl-.

Ar very particularly preferably denotes one of the following groups:

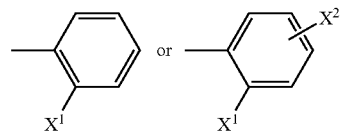

preferably

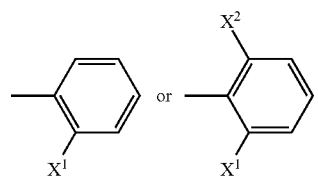

wherein X$^1$, and X$^2$ denote independently of one another F, Cl, —OCH$_3$, —CH$_3$, —C$_2$H$_5$, —CF$_3$, —OCF$_3$, —O-isoPropyl, —O-isobutyl, —OCH$_2$CN, —OCH$_2$cyclopropyl, —CH$_2$OH, —CH$_2$O-isoPropyl, —CH$_2$O-isobutyl, —CH$_2$OCH$_2$cyclopropyl, —CH$_2$NMe$_2$, —CH$_2$OC$_2$H$_5$, —NHCOMe, —NHCOEt, —NHSO$_2$NMe$_2$, —NHSO$_2$propyl, —CH$_2$-morpholine, —CH$_2$pirolidine, —CH$_2$NHMe, —SO$_2$Me, —CH$_2$SO$_2$Me, —C≡C—CH$_2$OMe, —(CH$_2$)$_3$OMe, —O(CH$_2$)$_2$OMe, —CO$_2$H, —OH, —NO$_2$, —CN, —NHSO$_2$CH$_3$, and/or phenyl or pyridyl or piperidine, or morpholine which is preferably unsubstituted.

Het is preferably a 6 to 14 membered ring system and denotes, notwithstanding further substitutions, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, indazolyl, 4- or 5-isoindolyl, 1-, 2-, 4- or 5-benzimidazolyl, 1-, 3-, 4-, 5-, 6- or 7-benzpyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-iso-quinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxane-6-yl, 2,1,3-benzothiadiazol-4- or -5-yl or 2,1,3-benzoxadiazol-5-yl.

The heterocyclic radicals may also be partially or fully hydrogenated.

Het can thus also denote, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxaneyl, 1,3-dioxane-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Het very particularly denotes one of the following groups:

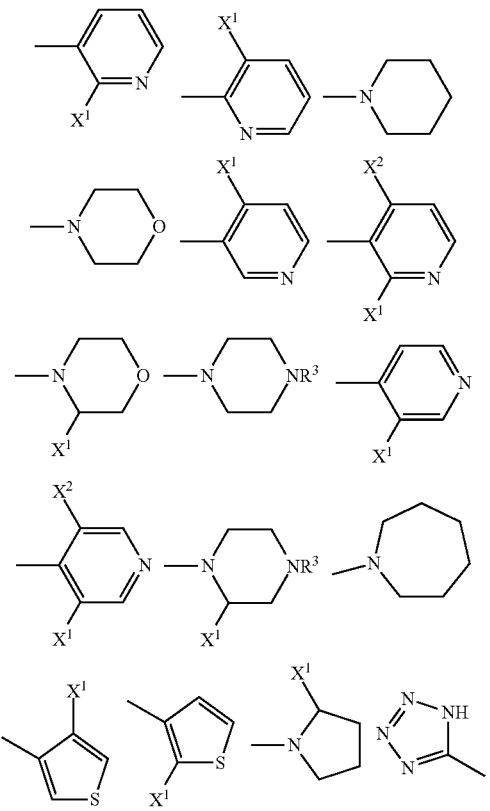

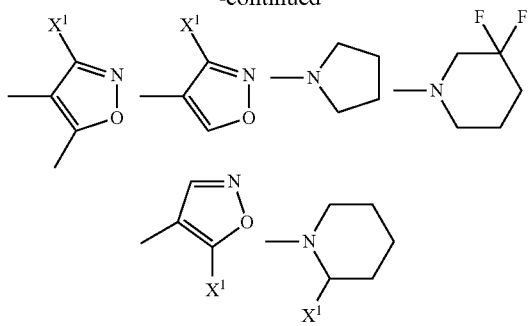

wherein $X^1$, $X^2$, and $R^3$ are as defined above.

The compounds of the formula I can have one or more centres of chirality and can therefore occur in various stereoisomeric forms. The formula I covers all these forms.

Accordingly, the invention relates, in particular, to Formula (I) and its use, in which at least one of the said radicals has one of the preferred meanings indicated above. Some preferred groups of compounds can be expressed by the following sub-formula Ia to Io, which conform to the formula (I) and in which the radicals not designated in greater detail have the meaning indicated under the formula I, but in which in Ia $R^a$ is Ar or Het.

in Ib $R^a$ is phenyl which is unsubstituted or monosubstituted or disubstituted, preferably monosubstituted, by F, $OCH_3$, $CH_3$, $CF_3$, such as, for example, 2'-methoxy-phenyl-, 2'-trifluoromethyl-phenyl-, 2'-chloro-phenyl, 2',6'-methyl-phenyl-, 2'-alkyl-phenyl-, or pyridyl, in Ic $R^1$ denotes F, in Id $R^2$ denotes H, in Ie Q denotes a single bond in para-position to the oxadiazole-moiety, S denotes COOH, in If $R^a$ denotes heterocyloalkyl preferably bearing at least an alpha-substituent, such as 2-methyl-piperidin-1-yl, in Ig $R^1$ is F, $R^2$ is H, $R^a$ denotes heterocyloalkyl, preferably bearing at least an alpha-substituent, such as 2-methyl-piperidin-1-yl, $R^b$ is trifluoroalkyl, in Ih $R^1$ is F, $R^2$ is H, $R^a$ denotes heterocyloalkyl, preferably bearing at least an alpha-substituent, such as 2-methyl-piperidin-1-yl, $R^b$ is nitro, in Ii $R^1$ is F, $R^2$ is H, $R^a$ is Ar, preferably bearing at least a 2' substituent, such as 2'-methyl-phenyl-, 2'-methoxy-phenyl-, 2'-trifluoromethyl-phenyl- $R^b$ is alkyl, nitro, alkoxy, in Ij $R^1$ is F, $R^2$ is H, $R^a$ is Het, such as 4-methyl-3-thienyl- $R^b$ is alkyl, alkoxy, in Ik $R^1$ is F, $R^2$ is H, $R^a$ is Ar, such as 2'-trifluoromethyl-phenyl-, 2'-chloro-phenyl, 2',6'-methyl-phenyl-, 2'-methyl-phenyl, $R^b$ is H, in Il R¹ is F,
R² is H,
Rᵃ is heterocycloalkyl, preferably non-substituted heterocycloakyl, such as piperidin-1-yl, morpholinyl
Rᵇ is nitro, methyl, trifluoromethyl,
in Im R¹ is F,
R² is H,
Rᵃ is Ar such as 2'-alkyl-phenyl-,
Rᵇ is alkyl,
in In R¹ is F,
R² is H,
Rᵃ is A or heterocycloalkyl, preferably unsubstituted such as phenyl, piperidin-1-yl,
Rᵇ is methyl,
In Io R¹ is F
R² is H
Rᵃ is ortho substituted Ar or orthosubstituted Het such as 2-methylphenyl, 2-methylpiperidine, 2-methylmorpholine, 2-methylthienyl.
Rᵇ is —CH₂OCH₃.

Alternatively, in Formula Ig, Ih, Ii, Ij, Ik, Il, Im, In, and Io, W is CH, Q is a single bond in para position to the oxadiazole moiety and S is COOH.

Alternatively, in Formula Ig, Ih, Ii, Ij, Ik, Il, Im, In, and Io, QS denotes

—COOR³, —CON(R³)(CH₂)ₙCO₂R³, —CONR³(C₃-C₆cycloalkyl)CO₂R³, —CH₂N(R³)(CH₂)ₙCO₂R³, —CH₂NR³(C₃-C₆cycloalkyl)CO₂R³, —CH₂—O—(CH₂)ₙCO₂R³, —CH₂O(C₃-C₆cycloalkyl)CO₂R³, —O(CH₂)ₙCO₂R³, —O(C₃-C₆cycloalkyl)CO₂R³ wherein n and R³ are as above defined.

and pharmaceutically usable derivatives, solvates, salts and stereoisomers thereof, including mixtures thereof in all ratios.

The compounds of the formula I and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), under reaction conditions which are known and suitable for the said reactions. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3ʳᵈ Edition 1999.

Use can also be made here of variants which are known per se, but are not mentioned here in greater detail.

If desired, the starting materials can also be formed in situ so that they are not isolated from the reaction mixture, but instead are immediately converted further into the compounds of the formula I.

The starting compounds for the preparation of compounds of formula I are generally known. If they are novel, they can, however, be prepared by methods known per se.

The reactions are preferably carried out in an inert solvent.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or DCM; alcohols, such as methanol, ethanol, isopropanol, n-propanol, n-butanol or tert-butanol; ethers, such as diethyl ether, diisopropyl ether, THF (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as EtOAc, or mixtures of the said solvents.

Pharmaceutical Salts and Other Forms

The said compounds of the formula I can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains an acidic center, such as a carboxyl group, one of its suitable salts can be formed by reacting the compound with a suitable base to give the corresponding base-addition salt. Such bases are, for example, alkali metal hydroxides, including potassium hydroxide and sodium hydroxide; alkaline earth metal hydroxides, such as magnesium hydroxide and calcium hydroxide; and various organic bases, such as piperidine, diethanolamine and N-methyl-glucamine (meglumine), benzathine, choline, diethanolamine, ethylenediamine, benethamine, diethylamine, piperazine, lysine, L-arginine, ammonia, triethanolamine, betaine, ethanolamine, morpholine and tromethamine. In the case of certain compounds of the formula I, which contain a basic center, acid-addition salts can be formed by treating these compounds with pharmaceutically acceptable organic and inorganic acids, for example hydrogen halides, such as hydrogen chloride or hydrogen bromide, other mineral acids and corresponding salts thereof, such as sulfate, nitrate or phosphate and the like, and alkyl- and monoaryl-sulfonates, such as methanesulfonate, ethanesulfonate, toluenesulfonate and benzene-sulfonate, and other organic acids and corresponding salts thereof, such as carbonate, acetate, trifluoro-acetate, tartrate, maleate, succinate, citrate, benzoate, salicylate, ascorbate and the like. Accordingly, pharmaceutically acceptable acid-addition salts of the compounds of the formula I include the following: acetate, adipate, alginate, aspartate, benzoate, benzene-sulfonate (besylate), bisulfate, bisulfite, bromide, camphorate, camphor-sulfonate, caprate, caprylate, chloride, chlorobenzoate, citrate, cyclamate, cinnamate, digluconate, dihydrogen-phosphate, dinitrobenzoate, dodecyl-sulfate, ethanesulfonate, formate, glycolate, fumarate, galacterate (from mucic acid), galacturonate, glucoheptanoate, gluco-nate, glutamate, glycerophosphate, hemi-succinate, hemisulfate, heptanoate, hexanoate, hippurate, hydrochloride, hydrobromide, hydroiodide, 2-hydroxy-ethanesulfonate, iodide, isethionate, isobutyrate, lactate, lactobionate, malate, maleate, malonate, mandelate, metaphosphate, methanesulfonate, methylbenzoate, mono-hydrogen-phosphate, 2-naphthalenesulfonate, nicotinate, nitrate, oxalate, oleate, palmo-ate, pectinate, persulfate, phenylacetate, 3-phenylpropionate, phosphate, phosphonate, phthalate, but this does not represent a restriction. Both types of salts may be formed or interconverted preferably using ion-exchange resin techniques.

Furthermore, the base salts of the compounds of the formula I include aluminum, ammonium, calcium, copper, iron (III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzyl-ethylen-ediamine (benzathine), dicyclohexylamine, diethanol-amine, diethyl-amine, 2-diethyl-amino-ethanol, 2-dimethyl-amino-ethanol, ethanolamine, ethylenediamine, N-ethylmorpholine, N-ethyl-piperidine, glucamine, glucosamine, histidine, hydrabamine, isopropyl-amine, lido-caine, lysine, meglu-mine (N-methyl-D-glucamine), morpholine, piperazine, pip-eridine, polyamine resins, procaine, purines, theobromine, triethanol-amine, triethylamine, trimethylamine, tripropyl-amine and tris(hydroxy-methyl)-methylamine (tromethamine), but this is not intended to represent a restric-tion.

Compounds of the formula I of the present invention which contain basic $N_2$-containing groups can be quaternised using agents such as (C1-C4)-alkyl halides, for example methyl, ethyl, isopropyl and tert-butyl chloride, bromide and iodide; di(C1-C4)alkyl sulfates, for example dimethyl, diethyl and diamyl sulfate; (C10-C18)alkyl halides, for example decyl, do-decyl, lauryl, myristyl and stearyl chloride, bromide and iodide; and aryl-(C1-C4)alkyl halides, for example benzyl chloride and phenethyl bromide. Both water- and oil-soluble compounds of the formula I can be prepared using such salts.

The above-mentioned pharmaceutical salts which are pre-ferred include acetate, trifluoroacetate, besylate, citrate, fumarate, gluconate, hemisuccinate, hippurate, hydrochlo-ride, hydrobromide, isethionate, mandelate, me-glumine, nitrate, oleate, phosphonate, pivalate, sodium phosphate, stearate, sulfate, sulfosalicylate, tartrate, thiomalate, tosylate and tro-meth-amine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts other-wise correspond to the respective free base forms thereof.

As mentioned, the pharmaceutically acceptable base-addi-tion salts of the compounds of the formula I are formed with metals or amines, such as alkali metals and alkaline earth metals or organic amines. Preferred metals are sodium, potas-sium, magnesium and calcium. Preferred organic amines are N,N'-dibenzylethylenediamine, chloroprocaine, choline, diethanol-amine, ethylenediamine, N-methyl-D-glucamine and procaine.

The base-addition salts of acidic compounds of the formula I are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts other-wise correspond to the respective free acid forms thereof.

If a compound of the formula I contains more than one group which is capable of forming pharmaceutically accept-able salts of this type, the formula I also encompasses mul-tiple salts. Typical multiple salt forms include, for example, bitartrate, diacetate, difumarate, dimeglumine, di-phosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically accept-able salt form of the active ingredient can also provide this active ingredient for the first time with a desired pharmaco-kinetic property which it did not have earlier and can even have a positive influence on the pharmacodynamics of this active ingredient with respect to its therapeutic efficacy in the body.

Owing to their molecular structure, the compounds of the formula I can be chiral and can accordingly occur in various enantiomeric forms. They can therefore exist in racemic or in optically active form.

Since the pharmaceutical activity of the racemates or ste-reoisomers of the compounds according to the invention may differ, it may be desirable to use the enantiomers. In these cases, the end product or even the Intermediates can be sepa-rated into enantiomeric compounds by chemical or physical measures known to the person skilled in the art or even employed as such in the synthesis.

In the case of racemic amines, diastereomers are formed from the mixture by reaction with an optically active resolv-ing agent. Examples of suitable resolving agents are optically active acids, such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacry-late polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of compounds of formula I, in combination with at least one further medi-cament active ingredient, preferably medicaments used in the treatment of multiple sclerosis such as cladribine or another co-agent, such as interferon, e.g. pegylated or non-pegylated interferons, preferably interferon beta and/or with com-pounds improving vascular function. These further medica-ments, such as interferon beta, may be administered concomi-tantly or sequentially, e.g. by subcutaneous, intramuscular or oral routes. These compositions can be used as medicaments in human and veterinary medicine.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condi-tion treated, the method of administration and the age, weight and condition of the patient, or pharmaceutical formulations can be administered in the form of dosage units which com-prise a predetermined amount of active ingredient per dosage unit. Preferred dosage unit formulations are those which com-prise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medica-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape which are broken up to form granules.

The granules can be lubricated by addition of stearic acid, a stearate salt, talc or mineral oil in order to prevent sticking to the tablet casting molds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds.

Syrups can be prepared by dissolving the compounds in an aqueous solution with a suitable flavour, while elixirs are prepared using a non-toxic alcoholic vehicle. Suspensions can be for-mulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof and the other active ingredients can also be administered in the form of liposome delivery systems, such as, for exam-ple, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or sus-pended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insuf-flators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a sphingosine 1-phosphate associated disorder, comprising administering to said subject an effective amount of a compounds of formula I. The present invention preferably relates to a method, wherein the sphingosine 1-phosphate-1 associated disorder is an autoimmune disorder or condition associated with an overactive immune response.

The present invention furthermore relates to a method of treating a subject suffering from an immunerogulatory abnormality, comprising administering to said subject a compounds of formula I in an amount that is effective for treating said immunoregulatory abnormality. The present invention preferably relates to a method wherein the immunoregulatory abnormality is an autoimmune or chronic inflammatory disease selected from the group consisting of: amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves' ophthalmopathy and asthma. The present invention furthermore relates to a method wherein the immunoregulatory abnormality is bone marrow or organ transplant rejection or graft-versus-host disease. The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

Preferred compounds of formula (I) exhibit a EC50 in GTPγS for the binding to the $S1P_1$ receptor of less than about 10 μM, preferably less than about 5 μM, more preferably less than about 1 μM and even more preferred less than about 0.1 μM. Most preferably, compounds of Formula (I) exhibit a EC50 for the binding of S1P1 less than 0.01 μM.

Preferred compounds of Formula (I) exhibit a selectivity on S1P1 receptor over the S1P3 receptor of a magnitude of more than about 20. More preferably, compounds of formula (I) are 50 fold selective for S1P1 compare to S1P3, more preferably, 100 fold.

The compounds of invention have been named according the standards used in the program "ACD/Name Batch" from Advanced Chemistry Development Inc., ACD/Labs (7.00 Release). Product version: 7.10, build: 15 Sep. 2003.

In the following the present invention shall be illustrated by means of some examples, which are not construed to be viewed as limiting the scope of the invention.

EXAMPLES

Compounds of the present invention are synthesized according to the protocols described in the patent application PCT/EP2008/063180

The oxadiazole compounds according to formula (I) can be prepared from readily available starting materials by several synthetic approaches, using both solution-phase and solid-phase chemistry protocols or mixed solution and solid phase protocols. Examples of synthetic pathways are described below in the examples.

The commercially available starting materials used in the following experimental description were purchased from Aldrich or Fluka unless otherwise reported.

The HPLC, NMR and MS data provided in the examples described below are obtained as followed:

HPLC Data:

Method A: HPLC columns: Xbridge™ C8 column 50 mm×4.6 mm at a flow of 2 mL/min; 8 min gradient from 0.1% TFA in $H_2O$ to 0.07% TFA in ACN.

Method B: HPLC columns: ATLANTIS C18 75×4.6 mm 5 U at a flow of 1 mL/min; A-0.1% HCOOH B-ACN.

Method C: HPLC columns: C18 BDS, 50×4.6 mm, SC\307 at a flow of 0.8 mL/min; A-0.1% TFA, B-ACN: Flow –0.8 mL/min.

Method D: HPLC columns: ATLANTIS C18 75×4.6 mm, 5 U at a flow of 0.8 ml/min; A-0.1% TFA, B-ACN Method: E: HPLC columns: ATLANTIS C18 75×4.6 mm, 5 U at a flow of 0.8 ml/min; A-10 mM $NH_4OAC$, B-ACN Method F: HPLC columns: Phenomenex Luna 5 μm C18 (2), 100×4.6 mm (plus guard cartridge) at a flow of 2 ml/min; 3.5 min gradient from 95:5 ([0.1% (V/V) formic acid in $H_2O$]: [0.1% (V/V) formic acid in MeCN]) to 5:95 ([0.1% (V/V) formic acid in $H_2O$]: [0.1% (V/V) formic acid in MeCN]) then held for 2 minutes at 5:95 ([0.1% (V/V) formic acid in $H_2O$]: [0.1% (V/V) formic acid in MeCN]).

Method G: HPLC columns: Waters Xterra MS 5 μm C18, 100×4.6 mm (plus guard cartridge) at a flow of 2 ml/min; 3.5 min gradient from 95:5 ([10 mM ammonium bicarbonate in $H_2O$]: MeCN) to 5:95 ([10 mM ammonium bicarbonate in $H_2O$]: MeCN) then held for 1.5 minutes at 5:95 ([10 mM ammonium bicarbonate in $H_2O$]: MeCN).

Method H: HPLC columns: Waters Sunfire 5 μm C18, 150×4.6 mm (plus guard cartridge) at a flow of 1 ml/min; 30 min gradient from 95:5 ([0.1% (V/V) formic acid in $H_2O$]: [0.1% (V/V) formic acid in MeOH]) to 0.1% (V/V) formic acid in MeOH then held for 5 minutes at 0.1% (V/V) formic acid in MeOH.

Method I: Gradient of Method H applied to HPLC columns: Supelco, Ascentis® Express 018 or Hichrom Halo C18, 2.7 μm 018, 100×4.6 mm.

Method J: HPLC columns: Waters Xterra 5 μm C18 (2), 250×4.6 mm (plus guard cartridge) at a flow of 1 ml/min; 19.5 min gradient from 95:5 ([10 mM ammonium bicarbonate in $H_2O$]: MeCN) to MeCN then held for 4 minutes at MeCN.

Method K: HPLC columns: Waters Xbridge 5 μm C18, 150×4.6 mm (plus guard cartridge) at a flow of 1 ml/min; 22 min gradient from 95:5 ([10 mM ammonium bicarbonate in $H_2O$]: MeOH) to MeOH then held for 4 minutes at MeOH.

UV detection (maxplot) for all methods.

Mass Spectrum:

Method A: LC/MS Waters ZMD (ESI); GC/MS: GC Agilent 6890N & MS Agilent 5973.

Method B: HPLC/MS: Waters Acquity, column Waters Acquity HPLC BEH C18 1.7 m 2.1×50 mm, conditions: solvent A (10 mM ammonium acetate in water+5% ACN), solvent B (ACN), gradient 5% B to 100% B over 3 min, UV detection (PDA, 230-400 nm) and MS detection (SQ detector, positive and negative ESI modes, cone voltage 30 V).

$^1$H-NMR Data:

Bruker DPX-300 MHz unless otherwise reported.

Preparative HPLC Purifications:

Preparative HPLC purifications were performed with HPLC waters Prep LC 4000 System equipped with Columns® PrepMS C18 10 m, 50×300 mm, unless otherwise reported. All HPLC purifications were performed with a gradient of ACN/$H_2O$ or ACN/$H_2O$/TFA (0.1%).

Mass Directed Autoprep Purifications:

Preparative HPLC purifications are performed with a mass directed autopurification Fractionlynx from Waters equipped with a Sunfire Prep C18 OBD column 19×100 mm 5 m, unless otherwise reported. All HPLC purifications were performed with a gradient of ACN/$H_2O$ or ACN/$H_2O$/HCOOH (0.1%).

The microwave chemistry was performed on a single mode microwave reactor Emrys™ Optimiser from Personal Chemistry.

General Procedures:

Procedure 1: Amidoxime Moiety Formation

To a solution of nitrile derivative (1 eq) in EtOH (1-5 mL/mmol of nitrile derivative) was added a 50% aqueous solution of $NH_2OH$ (5 eq). The resulting mixture was stirred at a temperature ranging from RT to 80° C. for 1 to 72 hours. In case a precipitation of the expected compound was observed, the precipitate was filtered off and washed with an adequate solvent, such as EtOH, iPrOH or water, and then dried under reduced pressure to give the expected amidoxime derivative. In all other cases, the reaction mixture was concentrated under reduced pressure, diluted with an adequate solvent, such as water or iPrOH, until the precipitation of the expected compound was observed. The precipitate was filtered off and washed with an adequate solvent, such as iPrOH or water, and then dried under reduced pressure to give the expected amidoxime derivative. When no precipitation occurred, the concentrated mixture was dissolved in EtOAc and water, the organic layer was washed with water (twice) and brine (twice), then dried over $MgSO_4$, filtered and concentrated under vacuum to give the expected amidoxime derivative.

Procedure 2: Amidoxime Moiety Formation

To a solution of nitrile derivative (1 eq) in EtOH (1-5 mL/mmol of nitrile derivative) was added $NH_2OH.HCl$ (1.1 eq) and $Et_3N$ (1.2 eq). The resulting mixture was stirred at a temperature ranging from RT to 80° C. for 1 to 72 hours. In case of precipitation of the expected compound, the precipitate was filtered off and washed with an adequate solvent, such as EtOH, iPrOH or water, and then dried under reduced pressure to give the expected amidoxime derivative. In all other cases, the reaction mixture was concentrated under reduced pressure, diluted with an adequate solvent, such as water or iPrOH, until precipitation. The precipitate was filtered off and washed with an adequate solvent, such as iPrOH or water, and then dried under reduced pressure to give the expected amidoxime derivative. When no precipitation occurred, the concentrated mixture was dissolved in EtOAc and water, the organic layer was washed with water (twice) and brine (twice), then dried over $MgSO_4$, filtered and concentrated under vacuum to give the expected amidoxime derivative.

Procedure 3: Oxadiazole Ring Formation

DIEA (2.0 to 2.2 eq) and HATU (1.0 to 1.1 eq) were added into a solution of the carboxylic acid derivative (1 eq) in anhydrous DMF (4 mL/mmol of carboxylic acid derivative) cooled at 0° C. The resulting mixture was stirred at 0° C. for a period of 5 to 30 minutes. Then the amidoxime derivative (1.0 to 1.2 eq) was added neat or as a DMF solution. The resulting mixture was stirred at 0° C. or RT for a period of 30 minutes to 18 hours. The reaction mixture was diluted with an adequate solvent, such as $Et_2O$, MTBE or EtOAc, and then washed with water and brine. The aqueous layers were extracted once. The organic layers were combined, dried ($MgSO_4$ or $Na_2SO_4$) and the solvents were removed under reduced pressure. The residue was either taken up with toluene (6 mL/mmol of carboxylic acid derivative) and pyridine (2 mL/mmol of carboxylic acid derivative) or with ACN (8.5 mL/mmol of carboxylic acid derivative). The resulting mixture was heated at a temperature between 80° C. to reflux for a period of 12 to 72 hours. The reaction mixture was diluted with an adequate solvent, such as $Et_2O$, MTBE or EtOAc, and then washed with water and brine. The aqueous layers were extracted once. The organic layers were combined, dried ($MgSO_4$ or $Na_2SO_4$) and the solvents were evaporated under reduced pressure. Purification by flash chromatography or precipitation gave the expected oxadiazole derivative.

Procedure 4: Oxadiazole Ring Formation

DIEA (2.0 to 2.2 eq) and HATU (1.0 to 1.1 eq) were added into a solution of the carboxylic acid derivative (1 eq) in anhydrous DMF (4 mL/mmol of carboxylic acid derivative) cooled at 0° C. The resulting mixture was stirred at 0° C. for a period of 5 to 30 minutes. Then the amidoxime derivative (1.0 to 1.2 eq) was added neat or as a DMF solution. The resulting mixture was stirred at 0° C. or RT for a period of 30 minutes to 18 hours. The reaction mixture was diluted with an adequate solvent, such as $Et_2O$, MTBE or EtOAc, and then washed with water and brine. The aqueous layers were extracted once. The organic layers were combined, dried ($MgSO_4$ or $Na_2SO_4$) and the solvents were removed under reduced pressure. The residue was taken up with ACN (8.5 mL/mmol of carboxylic acid derivative). The resulting mixture was heated at 150° C. for 30 min under MW irradiation. The reaction mixture was diluted with an adequate solvent, such as $Et_2O$, MTBE or EtOAc, and then washed with water and brine. The aqueous layers were extracted once. The organic layers were combined, dried ($MgSO_4$ or $Na_2SO_4$) and the solvents were evaporated under reduced pressure. Purification by flash chromatography or precipitation gave the expected oxadiazole derivative.

Procedure 5: Oxadiazole Ring Formation

To a suspension of carboxylic acid derivative (1 eq) in dry toluene (3.5 mL/mmol of carboxylic acid) at RT under $N_2$ was added oxalyl chloride (1.5 eq) and DMF (0.02 eq). The reaction mixture was stirred at RT for 2 hours and then concentrated under vacuum. The resulting acid chloride was then dissolved in dry toluene (2.5 mL/mmol of carboxylic acid) and added dropwise at RT under $N_2$ to a solution of amidoxime derivative (1 eq) in pyridine (1.3 mL/mmol of amidoxime) and toluene (1.3 mL/mmol of amidoxime). The reaction mixture was stirred at RT for 1 hour and then refluxed overnight. The reaction mixture was cooled to RT and concentrated under vacuum. The resulting oil was taken in EtOAc, washed with water, saturated solution of $NaHCO_3$ (twice), saturated solution of NaCl, then dried over $MgSO_4$, filtered and concentrated under vacuum. Purification by flash chromatography or precipitation gave the expected oxadiazole derivative.

Procedure 6: Oxadiazole Ring Formation

NMM (3 to 5 eq) and isobutyl chloroformate (1.0 to 1.1 eq) were added into a solution of the carboxylic acid derivative (1.0 eq) in a suitable solvent, such as dioxane or isopropyl acetate and stirred at a temperature comprised between 0° C. and RT for 10 minutes to a few hours. Then the amidoxime derivative (1.0 to 1.2 eq) was added in one portion and the reaction mixture was stirred at a temperature comprised between 0° C. and RT for 20 min to a few hours, and then heated at a temperature comprised between 80° C. to reflux for a period of 12 to 24 hours. The reaction mixture was diluted with an adequate solvent, such as $Et_2O$, MTBE or EtOAc, and then washed with water and brine. The aqueous layers were extracted once. The organic layers were combined, dried ($MgSO_4$ or $Na_2SO_4$) and the solvents were evaporated under reduced pressure. Purification by flash chromatography or precipitation gave the expected oxadiazole derivative.

Procedure 7: Oxadiazole Ring Formation

In a microwave vessel was added carboxylic acid derivative (1 eq), amidoxime derivative (1.1 eq), 1-ethyl-3-(3-dimethylaminopropyl)carbodiimide hydrochloride (1.1 eq), THF (2.7 mL/mmol of carboxylic acid) and CH₃CN (2.7 mL/mmol of carboxylic acid). The reaction mixture was stirred at RT for 2 hours and was then heated at 150° C. for 30 minutes under microwave irradiation. The reaction mixture was passed through SPE NH₂ and SPE SCX rinsed with ACN and the solvents were evaporated. Purification by flash chromatography or precipitation gave the expected oxadiazole derivative.

Procedure 8: Tert-Butyl Ester Hydrolysis

To tert-butyl ester derivative (1 eq) was added hydrochloric acid in dioxane (4N, 20-50 eq) and the reaction mixture was stirred at RT for 1 hour to 24 hours. The solution was then evaporated to dryness and the residue was purified by precipitation from a solvent such as CH₃CN, DCM, MTBE or Et₂O to afford the title compound.

Procedure 9: Methyl or Ethyl Ester Hydrolysis

To the methyl or ethyl ester derivative (1 eq) in a solution of MeOH or EtOH (5 mL/mmol of ester derivative) or MeOH/THF 1:1 or EtOH/THF 1:1 (5 mL/mmol of ester derivative) was added sodium hydroxide (5M, 5 eq) and the reaction mixture was stirred at RT for 1 hour to 24 hours. The solution was evaporated to dryness. The residue was taken up with EtOAc and washed with a 1N aqueous solution of HCl and brine. The organic layer was dried (MgSO₄) and concentrated under vacuum to afford the title compound.

Procedure 10: Substitution of Benzyl Bromides with Primary and Secondary Amines

To a solution of bromobenzyl derivative (1 eq) in CH₃CN or DMF (1.5-3 mL/mmol of bromobenzyl derivative) was added K₂CO₃ or NaHCO₃ (2-3 eq) and a primary or secondary amine (1.2 eq). The reaction mixture was stirred at RT or at 60° C. overnight. Solvent was removed under vacuum and the resulting mixture was diluted with water, extracted with EtOAc, washed with a saturated solution of NaCl, dried over MgSO₄ and concentrated under vacuum. Purification by flash chromatography or recristallization afforded the expected benzyl amine derivative.

Procedure 11: Suzuki Cross-Coupling Reaction

A mixture of the aryl bromide (1 eq), the boronic acid or ester derivative (1.2 to 2.0 eq), cesium fluoride (3 eq) and bis(triphenylphosphine)palladium(II) chloride (0.01 to 0.05 eq) was prepared in dioxane (10 mL/g of aryl bromide) and water (4 mL/g of aryl bromide) under nitrogen atmosphere. The resulting mixture was heated at a temperature comprised between 80° C. to reflux for 1 to 15 hours. The reaction mixture was diluted with MTBE (40 mL/g of aryl bromide) and the aqueous layer was removed. The organic layer was dried (MgSO₄ or Na₂SO₄) and concentrated under vacuum. The residue was purified by flash chromatography.

Procedure 12: Aromatic Cyanation

A mixture of aryl halide (leg), sodium cyanide (1.5 eq) and tetrabutylammonium bromide (1.5 eq) was dissolved in DMA (2 mL/mmol of aryl halide) and heated at 120° C. for 1 to 3 hours under microwave irradiation. The resulting mixture was diluted with EtOAc, washed with a saturated solution of NaCl, dried over MgSO₄ and concentrated under vacuum. Purification by flash chromatography or recristallization afforded the expected aryl cyanide derivative.

Procedure 13: Benzylic Bromation

To a solution of toluoyl derivative (1 eq) in CH₃CN (1.5 mL/mmol of toluoyl derivative) was added N-bromosuccinimide (1.2 eq) and 2,2'-azobis(2-methylpropionitrile) (0.02 eq). The reaction mixture was heated at 70° C. for 1 to 48 hours. The reaction mixture was then cooled to RT and water was added and the mixture was concentrated under vacuum. The residue was taken up in DCM and washed with a 10% aqueous solution of NaHCO₃ and brine, dried over MgSO₄ and concentrated under vacuum. Purification by flash chromatography or recristallization afforded the expected benzyl bromide derivative.

Procedure 14: Amide Formation

To a solution of the carboxylic acid derivative (1 eq) in DCM (40 mL/mmol) was added oxalyl chloride (3 eq) and DMF (0.04 eq) in DCM (10 mL) and the resulting mixture was stirred at RT for 1 hour. The solution was evaporated to dryness, the residue taken up in THF (10 mL/mmol) and then added to a mixture of the amine derivative (1 eq) and DIEA (4 eq) in THF (8 mL/mmol). The reaction mixture was stirred at RT for 2 to 24 hours, filtered through a SPE NH₂ column and rinsed with ACN. After evaporation of the solvents, the crude product was purified by flash chromatography affording the title compound.

Procedure 15: Suzuki Cross-Coupling Reaction

A mixture of the aryl bromide (1 eq), the boronic acid or ester derivative (1.2 to 2.0 eq), cesium fluoride (3 eq), palladium acetate (0.05 to 0.2 eq) and 2-dicyclohexylphosphino-2',6'-dimethoxybiphenyl (0.1 to 0.4 eq) was prepared in dioxane (10 mL/g of aryl bromide) and water (5 mL/g of aryl bromide) under nitrogen atmosphere. The resulting mixture was heated at a temperature comprised between 80° C. to reflux for 1 to 15 hours. The reaction mixture was diluted with MTBE (40 mL/g of aryl bromide) and the aqueous layer was removed. The organic layer was dried (MgSO₄ or Na₂SO₄) and concentrated under vacuum. The residue was purified by flash chromatography.

Intermediate 1: 3'-fluoro-2-(methoxymethyl)-2'-methylbiphenyl-4-carboxylic acid

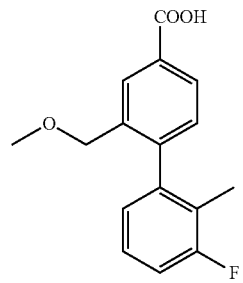 [SMILES: COCc1cc(C(=O)O)ccc1-c1cccc(F)c1C]

Step 1: Methyl 4-bromo-3-(bromomethyl)benzoate

Under N₂, to a solution of methyl 4-bromo-3-methylbenzoate (Aldrich 532878, 50.0 g, 218.3 mmol) in CHCl₃ (1 L) were added NBS (46.6 g, 261.9 mmol) in one portion and α,α'-azoisobutyronitrile (0.72 g, 4.37 mmol). The mixture was stirred at 70° C. for 2 days. The reaction mixture was cooled to RT and water (500 mL) was added. The organic layer was washed with a saturated aqueous solution of NaHCO₃ (500 mL), water (340 mL), then brine (500 mL), dried over MgSO₄ and concentrated affording the title compound as a yellow solid. It was washed with pentane (2×500 mL) affording the title compound as a yellow solid. ¹H NMR (DMSO-d₆, 300 MHz) δ 8.24 (d, J=1.91 Hz, 1H), 7.88-7.82 (m, 2H), 4.87 (s, 2H), 3.91 (s, 3H). HPLC (Method A) Rt 4.44 min (Purity: 97.9%).

Step 2: Methyl 4-bromo-3-(methoxymethyl)benzoate

A solution of methyl 4-bromo-3-(bromomethyl)benzoate (37.5 g, 121.8 mmol) in MeOH (1 125 mL) was refluxed for 4 days. After concentration, the mixture was partitioned between EtOAc (500 mL) and water (200 mL). The organic layer was washed with a 5% aqueous solution of NaHCO₃ (200 mL), brine (200 mL), dried over MgSO₄ and concentrated affording the title compound as a beige solid (29.8 g, 94%). ¹H NMR (DMSO-d₆, 300 MHz) δ 8.06-8.05 (m, 1H), 7.83 (d, J=1.23 Hz, 2H), 4.54 (m, 2H), 3.90 (s, 3H), 3.45 (s, 3H). LC/MS (Method B): 227.2 (M−H)⁻. HPLC (Method A) Rt 4.42 min (Purity: 93.0%).

Step 3: methyl 3'-fluoro-2-(methoxymethyl)-2'-methylbiphenyl-4-carboxylate

A mixture of methyl 4-bromo-3-(methoxymethyl)benzoate (Intermediate 1, Step 2, 5.00 g, 19.3 mmol), 3-fluoro-2-methylphenylboronic acid (4.46 g, 29.0 mmol), bis(triphenylphosphine)palladium(II) chloride (271 mg, 0.39 mmol) and cesium fluoride (8.79 g, 57.9 mmol) was prepared in dioxane (50 mL) and water (20 mL) under nitrogen atmosphere. The reaction mixture was heated at 100° C. for 1 hour. The reaction mixture was cooled at RT, diluted with MTBE (250 mL) and the layers were separated. The organic layer was washed with water (100 mL) and brine (100 mL). The aqueous layers were extracted with MTBE (150 mL). The organic layers were combined, dried over MgSO₄ and concentrated under reduced pressure. After purification by flash chromatography (silica, EtOAc/n-hexane), the title compound was obtained as a colorless oil (4.85 g, 87%). HPLC (Method A), Rt 5.0 min (purity: 99.5%). LC/MS (Method B): 289.0 (M+H)⁺.

Step 4: 3'-fluoro-2-(methoxymethyl)-2'-methylbiphenyl-4-carboxylic acid

A 5 N aqueous solution of NaOH (5.0 mL, 25 mmol) was added into a solution of methyl 3'-fluoro-2-(methoxymethyl)-2'-methylbiphenyl-4-carboxylate (4.85 g, 16.8 mmol) in EtOH (50 mL). The reaction mixture was heated at 60° C. for 1 hour, and then was concentrated under reduced pressure. The residue was taken up with MTBE (100 mL), water (50 mL) and a 5N aqueous solution of HCl (6 mL). The layers were separated and the organic layer was washed with water (50 mL) and brine (50 mL). The aqueous layers were extracted with MTBE (50 mL). The organic layers were combined, dried over MgSO₄ and concentrated under reduced pressure. After purification by crystallization from a mixture of MTBE and pentane, the title compound was obtained as a white powder (3.85 g, 83%). HPLC (Method A), Rt 4.2 min (purity: 99.8%). LC/MS (Method B) 273.0. (M−H)⁻.

Intermediate 2: 3-(methoxymethyl)-4-(2-methylpiperidin-1-yl)benzoic acid

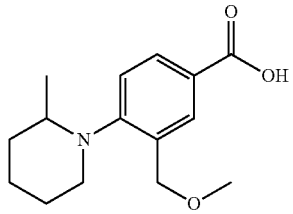 [SMILES: COCc1cc(C(=O)O)ccc1N1CCCCC1C]

Step 1: 5-bromo-2-(2-methylpiperidin-1-yl)benzaldehyde

2-Methylpiperidine (15.4 mL, 130.0 mmol) and anhydrous sodium carbonate (13.8 g, 130.0 mmol) were added into a solution of 5-bromo-2-fluorobenzaldehyde (13.2 g, 65.0 mmol) in DMSO (160 mL) and water (40 mL). The resulting mixture was heated at 120° C. for 16 hours. The reaction mixture was diluted with water (1 L) and extracted with Et₂O (2×750 mL). The organic layers were washed with brine (500 mL, pH 5-6 adjusted with a 5N aqueous solution of HCl), combined and dried (MgSO₄). The solvents were removed under reduced pressure to give the title compound as a brown yellow oil (16.3 g, 89%) used without further purification in the next step. HPLC (Method A), Rt 2.20 min (purity: 93.7%). HPLC/MS, M+(ESI): 282.1, 284.1. ¹H NMR (CDCl₃, 300 MHz) δ 10.40 (s, 1H), 7.93 (d, J=2.5 Hz, 1H), 7.62 (dd, J=8.6, 2.5 Hz, 1H), 7.12 (d, J=8.6 Hz, 1H), 3.17 (m, 1H), 3.06 (m, 1H), 2.81 (ddd, J=11.7, 7.6, 3.9 Hz, 1H), 1.89 (m, 1H), 1.83-1.65 (m, 3H), 1.58-1.42 (m, 2H), 0.91 (d, J=6.3 Hz, 3H).

Step 2: [5-bromo-2-(2-methylpiperidin-1-yl)phenyl]methanol

Sodium borohydride (2.2 g, 57.8 mmol) was added portion-wise into a solution of 5-bromo-2-(2-methylpiperidin-1-yl)benzaldehyde (16.3 g, 57.8 mmol) in MeOH (300 mL) cooled at 5° C. After 30 min, the reaction mixture was diluted with a saturated aqueous solution of NH₄Cl (300 mL) and extracted with EtOAc (600 mL+300 mL). The organic layers were washed with a saturated aqueous solution of NH₄Cl (150 mL) and brine (300 mL). The organic layers were combined, dried (MgSO₄) and the solvents were removed under reduced pressure to give the title compound as a yellow oil (15.9 g, 97%) used without further purification in the next step. HPLC (Method A), Rt 2.1 min (Purity: 94.9%). HPLC/MS, M+(ESI): 284.1, 286.0. ¹H NMR (CDCl₃, 300 MHz) δ 7.38 (dd, J=8.5, 2.4 Hz, 1H), 7.26 (d, J=2.4 Hz, 1H), 7.13 (d, J=8.5 Hz, 1H), 6.40 (brs, 1H), 4.86 (d, J=13.9 Hz, 1H), 4.67 (d, J=13.9 Hz, 1H), 3.06-2.88 (m, 2H), 2.61 (td, J=11.4, 3.2 Hz, 1H), 1.88-1.58 (m, 4H), 1.53-1.32 (m, 2H), 0.90 (d, J=6.2 Hz, 3H).

Step 3: 1-[4-bromo-2-(methoxymethyl)phenyl]-2-methylpiperidine

Methanesulfonyl chloride (4.0 mL, 51.6 mmol) was added into a solution of [5-bromo-2-(2-methylpiperidin-1-yl)phenyl]methanol (13.43 g, 47.3 mmol) and DIEA (17.7 mL, 104 mmol) in anhydrous DCM (130 mL) cooled at 0° C. After 1 hour, the reaction mixture was diluted with MeOH (150 mL)

and heated at 50° C. for 3 hours. The solvents were removed under reduced pressure to give a brown oil. The residue was taken up with Et$_2$O (450 mL), and then washed with water (150 mL, pH 8 adjusted with a 5N aqueous solution of NaOH), saturated aqueous solution of NH$_4$Cl (2×150 mL) and brine (150 mL). The aqueous layers were extracted with Et$_2$O (150 mL). The combined organic layers were dried (MgSO$_4$) and the solvent was removed under reduced pressure to give the title compound as a brown yellow oil (13.0 g, 92%) used without further purification in the next step. HPLC (Method A), Rt 2.9 min (Purity: 97.1%). HPLC/MS, M+(ESI): 298.1, 300.1. $^1$H NMR (CDCl$_3$, 300 MHz) δ 7.59 (d, J=2.5 Hz, 1H), 7.36 (dd, J=8.5, 2.5 Hz, 1H), 7.03 (d, J=8.5 Hz, 1H), 4.60 (d, J=12.8 Hz, 1H), 4.52 (d, J=12.8 Hz, 1H), 3.44 (s, 3H), 2.96-2.81 (m, 2H), 2.51 (m, 1H), 1.77 (m, 2H), 1.64 (m, 2H), 1.50-1.30 (m, 2H), 0.79 (d, J=6.1 Hz, 3H).

Step 4: 3-(methoxymethyl)-4-(2-methylpiperidin-1-yl)benzoic acid

A 1.5M solution of tert-butyllithium in pentane (64 mL, 95 mmol) was added into anhydrous Et$_2$O (130 mL) cooled at −78° C. A solution of 1-[4-bromo-2-(methoxymethyl)phenyl]-2-methylpiperidine (13.0 g, 43.5 mmol) in anhydrous Et$_2$O (20 mL) was added slowly. After 40 minutes, the reaction mixture was poured on an excess of freshly crushed dry ice and stirred for 30 min. The mixture was diluted with Et$_2$O/EtOAc (1:1, 800 mL) and washed with water (200 mL, pH=4-5 adjusted with a 5N aqueous solution of HCl). The aqueous layer was extracted with EtOAc (400 mL). The organic layers were combined, dried (MgSO$_4$) and the solvents were removed under reduced pressure to give a yellow oil, which was triturated in iPr$_2$O (~20 mL) and pentane (~20 mL). The precipitate was filtered off, washed with pentane and dried under reduced pressure to give the title compound as a beige powder. HPLC (Method A), Rt: 1.6 min (purity: 93.5%). HPLC/MS, M+(ESI): 264.2, M−(ESI): 262.2. $^1$H NMR (CDCl$_3$, 300 MHz) δ 8.22 (d, J=2.1 Hz, 1H), 8.00 (dd, J=8.3, 2.1 Hz, 1H), 7.17 (d, J=8.3 Hz, 1H), 4.60 (d, J=12.3 Hz, 1H), 4.55 (d, J=12.3 Hz, 1H), 3.46 (s, 3H), 3.17 (m, 1H), 3.02 (m, 1H), 2.63 (m, 1H), 1.88-1.65 (m, 4H), 1.55-1.40 (m, 2H), 0.88 (d, J=6.2 Hz, 3H).

Intermediate 3: 2-(methoxymethyl)-2'-methyl biphenyl-4-carboxylic acid

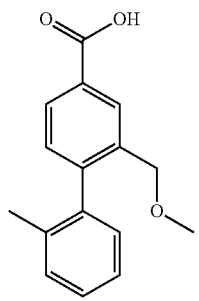

Step 1: Methyl 2-(methoxymethyl)-2'-methylbiphenyl-4-carboxylat:e

Methyl 4-bromo-3-(methoxymethyl)benzoate (Intermediate 1 Step 2, 40.0 g, 154.4 mmol), o-tolylboronic acid (23.1 g, 169.8 mmol), K$_2$CO$_3$ (106.7 g, 772 mmol), tetrakis(triphenylphosphine)palladium(0) (1.78 g, 1.54 mmol) were taken up in toluene (200 mL) and water (200 mL) under N$_2$ atmosphere. The reaction mixture was refluxed for 1 hour. The reaction mixture was cooled to RT, filtered over a pad of Celite and washed with EtOAc (1 L). The filtrate was concentrated to afford a yellow oil which was taken in EtOAc (800 mL). The organic layer was washed with a saturated aqueous solution of NaHCO$_3$ solution (250 mL), water (250 mL) and brine (250 mL), dried over MgSO$_4$ and concentrated affording the title compound as a yellow oil used without further purification (41.9 g, quantitative). HPLC (Method A) Rt 5.34 min (Purity: 89.4%).

Step 2: 2-(methoxymethyl)-2'-methylbiphenyl-4-carboxylic acid

A solution of methyl 2-(methoxymethyl)-2'-methylbiphenyl-4-carboxylate (40.0 g, 148.0 mmol) in EtOH (1.2 L) at RT was treated with a 5N aqueous solution of NaOH (90 mL, 450 mmol). The reaction mixture was stirred at 60° C. for 1 hour. The reaction mixture was cooled to RT and concentrated to give a yellow solid which was taken up in water (800 mL) and the aqueous phase was washed twice with EtOAc. The aqueous phase was acidified with a concentrated aqueous solution of HCl (40 mL, pH~2) and it was extracted with EtOAc (2×400 mL). The combined organics were washed with brine, dried over MgSO$_4$ and concentrated affording the title compound as a yellow solid (35.1 g, 92%). $^1$H NMR (DMSO-d$_6$, 300 MHz) δ 12.99 (br s, 1H), 8.09 (s, 1H), 7.91 (m, 1H), 7.33-7.22 (m, 4H), 7.09 (m, 1H), 4.11 (m, 2H), 3.18 (s, 3H), 1.99 (s, 3H). LC/MS (Method B): 255.2 (M−H)$^−$. HPLC (Method A) Rt 4.52 min (Purity: 96.4%).

Intermediate 4: 4-(2-Methylpiperidin-1-yl)-3-(trifluoromethyl)benzoic acid

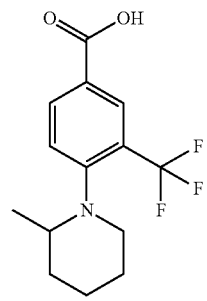 [SMILES: CC1CCCCN1c1ccc(C(=O)O)cc1C(F)(F)F]

Step 1: 4-(2-methylpiperidin-1-yl)-3-(trifluoromethyl)benzonitrile

A mixture of 4-fluoro-3-trifluoro-methylbenzonitrile (5 g, 26.4 mmol) and 2-methylpiperidine (6.25 mL, 52.9 mmol) was heated at 100° C. under N$_2$ for 12 hours. The reaction mixture was diluted with water (100 mL) and was extracted with EtOAc (2×100 mL). The organic layer was washed with water (2×100 mL) and brine solution (100 mL). The solvent was dried over sodium sulphate and concentrated. The residue was purified by flash chromatography using silica-gel (60-120 mesh) and pet-ether/EtOAc as eluent to afford the title compound as an off-white solid. $^1$H NMR (CDCl$_3$, 400 MHz) δ 7.87 (s, 1H), 7.73 (d, 1H), 7.50 (br s, 1H), 2.95-3.03

(m, 2H), 2.52 (m, 1H), 1.71-1.77 (m, 3H), 1.59 (m, 1H), 1.38 (m, 2H), 0.76 (d, 3H). HPLC (Method C)Rt 5.09 min (Purity: 98.8%).

Step 2: Methyl 4-(2-methylpiperidin-1-yl)-3-(trifluoromethyl)benzoate

A mixture of 4-(2-methylpiperidin-1-yl)-3-(trifluoromethyl)benzonitrile (7.4 g, 27.6 mmol) and HCl in methanol (250 mL) was heated at 75° C. for 48 hours. The reaction mixture evaporated to dryness and the residue was partitioned between EtOAc (200 mL) and a 10% aqueous solution of NaHCO$_3$ (100 mL). The organic layer was washed with water, brine and concentrated under vacuum to afford the title compound as yellow oil. It was used in the next step without further purification. $^1$H NMR (CDCl$_3$, 400 MHz) δ 8.38 (s, 1H), 8.21-8.25 (d, 1H), 7.45-7.47 (d, 1H), 3.94 (s, 3H), 2.99-3.04 (m, 3H), 2.50 (t, 1H), 1.78-1.81 (m, 3H), 1.72-1.77 (m, 3H), 1.42-1.45 (m, 3H).

Step 3: 4-(2-Methylpiperidin-1-yl)-3-(trifluoromethyl)benzoic acid

To a stirred solution of methyl 4-(2-methylpiperidin-1-yl)-3-(trifluoromethyl)benzoate (6.6 g, 21.9 mmol) in THF (50 mL) and water (5 mL) was added lithium hydroxide (1.84 g, 43.8 mmol). The resulting mixture was stirred at RT for 12 hours. Solvents were removed under vacuum and the resulting mass was diluted with water. The aqueous layer was washed with DCM (2×50 mL), and then acidified with a concentrated aqueous solution of HCl (pH=4). It was extracted with EtOAc (2×100 mL). The EtOAc layer was washed with brine and dried over sodium sulfate, affording the title compound as a white solid. $^1$H NMR (DMSO-d$_6$, 400 MHz) δ 13.30 (bs, 1H), 8.17 (m, 2H), 7.69 (d, 1H), 3.08 (m, 1H), 2.88 (m, 1H), 2.50 (m, 1H), 1.90 (m, 2H), 1.75 (m, 2H), 1.45 (m, 1H), 1.41 (m, 1H), 0.77 (d, 3H). LC/MS (Method A): 288.1 (M+H)$^+$. HPLC (Method B) Rt 3.71 min (Purity: 98.3%).

Intermediate 6: ethyl N-{4-[amino(hydroxyimino)methyl]-2-fluorobenzoyl}-beta-alaninate

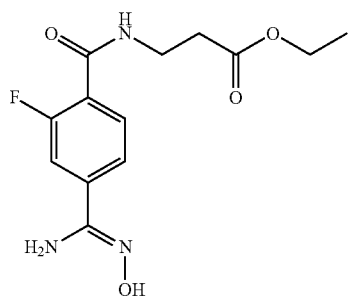 [SMILES: CCOC(=O)CCNC(=O)c1ccc(/C(N)=N/O)cc1F]

Step 1: ethyl N-(4-cyano-2-fluorobenzoyl)-beta-alaninate

4-Cyano-2-fluorobenzoic acid (ABCR, 1.65 g, 10 mmol) was dissolved in DCM (40 mL). DMF (8 μl) was added at RT followed by oxalyl chloride (0.98 mL, 11.6 mmol). Once the gas evolution has ceased, the reaction mixture was evaporated to dryness. The residue was then dissolved in DCM (10 mL) and beta-alanine ethyl ester hydrochloride (1.54 g, 10 mmol) was added followed by dropwise addition of N-ethyldiisopropylamine (3.40 mL, 20 mmol) over 10 minutes. The reaction mixture was then washed with water and a saturated aqueous solution of NaHCO$_3$, dried with MgSO$_4$ and evaporated in vaccuo affording the title compound (2.27 g, 86%) as a white powder. $^1$H NMR (DMSO-d$_6$, 300 MHz) δ 8.67 (t, J=5.0 Hz, 1H), 7.97 (dd, J=10.0, 1.3 Hz, 1H), 7.79 (dd, J=7.9, 1.4 Hz, 1H), 7.71 (m, 1H), 4.08 (q, J=7.2 Hz, 2H), 3.49 (m, 2H), 2.57 (t, J=6.9 Hz, 2H), 1.19 (t, J=7.2 Hz, 3H). LC/MS (Method B): 263.2 (M−H)$^−$. HPLC (Method A) Rt 2.68 min (Purity: 98.5%).

Step 2: ethyl N-{4-[amino(hydroxyimino)methyl]-2-fluorobenzoyl}-beta-alaninate The title compound was prepared following the general procedure 2 starting from ethyl N-(4-cyano-2-fluorobenzoyl)-beta-alaninate (2.0 g, 7.4 mmol). It was obtained as a white solid (2.1 g, 95%). $^1$H NMR (DMSO-d$_6$, 300 MHz) δ 9.93 (s, 1H), 8.39 (m, 1H), 7.60 (m, 2H), 7.53 (d, J=12.4 Hz, 1H), 5.97 (s, 2H), 4.08 (q, J=7.2 Hz, 2H), 3.48 (m, 2H), 2.57 (t, J=6.9 Hz, 2H), 1.19 (t, J=7.2 Hz, 3H). LC/MS (Method B): 296.2 (M−H)$^−$, 298.2 (M+H)$^+$.

Intermediate 7: 2'-Ethyl-2-(methoxymethyl)-1,1'-biphenyl-4-carboxylic acid

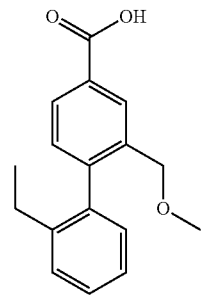 [SMILES: CCc1ccccc1-c1ccc(C(=O)O)cc1COC]

Step 1: Methyl 2'-ethyl-2-(methoxymethyl)-1,1'-biphenyl-4-carboxylate

To a solution of methyl 4-bromo-3-(methoxymethyl)benzoate (Intermediate 1 Step 2, 12.0 g, 46.3 mmol) in toluene (150 mL) and water (35 mL) under N$_2$, was added 2-ethylbenzene boronic acid (9.02 g, 60.1 mmol) followed by potassium carbonate (19 g, 139 mmol) and Pd(PPh$_3$)$_4$ (2.67 g, 2.31 mmol). The reaction mixture was degassed with N$_2$ and heated at 100° C. for 12 hours. The reaction mixture was diluted with EtOAc. The organic layer was washed with a saturated aqueous solution of sodium bicarbonate (100 mL), water (2×100 mL) and brine (100 mL). It was then dried over sodium sulphate and concentrated under reduced pressure. The residue was purified by chromatography (silica gel, pet ether/EtOAc) to afford the title compound as a pale yellow liquid (12.0 g, 83%). $^1$H NMR (CDCl$_3$, 400 MHz) δ 8.25 (1H, s), 8.00 (1H, d), 7.35 (2H, m), 7.25 (2H, m), 7.08 (1H, d), 4.12-4.21 (2H, m), 3.94 (3H, s), 3.29 (3H, s), 2.28-2.43 (2H, m), 1.03 (3H, t).

Step 2: 2'-Ethyl-2-(methoxymethyl)-1,1'-biphenyl-4-carboxylic acid

To a solution of methyl 2'-ethyl-2-(methoxymethyl)-1,1'-biphenyl-4-carboxylate (12.0 g, 42.2 mmol) in THF (150 mL)

and water (30 mL), was added lithium hydroxide monohydrate (5.31 g, 126.6 mmol) in portions. After 12 hours at RT, the reaction mixture was concentrated and the aqueous phase was acidified with a concentrated aqueous solution of HCl and extracted with EtOAc. The organic layers were washed with water and brine. The solvents were dried over sodium sulphate and concentrated under reduced pressure to afford the title compound as a white solid (9.0 g, 80%). $^1$H NMR (DMSO-$d_6$, 300 MHz) δ 12.9 (1H, bs), 8.08 (1H, s), 7.89 (1H, m), 7.35 (2H, m), 7.23 (2H, m), 7.04 (1H, m), 4.04-4.13 (2H, m), 3.17 (3H, s), 2.29-2.38 (1H, m), 2.22 (1H, m), 0.94 (3H, m). LC/MS (Method A): 269.0 (M−H)$^−$. HPLC (Method B) Rt 5.06 min (Purity: 97.4%).

Intermediate 8: 2-[(dimethylamino)methyl]-2'-methylbiphenyl-4-carboxylic acid

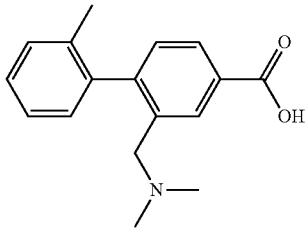 [SMILES: Cc1ccccc1-c1ccc(C(=O)O)cc1CN(C)C]

Step 1: Methyl 3-[(acetyloxy)methyl]-4-bromobenzoate

To a solution of methyl 4-bromo-3-(bromomethyl)benzoate (Intermediate 1 Step 1, 6.5 g, 21 mmol) in AcOH (32.5 mL) was added sodium acetate (3.46 g, 42 mmol) and the reaction mixture was stirred at 100° C. for 15 hours. After concentration in vacuo, the residue was partitioned between EtOAc and water. The organic layer was washed with a 5% aqueous solution of NaHCO$_3$ and brine, dried over MgSO$_4$ and concentrated in vacuo. Purification by chromatography (silica, chex/EtOAc) afforded the title compound as a white solid (4.78 g, 79%). $^1$H NMR (DMSO-$d_6$) δ 8.03 (m, 1H), 7.85 (m, 2H), 5.18 (s, 2H), 3.87 (s, 3H), 2.11 (s, 3H). HPLC (Method A) Rt 4.37 min (purity 98.1%).

Step 2: 2-(hydroxymethyl)-2'-methylbiphenyl-4-carboxylic acid

A mixture of methyl 3-[(acetyloxy)methyl]-4-bromobenzoate (4.7 g, 16.4 mmol), o-tolylboronic acid (2.45 g, 18 mmol), potassium carbonate (11.3 g, 82 mmol) and Pd(PPh$_3$)$_4$ (1.89 g, 1.64 mmol) in toluene (23.5 mL) and water (23.5 mL) was refluxed for 2 hours. After cooling to RT, the reaction mixture was filtered through a pad of Celite which was further washed with toluene (50 mL). The filtrate was concentrated in vacuo. The residue taken up in EtOAc (250 mL) and washed with a saturated aqueous solution of NaHCO$_3$, water and brine, dried over magnesium sulphate and concentrated under vacuum. The residue was taken up with EtOH (180 mL) and treated with a 5N aqueous solution of NaOH (12 mL, 60 mmol) at 60° C. for 1.5 hours. The reaction mixture was concentrated under vacuum. The residue was taken up in water (500 mL) and the aqueous layer was washed twice with EtOAc (2×200 mL). The aqueous layer was acidified with a concentrated aqueous solution of HCl until pH 2 and extracted with EtOAc (2×100 mL). The combined organic layer were dried (MgSO$_4$) and concentrated under vacuum to afford the title compound as a yellow solid (3.46 g, 87%). HPLC (Method A) Rt 3.77 min (purity 96.1%).

Step 3: methyl 2-(hydroxymethyl)-2'-methylbiphenyl-4-carboxylate (Trimethylsilyl)diazomethane (21 mL, 12.4 mmol) was added dropwise into a solution of 2-(hydroxymethyl)-2'-methylbiphenyl-4-carboxylic acid (2.0 g, 8.3 mmol) in MeOH (20 mL) and toluene (20 mL) at 0° C. After 10 minutes at 0° C., the resulting mixture was stirred at RT for 2 hours. The reaction mixture was concentrated under vacuum to give the title compound (2.1 g, quantitative), used without further purification in the next step. HPLC (Method A) Rt 3.95 min (purity 95.5%). $^1$H NMR (CDCl$_3$, 300 MHz) δ 8.23 (d, J=1.3 Hz, 1H), 7.98 (dd, J=7.8, 1.9 Hz, 1H), 7.28-7.18 (m, 4H), 7.08 (d, J=7.3 Hz, 1H), 4.42 (d, J=5.7 Hz, 2H), 3.92 (s, 3H), 2.01 (s, 3H), 1.61 (t, J=5.7 Hz, 1H).

Step 4: methyl 2-[(dimethylamino)methyl]-2'-methylbiphenyl-4-carboxylate

To a solution of methyl 2-(hydroxymethyl)-2'-methylbiphenyl-4-carboxylate (2.12 g, 8.27 mmol) in DCM (65 mL) was added DIEA (7.03 mL, 41.4 mmol) and methanesulfonyl chloride (768 µL, 9.93 mmol) at 0° C. and stirred for 25 min. After this time, a 2M solution of dimethylamine in THF (12.4 mL, 24.8 mmol) was added and the resulting mixture was stirred at RT for 16 hours. The reaction mixture was partitioned between DCM and a 5N aqueous solution of NaOH. The organic layer was dried (MgSO4) and concentrated under vacuum. A purification by chromatography (silica, DCM/MeOH) gave the title compound as a light yellow solid (2.03 g, 86%). $^1$H NMR (DMSO-$d_6$) δ 8.27 (d, J=1.4 Hz, 1H), 7.95 (dd, J=7.8, 1.9 Hz, 1H), 7.32-7.18 (m, 4H), 7.06 (d, J=7.3 Hz, 1H), 3.94 (s, 3H), 3.24-3.10 (m, 2H), 2.11 (s, 6H), 2.01 (s, 3H). HPLC (Method A) Rt 2.90 min (Purity 100.0%). LC/MS (Method B): 284.1 (M−H)$^−$.

Step 5: 2-[(dimethylamino)methyl]-2'-methylbiphenyl-4-carboxylic acid

To a solution of methyl 2-[(dimethylamino)methyl]-2'-methylbiphenyl-4-carboxylate (687 mg, 2.42 mmol) in water (20 mL) at RT was treated with a 5N aqueous solution of HCl (12 mL, 60 mmol). The reaction mixture was refluxed for 4 hours, and then evaporated under vacuum. The residue was taken up in ACN and evaporated under vacuum to give the title compound as a light yellow powder (719 mg, 96%). $^1$H NMR (DMSO-$d_6$) δ 13.23 (br s, 1H), 10.31 (br s, 1H), 8.47 (s, 1H), 8.03 (d, J=7.2 Hz, 1H), 7.38-7.31 (m, 4H), 7.20 (d, J=7.2 Hz, 1H), 4.32 (d, J=13.2 Hz, 1H), 3.87 (d, J=13.2 Hz, 1H), 2.61 (s, 3H), 2.50 (s, 3H), 1.98 (s, 3H). HPLC (Method A) Rt 2.52 min (Purity 100.0%).

Intermediate 9: 4-(2-ethylpiperidin-1-yl)-3-(methoxymethyl)benzoic acid, hydrochloride salt

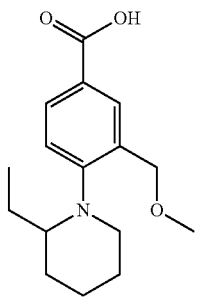 [SMILES: CCC1CCCCN1c1ccc(C(=O)O)cc1COC]

Step 1: 5-bromo-2-(2-ethylpiperidin-1-yl)benzaldehyde

To a solution of 5-bromo-2-fluorobenzaldehyde (20 g, 99 mmol) in DMSO (230 mL) and water (70 mL) were added 2-ethylpiperidine (14.4 mL, 108 mmol) and sodium carbonate (20.9 g, 197 mmol). The resulting mixture was heated at 110° C. for 30 hours. The reaction mixture was cooled at RT, diluted with water (1000 mL) and extracted with MTBE (2×500 mL). The organic layers were combined, dried (Na$_2$SO$_4$) and concentrated under reduced pressure. After purification by flash chromatography (silica, pet ether), the title compound was obtained as a yellow oil. $^1$H NMR (DMSO-d$_6$, 400 MHz) δ 10.15 (1H, s), 7.72 (2H, d), 7.24 (1H, m), 3.11 (2H, m), 2.85 (1H, m), 1.84 (1H, m), 1.34-1.67 (7H, m), 0.64 (3H, t).

Step 2: [5-bromo-2-(2-ethylpiperidin-1-yl)phenyl]methanol

To a solution of 5-bromo-2-(2-ethylpiperidin-1-yl)benzaldehyde (10 g, 48.4 mmol) in methanol (100 mL) under nitrogen was added sodium borohydride (1.28 g, 48.4 mmol) at 0° C. in portions. The reaction mixture was stirred at RT for 1 hour, then evaporated to remove methanol. The resulting crude was taken up with water (100 mL) and extracted with EtOAc. The organic layer was washed with water, then dried (Na$_2$SO$_4$) and concentrated under reduced pressure to afford the title compound as a yellow oil (8.8 g, 88%). $^1$H NMR (DMSO-d$_6$, 400 MHz) δ 7.55 (1H, s), 7.34-7.54 (1H, m), 7.08 (1H, d), 5.19 (1H, t), 4.62 (1H, d), 4.46 (1H, d), 2.77-2.84 (2H, m), 2.45 (1H, m), 1.74 (2H, t), 1.55 (2H, t), 1.33 (2H, m), 1.17 (2H, m), 0.62 (3H, t).

Step 3: 1-[4-bromo-2-(methoxymethyl)phenyl]-2-ethylpiperidine

To a solution of sodium hydride (2.3 g, 93 mmol) in anhydrous DMF (130 mL) was added a solution of [5-bromo-2-(2-ethylpiperidin-1-yl)phenyl]methanol (15 g, 48.3 mmol) in DMF (20 mL) drop wise at 0° C. After 30 minutes, methyl iodide was added drop wise at 0° C. The reaction mixture was quenched with a saturated aqueous solution of NH$_4$Cl (30 mL), then diluted with water (100 mL) and extracted with EtOAc. The organic layer was dried (Na$_2$SO$_4$) and concentrated under reduced pressure to afford the title compound as a yellow oil (15.2 g, 97%).

$^1$H NMR (CDCl$_3$, 400 MHz) δ 7.59 (1H, s), 7.35 (1H, d), 7.02 (1H, d), 4.49-4.59 (2H, m), 3.43 (3H, s), 2.88 (1H, d), 2.75 (1H, bs), 2.51 (1H, bs), 1.79-1.86 (2H, m), 1.62 (2H, m), 1.40 (2H, m), 0.88 (2H, m), 0.70 (3H, t).

Step 4: 4-(2-ethylpiperidin-1-yl)-3-(methoxymethyl)benzoic acid, hydrochloride salt To a solution of 1-[4-bromo-2-(methoxymethyl)phenyl]-2-ethylpiperidine (1.42 g, 4.55 mmol) in anhydrous THF was added n-butyl lithium (2.4 mL, 6.82 mmol) in drops at −78° C. After 1 hour at −78° C., the reaction mixture was poured onto crushed dry-ice (100 g). Once the excess carbon dioxide was escaped, the reaction mixture was acidified with a 2N aqueous solution of HCl. The precipitate was filtered off and dried to afford the title compound as a solid (1.0 g, 70%). HPLC (Method A), Rt: 2.5 min (purity: 97.7%). LC/MS (Method A): 278.0 (M+H)$^+$. $^1$H NMR (CD$_3$OD, 400 MHz) δ 8.20 (1H, d), 8.07 (1H, s), 7.92 (1H, d), 5.05 (2H, m), 3.89 (1H, bs), 3.69 (4H, m), 2.39 (1H, d), 2.02-2.14 (2H, m), 1.72-1.95 (3H, m), 1.46 (2H, m), 0.88 (3H, t).

Intermediate 10: 4-[(2R)-2-methylpiperidin-1-yl]-3-(trifluoromethyl)benzoic acid

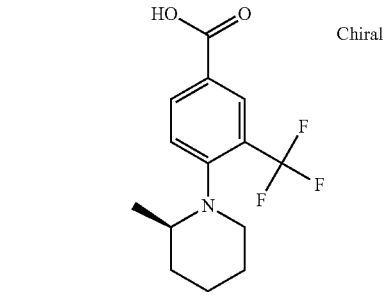 [SMILES: C[C@@H]1CCCCN1c1ccc(C(=O)O)cc1C(F)(F)F]

Step 1: 4-[(2R)-2-methylpiperidin-1-yl]-3-(trifluoromethyl)benzonitrile

A mixture of 4-fluoro-3-(trifluoromethyl)benzonitrile (1.0 g, 5.29 mmol) and (R)-(−)-2-methylpiperidine (3.1 mL, 26.4 mmol) was prepared in DMSO (10 mL) and heated at 100° C. under nitrogen for 12 hours. The reaction mixture was diluted with EtOAc, and then washed with water, a saturated aqueous solutions of NaHCO$_3$ and a saturated aqueous solution of NH$_4$Cl. The organic layer was dried (MgSO$_4$) and concentrated under vacuum to give the title compound as a yellow oil, which was used without further purification in the next step. HPLC (Method A) Rt 5.65 min (82.6%). LC/MS (Method B): 269.1 (M+H)$^+$.

Step 2: 4-[4(2R)-2-methylpiperidin-1-yl]-3-(trifluoromethyl)benzoic acid

Crude 4-[(2R)-2-methylpiperidin-1-yl]-3-(trifluoromethyl)benzonitrile (1.40 g, 5.22 mmol) was dissolved in MeOH (7 mL) and a 5N aqueous solution of NaOH (7 mL, 35 mmol). The resulting mixture was heated to 100° C. for 7 hours. The reaction mixture was acidified to pH 2 with a 5N aqueous solution of HCl. The resulting precipitate was filtered off and washed with water to give a pale brown solid. After recrystallization from a mixture of Et$_2$O and cHex, the title compound was obtained as a beige solid. ¹H NMR (DMSO-d₆) δ 13.29 (s, 1H), 8.23-8.12 (m, 2H), 7.68 (d, J=8.4 Hz, 1H), 3.07 (m, 1H), 2.94-2.81 (m, 1H), 2.61-2.45 (m, 2H), 1.75 (m, 1H), 1.67-1.18 (m, 4H), 0.71 (d, J=6.1 Hz, 3H). HPLC (Method A), Rt 4.80 min (Purity: 99.9%). LC/MS (Method B): 286.2 (M−H)⁻, 288.0 (M+H)⁺.

Intermediate 11: 4-[(2S)-2-methylpiperidin-1-yl]-3-(trifluoromethyl)benzoic acid

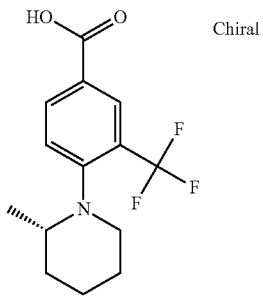 [SMILES: C[C@H]1CCCCN1c1ccc(C(=O)O)cc1C(F)(F)F]

Chiral

The title compound was prepared following the procedure described in Intermediate 10 Steps 1 and 2, but starting from (S)-(+)-2-methylpiperidine. It was isolated as a beige powder. ¹H NMR (DMSO-d₆) δ 13.29 (s, 1H), 8.23-8.12 (m, 2H), 7.68 (d, J=8.4 Hz, 1H), 3.07 (m, 1H), 2.94-2.81 (m, 1H), 2.61-2.45 (m, 2H), 1.75 (m, 1H), 1.67-1.18 (m, 4H), 0.71 (d, J=6.1 Hz, 3H). HPLC (Method A), Rt 4.79 min (Purity: 99.9%). LC/MS (Method B): 286.2 (M−H)⁻, 288.0 (M+H)⁺.

Intermediate 12: 2'-fluoro-2-(methoxymethyl)biphenyl-4-carboxylic acid

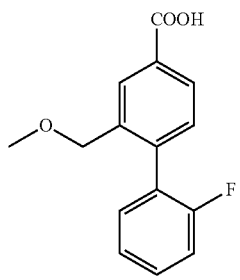 [SMILES: COCc1cc(C(=O)O)ccc1-c1ccccc1F]

Step 1: methyl 2'-fluoro-2-(methoxymethyl)biphenyl-4-carboxylate

To a solution of methyl 4-bromo-3-(methoxymethyl)benzoate (Intermediate 1 Step 2, 10 g, 38.6 mmol) in toluene (80 mL) and water (20 mL) under nitrogen was added 2-fluorophenylboronic acid (7.0 g, 50.2 mmol), followed by potassium carbonate (16 g, 115.8 mmol) and Pd(PPh₃)₄ (2.23 g, 1.9 mmol). After 3 hours at 100° C., the reaction mixture was diluted with EtOAc (200 mL) and washed with a saturated aqueous solution of NaHCO₃ (100 mL), water (2×100 mL) and brine. The organic layer was dried (Na₂SO₄) and concentrated under reduced pressure. The residue was purified by chromatography (silica, pet ether/EtOAc) to afford of the title compound as a pale yellow oil. ¹H NMR (CDCl₃, 400 MHz) δ 8.26 (1H, s), 8.04 (1H, d), 7.42 (1H, m), 7.35 (1H, d), 7.14-7.27 (3H, m), 4.34 (2H, s), 3.95 (3H, s), 3.30 (3H, s).

Step 2: 2'-fluoro-2-(methoxymethyl)biphenyl-4-carboxylic acid

To a solution of methyl 2'-fluoro-2-(methoxymethyl)biphenyl-4-carboxylate (12.0 g, 43.7 mmol) in a mixture of THF (50 ml), MeOH (50 ml) and water (25 ml) was added lithium hydroxide monohydrate (5.50 g, 131.2 mmol) in portions. After 12 hours at RT, the reaction mixture was concentrated and the aqueous residual layer was acidified with a concentrated aqueous solution of HCl, and then extracted with EtOAc. The organic layers were washed with water and brine, combined, dried (Na₂SO₄) and concentrated under reduced pressure to afford of the title compound as a white solid (10.5 g, 92%). LC/MS (Method B): 259.0 (M−H)⁻. ¹H NMR (DMSO-d₆, 400 MHz) δ 13.07 (1H, brs), 8.10 (1H, s), 7.92 (1H, d), 7.48 (1H, m), 7.27-7.37 (4H, m), 4.26 (2H, s), 3.18 (3H, s).

Intermediate 13: 2'-Chloro-2-(methoxymethyl)biphenyl-4-carboxylic acid

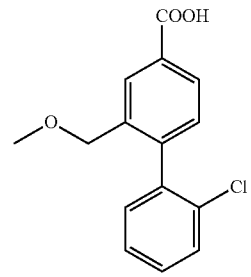 [SMILES: COCc1cc(C(=O)O)ccc1-c1ccccc1Cl]

Step 1: methyl 2'-chloro-2-(methoxymethyl)biphenyl-4-carboxylate

To a solution of methyl 4-bromo-3-(methoxymethyl)benzoate (Intermediate 1 Step 2, 15.0 g, 57.9 mmol) in toluene (120 mL) and water (30 mL) under nitrogen was added 2-chlorophenylboronic acid (19.9 g, 127.4 mmol), followed by potassium carbonate (16 g, 115.8 mmol) and Pd(PPh₃)₄ (3.34 g, 2.8 mmol). After 3 hours at 100° C., the reaction mixture was diluted with EtOAc (200 mL) and washed with a saturated aqueous solution of NaHCO₃ (100 mL), water (2×100 mL) and brine. The organic layer was dried (Na₂SO₄) and concentrated under reduced pressure. The residue was purified by chromatography (silica gel, pet ether/EtOAc) to afford of the title compound as a pale yellow oil. LC/MS (Method B): 291.0 (M+H)⁺. ¹H NMR (CDCl₃, 400 MHz) δ 8.21 (1H, s), 8.01 (1H, d), 7.48 (1H, m), 7.34 (2H, m), 7.26 (2H, m), 4.33 (1H, d), 4.20 (1H, d), 3.94 (3H, s), 3.27 (3H, s).

Step 2: 2'-chloro-2-(methoxymethyl)biphenyl-4-carboxylic acid

To a solution of methyl 2'-chloro-2-(methoxymethyl)biphenyl-4-carboxylate (11 g, 37.8 mmol) in a mixture of THF (50 ml), MeOH (50 ml) and water (25 ml) was added lithium hydroxide monohydrate (4.76 g, 113.5 mmol) in portions. After 12 hours at RT, the reaction mixture was concentrated and the aqueous residual layer was acidified with a concentrated aqueous solution of HCl, and then extracted with EtOAc (2×100 mL). The organic layers were washed with water and brine, combined, dried (Na$_2$SO$_4$) and concentrated under reduced pressure to afford of the title compound as a white solid (7.5 g, 72%). LC/MS (Method B): 275.0 (M−H)$^-$. $^1$H NMR (DMSO-d$_6$, 400 MHz) δ 13.0 (1H, brs), 8.08 (1H, s), 7.92 (1H, d), 7.58 (1H, d), 7.44 (2H, m), 7.29 (2H, m), 4.21 (1H, d), 4.13 (1H, d), 3.16 (3H, s).

Intermediate 14: 3-(methoxymethyl)-4-(2-methylpyrrolidin-1-yl)benzoic acid

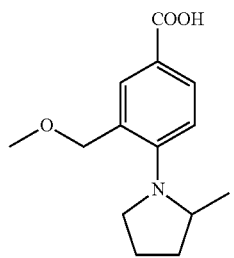

Step 1: 5-bromo-2-(2-methylpyrrolidin-1-yl)benzaldehyde

To a solution of 5-bromo-2-fluorobenzaldehyde (15 g, 73.8 mmol) in DMSO (150 mL) and water (40 mL) were added 2-methylpyrrolidine (9.8 mL, 96 mmol) and sodium carbonate (15.7 g, 148 mmol). The resulting mixture was heated at 110° C. for 8 hours. The reaction mixture was cooled at RT, diluted with water (1000 mL) and extracted with MTBE (2×100 mL). The organic layers were combined, dried (Na$_2$SO$_4$) and concentrated under reduced pressure. After purification by flash chromatography (silica, pet ether/ EtOAc), the title compound was obtained as a yellow oil (17 g, 85%). $^1$H NMR (DMSO-d$_6$, 400 MHz) δ 9.94 (1H, s), 7.75 (1H, s), 7.51 (1H, d), 6.93 (1H, d), 3.92 (1H, m), 3.68 (1H, m), 2.97 (1H, t), 2.49-2.18 (1H, m), 1.88 (1H, m), 1.57-1.68 (2H, m), 1.10 (3H, d).

Step 2: [5-bromo-2-(2-methylpyrrolidin-1-yl)phenyl] methanol

To a solution of 5-bromo-2-(2-methylpyrrolidin-1-yl)benzaldehyde (17 g, 63.4 mmol) in methanol (150 mL) under nitrogen was added sodium borohydride (2.41 g, 63.4 mmol) at 0° C. in portions. The reaction mixture was stirred at RT for 1 hour, then evaporated to remove methanol. The resulting crude was taken up with water (250 mL) and extracted with EtOAc (150 mL). The organic layer was washed with water, then dried (Na$_2$SO$_4$) and concentrated under reduced pressure to afford the title compound as a yellow oil (16 g, 93%). $^1$H NMR (DMSO-d$_6$, 400 MHz) δ 7.53 (1H, d), 7.27 (1H, d), 6.87 (1H, d), 5.22 (1H, t), 4.42 (2H, m), 3.56 (1H, m), 3.36 (1H, m), 2.70 (1H, m), 2.49 (1H, m) 2.09 (1H, m), 1.83 (1H, m), 1.73 (1H, m), 1.47 (1H, m), 0.90 (3H, d).

Step 3: 1-[4-bromo-2-(methoxymethyl)phenyl]-2-methylpyrrolidine

To a solution of sodium hydride (2.84 g, 119 mmol) in anhydrous DMF (80 mL) was added a solution of [5-Bromo-2-(2-methylpyrrolidin-1-yl)phenyl]methanol (16 g, 59.2 mmol) in DMF (50 mL) drop wise at 0° C. After 30 minutes, methyl iodide (7.3 mL, 119 mmol) was added drop wise at 0° C. The reaction mixture was quenched with a saturated aqueous solution of NH$_4$Cl (20 mL), then diluted with water (200 mL) and extracted with EtOAc (150 ml). The organic layer was dried (Na$_2$SO$_4$) and concentrated under reduced pressure to afford the title compound as a yellow oil (16.5 g, 98%). $^1$H NMR (CDCl$_3$, 400 MHz) δ 7.55 (1H, s), 7.29 (1H, m), 6.86 (1H, d), 4.45 (2H, s), 3.55 (1H, m), 3.41 (1H, m), 2.82 (1H, m), 2.12-2.51 (1H, m), 1.91 (1H, m) 1.81 (1H, m), 1.58 (1H, m), 0.99 (3H, d).

Step 4: 3-(methoxymethyl)-4-(2-methylpyrrolidin-1-yl)benzoic acid

To a solution of 1-[4-Bromo-2-(methoxymethyl)phenyl]-2-methylpyrrolidine (16.5 g, 58 mmol) in anhydrous THF (160 mL) was added n-butyl lithium in drops at −78° C. After 3 hours at −78° C., the reaction mixture was poured onto crushed dry-ice (100 g). Once the excess carbon dioxide was escaped, the reaction mixture was evaporated, and then acidified with 1.5 N HCl. The precipitate was filtered off and washed with pet ether to afford title compound as a solid. LC/MS (Method B): 249.9 (M+H)$^+$. $^1$H NMR (DMSO-d$_6$, 400 MHz) δ 12.4 (1H, brs), 7.84 (1H, s), 7.70 (1H, d), 6.85 (1H, d), 4.32-4.42 (2H, m), 3.59-3.87 (1H, m), 3.56 (1H, m), 3.29 (3H, s), 3.13 (1H, m), 2.14 (1H, m), 1.89 (1H, m), 1.74 (1H, m), 1.55 (1H, m), 0.99 (3H, d).

Intermediate 15: tert-butyl ({4-[amino(hydroxyimino)methyl]benzyl}oxy)acetate

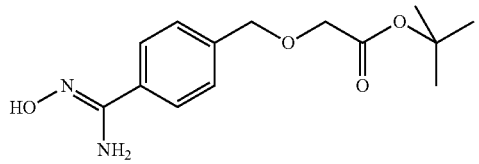 [SMILES: CC(C)(C)OC(=O)COCc1ccc(/C(N)=N/O)cc1]

Step 1: tert-butyl [(4-cyanobenzyl)oxy]acetate

An aqueous solution of NaOH (30 g in 60 mL of water) and tert-butyl bromoacetate (3.75 mL, 25.2 mmol) were added into a solution of 4-(hydroxymethyl)benzonitrile (3.0 g, 22.53 mmol) and tetrabutylammonium hydrogen sulfate (765 mg, 2.25 mmol) in toluene (60 mL). The reaction mixture was stirred at RT for 2 hours. The aqueous layer was removed and extracted twice with EtOAc. The organic layers were combined and washed with a saturated aqueous solution of NH$_4$Cl and brine, and then dried (MgSO$_4$) and concentrated to give the title compound as a colorless oil (4.37 g, 78%). HPLC (Method A) Rt 4.7 min (purity: 95.2%). $^1$H NMR (CDCl$_3$, 300 MHz) δ 7.65 (d, J=8.4 Hz, 2H), 7.50 (d, J=8.4 Hz, 2H), 4.68 (s, 2H), 4.05 (s, 2H), 1.50 (s, 9H).

Step 2: tert-butyl ({4-[amino(hydroxyimino)methyl] benzyl}oxy)acetate

The title compound was prepared following general procedure 1, starting from tert-butyl [(4-cyanobenzyl)oxy]acetate. It was obtained as a white solid (4.50 g, 91%). HPLC (Method A) Rt 2.8 min (purity: 99.2%). LC/MS (Method B): 279.1 (M−H)⁻, 281.0 (M+H)⁺. ¹H NMR (CDCl₃, 300 MHz) δ 8.58 (brs, 1H), 7.61 (d, J=8.4 Hz, 2H), 7.40 (d, J=8.4 Hz, 2H), 4.90 (brs, 2H), 4.63 (s, 2H), 3.99 (s, 2H), 1.48 (s, 9H).

Intermediate 16: tert-butyl 3-[{3-[amino(hydroxyimino)methyl]benzyl}(methyl)amino]propanoate

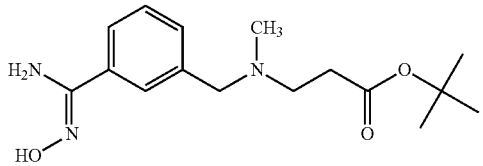 [SMILES: CN(CCC(=O)OC(C)(C)C)Cc1cccc(/C(N)=N/O)c1]

Step 1: 3-[(Methylamino)methyl]benzonitrile

To a stirred solution of methylamine (40% in water, 200 mL) under N₂, was added 3-(bromomethyl)benzonitrile (10 g, 51 mmol) slowly in portions over 10 minutes at 0° C. After being stirred at RT for 3 hours, the reaction mixture was extracted with DCM. Then the organic layer was washed with brine and dried over sodium sulphate and concentrated under reduced pressure. The residue was purified by chromatography (silica, pet ether/EtOAc) to afford the title compound as a pale yellow liquid (6.1 g, 82%). ¹H NMR (DMSO-d₆, 400 MHz) δ 7.74 (s, 1H), 7.63-7.68 (m, 2H), 7.48-7.52 (m, 1H), 3.66 (s, 2H), 2.22 (s, 3H).

Step 2: tert-butyl 3-[(3-cyanobenzyl)(methyl)amino]propanoate

To a stirred mixture of 3-[(methylamino)methyl]benzonitrile (6.1 g, 41.7 mmol) and sodium bicarbonate (7.0 g, 83.4 mmol) in ACN (70 mL) was added dropwise tert-butyl 3-bromo-propanoate (7 mL, 41.7 mol). After being stirred at RT for 12 hours, the reaction mixture was filtered and the filtrate was concentrated under reduced pressure. The residue was purified by chromatography (silica, pet ether/EtOAc) to afford the title compound as a pale yellow liquid. ¹H NMR (DMSO-d₆, 400 MHz) δ 7.70 (s, 2H), 7.60 (m, 1H), 7.51 (m, 1H), 3.49 (s, 2H), 2.58 (m, 2H), 2.36 (m, 2H), 2.09 (s, 3H), 1.38 (s, 9H).

Step 3: tert-butyl 3-[{3-[amino(hydroxyimino)methyl]benzyl}(methyl)amino]propanoate The title compound was prepared following the general procedure 1, starting from tert-butyl 3-[(3-cyanobenzyl)(methyl)amino]propanoate. It was obtained as a white gummy solid (4.50 g, 84%). ¹H NMR (DMSO-d₆, 400 MHz) δ 9.56 (s, 1H), 7.52 (m, 2H), 7.29 (m, 2H), 5.74 (s, 2H), 3.44 (s, 2H), 2.57 (m, 2H), 2.36 (m, 2H), 2.09 (s, 3H), 1.37 (s, 9H). LC/MS (Method B): 308.2 (M+H)⁺. HPLC (Method B) Rt 5.18 min (Purity: 96.5%).

Intermediate 17: tert-butyl ({3-[amino(hydroxyimino)methyl]benzyl}oxy)acetate

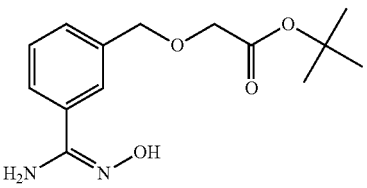 [SMILES: CC(C)(C)OC(=O)COCc1cccc(/C(N)=N\O)c1]

Step 1: tert-butyl [(3-cyanobenzyl)oxy]acetate

The title compound was prepared following the procedure described for Intermediate 15 Step 1, but starting from 3-cyanobenzyl alcohol. It was obtained as a colorless oil (4.4 g, 78%). HPLC (Method A) Rt 4.55 min (Purity: 98.3%).

Step 2: tert-butyl ({-[amino(hydroxyimino)methyl]benzyl}oxy)acetate

The title compound was prepared following the general procedure 1, starting from tert-butyl [(3-cyanobenzyl)oxy] acetate. It was isolated as a white powder (4.48 g, 90%). LC/MS (Method B): 281.2 (M+H)⁺, 279.2 (M−H)⁻. HPLC (Method B) Rt 2.75 min (Purity: 100%).

Intermediate 18: ethyl 4-{5-[amino(hydroxyimino)methyl]-2,3-difluorophenoxy}butanoate

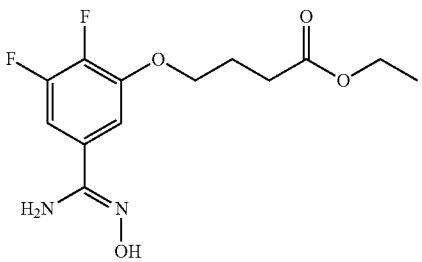 [SMILES: CCOC(=O)CCCOc1cc(/C(N)=N/O)cc(F)c1F]

Step 1: ethyl 4-(5-bromo-2,3-difluorophenoxy)butanoate

To a solution of 5-bromo-2,3-difluorophenol (Avocado, 2.5 g, 12.0 mmol) in DMF (50 mL) was added ethyl 4-bromobutyrate (2.57 g, 13.2 mmol) and K₂CO₃ (2.5 g, 18 mmol). The reaction mixture was heated at 80° C. for 3 hours. The reaction mixture was diluted with EtOAc and washed with water (3×) and brine, dried (MgSO₄) and concentrated under vacuum affording the title compound as a colorless oil (3.53 g, 91%). ¹H NMR (DMSO-d₆, 300 MHz) δ 7.36 (m, 1H), 7.28 (m, 1H), 4.16-4.03 (m, 4H), 2.45 (t, 2H), 2.03-1.94 (m, 2H), 1.18 (t, 3H). LC/MS (Method B): 323.1, 325.0 (M+H)⁺. HPLC (Method A) Rt 4.94 min (Purity: 99.8%).

Step 2: ethyl 4-(5-cyano-2,3-difluorophenoxy)butanoate

To a solution of ethyl 4-(5-bromo-2,3-difluorophenoxy) butanoate (2.9 g, 9.0 mmol) in anhydrous DMF (30 mL) was added copper(I) cyanide (1.6 g, 18.0 mmol) under nitrogen atmosphere. The resulting mixture was heated to 120° C. for 16 hours. Additional amount of copper(I) cyanide (0.8 g, 9.0 mmol) was added and the reaction mixture was stirred at 120° C. for 24 hours. A second additional amount of copper(I) cyanide (0.8 g, 9.0 mmol) was added. After 24 additional hours at 120° C., the reaction mixture was cooled down and filtered through a pad of Celite, which was rinsed with EtOAc. The organic layer was washed many times with an aqueous solution of NH$_4$OH and brine, dried (MgSO$_4$) and concentrated under vacuum affording the title compound as a beige solid (2.29 g, 95%). HPLC (Method A) Rt 4.73 min (Purity: 84.4%).

Step 3: ethyl 4-{5-[amino(hydroxyimino)methyl]-2,3-difluorophenoxy}butanoate

The title compound was prepared following the general procedure 1, starting from ethyl 4-(5-cyano-2,3-difluorophenoxy)butanoate (2.20 g, 8.17 mmol). It was obtained as a white solid (2.39 g, 97%). $^1$H NMR (DMSO-d$_6$, 300 MHz) δ 9.78 (br s, 1H), 7.30-7.23 (m, 2H), 5.95 (br s, 2H), 4.16-4.03 (m, 4H), 2.47-2.44 (m, 2H), 2.06-1.99 (m, 2H), 1.18 (t, J=7.0 Hz, 3H). LC/MS (Method B): 301.2 (M−H)$^−$, 303.2 (M+H)$^+$. HPLC (Method A) Rt 3.01 min (Purity: 88.2%).

Intermediate 19: N'-hydroxy-3-(methylsulfonyl)benzenecarboximidamide

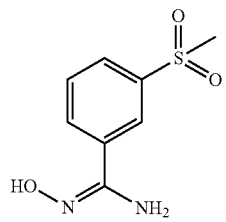

The title compound was prepared following the general procedure 1, starting from 3-methylsulfonylbenzonitrile. It was obtained as a white powder (2.69 g, 75%). $^1$H NMR (DMSO-d$_6$, 300 MHz) δ 9.88 (s, 1H), 8.21 (m, 1H), 8.00 (m, 1H), 7.91 (m, 1H), 7.66 (m, 1H), 6.03 (s, 2H), 3.23 (s, 3H).

Intermediate 20: tert-butyl 3-({3-[amino(hydroxyimino)methyl]benzyl}oxy)propanoate

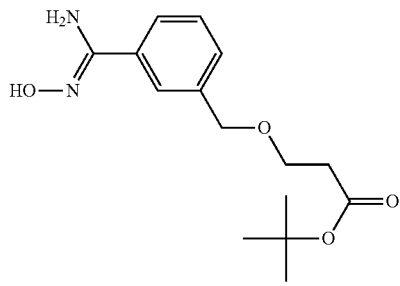 [SMILES: CC(C)(C)OC(=O)CCOCc1cccc(/C(N)=N/O)c1]

Step 1: tert-butyl 3-[(3-cyanobenzyl)oxy]propanoate

The title compound was prepared according the procedure described for Intermediate 15 Step 1, but starting from 3-cyanobenzyl alcohol and tert-butyl 3-bromopropionate. It was isolated as a colorless oil (630 mg, 32%). $^1$H NMR (DMSO-d$_6$, 300 MHz) δ 7.76 (m, 2H), 7.65 (m, 1H), 7.57 (m, 1H), 4.53 (brs, 2H), 3.64 (t, J=6.3 Hz, 2H), 2.49 (t, J=6.3 Hz, 2H), 1.40 (s, 9H). LC/MS (Method B) 262.2 (M+H)$^+$. HPLC (Method A) Rt 4.75 min (Purity: 99.9%).

Step 2: tert-butyl 3-({3-[amino(hydroxyimino)methyl]benzyl}oxy)propanoate

The title compound was prepared according the general procedure 2, starting from tert-butyl 3-[(3-cyanobenzyl)oxy]propanoate. It was isolated as a colorless oil (640 mg, 91%). $^1$H NMR (DMSO-d$_6$, 300 MHz) δ 9.60 (s, 1H), 7.59 (m, 2H), 7.34 (m, 2H), 5.80 (brs, 2H), 4.47 (brs, 2H), 3.63 (t, J=6.3 Hz, 2H), 2.47 (t, J=6.3 Hz, 2H), 1.40 (s, 9H). HPLC (Method A) Rt 2.89 min (Purity: 97%).

Intermediate 21: tert-butyl [{3-[amino(hydroxyimino)methyl]benzyl}(methyl)amino]acetate

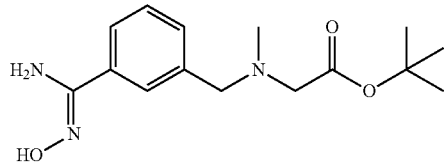 [SMILES: CN(CC(=O)OC(C)(C)C)Cc1cccc(/C(N)=N/O)c1]

Step 1: tert-butyl [(3-cyanobenzyl)(methyl)amino]acetate

To a stirred solution of sarcosine tert-butyl ester hydrochloride (8.1 g, 44.9 mmol) and triethylamine (17 mL, 122.4 mmol) in ACN (100 mL) was added 3-(bromomethyl)benzonitrile (8.0 g, 40.8 mmol) portionwise over a period of 10 minutes at 0° C. After being stirred at RT for 3 hours, the reaction mixture was poured into water and extracted with DCM. Then the organic layer was washed with brine, dried over sodium sulphate and concentrated under reduced pressure to afford the title compound as a pale green liquid (9.0 g, 85%). $^1$H NMR (DMSO-d$_6$, 400 MHz) δ 7.72 (2H, m), 7.64 (1H, m), 7.54 (1H, m), 3.66 (2H, s), 3.18 (2H, s), 2.22 (3H, s), 1.41 (9H, s).

Step 2: tert-butyl [{3-[amino(hydroxyimino)methyl]benzyl}(methyl)amino]acetate

The title compound was prepared according the general procedure 1, starting from tert-butyl [(3-cyanobenzyl)(methyl)amino]acetate. It was obtained as a white powder (8.5 g, 84%). $^1$H NMR (DMSO-d$_6$, 400 MHz) δ 9.57 (1H, s), 7.59 (1H, s), 7.53 (1H, m), 7.30 (2H, m), 5.75 (2H, s), 3.61 (2H, s), 3.15 (2H, s), 2.23 (3H, s), 1.41 (9H, s). LC/MS (Method B): 294.0 (M+H)$^+$. HPLC (Method A) Rt 3.31 min (Purity: 97.5%).

Intermediate 22: tert-butyl N-{3-[amino(hydroxyimino)methyl]benzyl}-N-(tert-butoxycarbonyl)-beta-alaninate

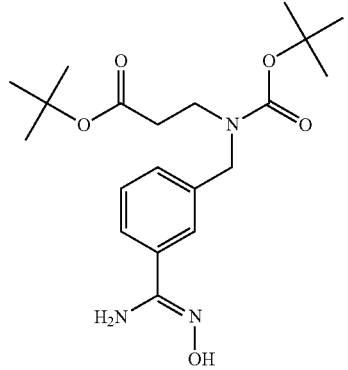 [SMILES: CC(C)(C)OC(=O)CCN(Cc1cccc(/C(N)=N/O)c1)C(=O)OC(C)(C)C]

Step 1: tert-butyl 3-[(3-cyanobenzyl)amino]propanoate

To a stirred solution of β-alanine tert-butyl ester hydrochloride (7.1 g, 39.2 mmol) and triethylamine (14.2 mL, 107 mmol) in dry acetonitrile (100 mL) was added 3-(bromomethyl)benzonitrile (7.0 g, 35.7 mmol) in portions over 10 minutes at 0° C. After being stirred at RT for 5 hours, the reaction mixture was diluted with water (100 mL) and extracted with dichloromethane (2×100 mL) The organic layers were combined, dried using sodium sulphate and concentrated under reduced pressure. The residue was purified by flash chromatography affording the title compound as a pale yellow liquid. $^1$H NMR (DMSO-$d_6$, 400 MHz) δ 7.75 (s, 1H), 7.66 (m, 2H), 7.50 (m, 1H), 3.71 (s, 2H), 2.64 (t, 2H), 2.32 (m, 2H), 1.37 (s, 9H).

Step 2: tert-butyl N-(tert-butoxycarbonyl)-N-(3-cyanobenzyl)-beta-alaninate

To a solution of tert-butyl 3-[(3-cyanobenzyl)amino]propanoate (3.7 g, 14.2 mmol) in anhydrous THF (100 mL) was added di-tert-butyl dicarbonate (3.1 g, 14.2 mmol). The resulting mixture was heated at 50° C. for 6 hours. The reaction mixture was then concentrated under reduced pressure affording the title compound as a pale yellow liquid (5.0 g, 98%). $^1$H NMR (DMSO-$d_6$, 400 MHz) δ 7.73 (t, 1H), 7.63 (s, 1H), 7.55 (d, 2H), 4.41 (s, 2H), 3.31 (t, 2H), 2.40 (t, 2H), 1.36 (m, 18H).

Step 3: tert-butyl N-{3-[amino(hydroxyimino)methyl]benzyl}-N-(tert-butoxycarbonyl)-beta-alaninate The title compound was prepared following the general procedure 1, starting from tert-butyl N-(tert-butoxycarbonyl)-N-(3-cyanobenzyl)-beta-alaninate (5.0 g, 13.8 mmol). It was isolated as a pale yellow oil (5.1 g, 93%). $^1$H NMR (DMSO-$d_6$, 400 MHz) δ 9.61 (s, 1H), 7.54 (m, 2H), 7.33 (m, 1H), 7.19 (d, 1H), 5.78 (s, 2H), 4.38 (s, 2H), 3.33 (m, 2H), 2.40 (m, 2H), 1.33-1.42 (m, 18H). LC/MS (Method B): 394.0 (M+H)$^+$. HPLC (Method A) Rt 3.47 min (Purity: 97.7%). HPLC (Method E) Rt 3.71 min (Purity: 97.2%).

Intermediate 23: tert-butyl N-{5-[amino(hydroxyimino)methyl]-2-fluorobenzyl}-N-methyl-beta-alaninate

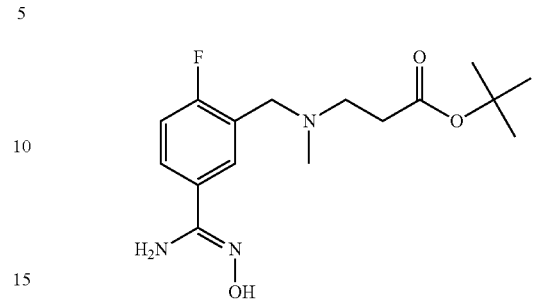

Step 1: tert-butyl N-(5-cyano-2-fluorobenzyl)-N-methyl-beta-alaninate

The title compound was prepared following the general procedure 10 starting from 5-cyano-2-fluorobenzylbromide (1.5 g, 7.0 mmol) and tert-butyl N-methyl-beta-alaninate (1.3 g, 8.4 mmol, prepared as described in Biorg. Med. Chem. (11) 2003, 3083-3099). It was isolated as a pale yellow oil (1.9 g, 92%). $^1$H NMR (CDCl$_3$, 300 MHz) δ 7.79 (dd, J=6.7, 2.1 Hz, 1H), 7.57-7.52 (m, 1H), 7.11 (m, 1H), 3.57 (s, 2H), 2.74 (t, J=7.1 Hz, 2H), 2.43 (t, J=7.1 Hz, 2H), 2.22 (s, 3H), 1.45 (s, 9H). LC/MS (Method B): 293.2 (M+H)$^+$. HPLC (Method A) Rt 2.44 min (Purity: 86.4%).

Step 2: tert-butyl N-{5-[amino(hydroxyimino)methyl]-2-fluorobenzyl}-N-methyl-beta-alaninate The title compound was prepared following the general procedure 1 starting from tert-butyl N-(5-cyano-2-fluorobenzyl)-N-methyl-beta-alaninate (1.39 g, 4.75 mmol). It was isolated as a colorless oil (1.6 g, quantitative). $^1$H NMR (CDCl$_3$, 300 MHz) δ 7.73 (dd, J=7.0, 2.3 Hz, 1H), 7.58-7.53 (m, 1H), 7.03 (dd, J=9.5, 8.7 Hz, 1H), 5.11 (br s, 2H), 3.59 (s, 2H), 2.69 (t, J=7.0 Hz, 2H), 2.45 (t, J=7.0 Hz, 2H), 2.28 (s, 3H), 1.45 (s, 9H). LC/MS (Method B): 324.3 (M−H)$^-$, 326.2 (M+H)$^+$.

Intermediate 24: tert-butyl N-{3-[amino(hydroxyimino)methyl]-5-fluorobenzyl}-N-methylglycinate

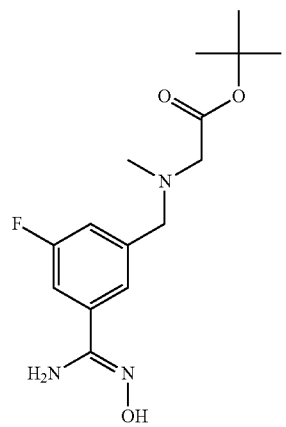 [SMILES: CN(CC(=O)OC(C)(C)C)Cc1cc(F)cc(/C(N)=N/O)c1]

Step 1: 3-(bromomethyl)-5-fluorobenzonitrile

A solution of 3-fluoro-5-methylbenzonitrile (Hognda Trading Co) (100 g, 0.74 mol) was prepared in ACN (1 L) under nitrogen atmosphere. N-Bromosuccinimide (105 g, 0.59 mol) and AIBN (2.4 g, 0.014 mol) were added and the reaction mixture was heated at 70° C. for 90 minutes. The reaction mixture was concentrated under vacuum. The residue was diluted in DCM, cooled at 0° C. and stirred for 15 minutes. The precipitated succinimide was filtered off and the filtrate was concentrated to give a yellow oil. The crude product was taken up with pet ether (200 mL), cooled at −20° C. and stirred for 30 minutes. The precipitate was filtered off and dried under vacuum to give the title compound as a white solid. $^1$H NMR (DMSO-$d_6$, 400 MHz) δ 7.83 (m, 2H) 7.73 (m, 1H), 4.72 (s, 2H). HPLC (Method A) Rt 4.17 min (Purity: 99.4%).

Step 2: tert-butyl N-(3-cyano-5-fluorobenzyl)-N-methylglycinate

The title compound was prepared according the general procedure 10, starting from 3-(bromomethyl)-5-fluorobenzonitrile and sarcosine tert-butyl ester hydrochloride. It was isolated as a yellow oil (3.5 g, 98%). $^1$H NMR (DMSO-$d_6$, 400 MHz) δ 7.74 (m, 1H), 7.63 (m, 1H), 7.54 (m, 1H), 3.70 (brs, 2H), 3.22 (brs, 2H), 2.24 (s, 3H), 1.42 (s, 9H). LC/MS (Method B) 262.2 (M+H)$^+$. HPLC (Method A) Rt 2.42 min (Purity: 93.3%).

Step 3: tert-butyl N-{3-[amino(hydroxyimino)methyl]-5-fluorobenzyl}-N-methylglycinate The title compound was prepared according general procedure 2, starting from tert-butyl N-(3-cyano-5-fluorobenzyl)-N-methylglycinate. It was isolated as a yellow solid. $^1$H NMR (DMSO-$d_6$, 400 MHz) δ 9.75 (br s, 1H), 7.49 (s, 1H), 7.34 (m, 1H), 7.13 (m, 1H), 5.87 (brs, 2H), 3.65 (s, 2H), 3.19 (s, 2H), 2.25 (s, 3H), 1.43 (s, 9H). LC/MS (Method B): 311.9 (M+H)$^+$, 310.0 (M−H$^-$). HPLC (Method A) Rt 1.89 min (Purity: 53%).

Intermediate 25: tert-butyl N-{3-[amino(hydroxyimino)methyl]-5-fluorobenzyl}-N-methyl-beta-alaninate

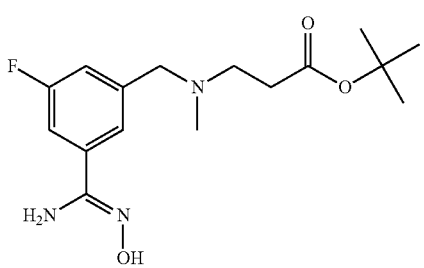 [SMILES: CN(CCC(=O)OC(C)(C)C)Cc1cc(F)cc(/C(N)=N/O)c1]

Step 1: tert-butyl N-(3-cyano-5-fluorobenzyl)-N-methyl-beta-alaninate

The title compound was prepared according the general procedure 10, starting from 3-(bromomethyl)-5-fluorobenzonitrile (Intermediate 24 Step 1, 750 mg, 3.5 mmol) and tert-butyl N-methyl-beta-alaninate (670 mg, 4.2 mmol, prepared as described in Biorg. Med. Chem. (11) 2003, 3083-3099). It was isolated as a pale yellow oil. $^1$H NMR (DMSO-$d_6$, 300 MHz) δ 7.73 (ddd, J=8.6, 2.6, 1.4 Hz, 1H), 7.61 (s, 1H), 7.56-7.45 (m, 1H), 3.53 (s, 2H), 2.60 (t, J=6.7 Hz, 2H), 2.38 (t, J=6.7 Hz, 2H), 2.12 (s, 3H), 1.40 (s, 9H). LC/MS (Method B): 293.3 (M+H)$^+$. HPLC (Method A) Rt 2.61 min (Purity: 96.2%).

Step 2: tert-butyl N-{3-[amino(hydroxyimino)methyl]-5-fluorobenzyl}-N-methyl-beta-alaninate The title compound was prepared following the general procedure 2, starting from tert-butyl N-(3-cyano-5-fluorobenzyl)-N-methyl-beta-alaninate (495 mg, 1.7 mmol). It was isolated as a yellow oil (524 mg, 95%). $^1$H NMR (DMSO-$d_6$, 300 MHz) δ 9.73 (s, 1H), 7.45 (s, 1H), 7.38-7.28 (m, 1H), 7.11 (d, J=9.7 Hz, 1H), 5.85 (s, 2H), 3.48 (s, 2H), 2.60 (t, J=6.9 Hz, 2H), 2.38 (t, J=6.9 Hz, 2H), 2.12 (s, 3H), 1.39 (s, 9H). LC/MS (Method B): 324.3 (M−H)$^-$.

Intermediate 26: 3-[(2,3-dihydroxypropyl)amino]-N'-hydroxybenzenecarboximidamide

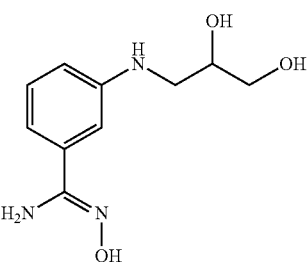 [SMILES: N/C(=N\O)c1cccc(NCC(O)CO)c1]

The title compound was prepared following the general procedure 1, starting from 3-(2,3-dihydroxy-propylamino) benzonitrile (1.0 g, 5.2 mmol). It was isolated as a white solid (476 mg, 41%). LC/MS (Method B): 226.2 (M+H)+.

Intermediate 27: N'-hydroxy-4-(2-hydroxyethoxy)benzenecarboximidamide

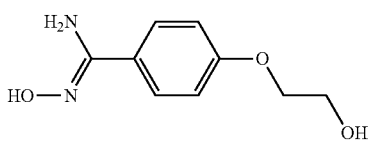

The title compound was prepared following the general procedure 1, starting from 4-(2-hydroxy-ethoxy)benzonitrile (1.0 g, 6.1 mmol, prepared as described in Org. Lett. 2004, 6 (11), pp 1693-1696). It was isolated as a white solid.

Intermediate 28: 4-(2-{[tert-butyl(dimethyl)silyl]oxy}ethoxy)-3-fluoro-N'-hydroxybenzenecarboximidamide

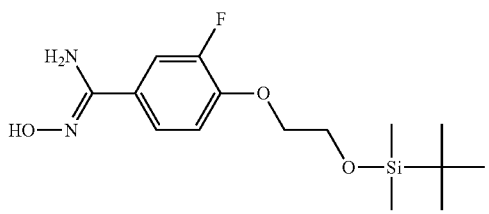 [SMILES: CC(C)(C)[Si](C)(C)OCCOc1ccc(/C(N)=N/O)cc1F]

Step 1: 4-(2-{[tert-butyl(dimethyl)silyl]oxy}ethoxy)-3-fluorobenzonitrile

A solution of 3-fluoro-4-hydroxybenzonitrile (ABCR, 2.0 g, 14.6 mmol) was prepared in anhydrous DMF (40 mL), and then (2-bromoethoxy)-tert-butyldimethylsilane (3.3 mL, 15.3 mmol) and $K_2CO_3$ (3.0 g, 21.9 mmol) were added. The reaction mixture was stirred at 80° C. for 4 hours. The reaction mixture was diluted with EtOAc, washed with water and brine, dried over $MgSO_4$ and concentrated under vacuum to give the title compound (4.3 g, 99%). HPLC (Method A) Rt 6.19 min (Purity: 94.2%).

Step 2: 4-(2-{[tert-butyl(dimethyl)silyl]oxy}ethoxy)-3-fluoro-N'-hydroxybenzene carboximidamide The title compound was prepared following the general procedure 1, starting from 4-(2-{[tert-butyl(dimethyl)silyl]oxy}ethoxy)-3-fluorobenzonitrile. It was isolated as a pale pink solid (4.4 g, 92%). $^1$H NMR (DMSO-$d_6$, 300 MHz) δ 9.53 (br s, 1H), 7.43-7.36 (m, 2H), 7.13-7.07 (m, 1H), 5.74 (br s, 2H), 4.07 (m, 2H), 3.88 (m, 2H), 0.79 (s, 9H), 0.00 (s, 6H). LC/MS (Method B): 327.3 (M–H)$^-$, 329.2 (M+H)$^+$. HPLC (Method A) Rt 4.38 min (Purity: 96.2%).

Intermediate 29: 3-{[(2,3-dihydroxypropyl)(methyl)amino]methyl}-N'-hydroxybenzenecarboximidamide

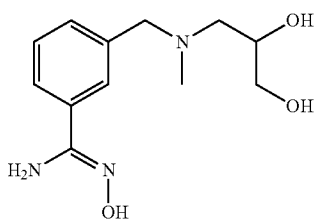 [SMILES: CN(Cc1cccc(/C(N)=N/O)c1)CC(O)CO]

Step 1: 3-{[(2,3-dihydroxypropyl)(methyl)amino]methyl}benzonitrile

The title compound was prepared following the general procedure 10, starting from 3-(bromomethyl)benzonitrile and 3-(methylamino)-1,2-propanediol. It was isolated as a colorless oil (920 mg, 82%). LC/MS (Method B): 221.1 (M+H)$^+$.

Step 2: 3-{[(2,3-dihydroxypropyl)(methyl)amino]methyl}-N'-hydroxybenzenecarboximidamide The title compound was prepared following the general procedure 1, starting from 3-{[(2,3-dihydroxypropyl)(methyl)amino]methyl}benzonitrile. It was isolated as a colorless oil. LC/MS (Method B): 254.1 (M+H)$^+$.

Intermediate 30: 3-{[bis(2-hydroxyethyl)amino]methyl}-N'-hydroxybenzenecarboximidamide

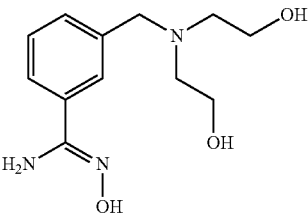 [SMILES: N/C(=N\O)c1cccc(CN(CCO)CCO)c1]

Step 1: 3-{[bis(2-hydroxyethyl)amino]methyl}benzonitrile

The title compound was prepared following the general procedure 10, starting from 3-(bromomethyl)benzonitrile and diethanolamine. It was obtained as a colorless oil (820 mg, 73%). LC/MS (Method B): 219.1 (M–H)$^-$, 221.1 (M+H)$^+$.

Step 2: 3-{[bis(2-hydroxyethyl)amino]methyl}-N'-hydroxybenzenecarboximidamide The title compound was prepared following the general procedure 2, starting from 3-{[bis(2-hydroxyethyl)amino]methyl}benzonitrile. It was obtained as a colorless oil.

Intermediate 31: tert-butyl N-{4-[amino(hydroxyimino)methyl]benzyl}-N-methylglycinate

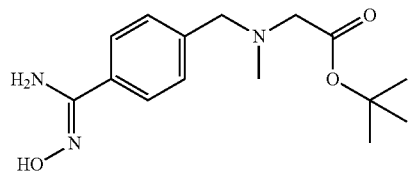 [SMILES: CN(CC(=O)OC(C)(C)C)Cc1ccc(/C(N)=N/O)cc1]

Step 1: tert-butyl N-(4-cyanobenzyl)-N-methylglycinate

A mixture of alpha-bromo-p-tolunitrile (10.0 g, 51 mmol), sarcosine tert-butyl ester hydrochloride (10.2 g, 56 mmol) and potassium carbonate (21.2 g, 153 mmol) in acetone (100 mL) was stirred at 60° C. overnight. Resulting suspension was filtered off and salts were washed with acetone (2×150 mL). The filtrate was concentrated under reduced pressure. The residue was diluted with water (200 mL) and extracted with EtOAc (2×150 mL). The combined organic layers were washed with water (200 mL), dried ($MgSO_4$) and the solvents were removed under reduced pressure to give the title compound as a yellow oil used without further purification (11.7 g, 88%). ¹H NMR (DMSO-d₆, 300 MHz) δ 7.79 (d, J=8.4 Hz, 2H), 7.51 (d, J=8.4 Hz, 2H), 3.71 (s, 2H), 3.20 (s, 2H), 2.23 (s, 3H), 1.42 (s, 9H). LC/MS (Method B): 260.9 (M+H)⁺.

Step 2: tert-butyl N-{4-[amino(hydroxyimino)methyl]benzyl}-N-methylglycinate

A 50% aqueous solution of hydroxylamine (13.25 mL, 225 mmol) was added at once into a solution of tert-butyl N-(4-cyanobenzyl)-N-methylglycinate (11.70 g, 45 mmol) in EtOH (75 mL).

The reaction mixture was stirred at RT overnight. The solvents were removed under reduced pressure to give a white solid. The solid was suspended in water (200 mL) and stirred for 20 minutes, then filtered off, washed with water and dried to give the title compound as a white powder (12.54 g, 95%). ¹H NMR (DMSO-d₆, 300 MHz) δ 9.58 (s, 1H), 7.62 (d, J=8.3 Hz, 2H), 7.28 (d, J=8.3 Hz, 2H), 5.78 (s, 2H), 3.62 (s, 2H), 3.15 (s, 2H), 2.24 (s, 3H), 1.42 (s, 9H). LC/MS (Method B): 294.0 (M+H)⁺.

Intermediate 32: tert-butyl N-{4-[amino(hydroxyimino)methyl]-2-fluorobenzyl}-N-methylglycinate

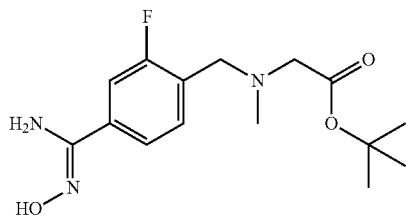 [SMILES: CN(CC(=O)OC(C)(C)C)Cc1ccc(/C(N)=N/O)cc1F]

Step 1: tert-butyl N-(4-cyano-2-fluorobenzyl)-N-methylglycinate

A mixture of 4-cyano-2-fluorobenzyl bromide (250 g, 1.17 mol), sarcosine tert-butyl ester hydrochloride (212.2 g, 1.17 mol) and potassium carbonate (484 g, 3.50 mol) in acetone (2 L) was stirred 24 hours at 50° C. and 18 hours at RT. The reaction mixture was filtered and the filtrate was concentrated under vacuum. The residue was taken up with water (1 L) and extracted with ethyl acetate (2×1 L). The combined organic layers were washed with water (1 L), dried (MgSO₄) and concentrated under vacuum to give the title compound as a yellow-brown oil (325 g, quantitative). ¹H NMR (DMSO-d₆, 300 MHz) δ 7.82 (dd, J=9.9, 1.4 Hz, 1H), 7.70 (dd, J=7.9, 1.5 Hz, 1H), 7.64 (m, 1H), 3.78 (s, 2H), 3.23 (s, 2H), 2.27 (s, 3H), 1.42 (s, 9H). LC/MS (Method B): 279.2 (M+H)⁺.

Step 2: tert-butyl N-{4-[amino(hydroxyimino)methyl]-2-fluorobenzyl}-N-methylglycinate A 50% aqueous solution of hydroxylamine (345 mL, 5.85 mol) was added dropwise over 10 minutes into a solution of tert-butyl N-(4-cyano-2-fluorobenzyl)-N-methylglycinate (325 g, 1.17 mol) in EtOH (2.1 L). The reaction mixture was stirred at RT for 20 hours. Solvents were concentrated under vacuum and water (2 L) was added. The resulting suspension was filtered off, washed with water (1 L) and dried under vacuum to give title compound as white powder (323 g, 89%). ¹H NMR (DMSO-d₆, 300 MHz) δ 9.74 (s, 1H), 7.51 (dd, J=8.0, 1.6 Hz, 1H), 7.45-7.36 (m, 2H), 5.87 (s, 2H), 3.70 (s, 2H), 3.17 (s, 2H), 2.26 (s, 3H), 1.42 (s, 9H). LC/MS (Method B): 312.3 (M+H)⁺.

Intermediate 33: tert-butyl N-{4-[amino(hydroxyimino)methyl]-2-bromobenzyl}-N-methylglycinate

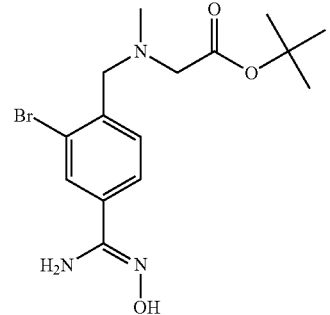 [SMILES: CN(CC(=O)OC(C)(C)C)Cc1ccc(/C(N)=N/O)cc1Br]

Step 1: tert-butyl N-(2-bromo-4-cyanobenzyl)-N-methylglycinate

The title compound was prepared following the general procedure 10, starting from 2-bromo-4-cyanobenzyl bromide (Carbocor) and sarcosine tert-butyl ester hydrochloride. It was obtained as a white solid. ¹H NMR (DMSO-d₆, 300 MHz) δ 8.17 (d, J=1.6 Hz, 1H), 7.88 (dd, J=8.0, 1.6 Hz, 1H), 7.69 (d, J=8.0 Hz, 1H), 3.82 (s, 2H), 3.31 (s, 2H), 2.31 (s, 3H), 1.43 (s, 9H). LC/MS (Method B): 338.9, 340.9 (M+H)⁺. HPLC (Method A) Rt 3.10 min (Purity: 99.6%).

Step 2: tert-butyl N-{4-[amino(hydroxyimino)methyl]-2-bromobenzyl}-N-methylglycinate The title compound was prepared following the general procedure 2, starting from tert-butyl N-(2-bromo-4-cyanobenzyl)-N-methylglycinate. It was isolated as a colorless oil (303 mg, 97%). ¹H NMR (DMSO-d₆, 300 MHz) δ 9.74 (s, 1H), 7.87 (d, J=1.7 Hz, 1H), 7.67 (dd, J=8.0, 1.7 Hz, 1H), 7.47 (d, J=8.0 Hz, 1H), 5.88 (s, 2H), 3.75 (s, 2H), 3.26 (s, 2H), 2.31 (s, 3H), 1.43 (s, 9H). LC/MS (Method B): 371.9, 373.9 (M+H)⁺. HPLC (Method A) Rt 1.53 min (Purity: 98.6%).

Intermediate 34: methyl 4-[amino(hydroxyimino)methyl]-2-chlorobenzoate

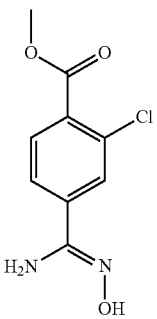

Step 1: methyl 4-bromo-2-chlorobenzoate

Thionyl chloride (1.23 mL, 17.0 mmol) was added dropwise into a solution of 4-bromo-2-chlorobenzoic acid (Combi-Blocks CA-4187, 1.0 g, 4.25 mmol) in MeOH (20 mL) at 0° C. The reaction mixture was then stirred at RT until completion. The reaction mixture was concentrated under reduced pressure. The residue was dissolved in EtOAc and washed with a saturated aqueous solution of $NaHCO_3$ and brine. The organic layer was dried ($MgSO_4$) and concentrated under vacuum to give the title compound (871 mg, 82%). $^1$H NMR ($CDCl_3$, 300 MHz) δ 7.72 (d, J=8.4 Hz, 1H), 7.64 (d, J=1.9 Hz, 1H), 7.46 (dd, J=8.4, 1.9 Hz, 1H), 3.93 (s, 3H). HPLC (Method A) Rt 4.22 min (Purity: 98.5%).

Step 2: methyl 2-chloro-4-cyanobenzoate

A mixture of triphenylphosphine polymer bound (239 mg, 0.72 mmol) and palladium(II) acetate (75 mg, 0.33 mmol) was prepared in DMF (12 mL) under nitrogen atmosphere and stirred at RT for 2 hours. Zinc cyanide (561 mg, 4.77 mmol) and methyl 4-bromo-2-chlorobenzoate (1.19 g, 4.77 mmol) were added and the resulting mixture was heated under microwave irradiation at 140° C. for 50 minutes. The reaction mixture was filtered and the resin was washed with $Et_2O$ (3×10 mL). The combined organic layers were washed with water (3×5 mL) and brine (10 mL), dried ($MgSO_4$) and concentrated under vacuum to give the title compound as a white powder. $^1$H NMR (DMSO-$d_6$, 300 MHz) δ 8.23 (m, 1H), 7.96 (m, 2H), 3.90 (s, 3H). HPLC (Method A) Rt 3.39 min (Purity: 97.6%).

Step 3: methyl 4-[amino(hydroxyimino)methyl]-2-chlorobenzoate

The title compound was prepared according the general procedure 1, starting from methyl 2-chloro-4-cyanobenzoate. It was obtained as a beige solid (631 mg, quantitative). $^1$H NMR (DMSO-$d_6$, 300 MHz) δ 10.02 (br s, 1H), 7.84 (d, J=1.6 Hz, 1H), 7.83 (d, J=8.2 Hz, 1H), 7.75 (dd, J=8.2, 1.6 Hz, 1H), 6.03 (br s, 2H), 3.86 (s, 3H). LC/MS (Method B): 227.2 (M−H)⁻, 229.1 (M+H)⁺. HPLC (Method A) Rt 1.44 min (Purity: 63.4%).

Intermediate 35: methyl 4-[amino(hydroxyimino)methyl]-2-fluorobenzoate

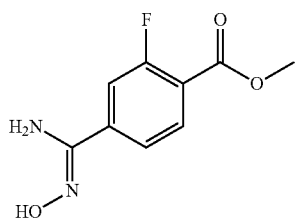

Step 1: methyl 4-cyano-2-fluorobenzoate

Oxalyl chloride (9.0 mL, 106.6 mmol) and DMF (0.5 mL) were added into a suspension of 4-cyano-2-fluorobenzoic acid (ABCR, 16 g, 96.9 mmol) in anhydrous DCM (300 mL) The resulting mixture was stirred at RT, and then evaporated under reduced pressure. The residue was taken up with anhydrous THF (150 mL) and added dropwise into a solution of methanol (50 mL) and triethylamine (25.8 mL, 193.8 mmol) at 4° C. The reaction mixture was diluted with a 0.1N aqueous solution of HCl (200 mL) and extracted with EtOAc (3×100 mL). The combined organic layers were washed with a semi-saturated aqueous solution of $NaHCO_3$ (200 mL) and water (200 mL), dried ($MgSO_4$) and concentrated under vacuum to give the title compound as a pale yellow solid (17.8 g, quantitative). HPLC (Method A) Rt 2.81 min (Purity: 93.9%).

Step 2: methyl 4-[amino(hydroxyimino)methyl]-2-fluorobenzoate

The title compound was prepared according the general procedure 1, starting from methyl 4-cyano-2-fluorobenzoate. It was obtained as white solid. $^1$H NMR (DMSO-$d_6$, 300 MHz) δ 10.09 (s, 1H), 7.92 (m, 1H), 7.70-7.62 (m, 2H), 6.05 (s, 2H), 3.89 (s, 3H). LC/MS (Method B): 210.9 (M−H)⁻, 212.9 (M+H)⁺. HPLC (Method A), Rt 0.97 min (purity: 100%).

Intermediate 36: tert-butyl N-{4-[amino(hydroxyimino)methyl]benzyl}-N-(tert-butoxycarbonyl)glycinate

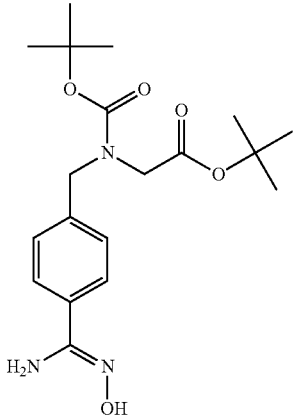 [SMILES: CC(C)(C)OC(=O)CN(Cc1ccc(/C(N)=N/O)cc1)C(=O)OC(C)(C)C]

Step 1: tert-butyl N-(4-cyanobenzyl)glycinate

The title compound was prepared following the general procedure 10, starting from 4-cyanobenzyl bromide and tert-butyl glycinate. It was isolated as a colorless oil. $^1$H NMR (DMSO-$d_6$, 300 MHz) δ 7.78 (d, J=8.3 Hz, 2H), 7.52 (d, J=8.3 Hz, 2H), 3.79 (s, 2H), 3.19 (s, 2H), 2.60 (br s, 1H), 1.41 (s, 9H). HPLC (Method A) Rt 2.17 min (Purity: 97.2%).

Step 2: tert-butyl N-(tert-butoxycarbonyl)-N-(4-cyanobenzyl)glycinate

A mixture of tert-butyl N-(4-cyanobenzyl)glycinate (1.1 g, 4.5 mmol), di-tert-butyl dicarbonate (1.1 g, 4.9 mmol) and N-ethyldiisopropylamine (1.1 mL, 6.7 mmol) was prepared in DCM (22 mL) and stirred at RT for 3.5 hours. The reaction mixture was diluted with DCM and washed with a saturated aqueous solution of $NaHCO_3$ (2×) and brine. The organic layer was dried ($MgSO_4$) and concentrated to afford the title compound as a colorless oil (1.2 g, 77%). $^1$H NMR (DMSO-$d_6$, 300 MHz) δ 7.84-7.78 (m, 2H), 7.48 (d, J=8.0 Hz, 2H), 4.50-4.45 (m, 2H), 3.93-3.83 (m, 2H), 1.41-1.29 (m, 18H). LC/MS (Method B): 347.1 (M+H)⁺. HPLC (Method A) Rt 5.10 min (Purity: 100.0%).

Step 3: tert-butyl N-{4-[amino(hydroxyimino)methyl]benzyl}-N-(tert-butoxycarbonyl)glycinate The title compound was prepared following the general procedure 2, starting from tert-butyl N-(tert-butoxycarbonyl)-N-(4-cyanobenzyl)glycinate. It was obtained as a colorless oil (1.26 g, 97%). $^1$H NMR (DMSO-$d_6$, 300 MHz) δ 9.59 (s, 1H), 7.65-7.60 (m, 2H), 7.26 (d, J=8.3 Hz, 2H), 5.77 (s, 2H), 4.40 (s, 2H), 3.84-3.75 (m, 2H), 1.41-1.34 (m, 18H). LC/MS (Method B): 380.1 (M+H)$^+$. HPLC (Method A) Rt 3.31 min (Purity: 98.1%).

Intermediate 37: tert-butyl N-{3-[amino(hydroxyimino)methyl]benzyl}-N-ethyl-beta-alaninate

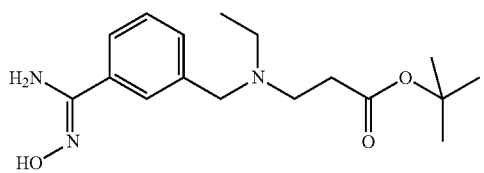 [SMILES: CCN(CCC(=O)OC(C)(C)C)Cc1cccc(/C(N)=N/O)c1]

Step 1: 3-[(ethylamino)methyl]benzonitrile 3-(Bromomethyl)benzonitrile (20.0 g, 0.1 mol) was added portion wise into a 2M solution of ethylamine in THF (150 mL) at 0° C. After 5 hours, the reaction mixture was concentrated under vacuum. The residue was taken up with water and extracted with DCM. The organic layer was dried over sodium sulphate and evaporated under reduced pressure to afford the title compound as yellow liquid (12 g, 73%). $^1$H NMR (DMSO-$d_6$, 400 MHz) δ 7.75 (s, 1H), 7.67 (d, 2H), 7.50 (m, 1H), 3.71 (s, 2H), 2.46 (m, 2H), 0.99 (m, 3H).

Step 2: tert-butyl N-(3-cyanobenzyl)-N-ethyl-beta-alaninate

A mixture of 3-[(ethylamino)methyl]benzonitrile (5 g, 31 mmol) and tert-butyl acrylate (4.6 mL, 31 mmol) was heated neat at 80° C. for 12 hours. The crude mixture was purified by flash chromatography (silica, pet ether/EtOAc) to afford the title compound as colorless oil. $^1$H NMR (DMSO-$d_6$, 400 MHz) δ 7.69 (m, 2H), 7.62 (d, J=7.8 Hz, 1H), 7.50 (m, 1H), 3.56 (s, 2H), 2.64 (t, 2H), 2.40 (m, 2H), 2.32 (t, 2H), 1.39 (s, 9H), 0.93 (t, 3H).

Step 3: tert-butyl N-{3-[amino(hydroxyimino)methyl]benzyl}-N-ethyl-beta-alaninate The title compound was prepared according the general procedure 2, starting from tert-butyl N-(3-cyanobenzyl)-N-ethyl-beta-alaninate. It was isolated as a colorless oil (5.2 g, 86%). $^1$H NMR (DMSO-$d_6$, 400 MHz) δ 9.59 (1H, s), 7.59 (2H, m), 7.52 (d, J=5.8 Hz, 1H), 7.29 (d, J=5.8 Hz, 1H), 5.74 (s, 2H), 3.51 (s, 2H), 2.66 (t, 2H), 2.41 (m, 2H), 2.32 (t, 2H), 1.38 (s, 9H), 0.95 (t, 3H). LC/MS (Method A) 322.0 (M+H)$^+$. HPLC (Method A) Rt 2.09 min (Purity: 97.2%).

Intermediate 38: tert-butyl N-{3-[amino(hydroxyimino)methyl]benzyl}-N-(2-hydroxyethyl)-beta-alaninate

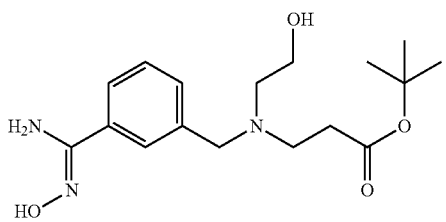 [SMILES: CC(C)(C)OC(=O)CCN(CCO)Cc1cccc(/C(N)=N/O)c1]

Step 1: 3-{[(2-hydroxyethyl)amino]methyl}benzonitrile 3-(Bromomethyl)benzonitrile (20.0 g, 0.125 mol) was added portion wise into a mixture of ethanolamine (11.4 g, 0.19 mol) and sodium bicarbonate (21.0 g, 0.25 mol) in ACN (200 mL) at 0° C. The resulting mixture was stirred for 4 hours. The reaction mixture was concentrated under vacuum. The residue was taken up with water and extracted with DCM (200 mL). The organic layer was dried over sodium sulfate and evaporated under reduced pressure. The residue was purified by chromatography to afford the title compound as white solid (9.8 g, 54%). $^1$H NMR (DMSO-$d_6$, 400 MHz) δ 7.76 (s, 1H), 7.67 (m, 2H), 7.51 (m, 1H), 4.47 (brs, 1H), 3.74 (s, 2H), 3.44 (m, 2H), 2.51 (m, 2H), 2.12 (brs, 1H).

Step 2: tert-butyl N-(3-cyanobenzyl)-N-(2-hydroxyethyl)-beta-alaninate

Tert-butyl acrylate (3.56 ml, 29 mmol) was added into a solution of 3-{[(2-hydroxyethyl)amino]methyl}benzonitrile (4.9 g, 28 mmol) in anhydrous DMF (5 mL) under nitrogen atmosphere. The resulting mixture was heated at 80° C. for 12 hours. The reaction mixture was diluted with water (100 mL) and extracted with ethyl acetate (100 mL). The organic layer was dried over sodium sulfate and concentrated under reduced pressure to afford the title compound as colorless liquid. $^1$H NMR (DMSO-$d_6$, 400 MHz) δ 7.75 (s, 1H), 7.69 (d, J=7.6 Hz, 1H), 7.62 (d, J=7.9 Hz, 1H), 7.50 (m, 1H), 4.36 (t, 1H), 3.62 (s, 2H), 3.43 (m, 2H), 2.69 (t, 2H), 2.47 (m, 2H), 2.34 (t, 2H), 1.38 (s, 9H).

Step 3: tert-butyl N-{3-[amino(hydroxyimino)methyl]benzyl}-N-(2-hydroxyethyl)-beta-alaninate The title compound was prepared following the general procedure 2, starting from tert-butyl N-(3-cyanobenzyl)-N-(2-hydroxyethyl)-beta-alaninate. It was isolated as a colorless oil (4.0 g, 87%). $^1$H NMR (DMSO-$d_6$, 400 MHz) δ 9.57 (s, 1H), 7.58 (s, 1H), 7.51 (t, 1H), 7.28 (d, 2H), 5.74 (s, 2H), 4.30 (t, 1H), 3.57 (s, 2H), 3.41 (m, 2H), 2.70 (t, 2H), 2.47 (m, 2H), 2.34 (t, 2H), 1.37 (s, 9H). LC/MS (Method A) 338.1 (M+H)$^+$. HPLC (Method A) Rt 1.89 min (Purity: 98.2%).

Intermediate 39: tert-butyl N-{4-[amino(hydroxyimino)methyl]-2-fluorobenzyl}-N-methyl-beta-alaninate

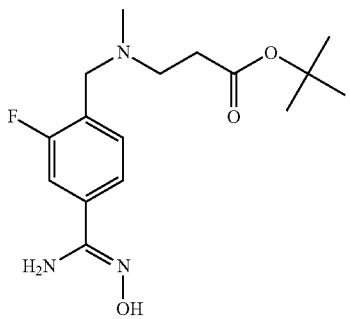 [SMILES: CN(CCC(=O)OC(C)(C)C)Cc1ccc(/C(N)=N/O)cc1F]

Step 1: tert-butyl N-(4-cyano-2-fluorobenzyl)-N-methyl-beta-alaninate

The title compound was prepared following the general procedure 10, starting from 4-cyano-2-fluorobenzyl bromide (Fluorochem, 2.0 g, 9.3 mmol) and tert-butyl N-methyl-beta-alaninate (1.8 g, 11.2 mmol, prepared as described in Biorg. Med. Chem. (11) 2003, 3083-3099). It was isolated as a yellow oil (2.4 g, 87%). $^1$H NMR (CDCl$_3$, 300 MHz) δ 7.82 (dd, J=10.0, 1.6 Hz, 1H), 7.69 (dd, J=7.8, 1.6 Hz, 1H), 7.60 (m, 1H), 3.58 (s, 2H), 2.61 (t, J=6.9 Hz, 2H), 2.38 (t, J=6.9 Hz, 2H), 2.14 (s, 3H), 1.38 (s, 9H). LC/MS (Method B): 293.0 (M+H)$^+$. HPLC (Method A) Rt 2.44 min (Purity: 88.5%).

Step 2: tert-butyl N-{4-[amino(hydroxyimino)methyl]-2-fluorobenzyl}-N-methyl-beta-alaninate The title compound was prepared following the general procedure 2, starting from tert-butyl N-(4-cyano-2-fluorobenzyl)-N-methyl-beta-alaninate (1.4 g, 4.8 mmol). It was obtained as a yellow oil (2.4 g, 90%). $^1$H NMR (DMSO-d$_6$, 300 MHz) δ 9.74 (br s, 1H), 7.49 (dd, J=8.0, 1.6 Hz, 1H), 7.42 (dd, J=11.6, 1.6 Hz, 1H), 7.37 (m, 1H), 5.87 (br s, 2H), 3.51 (s, 2H), 2.60 (t, J=7.0 Hz, 2H), 2.38 (t, J=7.0 Hz, 2H), 2.13 (s, 3H), 1.38 (s, 9H). LC/MS (Method B): 326.0 (M+H)$^+$. HPLC (Method A) Rt 1.57 min (Purity: 95.0%).

Intermediate 40: tert-butyl N-{4-[amino(hydroxyimino)methyl]benzyl}-N-methyl-beta-alaninate

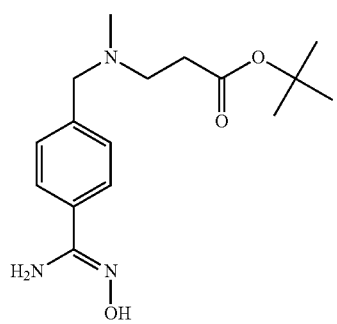 [SMILES: CN(CCC(=O)OC(C)(C)C)Cc1ccc(/C(N)=N/O)cc1]

Step 1: tert-butyl N-(4-cyanobenzyl)-N-methyl-beta-alaninate

The title compound was prepared following the general procedure 10, starting from 4-cyanobenzyl bromide (1.5 g, 7.7 mmol) and tert-butyl N-methyl-beta-alaninate (1.5 g, 9.2 mmol, prepared as described in Biorg. Med. Chem. (11) 2003, 3083-3099). It was isolated as a yellow oil (1.9 g, 89%). $^1$H NMR (DMSO-d$_6$, 300 MHz) δ 7.78 (d, J=8.3 Hz, 2H), 7.49 (d, J=8.3 Hz, 2H), 3.55 (s, 2H), 2.60 (t, J=6.9 Hz, 2H), 2.38 (t, J=6.9 Hz, 2H), 2.11 (s, 3H), 1.39 (s, 9H). LC/MS (Method B): 275.0 (M+H)$^+$. HPLC (Method A) Rt 2.40 min (Purity: 82.5%).

Step 2: tert-butyl N-{4-[amino(hydroxyimino)methyl]benzyl}-N-methyl-beta-alaninate The title compound was prepared following the general procedure 2, starting from tert-butyl N-(4-cyanobenzyl)-N-methyl-beta-alaninate (1.9 g; 6.8 mmol). It was isolated as a yellow oil (1.6 g, 77%). $^1$H NMR (DMSO-d$_6$, 300 MHz) δ 9.57 (br s, 1H), 7.61 (d, J=8.2 Hz, 2H), 7.27 (d, J=8.2 Hz, 2H), 5.77 (s, 2H), 3.51-3.45 (m, 2H), 2.59 (t, J=7.0 Hz, 2H), 2.38 (t, J=7.0 Hz, 2H), 2.10 (s, 3H), 1.40 (s, 9H). LC/MS (Method B): 308.0 (M+H)$^+$. HPLC (Method A) Rt 1.52 min (Purity: 82.3%).

Intermediate 41: tert-butyl N-(3-{5-[4-bromo-3-(methoxymethyl)phenyl]-1,2,4-oxadiazol-3-yl}benzyl)-N-methylglycinate

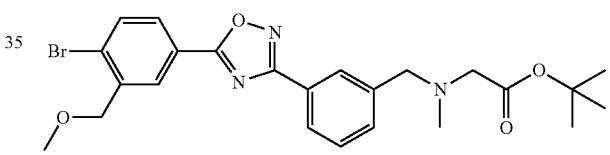

Step 1: 4-bromo-3-(methoxymethyl)benzoic acid

To a solution of methyl 4-bromo-3-(methoxymethyl)benzoate (Intermediate 1, Step 2, 7.0 g, 27.0 mmol) in EtOH (210 mL) was added a 5 N aqueous solution of NaOH (16 mL, 80.0 mmol). The resulting mixture was heated at 60° C. for 1 hour. The reaction mixture was cooled to RT and concentrated under vacuum. The residue was taken up with water and washed with EtOAc. The aqueous layer was then acidified with a 1N aqueous solution of HCl and extracted with EtOAc. The organic layer was dried (MgSO$_4$) and concentrated under vacuum to give the title compound as a yellow solid (5.81 g, 87%). $^1$H NMR (DMSO-d$_6$, 300 MHz) 13.19 (br s, 1H), 8.00 (m, 1H), 7.77 (m, 2H), 4.49 (s, 2H), 3.40 (s, 3H). LC/MS (Method B): 245.0 (M−H)$^-$. HPLC (Method A) Rt 3.63 min (purity: 97.4%).

Step 2: tert-butyl N-(3-{5-[4-bromo-3-(methoxymethyl)phenyl]-1,2,4-oxadiazol-3-yl}benzyl)-N-methylglycinate Oxalyl chloride (7.8 mL, 91.8 mmol) and DMF (100 μL) were added into a solution of 4-bromo-3-(methoxymethyl) benzoic acid (15.0 g, 61.2 mmol) in anhydrous toluene (225 mL). The resulting mixture was stirred at RT for 2 hours, and then concentrated under vacuum to give the acyl chloride derivative as a yellow oil. This acyl chloride was taken up with anhydrous toluene (150 mL) and added drop wise into a solution of Intermediate 21 (18.0 g, 61.2 mmol) in toluene (75 mL) and pyridine (75 mL). The resulting mixture was stirred at RT for 2 hours, and then heated at reflux for 18 hours. The reaction mixture was concentrated under vacuum. The residue was taken up with EtOAc (400 mL) and washed with water (150 mL), a saturated aqueous solution of $NaHCO_3$ (2×150 mL) and brine (150 mL). The organic layer was dried ($MgSO_4$) and concentrated under vacuum to give a yellow solid which was washed with MeOH to give the title compound as a beige powder. HPLC (Method A) Rt 4.8 min (purity: 96.3%). $^1$H NMR (DMSO-$d_6$, 300 MHz) δ 8.23 (s, 1H), 8.07-7.91 (m, 4H), 7.54 (m, 2H), 4.57 (s, 2H), 3.74 (s, 2H), 3.47 (s, 3H), 3.22 (s, 2H), 2.29 (s, 3H), 1.45 (s, 9H).

Intermediate 42: methyl 4-[amino(hydroxyimino)methyl]-2,5-difluorobenzoate

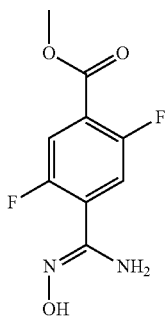

Step 1: methyl 4-cyano-2,5-difluorobenzoate

Methyl 2,4,5-trifluorobenzoate (DSL Chemicals, 950 mg, 5 mmol), sodium cyanide (306 mg, 6.25 mmol) and tetrabutylammonium bromide (2.01 g, 6.25 mmol) were dissolved in DMF (10 mL) and the resulting mixture was heated at 60° C. overnight. Additional amount of sodium cyanide (306 mg, 6.25 mmol) was added and the mixture was stirred at 60° C. for 24 additional hours. The reaction mixture was diluted with EtOAc and washed with brine several times. The organic layer was dried over $MgSO_4$ and concentrated under vacuum. The residue was purified by flash chromatography (silica, EtOAc/cHex) to give the title compound. $^1$H NMR (DMSO-$d_6$, 300 MHz) δ 7.77 (dd, J=8.4, 5.5 Hz, 1H), 7.42 (dd, J=8.9, 5.0 Hz, 1H), 3.96 (s, 3H). LC/MS (Method B): 463.2 (M−H)$^−$, 465.2 (M+H)$^+$. HPLC (Method A) Rt 3.63 min (Purity: 99.9%).

Step 2: methyl 4-[amino(hydroxyimino)methyl]-2,5-difluorobenzoate

The title compound was prepared following the general protocol 1, starting from methyl 4-cyano-2,5-difluorobenzoate. It was obtained as a white solid (304 mg, 98%). LC/MS (Method B): 229.0 (M−H)$^+$, 231.0 (M+H)$^+$. HPLC (Method A) Rt 1.08 min (Purity: 98.7%).

Intermediate 43: tert-butyl N-{3-[amino(hydroxyimino)methyl]-5-chlorobenzyl}-N-methylglycinate

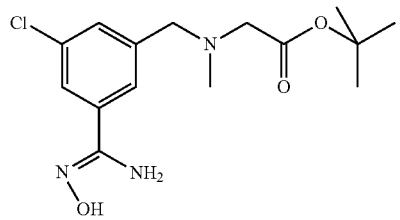 [SMILES: CN(CC(=O)OC(C)(C)C)Cc1cc(Cl)cc(/C(N)=N/O)c1]

Step 1: 3-(bromomethyl)-5-chlorobenzonitrile

The title compound was prepared following general procedure 13, starting from 3-chloro-5-methylbenzonitrile (FluoroChem Ltd). It was isolated as a yellow powder. LC/MS (Method B): 295.1 (M+H)$^+$. HPLC (Method A) Rt 4.61 min (Purity: 96.8%).

Step 2: tert-butyl N-(3-chloro-5-cyanobenzyl)-N-methylglycinate

The title compound was prepared following general procedure 10, starting from 3-(bromomethyl)-5-chlorobenzonitrile and sarcosine tert-butyl ester hydrochloride. It was isolated as a yellow oil (570 mg, 78%). LC/MS (Method B): 295.1 (M+H)$^+$.

Step 3: tert-butyl N-{3-[amino(hydroxyimino)methyl]-5-chlorobenzyl}-N-methylglycinate The title compound was prepared following general procedure 2, starting from tert-butyl N-(3-chloro-5-cyanobenzyl)-N-methylglycinate. It was isolated as a yellowish oil (550 mg, 88%). LC/MS (Method B): 326.2 (M−H)$^−$.

Intermediate 44: tert-butyl N-{4-[amino(hydroxyimino)methyl]-2-methoxybenzyl}-N-methylglycinate

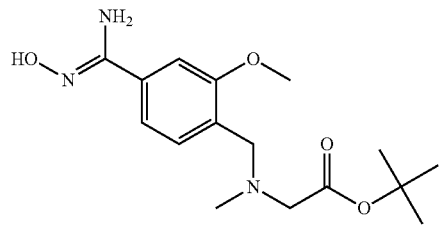 [SMILES: COc1cc(/C(N)=N/O)ccc1CN(C)CC(=O)OC(C)(C)C]

Step 1: tert-butyl N-(4-cyano-2-methoxybenzyl)-N-methylglycinate

The title compound was prepared following the general procedure 10, starting from 4-cyano-2-methoxybenzyl bromide (Carbocore) and sarcosine tert-butyl ester hydrochloride. It was isolated as a colorless oil. $^1$H NMR (DMSO-$d_6$, 300 MHz) δ 7.53 (d, J=7.7 Hz, 1H), 7.45-7.40 (m, 2H), 3.83 (s, 3H), 3.69 (s, 2H), 3.20 (s, 2H), 2.27 (s, 3H), 1.42 (s, 9H). LC/MS (Method B): 291.0 (M+H)$^+$. HPLC (Method A) Rt 2.52 min (Purity: 93.5%).

Step 2: tert-butyl N-{4-[amino(hydroxyimino)methyl]-2-methoxybenzyl}-N-methylglycinate The title compound was prepared following the general procedure 2, starting from tert-butyl N-(4-cyano-2-methoxybenzyl)-N-methylglycinate (1.0 g, 3.4 mmol). It was isolated as a yellow oil (860 mg, 77%). $^1$H NMR (DMSO-$d_6$, 300 MHz) δ 9.58 (s, 1H), 7.31-7.23 (m, 3H), 5.81 (s, 2H), 3.79 (s, 3H), 3.63 (s, 2H), 3.14 (s, 2H), 2.26 (s, 3H), 1.42 (s, 9H). LC/MS (Method B): 324.0 (M+H)$^+$. HPLC (Method A) Rt 1.49 min (Purity: 88.6%).

Intermediate 45: tert-butyl N-{4-[amino(hydroxyimino)methyl]-2-fluorobenzyl}-N-(tert-butoxycarbonyl)glycinate

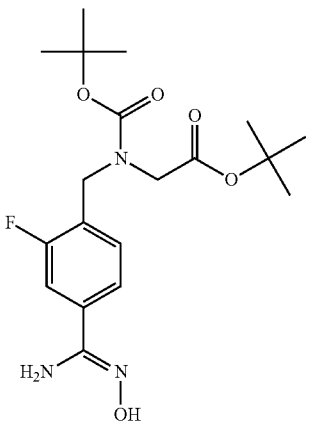 [SMILES: CC(C)(C)OC(=O)CN(Cc1ccc(/C(N)=N/O)cc1F)C(=O)OC(C)(C)C]

Step 1: tert-butyl N-(4-cyano-2-fluorobenzyl)glycinate

The title compound was prepared following the general procedure 10, starting from 4-cyano-2-fluorobenzyl bromide (Fluorochem) and tert-butyl glycinate. It was isolated as a yellow oil (1.8 g, 74%). $^1$H NMR (DMSO-$d_6$, 300 MHz) δ 7.82-7.77 (m, 1H), 7.71-7.63 (m, 2H), 3.82 (s, 2H), 3.22 (s, 2H), 2.58 (br s, 1H), 1.40 (s, 9H). LC/MS (Method B): 265.0 (M+H)$^+$. HPLC (Method A) Rt 2.23 min (Purity: 98.0%).

Step 2: tert-butyl N-(tert-butoxycarbonyl)-N-(4-cyano-2-fluorobenzyl)glycinate To a solution of tert-butyl N-(4-cyano-2-fluorobenzyl)glycinate (1.8 g, 6.8 mmol) and di-tert-butyl dicarbonate (1.6 g, 7.5 mmol) in DCM (36 mL) was added N-ethyldiisopropylamine (1.7 mL, 10.2 mmol). The resulting mixture was stirred at RT for 3.5 hours. The reaction mixture was diluted with DCM and washed with a saturated aqueous solution of NaHCO$_3$ (2×) and brine. The organic layer was dried (MgSO$_4$) and concentrated to give the title compound as a yellowish oil (2.1 g, 85%). $^1$H NMR (DMSO-$d_6$, 300 MHz) δ 7.84 (m, 1H), 7.71 (m, 1H), 7.58 (m, 1H), 4.52-4.48 (m, 2H), 3.95-3.87 (m, 2H), 1.48-1.31 (m, 18H). LC/MS (Method B): 365.1 (M+H)$^+$. HPLC (Method A) Rt 5.20 min (Purity: 97.1%).

Step 3: tert-butyl N-{4-[amino(hydroxyimino)methyl]-2-fluorobenzyl}-N-(tert-butoxycarbonyl)glycinate The title compound was prepared following the general procedure 2, starting from tert-butyl N-(tert-butoxycarbonyl)-N-(4-cyano-2-fluorobenzyl)glycinate (2.1 g, 5.8 mmol). It was isolated as a yellow oil (1.7 g, 74%). $^1$H NMR (DMSO-$d_6$, 300 MHz) δ 9.76 (s, 1H), 7.54-7.31 (m, 3H), 5.88 (s, 2H), 4.44 (s, 2H), 3.89-3.81 (m, 2H), 1.40-1.35 (m, 18H). LC/MS (Method B): 396.2 (M−H)$^-$, 398.0 (M+H)$^+$. HPLC (Method A) Rt 3.39 min (Purity: 95.6%).

Intermediate 46: 5'-fluoro-2-(methoxymethyl)-2'-methylbiphenyl-4-carboxylic acid

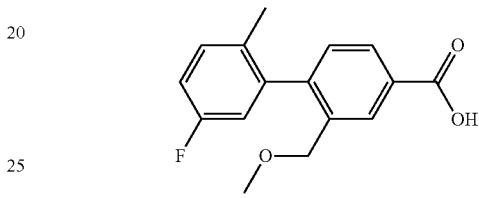

Step 1: methyl 5'-fluoro-2-(methoxymethyl)-2'-methylbiphenyl-4-carboxylate

A mixture of methyl 4-bromo-3-(methoxymethyl)benzoate (Intermediate 1, Step 2, 3.00 g, 11.6 mmol), 5-fluoro-2-methylphenylboronic acid (2.67 g, 17.4 mmol), bis(triphenylphosphine)palladium(II) chloride (162 mg, 0.23 mmol) and cesium fluoride (5.28 g, 34.7 mmol) was prepared in dioxane (30 mL) and water (12 mL) under nitrogen atmosphere. The reaction mixture was heated at 90° C. for 3 hours. The reaction mixture was cooled at RT, diluted with MTBE (150 mL) and the layers were separated. The organic layer was washed with brine (50 mL). The aqueous layers were extracted with MTBE (100 mL). The organic layers were combined, dried over MgSO$_4$ and concentrated under reduced pressure. After purification by flash chromatography (silica, EtOAc/heptane), the title compound was obtained as a colorless oil (2.88 g, 86%). HPLC (Method A), Rt 5.0 min (purity: 98.7%). LC/MS (Method B): 288.9 (M+H)$^+$.

Step 2: 5'-fluoro-2-(methoxymethyl)-2'-methylbiphenyl-4-carboxylic acid

A 5N aqueous solution of NaOH (3 mL, 15 mmol) was added into a solution of methyl 5'-fluoro-2-(methoxymethyl)-2'-methylbiphenyl-4-carboxylate (2.88 g, 10.0 mmol) in EtOH (30 mL) and stirred at 60° C. for 1 hour. The reaction mixture was concentrated under vacuum. The residue was taken up with MTBE (100 mL), water (50 mL) and a 5N aqueous solution of HCl (4 mL). The layers were separated. The organic layer was washed with water (50 mL) and brine (50 mL). The aqueous layers were extracted with MTBE (50 mL). The organic layers were combined, dried (MgSO$_4$) and concentrated under vacuum. After purification by crystallization from a mixture of MTBE and heptane, the title compound was obtained as a white powder (2.31 g, 84%). HPLC (Method A) Rt 3.9 min (Purity: 100%). LC/MS (Method B): 273.1 (M−H)$^-$. $^1$H NMR (DMSO-$d_6$, 300 MHz) δ 13.05 (s, 1H), 8.09 (d, J=1.7 Hz, 1H), 7.92 (dd, J=7.9, 1.7 Hz, 1H), 7.36

(dd, J=8.5, 6.0 Hz, 1H), 7.26 (d, J=7.9 Hz, 1H), 7.16 (m, 1H), 6.98 (dd, J=9.5, 2.8 Hz, 1H), 4.16 (d, J=12.5 Hz, 1H), 4.10 (d, J=12.5 Hz, 1H), 3.19 (s, 3H), 1.95 (s, 3H).

Intermediate 48: 2-ethoxy-2'-methyl-1,1'-biphenyl-4-carboxylic acid

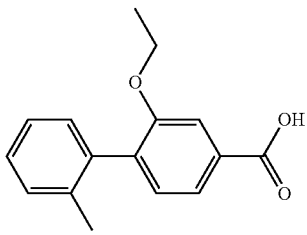 [SMILES: CCOc1cc(C(=O)O)ccc1-c1ccccc1C]

Step 1: methyl 2-hydroxy-2'-methyl-1,1'-biphenyl-4-carboxylate

A mixture of methyl 4-bromo-3-hydroxybenzoate (CombiBlocks, 25 g, 108 mmol), o-tolylboronic acid (22 g, 162 mmol), anhydrous potassium carbonate (44 g, 324 mmol) and Pd(PPh$_3$)$_4$ (6.25 g, 5.4 mmol) was prepared in a mixture of toluene (500 mL) and water (100 mL), and then degassed with N$_2$. The reaction mixture was heated at 110° C. for 12 hours. The reaction mixture was cooled at RT, filtered through a Celite pad and washed with a 10% aqueous solution of NaHCO$_3$, water and brine. The organic layer was dried (Na$_2$SO$_4$) and concentrated under vacuum. The residue was purified by chromatography (silica, pet ether/EtOAc) affording of the title compound as pale yellow solid (20 g, 77%). $^1$H-NMR (DMSO-d$_6$, 400 MHz) δ 9.85 (s, 1H), 7.52 (s, 1H), 7.45 (d, 1H), 7.20-7.25, (m, 3H), 7.15 (d, 1H), 7.10 (d, 1H), 3.84 (s, 3H), 2.09 (s, 3H).

Step 2: methyl 2-ethoxy-2'-methyl-1,1'-biphenyl-4-carboxylate

To a stirred solution of methyl 2-hydroxy-2'-methyl-1,1'-biphenyl-4-carboxylate (10 g, 41.2 mmol) in anhydrous ACN (100 mL) was added anhydrous potassium carbonate (17.1 g, 123.6 mmol) followed by ethyl bromide (15.4 mL, 206 mmol). The reaction mixture was heated at 50° C. for 48 hours, and then cooled to RT and filtered. The filtrate was concentrated under vacuum affording of the title compound as brown liquid (11 g, 98%). $^1$H-NMR (DMSO-d$_6$, 400 MHz) δ 7.70 (d, 1H), 7.62 (s, 1H), 7.16-7.29 (m, 5H), 4.09 (q, 2H), 3.95 (s, 3H), 2.15 (s, 3H), 1.30 (t, 3H).

Step 3: 2-ethoxy-2'-methyl-1,1'-biphenyl-4-carboxylic acid

To a stirred solution of methyl 2-ethoxy-2'-methyl-1,1'-biphenyl-4-carboxylate (11 g, 40.6 mmol) in a mixture of THF (100 mL) and water (10 mL) was added lithium hydroxide (6.82 g, 162.7 mmol) in portions. After 24 hours at RT, the reaction mixture was evaporated and the residue was taken up with water. The aqueous layer was acidified with a concentrated aqueous solution of HCl and extracted with EtOAc. The organic layer was washed with brine, dried (Na$_2$SO$_4$) and concentrated under vacuum affording of the title compound as pale yellow solid (9.7 g, 93%). LC/MS (Method B): 255.0 (M−H)$^−$. $^1$H-NMR (DMSO-d$_6$, 400 MHz) δ 13.02 (br s, 1H), 7.57 (m, 2H), 7.18-7.25 (m, 4H), 7.09 (d, 1H), 4.05 (q, 2H), 2.05 (s, 3H), 1.18 (t, 3H).

Intermediate 49: 2-ethoxy-2'-ethylbiphenyl-4-carboxylic acid

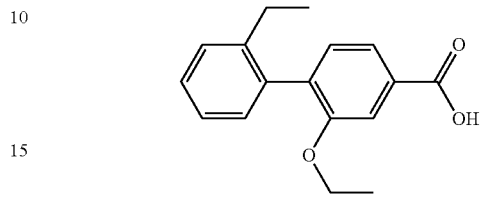

Step 1: methyl 2'-ethyl-2-hydroxybiphenyl-4-carboxylate

A mixture of methyl 4-bromo-3-hydroxybenzoate (Combi-Blocks CA-4189, 3.00 g, 13.0 mmol), 2-ethylphenylboronic acid (2.92 g, 19.5 mmol), cesium fluoride (5.92 g, 39.0 mmol; 3.00), palladium acetate (58 mg, 0.26 mmol) and 2-dicyclohexylphosphino-2',6'-dimethoxybiphenyl (320 mg, 0.78 mmol) was prepared in dioxane (30 mL) and water (15 mL) and heated at 90° C. for 2 hours. Additional amounts of 2-ethylphenylboronic acid (1.46 g, 9.7 mmol), palladium acetate (58 mg, 0.26 mmol) and 2-dicyclohexylphosphino-2',6'-dimethoxybiphenyl (320 mg, 0.78 mmol) were added, and the mixture was stirred for 2 additional hours. Additional amounts of 2-ethylphenylboronic acid (0.73 g, 4.9 mmol), palladium acetate (29 mg, 0.13 mmol) and 2-dicyclohexylphosphino-2',6'-dimethoxybiphenyl (160 mg, 0.39 mmol) were added, and the mixture was stirred for 2 additional hours. The reaction mixture was diluted with MTBE (150 mL), and then washed with water (50 mL) and brine (50 mL). The aqueous layers were extracted with MTBE (75 mL). The organic layers were combined, dried (MgSO$_4$) and concentrated under vacuum. After purification by flash chromatography (silica, heptane/EtOAc), the title compound was obtained as a yellow oil (3.13 g, 94%). HPLC (Method A) Rt 4.5 min (Purity: 99.2%). LC/MS (Method B): 255.1 (M−H)$^−$.

Step 2: methyl 2-ethoxy-2'-ethylbiphenyl-4-carboxylate

To a stirred solution of methyl 2'-ethyl-2-hydroxybiphenyl-4-carboxylate (3.13 g, 12.2 mmol) in anhydrous ACN (45 mL) was added anhydrous potassium carbonate (5.05 g, 36.6 mmol) followed by ethyl bromide (4.5 mL, 61 mmol). The reaction mixture was heated at 50° C. for 15 hours, and then cooled to RT and filtered. The filtrate was concentrated under vacuum. The oil was taken up with MTBE, treated with activated charcoal, filtered through a Celite pad and concentrated. After purification by flash chromatography (silica, heptane/EtOAc), the title compound was obtained as a colorless oil (2.73 g, 79%). HPLC (Method A) Rt 5.4 min (Purity: 99.7%).

Step 3: 2-ethoxy-2'-ethylbiphenyl-4-carboxylic acid

A 5N aqueous solution of NaOH (3 mL, 15 mmol) was added into a solution of methyl 2-ethoxy-2'-ethylbiphenyl-4-carboxylate (2.72 g, 9.6 mmol) in EtOH (30 mL). The resulting mixture was heated at 60° C. for 1 hour. The reaction mixture was concentrated under vacuum. The residue was taken up with water (50 mL) and a 5N aqueous solution of HCl (5 mL), and then extracted twice with MTBE (100 mL+50 mL). The organic layers were washed with brine (50 mL), combined, dried (MgSO$_4$) and concentrated under vacuum. After purification by crystallization from MTBE and heptane, the title compound was obtained as a white powder (2.04 g, 79%). HPLC (Method A) Rt 4.5 min (Purity: 100%). LC/MS (Method B): 269.1 (M−H)$^−$. $^1$H NMR (DMSO-d$_6$, 300 MHz) δ 13.00 (s, 1H), 7.58 (m, 2H), 7.30 (m, 2H), 7.22 (m, 2H), 7.06 (d, J=7.4 Hz, 1H), 4.05 (q, J=7.0 Hz, 2H), 2.45-2.32 (m, 2H), 1.17 (t, J=7.0 Hz, 3H), 0.97 (t, J=7.6 Hz, 3H).

Intermediate 53: 2,2'-dimethyl-1,1'-biphenyl-4-carboxylic acid

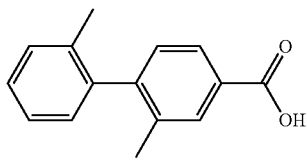 [SMILES: Cc1ccccc1-c1ccc(C(=O)O)cc1C]

Step 1: methyl 2,2'-dimethyl-1,1'-biphenyl-4-carboxylate

To a solution of methyl 4-bromo-3-methylbenzoate (ABCR, 15.0 g, 65 mmol) in toluene (200 mL) and water (200 mL), was added o-tolylboronic acid (10.7 g, 78 mmol) followed by potassium carbonate (45.3 g, 32.7 mmol) and tetrakis(triphenylphosphine)palladium(0) (3.78 g, 3.3 mmol). The mixture was degassed with N$_2$ and refluxed at 120° C. for 6 hours. After the completion of reaction, the reaction mixture was cooled to RT. The organic phase was separated and evaporated under reduced pressure. The crude compound was passed through a silica column using hexane as eluent to get the title compound as a white solid (15 g, 95%). $^1$H NMR (DMSO-d$_6$, 400 MHz) δ 7.91 (s, 1H), 7.82 (m, 1H), 7.32 (m, 2H), 7.27 (m, 1H), 7.24 (m, 1H), 7.06 (m, 1H), 3.84 (s, 3H), 2.09 (s, 3H), 1.95 (s, 3H). HPLC (Method B), Rt 3.01 min (purity: 98.71%).

Step 2: 2,2'-dimethyl-1,1'-biphenyl-4-carboxylic acid

To a solution of methyl 2,2'-dimethyl-1,1'-biphenyl-4-carboxylate (15 g, 62.2 mmol) in THF (100 mL) was added a 10% aqueous solution of sodium hydroxide (100 mL) and the mixture was heated at 100° C. overnight. THF was removed under reduced pressure and the aqueous residue was washed with EtOAc. The aqueous layer was then acidified with a 3N aqueous solution of HCl (until pH 2-3) and extracted with DCM. The organic phase was washed with water and dried over sodium sulfate and concentrated under reduced pressure to obtain get the title compound as a white solid (13.5 g, 95%). $^1$H NMR (DMSO-d$_6$, 400 MHz) δ 12.89 (bs, 1H), 7.89 (s, 1H), 7.81 (m, 1H), 7.32-7.23 (m, 3H), 7.19-7.11 (m, 1H), 7.06 (m, 1H), 2.04 (s, 3H), 1.98 (s, 3H). LC/MS (Method B): 227.0 (M+H)$^+$. HPLC (Method B), Rt 4.1 min (purity: 99.6%).

Intermediate 55: 2'-(difluoromethyl)-2-methylbiphenyl-4-carboxylic acid

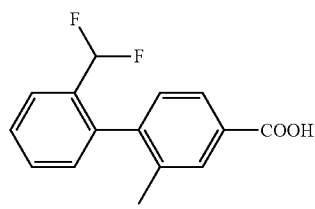 [SMILES: Cc1cc(C(=O)O)ccc1-c1ccccc1C(F)F]

Step 1: methyl 2'-(difluoromethyl)-2-methylbiphenyl-4-carboxylate

A mixture of methyl 3-methyl-4-(4,4,5,5-tetramethyl-1,3,2-dioxaborolan-2-yl)benzoate (Combiblocks PN-8756, 1.86 g, 6.74 mmol), 1-bromo-2-difluoromethyl-benzene (Fluorochem 023878, 1.67 g, 8.08 mmol), cesium fluoride (3.07 g, 20.2 mmol) and PdCl$_2$(PPh$_3$)$_2$ (142 mg, 0.20 mmol) was prepared in dioxane (20 mL) and water (10 mL) under nitrogen atmosphere. The resulting mixture was heated at 90° C. for 2 hours. The reaction mixture was diluted with MTBE (60 mL), and then washed with water (2×50 mL) and brine (50 mL). The aqueous layers were extracted with MTBE (50 mL). The organic layers were combined, dried (MgSO$_4$) and concentrated under reduced pressure. After purification by flash chromatography (silica, DCM/heptane), the title compound was obtained as a colorless oil (1.42 g, 76%). HPLC (Method A) Rt 5.0 min (purity: 99.1%). $^1$H NMR (DMSO-d$_6$, 300 MHz) δ 7.93 (s, 1H), 7.84 (dd, J=7.9, 1.4 Hz, 1H), 7.75 (m, 1H), 7.67-7.56 (m, 2H), 7.28 (m, 2H), 6.55 (t, J=54.7 Hz, 1H), 3.88 (s, 3H), 2.06 (s, 3H).

Step 2: 2'-(difluoromethyl)-2-methylbiphenyl-4-carboxylic acid

A 5 N aqueous solution of NaOH (1.5 mL, 7.5 mmol) was added into a solution of methyl 2% (difluoromethyl)-2-methylbiphenyl-4-carboxylate (1.42 g, 5.14 mmol) in EtOH (15 mL). The resulting mixture was heated at 70° C. for 1 hour, and then evaporated. The residue was taken up with water (25 mL) and a 5N aqueous solution of HCl (3 mL), and then extracted with MTBE (2×50 mL). The organic layers were washed with brine (25 mL), combined, dried (MgSO$_4$) and concentrated reduced pressure to give the title compound as a white powder (1.26 g, 93%). HPLC (Method A) Rt 4.2 min (purity: 98.9%). LC/MS (Method B): 261.1 (M−H)$^−$. $^1$H NMR (DMSO-d$_6$, 300 MHz) δ 13.1 (s, 1H), 7.90 (s, 1H), 7.82 (dd, J=7.9, 1.4 Hz, 1H), 7.74 (m, 1H), 7.66-7.55 (m, 2H), 7.26 (m, 2H), 6.55 (t, J=54.8 Hz, 1H), 2.05 (s, 3H).

Intermediate 58: tert-butyl N-{2-fluoro-3-[(hydroxyamino)(imino)methyl]benzyl}-N-methylglycinate

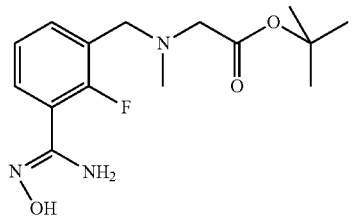 [SMILES: CN(CC(=O)OC(C)(C)C)Cc1cccc(/C(N)=N/O)c1F]

Step 1: 3-(bromomethyl)-2-fluorobenzonitrile

The title compound was prepared following the general procedure 13, starting from 2-fluoro-3-methylbenzonitrile (Matrix Scientific). It was obtained as an orange solid. HPLC (Method A) Rt 3.72 (Purity: 99.3%).

Step 2: tert-butyl N-{2-fluoro-3-[(hydroxyamino)(imino)methyl]benzyl}-N-methylglycinate Tert-butyl N-(3-cyano-2-fluorobenzyl)-N-methylglycinate was made following the general procedure 10, starting from 3-(bromomethyl)-2-fluorobenzonitrile and sarcosine tert-butyl ester hydrochloride. It was isolated as an oil (1.05 g, 88%). It was submitted to the general procedure 2, affording the title compound as a yellow oil (1 g, 85%). HPLC (Method A) Rt 1.09 (Purity: 92%).

Intermediate 59: tert-butyl N-{3-[amino(hydroxyimino)methyl]benzyl}-N-isopropyl-beta-alaninate

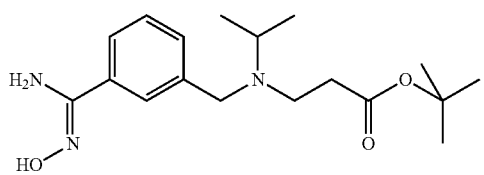 [SMILES: CC(C)N(CCC(=O)OC(C)(C)C)Cc1cccc(/C(N)=N/O)c1]

Step 1: 3-[(isopropylamino)methyl]benzonitrile

The title compound was prepared following general procedure 10, starting from 3-(bromomethyl)benzonitrile and isopropyl amine. It was isolated as a yellow liquid (5.7 g, 92%).
$^1$H NMR (DMSO-$d_6$, 400 MHz) δ 7.73 (s, 1H), 7.67 (d, J=7.7 Hz, 1H), 7.63 (d, J=7.8 Hz, 1H), 7.49 (m, 1H), 3.56 (s, 2H), 2.75 (m, 1H), 0.83 (d, J=8.8 Hz, 6H).

Step 2: tert-butyl N-(3-cyanobenzyl)-N-isopropyl-beta-alaninate

A mixture of 3-[(isopropylamino)methyl]benzonitrile (5.7 g, 32.7 mmol), tert-butyl acrylate (4.78 ml, 32.7 mmol) and DBU (5.0 ml, 32.7 mmol) was heated neat at 80° C. for 24 hours. The reaction mixture was diluted with water and extracted with DCM. The organic layer was dried over sodium sulfate and concentrated under reduced pressure. After purification by chromatography (silica, pet ether/EtOAc), the title compound was obtained as a colorless oil.
$^1$H NMR (DMSO-$d_6$, 400 MHz) δ 7.73 (s, 1H), 7.67 (d, J=7.7 Hz, 1H), 7.63 (d, J=7.8 Hz, 1H), 7.49 (t, J=7.7 Hz, 1H), 3.56 (s, 2H), 2.75 (m, 1H), 2.62 (t, J=6.5 Hz, 2H), 2.25 (t, J=6.4 Hz, 2H), 1.39 (s, 9H), 0.83 (d, J=8.8 Hz, 6H).

Step 3: tert-butyl N-{3-[amino(hydroxyimino)methyl]benzyl}-N-isopropyl-beta-alaninate The title compound was prepared following general procedure 2, starting from tert-butyl N-(3-cyanobenzyl)-N-isopropyl-beta-alaninate. It was obtained as a colorless oil (4.8 g, 90%). $^1$H NMR (DMSO-$d_6$, 400 MHz) δ 9.56 (s, 1H), 7.59 (s, 1H), 7.50 (d, J=7.6 Hz, 1H), 7.34 (d, J=7.6 Hz, 1H), 7.27 (m, 1H), 5.73 (s, 2H), 3.51 (s, 2H), 2.80 (m, 1H), 2.62 (t, J=6.8 Hz, 2H), 2.27 (t, J=6.8 Hz, 2H), 1.37 (s, 9H), 0.94 (d, J=6.6 Hz, 6H). LC/MS (Method A): 336.3 (M+H)$^+$. HPLC (Method A) Rt 2.19 min (Purity: 97.4%).

Intermediate 60: tert-butyl N-{5-[amino(hydroxyimino)methyl]-2-chlorobenzyl}-N-methylglycinate

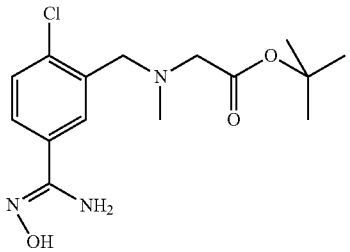 [SMILES: CN(CC(=O)OC(C)(C)C)Cc1cc(/C(N)=N/O)ccc1Cl]

Step 1: 3-(bromomethyl)-4-chlorobenzonitrile

The title compound was prepared following the general procedure 13, starting from 4-chloro-3-methylbenzonitrile (TransWorld Chemicals) and was isolated as a pale yellow powder (1.8 g, 59%). HPLC (Method A) Rt 4.05 (Purity: 97%).

Step 2: tert-butyl N-(2-chloro-5-cyanobenzyl)-N-methylglycinate

The title compound was prepared following general procedure 10, starting from 3-(bromomethyl)-4-chlorobenzonitrile and sarcosine tert-butyl ester hydrochloride. It was obtained as a colorless oil (1.9 g, 86%). LC/MS (Method B): 295.1 (M+H)$^+$.

Step 3: tert-butyl N-{5-[amino(hydroxyimino)methyl]-2-chlorobenzyl}-N-methylglycinate The title compound was prepared following general procedure 1, starting from tert-butyl N-(2-chloro-5-cyanobenzyl)-N-methylglycinate and was isolated as a colorless oil (1.55 g, 73%). LC/MS (Method B): 328.1 (M+H)$^+$.

Intermediate 61: tert-butyl 4-[{4-[amino(hydroxyimino)methyl]benzyl}(methyl)amino]butanoate

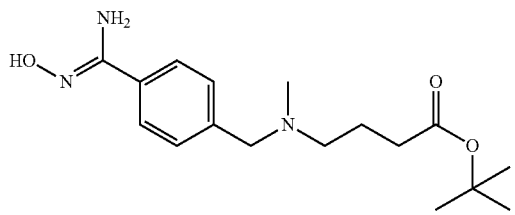 [SMILES: CN(CCCC(=O)OC(C)(C)C)Cc1ccc(/C(N)=N/O)cc1]

Step 1: tert-butyl 4-[(4-cyanobenzyl)(methyl)amino]butanoate

The title compound was prepared following general procedure 10, starting from 4-cyanobenzyl bromide and tert-butyl 4-(methylamino)butanoate hydrochloride (Watanabe). It was obtained as a yellow oil (586 mg, quantitative). LC/MS (Method B): 289.2 (M+H)$^+$. HPLC (Method A) Rt 3.02 (Purity: 91.8%).

Step 2: tert-butyl 4-[{4-[amino(hydroxyimino)methyl]benzyl}(methyl)amino]butanoate The title compound was prepared following general procedure 2, starting from tert-butyl 4-[(4-cyanobenzyl)(methyl)amino]butanoate and was isolated as an off-white solid (468 mg, 73%). HPLC (Method A) Rt 2.1 (Purity: 98.7%). LC/MS (Method B): 322.2 (M+H)$^+$.

Intermediate 62: 2'-chloro-3'-fluoro-2-(methoxymethyl)biphenyl-4-carboxylic acid

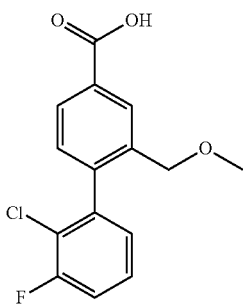 [SMILES: COCc1cc(C(=O)O)ccc1-c1cccc(F)c1Cl]

Step 1: methyl 2'-chloro-3'-fluoro-2-(methoxymethyl)biphenyl-4-carboxylate

A mixture of methyl 4-bromo-3-(methoxymethyl)benzoate (Intermediate 1, Step 2, 3.00 g, 11.6 mmol), 2-chloro-3-fluorophenylboronic acid (2.42 g, 13.9 mmol), cesium fluoride (5.27 g, 34.7 mmol), palladium acetate (52 mg, 0.23 mmol) and 2-dicyclohexylphosphino-2',6'-dimethoxybiphenyl (285 mg, 0.69 mmol) was prepared in dioxane (30 mL) and water (15 mL), and then heated at 90° C. for 1 hour. Additional amounts of 2-chloro-3-fluorophenylboronic acid (2.42 g, 13.9 mmol), palladium acetate (52 mg, 0.23 mmol) and 2-dicyclohexylphosphino-2',6'-dimethoxybiphenyl (285 mg, 0.69 mmol) were added, and then the resulting mixture was maintained at 90° C. for 1 additional hour. The reaction mixture was diluted with MTBE (200 mL) and washed with water (2×100 mL) and brine (100 mL). The aqueous layers were extracted with MTBE (100 mL). The organic layers were combined, dried (MgSO$_4$) and treated with activated charcoal. After filtration through a Celite pad, the solution was concentrated under vacuum. After purification by flash chromatography (silica, heptane/EtOAc), the title compound was obtained as a pale yellow oil. HPLC (Method A) Rt 4.9 min (Purity: 99.6%). LC/MS (Method B): 309.0 (M+H)$^+$.

Step 2: 2'-chloro-3'-fluoro-2-(methoxymethyl)biphenyl-4-carboxylic acid

A 5N aqueous solution of NaOH (2.3 mL, 11.5 mmol) was added into a solution of methyl 2'-chloro-3'-fluoro-2-(methoxymethyl)biphenyl-4-carboxylate (2.38 g, 7.7 mmol) in EtOH (25 mL) and heated at reflux for 30 minutes. The reaction mixture was concentrated under vacuum. The residue was taken up with water (30 mL) and a 5N aqueous solution of HCl (4 mL), and then extracted with MTBE (100 mL, then 50 mL). The organic layers were washed with brine, combined, dried (MgSO$_4$) and treated with activated charcoal. After filtration through a Celite pad, the solution was concentrated under vacuum. After purification by crystallization from a mixture of MTBE and heptane, the title compound was obtained as a white powder (2.01 g, 88%). HPLC (Method A) Rt 4.1 min (Purity: 99.5%). LC/MS (Method B): 293.0 (M−H)$^−$. $^1$H NMR (DMSO-d$_6$, 300 MHz) δ 13.13 (s, 1H), 8.10 (d, J=1.7 Hz, 1H), 7.94 (dd, J=8.0, 1.7 Hz, 1H), 7.54-7.44 (m, 2H), 7.33 (d, J=8.0 Hz, 1H), 7.23-7.18 (m, 1H), 4.23 (d, J=12.7 Hz, 1H), 4.15 (d, J=12.7 Hz, 1H), 3.17 (s, 3H).

Intermediate 63: tert-butyl N-{3-[amino(hydroxyimino)methyl]-4,5-difluorobenzyl}-N-methylglycinate

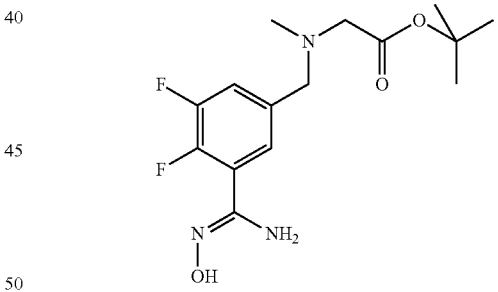

Step 1: 5-(bromomethyl)-2,3-difluorobenzonitrile

The title compound was prepared following the general procedure 13, starting from 2,3-difluoro-5-methylbenzonitrile (Capot Chemical Ltd) and was isolated as a colorless oil. HPLC (Method A) Rt 4.45 (Purity: 96.6%).

Step 2: tert-butyl N-(3-cyano-4,5-difluorobenzyl)-N-methylglycinate

The title compound was prepared following general procedure 10, starting from 5-(bromomethyl)-2,3-difluorobenzonitrile and tert-butyl N-methylglycinate hydrochloride. It was obtained as a yellow oil (618 mg, 88%). HPLC (Method A) Rt 2.75 (Purity: 97%).

Step 3: tert-butyl N-{3-[amino(hydroxyimino)methyl]-4,5-difluorobenzyl}-N-methylglycinate The title compound was prepared following general procedure 2, starting from tert-butyl N-(3-cyano-4,5-difluorobenzyl)-N-methylglycinate and was isolated as a colorless oil (630 mg, 93%). HPLC (Method A) Rt 1.61 (Purity: 59.6%).

Intermediate 65: tert-butyl 2-((3-chloro-4-(N'-hydroxycarbamimidoyl)benzyl)(methyl)amino)acetate

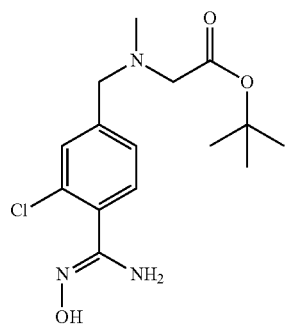 [SMILES: CN(CC(=O)OC(C)(C)C)Cc1ccc(/C(N)=N/O)c(Cl)c1]

Step 1: tert-butyl 2-((4-cyano-3-chlorobenzyl)(methyl)amino)acetate

A solution of 4-methyl-2-chlorobenzonitrile (1.51 g, 10 mmol), N-bromosuccinimide (2.14 g, 12.0 mmol) and AIBN (33 mg, 0.20 mmol) in ACN (40 mL) was heated under reflux for 18 hours. The reaction mixture was diluted with EtOAc and washed with a saturated aqueous solution of $Na_2CO_3$ and brine. The organic layer was dried ($MgSO_4$) and concentrated under vacuum. The residue was treated with sarcosine tert-butyl ester hydrochloride (1.44 g, 7.92 mmol) and $K_2CO_3$ (2.74 g, 19.8 mmol) in ACN (10 mL). The mixture was heated at 100° C. for 2 hours. The solvent was evaporated under vacuum. The residue was dissolved in a mixture of DCM and water and then poured through a hydrophobic frit. The solvent was evaporated under vacuum. The residue was purified by flash chromatography (silica, iso-hexane/$Et_2O$) to afford the title compound (1.95 g, quantitative). $^1$H NMR ($CDCl_3$, 400 MHz) δ 7.61 (1H, d, J=8.0 Hz), 7.57 (1H, s), 7.36 (1H, m), 3.73 (2H, s), 3.21 (2H, s), 2.36 (3H, s), 1.48 (9H, s).

Step 2: tert-butyl 2-((3-chloro-4-(N'-hydroxycarbamimidoyl)benzyl)(methyl)amino)acetate A solution of tert-butyl 2-((4-cyano-3-chlorobenzyl)(methyl)amino)acetate (1.95 g, 6.60 mmol) and 50% aqueous hydroxylamine (2.02 mL) in ethanol (10 mL) was heated at 80° C. for 5 hours. The solvent was evaporated in vacuo. The residue was partitioned between DCM and water. The organic phase was poured through a hydrophobic frit and evaporated in vacuo to afford the title compound (2.16 g, quantitative).

$^1$H NMR ($CDCl_3$, 400 MHz) δ 7.48-7.42 (2H, m), 7.28 (1H, m), 4.97 (2H, s), 3.69 (2H, s), 3.18 (2H, s), 2.37 (3H, s), 1.48 (9H, s).

Intermediate 66: N'-hydroxy-4-(hydroxymethyl)-3-methylbenzimidamide

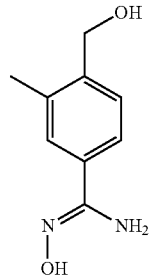

Step 1: (4-bromo-2-methylphenyl)methanol

To a solution of 4-bromo-2-methylbenzoic acid (1.0 g, 4.65 mmol) in $Et_2O$ (15 mL) was added lithium aluminiumhydride (370 mg, 10.23 mmol) and the mixture was stirred for 4 hours. The reaction mixture was diluted with water (100 mL) and extracted with EtOAc (4×100 mL). The combined organic fractions were dried ($MgSO_4$) and concentrated in vacuo. The residue was purified by flash chromatography (silica, petrol ether/EtOAc) to give the title compound as a colorless gum (752 mg, 80%). $^1$H NMR ($CDCl_3$, 400 MHz) δ 7.35-7.30 (2H, m), 7.24 (1H, m), 4.65 (2H, s), 2.32 (3H, s).

Step 2: 4-(hydroxymethyl)-3-methylbenzonitrile

A mixture of (4-bromo-2-methylphenyl)methanol (603 mg, 3.0 mmol), $Pd_2(dba)_3$ (110 mg, 0.12 mmol), S-Phos (99 mg, 0.24 mmol) and zinc cyanide (421 mg, 3.6 mmol) was prepared in a mixture of DMF/water (99:1, 5 mL) under nitrogen atmosphere and heated at 130° C. for 30 minutes under microwave irradiation. The suspension was filtered through a Celite pad and the filter-cake washed with EtOAc. The filtrate was washed with water and brine. The organic phase was passed through a hydrophobic frit and the solvent evaporated in vacuo. The residue was purified by flash chromatography (silica, petrol ether/EtOAc) to give the title compound. $^1$H NMR ($CDCl_3$, 400 MHz) δ 7.58-7.48 (2H, m), 7.44 (1H, s), 4.75 (2H, d, J=5.5 Hz), 2.33 (3H, s), 1.85-1.78 (1H, m).

Step 3: N'-hydroxy-4-(hydroxymethyl)-3-methylbenzimidamide

The amidoxime was prepared following the procedure 1, but starting from 4-(hydroxymethyl)-3-methylbenzonitrile. It was obtained as a white solid (741 mg, 71%). $^1$H NMR (DMSO-$d_6$, 400 MHz) δ 9.51 (1H, s), 7.46 (2H, m), 7.34 (1H, d, J=7.7 Hz), 5.72 (2H, s), 5.09 (1H, s), 4.50 (2H, s), 2.26 (3H, s).

Intermediate 67: tert-butyl N-{4-[amino(hydroxyimino)methyl]-2-ethylbenzyl}-N-methylglycinate

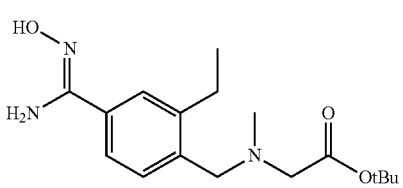 [SMILES: CCc1cc(/C(N)=N/O)ccc1CN(C)CC(=O)OC(C)(C)C]

Step 1: tert-butyl N-(4-cyano-2-vinylbenzyl)-N-methylglycinate

A mixture of tert-butyl N-(2-bromo-4-cyanobenzyl)-N-methylglycinate (Intermediate 33 Step 1, 658 mg, 1.94 mmol), vinyl boronic acid pinacol ester (597 mg, 3.88 mmol), $K_2CO_3$ (536 mg, 3.88 mmol) and tetrakis-triphenylphosphine palladium(0) (224 mg, 0.19 mmol) was prepared in a mixture of dioxane/water (5:1; 6 mL) and heated at 100° C. for 18 hours. The reaction mixture was diluted with DCM/water and separated. The organic phase was passed through a hydrophobic frit and the solvents evaporated in vacuo. The residue was purified by flash chromatography (silica, iso-hexane/EtOAc) to afford the title compound (508 mg, 92%). $^1$H NMR (CDCl$_3$, 400 MHz) δ 7.77 (1H, s), 7.58-7.43 (2H, m), 7.13 (1H, dd, J=17.4, 11.0 Hz), 5.69 (1H, d, J=17.4 Hz), 5.42 (1H, d, J=11.0 Hz), 3.80 (2H, s), 3.18 (2H, s), 2.36 (3H, s), 1.50 (9H, s).

Step 2: tert-butyl N-(4-cyano-2-ethylbenzyl)-N-methylglycinate

A mixture of tert-butyl N-(4-cyano-2-vinylbenzyl)-N-methylglycinate (500 mg, 1.75 mmol) and 10% palladium on carbon (50 mg) in methanol (5 mL) were stirred under an atmosphere of hydrogen for 18 hours. The suspension was filtered through a Celite pad and the filter-cake washed with DCM. The filtrate was evaporated in vacuo to afford the title compound (474 mg, 94%).

Step 3: tert-butyl N-{4-[amino(hydroxyimino)methyl]-2-ethylbenzyl}-N-methylglycinate A solution of tert-butyl N-(4-cyano-2-ethylbenzyl)-N-methylglycinate (570 mg, 1.98 mmol) and 50% aqueous hydroxylamine (0.6 mL, 10 mmol) in ethanol (10 mL) was heated at 80° C. for 18 hours. The solvent was evaporated in vacuo. The residue was partitioned between DCM and water. The organic phase was passed through a hydrophobic frit and evaporated in vacuo to afford the title compound (658 mg, quantitative). $^1$H NMR (CDCl$_3$, 400 MHz) δ 7.46 (1H, s), 7.39 (2H, s), 4.85 (2H, br s), 3.73 (2H, s), 3.16 (2H, s), 2.73 (2H, q, J=7.6 Hz), 2.37 (3H, s), 1.47 (9H, s), 1.25-1.19 (3H, m).

Intermediate 70: N'-hydroxy-3-(hydroxymethyl)benzimidamide

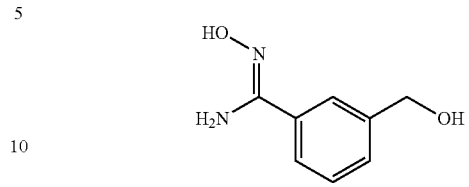

The title compound was prepared following the general procedure 1, but starting from 3-(hydroxymethyl)benzonitrile (8.43 g, 63.4 mmol). It was obtained as a white solid (9.15 g, 86%). $^1$H NMR (DMSO-d$_6$, 400 MHz) δ 9.63 (1H, s), 7.67 (1H, s), 7.56 (1H, m), 7.35 (2H, m), 5.82 (2H, s), 5.27 (1H, t, J=5.7 Hz), 4.54 (2H, d, J=5.7 Hz).

Intermediate 71: tert-butyl N-{4-[amino(hydroxyimino)methyl]benzyl}-N-(2-methoxyethyl)glycinate

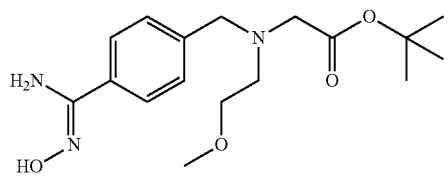 [SMILES: COCCN(CC(=O)OC(C)(C)C)Cc1ccc(/C(N)=N/O)cc1]

Step 1: 4-{[(2-methoxyethyl)amino]methyl}benzonitrile

2-Methoxyethylamine (2.2 mL, 25.5 mmol) was added into a solution of 4-cyanobenzyl bromide (1.0 g, 5.1 mmol) in ACN (10 mL) and the resulting mixture was stirred at RT for 1 hour. The reaction mixture was concentrated under vacuum. The crude product was dissolved in EtOAc, and then washed with a saturated aqueous solution of NaHCO$_3$ and brine, dried (MgSO$_4$) and concentrated under vacuum to give the title compound (958 mg, 99%). LC/MS (Method B): 191.0 (M+H)$^+$. HPLC (Method A) Rt 1.44 min (Purity: 93.4%).

Step 2: tert-butyl N-(4-cyanobenzyl)-N-(2-methoxyethyl)glycinate

Tert-butyl bromoacetate (1.64 mL, 11.1 mmol) was added into a mixture of 4-{[(2-methoxyethyl)amino]methyl}benzonitrile (958 mg, 5.04 mmol) and K$_2$CO$_3$ (3.06 g, 22.2 mmol) in ACN (20 mL). The resulting mixture was stirred at RT overnight. The reaction mixture was diluted with EtOAc, and then washed with water and brine, dried (MgSO$_4$) and concentrated under vacuum. The residue was purified by flash chromatography (silica, cHex/EtOAc) to give the title compound as a colorless oil. LC/MS (Method B): 305.1 (M+H)$^+$. HPLC (Method A) Rt 3.09 min (Purity: 91.1%).

Step 3: tert-butyl N-{4-[amino(hydroxyimino)methyl]benzyl}-N-(2-methoxyethyl)glycinate The title compound was prepared according the general procedure 1, starting from tert-butyl N-(4-cyanobenzyl)-N-(2-methoxyethyl)glycinate and was isolated as an oil. $^1$H NMR (DMSO-d$_6$, 400 MHz) δ 9.58 (br s, 1H), 7.61 (d, J=8.0 Hz, 1H), 7.29 (d, J=8.0 Hz, 1H), 5.78 (s, 2H), 3.77 (s, 2H), 3.44-3.36 (m, 2H), 3.25 (s, 2H), 3.20 (s, 3H), 2.79-2.71 (m, 2H), 1.42 (s, 9H). LC/MS (Method B): 338.2 (M+H)$^+$.

Intermediate 72: N'-hydroxy-4-(hydroxymethyl)benzenecarboximidamide

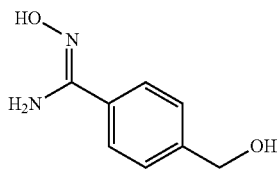 [SMILES: N/C(=N\O)c1ccc(CO)cc1]

The title compound was prepared according the general procedure 1, starting from 4-(hydroxymethyl)benzonitrile. It was obtained as a white solid (13.1 g, 95%). $^1$H NMR (DMSO-d$_6$, 400 MHz) δ 9.58 (1H, s), 7.66 (2H, m), 7.34 (2H, d, J=8.1 Hz), 5.79 (2H, s), 5.23 (1H, t, J=5.6 Hz), 4.54 (2H, d, J=5.6 Hz).

Intermediate 74: tert-butyl 2-((4-(N'-hydroxycarbamimidoyl)-2-(trifluoromethyl)benzyl)(methyl)amino)acetate

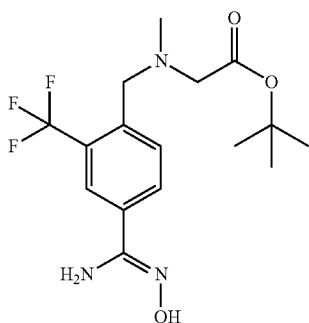 [SMILES: CN(CC(=O)OC(C)(C)C)Cc1ccc(/C(N)=N/O)cc1C(F)(F)F]

Step 1: tert-butyl 2-((4-cyano-2-(trifluoromethyl)benzyl)methyl)amino)acetate

A solution of 4-methyl-3-(trifluoromethyl)benzonitrile (1.85 g, 10 mmol), N-bromosuccinimide (2.14 g, 12.0 mmol) and AIBN (0.033 g, 0.2 mmol) in ACN (40 mL) was heated under reflux for 18 hours. The reaction mixture was diluted with EtOAc and water. The suspension was filtered and the filtrate was separated. The organic phase was washed with brine, dried (MgSO$_4$) and concentrated under vacuum. The residue was purified by flash chromatography (silica, iso-hexane/EtOAc). The material was treated with sarcosine tert-butyl ester hydrochloride (0.516 g, 2.84 mmol) and K$_2$CO$_3$ (0.980 g, 7.1 mmol) in ACN (10 mL). The mixture was heated at 70° C. for 18 hours. The solvent was evaporated under vacuum. The residue was dissolved in a mixture of DCM and water and then poured through a hydrophobic frit. The solvent was evaporated under vacuum. The residue was purified by flash chromatography (silica, iso-hexane/EtOAc) to afford the title compound (0.543 g, 70%). $^1$H NMR (CDCl$_3$, 400 MHz) δδ 8.15 (1H, d, J=8.2 Hz), 7.90 (1H, s), 7.83 (1H, d, J=8.2 Hz), 3.90 (2H, s), 3.26 (2H, s), 2.37 (3H, s), 1.48 (9H, s).

Step 2: tert-butyl 2-((4-(N'-hydroxycarbamimidoyl)-2-(trifluoromethyl)benzyl)(methyl)amino)acetate A solution of tert-butyl 2-((4-cyano-2-(trifluoromethyl)benzyl)(methyl)amino)acetate (0.541 g, 1.65 mmol) and 50% aqueous hydroxylamine (0.50 mL) in ethanol (2 mL) was heated at 75° C. for 2 hours. The solvent was evaporated in vacuo. The residue was partitioned between DCM and water. The organic phase was passed through a hydrophobic frit and evaporated in vacuo to afford the title compound (0.460 g, 77%). $^1$H NMR (CDCl$_3$, 400 MHz,) δ 7.97 (1H, d, J=8.1 Hz), 7.89 (1H, s), 7.78 (1H, d, J=8.1 Hz), 4.86 (2H, br s), 3.86 (2H, s), 3.23 (2H, s), 2.37 (3H, s), 1.48 (9H, s).

Intermediate 75: tert-butyl 2-((2-chloro-4-(N'-hydroxycarbamimidoyl)benzyl)(methyl)amino)acetate

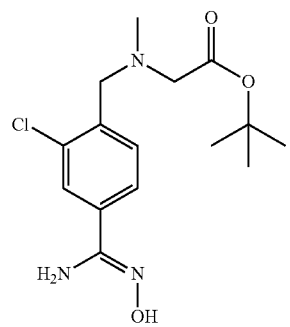 [SMILES: CN(CC(=O)OC(C)(C)C)Cc1ccc(/C(N)=N/O)cc1Cl]

Step 1: tert-butyl 2-((4-cyano-2-chlorobenzyl)(methyl)amino)acetate

A solution of 4-methyl-3-chlorobenzonitrile (4.69 g, 31 mmol), N-bromosuccinimide (6.04 g, 34.2 mmol) and benzoyl peroxide (0.750 g, 3.10 mmol) in ACN (20 mL) was heated under reflux for 18 hours. The reaction mixture was diluted with EtOAc and washed with a saturated aqueous solution of Na$_2$CO$_3$ and brine. The organic phase was dried (MgSO4) and concentrated under vacuum. A portion of the residue (1.0 g, 4.34 mmol) was treated with sarcosine tert-butyl ester hydrochloride (1.57 g, 8.69 mmol) and K$_2$CO$_3$ (2.39 g, 17.4 mmol) in dioxane (5 mL). The resulting mixture was heated at 100° C. for 2 hours, and then concentrated under vacuum. The residue was dissolved in a mixture of DCM and water, and then passed through a hydrophobic frit. The solvent was evaporated under vacuum to afford the title compound (0.952 g, 74%).

Step 2: tert-butyl 2-((2-chloro-4-(N'-hydroxycarbamimidoyl)benzyl)(methyl)amino)acetate A solution of tert-butyl 2-((4-cyano-2-chlorobenzyl)(methyl)amino)acetate (1.25 g, 4.25 mmol) and 50% aqueous hydroxylamine (1.30 mL) in ethanol (10 mL) was heated at 80° C. for 5 hours. The solvent was evaporated under vacuum. The residue was partitioned between DCM and water. The organic phase was passed through a hydrophobic frit and concentrated under vacuum to afford the title compound (1.34 g, 76%). $^1$H NMR (CDCl$_3$, 400 MHz) δ 7.63 (1H, d, J=1.8 Hz), 7.59 (1H, d, J=8.0 Hz), 7.50 (1H, dd, J=8.0, 1.8 Hz), 4.84 (2H, s), 3.83 (2H, s), 3.25 (2H, s), 2.42 (3H, s), 1.48 (9H, s).

Intermediate 76: tert-butyl 2-((2,6-difluoro-4-(N'-hydroxycarbamimidoyl)benzyl)(methyl)amino)acetate

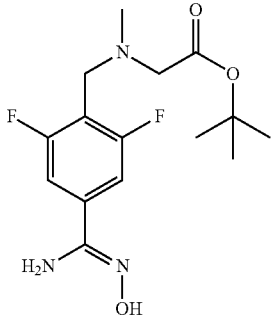 [SMILES: CN(CC(=O)OC(C)(C)C)Cc1c(F)cc(/C(N)=N/O)cc1F]

Step 1: tert-butyl 2-((4-cyano-2,6-difluorobenzyl)methyl)amino)acetate

To a degassed solution of 3,5-difluoro-4-methylbenzonitrile (1.53 g, 10 mmol) and AIBN (0.033 g; 0.20 mmol) in ACN (40 mL) was added N-bromo-succinimide (2.14 g, 12.0 mmol). The reaction mixture was heated at 90° C. for 24 hours. The solvent was evaporated in vacuo and the residue partitioned between water and DCM. The organic phase was passed through a hydrophobic frit and the solvent evaporated in vacuo. The residue was dissolved in CAN, and then sarcosine t-butyl ester hydrochloride (1.09 g, 6.0 mmol) and $K_2CO_3$ (2.07 g, 15 mmol) added. The reaction mixture was stirred at 70° C. for 18 hours. The suspension was filtered and the filtrate evaporated in vacuo. The residue was purified by flash chromatography (silica, iso-hexane/EtOAc) to afford the title compound. $^1$H NMR (CDCl$_3$, 400 MHz) δ 7.22 (2H, d, J=5.9 Hz), 3.94 (2H, s), 3.21 (2H, s), 2.41 (3H, s), 1.48 (9H, s).

Step 2: tert-butyl 2-((2,6-difluoro-4-(N'-hydroxycarbamimidoyl)benzyl)(methyl)amino)acetate A solution of tert-butyl 2-((4-cyano-2,6-difluorobenzyl)(methyl)amino)acetate (0.281 g, 0.95 mmol) and 50% aqueous hydroxylamine (0.32 mL) in ethanol (1.3 mL) was heated at 75° C. for 18 hours. The solvent was evaporated in vacuo. The residue was partitioned between EtOAc and water, and then the organic phase was passed through a hydrophobic frit. The solvent was evaporated in vacuo to afford the title compound. $^1$H NMR (CDCl$_3$, 400 MHz) δ 7.22-7.13 (2H, m), 4.81 (2H, br s), 3.91 (2H, s), 3.20 (2H, s), 2.40 (3H, s), 1.48 (9H, s).

Intermediate 77: 2-(1-methoxyethyl)-2'-methylbiphenyl-4-carboxylic acid

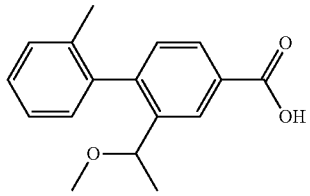 [SMILES: COC(C)c1cc(C(=O)O)ccc1-c1ccccc1C]

Step 1: 4-bromo-2'-methylbiphenyl-2-carbaldehyde

A mixture of 5-bromo-2-iodobenzaldehyde (3B Scientific Corp., 5.83 g, 18.8 mmol), o-tolylboronic acid (2.55 g, 18.8 mmol), cesium fluoride (8.55 g, 56.4 mmol) and bis(triphenylphosphine)palladium(II) chloride (263 mg, 0.38 mmol) was prepared in dioxane (60 mL) and water (25 mL) under nitrogen atmosphere and was heated at 50° C. for 16 hours. The reaction mixture was cooled at RT, diluted with MTBE (250 mL) and the layers were separated. The organic layer was washed with water (100 mL) and brine (100 mL). The aqueous layers were extracted with MTBE (150 mL). The organic layers were combined, dried (Na$_2$SO$_4$) and concentrated under vacuum. After purification by flash chromatography (silica, hexane/EtOAc), the title compound was obtained as a pale yellow solid (4.63 g, 90%). HPLC (Method A) Rt 5.6 min (Purity: 93%). $^1$H NMR (DMSO-d$_6$, 300 MHz) δ 9.57 (s, 1H), 8.02 (s, 1H), 7.94 (m, 1H), 7.39-7.27 (m, 4H), 7.20 (m, 1H), 2.06 (s, 3H).

Step 2: 1-(4-bromo-2'-methylbiphenyl-2-yl)ethyl methyl ether

A solution of methyllithium in Et$_2$O (1.6M, 6.8 mL, 10.9 mmol) was added dropwise into a solution of 4-bromo-2'-methylbiphenyl-2-carbaldehyde (2.0 g, 7.3 mmol) in anhydrous THF (30 mL) cooled at −78° C. under nitrogen atmosphere. The resulting mixture was stirred at −78° C. for 45 minutes and an additional amount of methyllithium in Et$_2$O (1.6M, 3.4 mL, 5.5 mmol) was added. After 10 minutes, iodomethane (4.1 ml, 65.4 mmol) was added. The cooling bath was removed and the reaction mixture was stirred at RT for 5 days. The reaction mixture was diluted with MTBE (100 mL), and then washed with water (2×50 mL) and brine (50 mL). The aqueous layers were extracted with MTBE (100 mL). The organic layers were combined, dried (MgSO$_4$) and concentrated under vacuum. After purification by flash chromatography (silica, heptane/MTBE), the title compound was obtained as a pale yellow oil (1.90 g, 86%). HPLC (Method A) Rt 5.7 min (Purity: 91%). $^1$H NMR (DMSO-d$_6$, 300 MHz) δ 7.62 (d, J=2.2 Hz, 0.4H), 7.59 (d, J=2.2 Hz, 0.6H), 7.52 (dd, J=8.1, 2.2 Hz, 1H), 7.35-7.21 (m, 3H), 7.13-7.02 (m, 2H), 4.05 (q, J=6.4 Hz, 0.4H), 3.84 (q, J=6.4 Hz, 0.6H), 3.05 (s, 1.2H), 3.03 (s, 1.8H), 2.03 (s, 1.8H), 1.98 (s, 1.2H), 1.17 (d, J=6.4 Hz, 1.8H), 1.11 (d, J=6.4 Hz, 1.2H).

Step 3: 2-(1-methoxyethyl)-2'-methylbiphenyl-4-carboxylic acid

A solution of tert-butyllithium in pentane (1.5M, 8.05 mL, 12.1 mmol) was added into anhydrous Et$_2$O (40 mL) cooled at −78° C. under nitrogen atmosphere. Then a solution of 1-(4-bromo-2'-methylbiphenyl-2-yl)ethyl methyl ether (1.84 g, 6.03 mmol) in anhydrous Et$_2$O (10 mL) was added dropwise over 10 minutes. The resulting mixture was stirred at −78° C. for 25 minutes, and then a large excess of dry ice was added and the cooling bath was removed. The reaction mixture was stirred until the temperature came back at RT, then diluted with water (20 ml) and a 5N aqueous solution of NaOH (0.5 mL). The layers were separated and the aqueous layer was washed with Et$_2$O (20 ml). The organic layers were extracted with a 0.1N aqueous solution of NaOH (20 mL). The combined aqueous layers were acidified with a 5N aqueous solution of HCl (until pH∼1) and extracted with MTBE (2×50 mL). The organic layers were washed with brine (30 mL), combined, dried (Na$_2$SO$_4$) and concentrated under vacuum to give a pale yellow solid. After crystallization from a mixture of Et$_2$O and heptane, the title compound was obtained as a white powder. HPLC (Method A) Rt 4.2 min (Purity: 98.2%). LC/MS (Method B): 269.1 (M−H)$^-$. $^1$H NMR (DMSO-d$_6$, 300 MHz) δ 13.03 (s, 1H), 8.09 (d, J=1.8

Hz, 0.4H), 8.07 (d, J=1.8 Hz, 0.6H), 7.89 (dd, J=7.9, 1.8 Hz, 1H), 7.36-7.24 (m, 3H), 7.22 (d, J=7.9 Hz, 0.4H), 7.20 (d, J=7.9 Hz, 0.6H), 7.13 (d, J=6.9 Hz, 0.4H), 7.07 (d, J=6.9 Hz, 0.6H), 4.12 (q, J=6.4 Hz, 0.4H), 3.92 (q, J=6.4 Hz, 0.6H), 3.05 (s, 1.2H), 3.04 (s, 1.8H), 2.03 (s, 1.8H), 1.98 (s, 1.2H), 1.19 (d, J=6.4 Hz, 1.8H), 1.13 (d, J=6.4 Hz, 1.2H).

Example 1

N-(3-{5-[2'-ethyl-2-(methoxymethyl)biphenyl-4-yl]-1,2,4-oxadiazol-3-yl}benzyl)-N-methyl-beta-alanine, hydrochloride salt

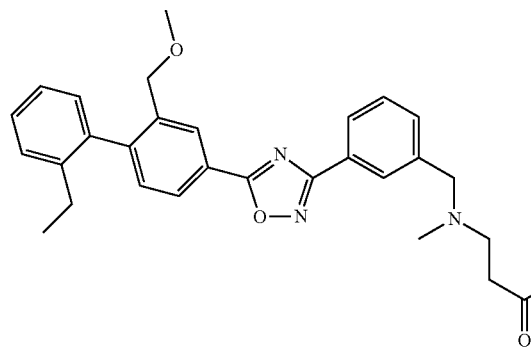

Tert-butyl N-(3-{5-[2'-ethyl-2-(methoxymethyl)biphenyl-4-yl]-1,2,4-oxadiazol-3-yl}benzyl)-N-methyl-beta-alaninate was prepared following the general procedure 3 starting from intermediate 7 and intermediate 16. It was hydrolyzed following the general procedure 8 affording the title compound as a slightly orange solid. $^1$H NMR (DMSO-$d_6$, 300 MHz) δ 12.75 (br s, 1H), 10.31 (br s, 1H), 8.36 (s, 1H), 8.34 (s, 1H), 8.22 (d, J=7.7 Hz, 1H), 8.17 (dd, J=7.9, 1.5 Hz, 1H), 7.86 (d, J=7.8 Hz, 1H), 7.73 (t, J=7.7 Hz, 1H), 7.46 (d, J=8.1 Hz, 1H), 7.42 (s, 1H), 7.40 (s, 1H), 7.33-7.27 (m, 1H), 7.12 (d, J=7.3 Hz, 1H), 4.50 (br s, 2H), 4.24 (d, J=12.8 Hz, 1H), 4.14 (d, J=12.9 Hz, 1H), 3.35 (br s, 2H), 3.27 (s, 3H), 2.87 (t, J=7.3 Hz, 2H), 2.71 (s, 3H), 2.46-2.23 (m, 2H), 1.00 (t, J=7.5 Hz, 3H). LC/MS (Method B): 484.5 (M−H)$^-$, 486.4 (M+H)$^+$. HPLC (Method A) Rt 4.31 min (Purity: 99.2%).

Example 2

N-(3-{5-[3-(methoxymethyl)-4-(2-methylpiperidin-1-yl)phenyl]-1,2,4-oxadiazol-3-yl}benzyl)-N-methyl-beta-alanine, hydrochloride salt

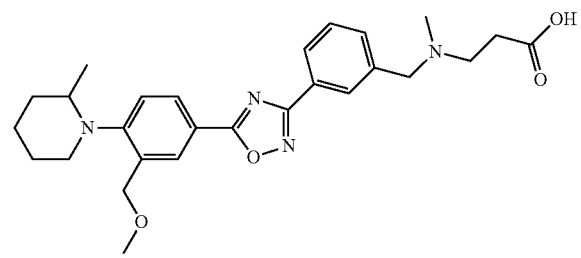 [SMILES: COCc1cc(-c2nc(-c3cccc(CN(C)CCC(=O)O)c3)no2)ccc1N1CCCCC1C]

Tert-butyl N-(3-{5-[3-(methoxymethyl)-4-(2-methylpiperidin-1-yl)phenyl]-1,2,4-oxadiazol-3-yl}benzyl)-N-methyl-beta-alaninate was prepared following the general procedure 3 starting from Intermediate 2 and Intermediate 16. It was hydrolyzed following general procedure 8 to afford the title compound as a white powder. $^1$H NMR (DMSO-$d_6$, 300 MHz) δ 8.18 (m, 1H), 8.07 (m, 1H), 8.02-7.95 (m, 2H), 7.54 (m, 2H), 7.38 (d, J=8.4 Hz, 1H), 4.56 (m, 2H), 3.62 (brs, 2H), 3.42 (s, 3H), 3.32 (m, 1H), 3.03 (m, 1H), 2.72-2.52 (m, 3H), 2.44 (m, 2H), 2.17 (s, 3H), 190-1.57 (m, 4H), 1.55-1.30 (m, 2H), 0.86 (d, J=6.2 Hz, 3H). LC/MS (Method B): 479.4 (M+H)$^+$, 477.5 (M−H)$^-$. HPLC (Method A) Rt 2.97 min (Purity: 100%).

Example 3

N-(2-fluoro-4-{5-[3-(methoxymethyl)-4-(2-methylpiperidin-1-yl)phenyl]-1,2,4-oxadiazol-3-yl}benzoyl)-beta-alanine

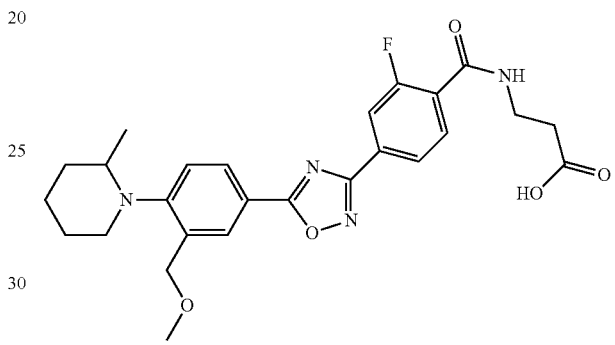

Ethyl N-(2-fluoro-4-{5-[3-(methoxymethyl)-4-(2-methylpiperidin-1-yl)phenyl]-1,2,4-oxadiazol-3-yl}benzoyl)-beta-alaninate was prepared following the general procedure 3 starting from Intermediate 2 and Intermediate 6. It was hydrolyzed following general procedure 9 to afford the title compound as a pale yellow powder. $^1$H NMR (DMSO-$d_6$, 300 MHz) δ 12.3 (brs, 1H), 8.56 (m, 1H), 8.18 (m, 1H), 8.06 (m, 1H), 7.97 (m, 1H), 7.90 (dd, J=8.0 Hz, 1H), 7.81 (t, 1H, J=7.6 Hz), 7.38 (d, J=8.5 Hz, 1H), 4.54 (m, 2H), 3.47 (m, 2H), 3.40 (s, 3H), 3.23 (m, 1H), 3.02 (m, 1H), 2.56-2.47 (m, 3H), 1.88-1.30 (m, 7H), 0.85 (d, J=6.2 Hz, 3H). LC/MS (Method B): 497.4 (M+H)$^1$, 495.4 (M−H)$^-$. HPLC (Method A) Rt 3.01 min (Purity: 97.2%).

Example 4

[(3-{5-[3-(methoxymethyl)-4-(2-methylpiperidin-1-yl)phenyl]-1,2,4-oxadiazol-3-yl}benzyl)oxy]acetic acid, hydrochloride salt

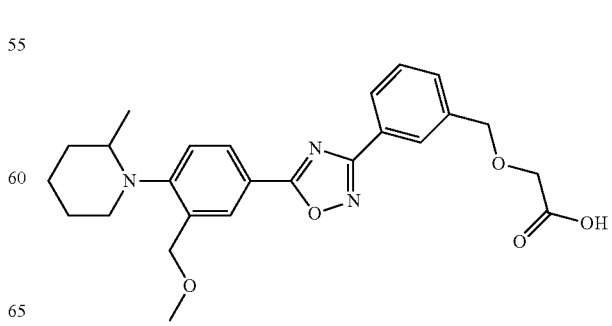

Tert-butyl [(3-{5-[3-(methoxymethyl)-4-(2-methylpiperidin-1-yl)phenyl]-1,2,4-oxadiazol-3-yl}benzyl)oxy]acetate was prepared following the general procedure 3 starting from Intermediate 2 and Intermediate 17. It was hydrolyzed following general procedure 8 to afford the title compound as a yellow powder. $^1$H NMR (DMSO-d$_6$, 300 MHz) δ 8.18 (m, 1H), 8.10 (m, 2H), 8.02 (m, 1H), 7.58 (m, 2H), 7.45 (d, J=8.4 Hz, 1H), 4.65 (s, 2H), 4.57 (s, 2H), 4.14 (s, 2H), 3.40 (s, 3H), 3.31 (m, 1H), 3.08 (m, 1H), 2.72 (m, 1H), 1.90-1.35 (m, 7H), 0.86 (d, J=6.2 Hz, 3H). LC/MS (Method B): 452.4 (M+H)$^+$, 450.4 (M−H)$^−$. HPLC (Method A) Rt 3.31 min (Purity: 94.6%).

Example 5

4-(2,3-difluoro-5-{5-[2-(methoxymethyl)-2'-methylbiphenyl-4-yl]-1,2,4-oxadiazol-3-yl}phenoxy)butanoic acid

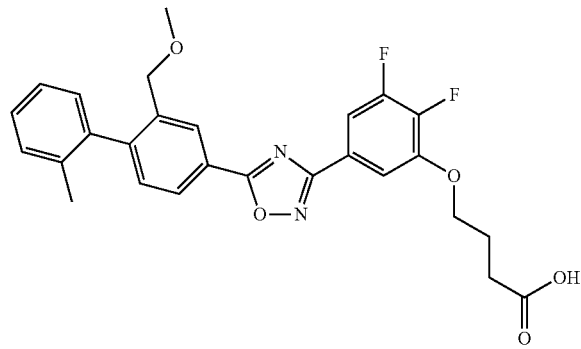 [SMILES: COCc1cc(-c2nc(-c3cc(F)c(F)c(OCCCC(=O)O)c3)no2)ccc1-c1ccccc1C]

Ethyl 4-(2,3-difluoro-5-{5-[2-(methoxymethyl)-2'-methylbiphenyl-4-yl]-1,2,4-oxadiazol-3-yl}phenoxy)butanoate was prepared following the general procedure 3 starting from intermediate 3 and intermediate 18. It was hydrolyzed following the general procedure 9 affording the title compound as a pale yellow powder. $^1$H NMR (DMSO-d$_6$, 300 MHz) δ 12.21 (br s, 1H), 8.32 (d, J=1.5 Hz, 1H), 8.18 (dd, J=7.9, 1.9 Hz, 1H), 7.74-7.65 (m, 2H), 7.43 (d, J=8.0 Hz, 1H), 7.37-7.27 (m, 3H), 7.15 (d, J=7.2 Hz, 1H), 4.27 (t, J=6.4 Hz, 2H), 4.20-4.14 (m, 2H), 3.25 (s, 3H), 2.44 (t, J=7.3 Hz, 2H), 2.08-1.99 (m, 5H). LC/MS (Method B): 493.3 (M−H)$^−$, 495.3 (M+H)$^+$. HPLC (Method A) Rt 5.79 min (Purity: 98.2%).

Example 6

1-(2-(methoxymethyl)-4-{3-[3-(methylsulfonyl)phenyl]-1,2,4-oxadiazol-5-yl}phenyl)-2-methylpiperidine, hydrochloride salt

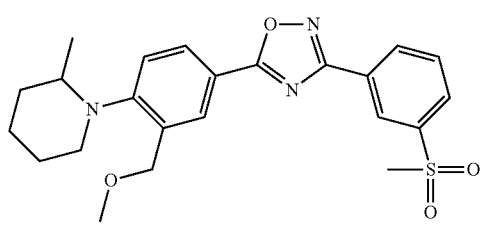 [SMILES: COCc1cc(-c2nc(-c3cccc(S(C)(=O)=O)c3)no2)ccc1N1CCCCC1C]

The title compound was prepared following the general procedure 3 starting from Intermediate 2 and Intermediate 19 and was isolated as a white powder. $^1$H NMR (DMSO-d$_6$, 300 MHz) δ 8.56 (t, J=1.3 Hz, 1H), 8.44 (dt, J=7.9, 1.3 Hz, 1H), 8.22-8.09 (m, 3H), 7.90 (t, J=7.9 Hz, 1H), 7.39 (d, J=8.0 Hz, 1H), 4.58 (d, J=12.8 Hz, 1H), 4.53 (d, J=12.8 Hz, 1H), 4.16 (bs, 1H), 3.42 (s, 3H), 3.34 (s, 3H), 3.24 (m, 1H), 3.04 (m, 1H), 2.64 (m, 1H), 1.84-1.30 (m, 6H), 0.86 (d, J=6.1 Hz, 3H). LC/MS (Method B): 442.3 (M+H)$^+$. HPLC (Method A) Rt 3.81 min (Purity: 99.3%).

Example 7

3-[(3-{5-[2-(methoxymethyl)-2'-methylbiphenyl-4-yl]-1,2,4-oxadiazol-3-yl}benzyl)oxy]propanoic acid

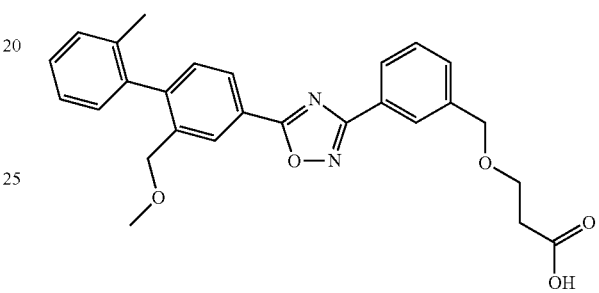

Tert-butyl 3-[(3-{5-[2-(methoxymethyl)-2'-methylbiphenyl-4-yl]-1,2,4-oxadiazol-3-yl}benzyl)oxy]propanoate was prepared following the general procedure 3 starting from intermediate 3 and Intermediate 20. It was hydrolyzed following general procedure 8 to afford the title compound as colorless oil.

$^1$H NMR (DMSO-d$_6$, 300 MHz) δ 12.25 (brs, 1H), 8.33 (m, 1H), 8.17 (dd, J=7.9 Hz, 1H), 8.06 (m, 2H), 7.59 (m, 2H), 7.43 (d, J=7.9 Hz, 1H), 7.36 (m, 2H), 7.30 (m, 1H), 7.15 (d, J=7.0 Hz, 1H), 4.62 (s, 2H), 4.20 (m, 2H), 3.71 (t, J=6.3 Hz, 2H), 3.25 (s, 3H), 2.55 (t, J=6.3 Hz, 2H), 2.04 (s, 3H). LC/MS (Method B): 459.3 (M+H)$^+$, 457.4 (M−H)$^−$. HPLC (Method A) Rt 5.62 min (Purity: 95.5%).

Example 8

N,N-dimethyl-1-(2'-methyl-4-{3-[3-(methylsulfonyl)phenyl]-1,2,4-oxadiazol-5-yl}biphenyl-2-yl)methanamine

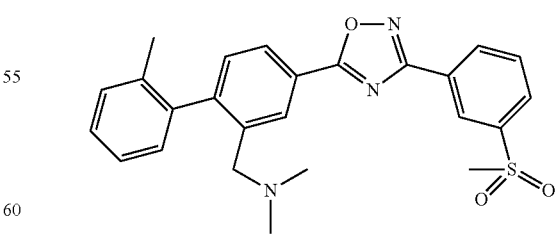

The title compound was prepared following the general procedure 3 starting from Intermediate 8 and Intermediate 19 and was isolated as a white powder. $^1$H NMR (DMSO-d$_6$, 300 MHz) δ 8.59 (t, J=1.7 Hz, 1H), 8.47 (m, 1H), 8.43 (d, J=1.6 Hz, 1H), 8.21 (m, 1H), 8.15 (dd, J=1.9, 7.9 Hz, 1H), 7.92 (t, J=7.9 Hz, 1H), 7.40 (d, J=8.0 Hz, 1H), 7.35-7.26 (m, 3H), 7.11 (d, J=7.1 Hz, 1H), 3.35 (s, 3H), 3.19 (brs, 2H), 2.09 (s, 6H), 2.02 (s, 3H). LC/MS (Method B): 448.3 (M+H)⁺. HPLC (Method A) Rt 3.51 min (Purity: 98.5%).

Example 9

3-[4(3-{5-[3-(methoxymethyl)-4-(2-methylpiperidin-1-yl)phenyl]-1,2,4-oxadiazol-3-yl}benzyl)oxy]propanoic acid, hydrochloride salt

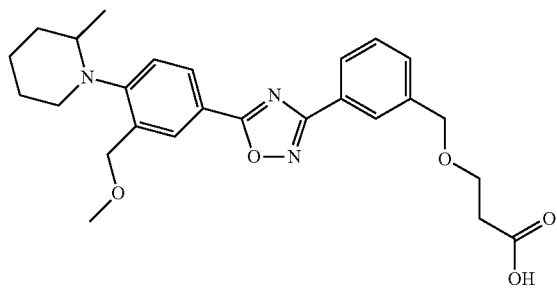 [SMILES: COCc1cc(-c2nc(-c3cccc(COCCC(=O)O)c3)no2)ccc1N1CCCCC1C]

Tert-butyl 3-[(3-{5-[3-(methoxymethyl)-4-(2-methylpiperidin-1-yl)phenyl]-1,2,4-oxadiazol-3-yl}benzyl)oxy]propanoate was prepared following the general procedure 3 starting from Intermediate 2 and Intermediate 20. It was hydrolyzed following general procedure 8 to afford the title compound as a pale yellow powder. ¹H NMR (DMSO-d₆, 300 MHz) δ 8.19 (m, 1H), 8.06 (m, 3H), 7.57 (m, 2H), 7.39 (m, 1H), 4.60 (s, 2H), 4.57 (m, 2H), 3.70 (t, J=6.2 Hz, 2H), 3.42 (s, 3H), 3.24 (m, 1H), 3.03 (m, 1H), 2.63 (m, 1H), 2.54 (t, J=6.2 Hz, 2H), 1.85-1.30 (m, 6H), 0.86 (d, J=6.1 Hz, 3H). LC/MS (Method B): 466.4 (M+H)⁺, 464.4 (M–H)⁻. HPLC (Method A) Rt 3.30 min (Purity: 98.3%).

Example 10

N-(3-{5-[2'-fluoro-2-(methoxymethyl)biphenyl-4-yl]-1,2,4-oxadiazol-3-yl}benzyl)-N-methylolycine, hydrochloride salt

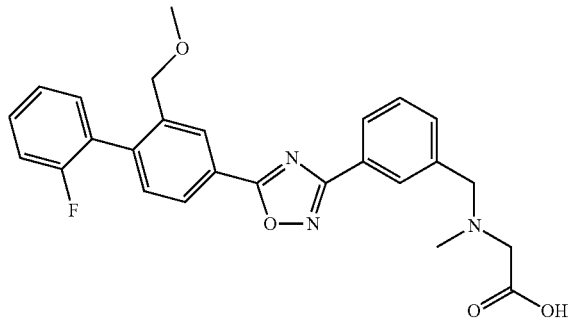 [SMILES: COCc1cc(-c2nc(-c3cccc(CN(C)CC(=O)O)c3)no2)ccc1-c1ccccc1F]

Tert-butyl N-(3-{5-[2'-fluoro-2-(methoxymethyl)biphenyl-4-yl]-1,2,4-oxadiazol-3-yl}benzyl)-N-methylglycinate was prepared following the general procedure 4 starting from intermediate 12 and intermediate 21. It was hydrolyzed following the general procedure 8 affording the title compound as a white powder. ¹H NMR (DMSO-d₆, 300 MHz) δ 8.33 (s, 2H), 8.23-8.18 (m, 2H), 7.78-7.68 (m, 2H), 7.58-7.49 (m, 2H), 7.43-7.32 (m, 3H), 4.47 (bs, 2H), 4.34 (s, 2H), 4.12 (s, 2H), 3.24 (s, 3H), 2.81 (s, 3H). LC/MS (Method B): 460.4 (M–H)⁻, 462.3 (M+H)⁺. HPLC (Method A) Rt 3.82 min (Purity: 96.0%).

Example 11

N-(3-{5-[2'-chloro-2-(methoxymethyl)biphenyl-4-yl]-1,2,4-oxadiazol-3-yl}benzyl)-N-methylglycine, hydrochloride salt

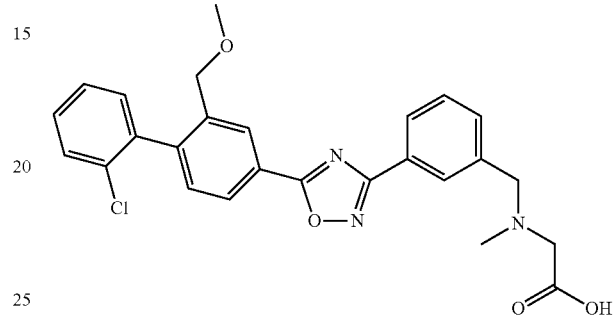

Tert-butyl N-(3-{5-[2'-chloro-2-(methoxymethyl)biphenyl-4-yl]-1,2,4-oxadiazol-3-yl}benzyl)-N-methylglycinate was prepared following the general procedure 4 starting from Intermediate 13 and Intermediate 21. It was hydrolyzed following the general procedure 8 affording the title compound as a white powder. ¹H NMR (DMSO-d₆, 300 MHz) δ 8.33 (s, 2H), 8.22 (m, 2H), 7.79-7.69 (m, 2H), 7.63 (m, 1H), 7.53-7.45 (m, 3H), 7.37 (m, 1H), 4.48 (s, 2H), 4.29 (d, J=13.1 Hz, 1H), 4.21 (d, J=13.1 Hz, 1H), 4.12 (s, 2H), 3.24 (s, 3H), 2.81 (s, 3H). LC/MS (Method B): 476.4 (M–H)⁻, 478.3 (M+H)⁺. HPLC (Method A) Rt 3.99 min (Purity: 98.4%).

Example 12

3-[(3-{5-[4-(2-methylpiperidin-1-yl)-3-(trifluoromethyl)phenyl]-1,2,4-oxadiazol-3-yl}benzyl)oxy]propanoic acid, hydrochloride salt

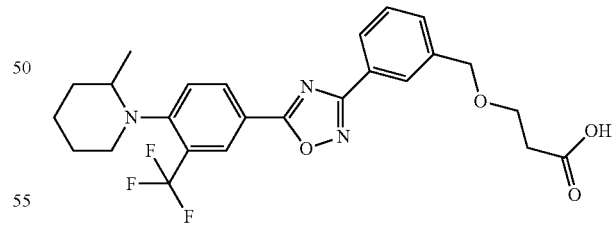

Tert-butyl 3-[(3-{5-[4-(2-methylpiperidin-1-yl)-3-(trifluoromethyl)phenyl]-1,2,4-oxadiazol-3-yl}benzyl)oxy]propanoate was prepared following the general procedure 3 starting from Intermediate 4 and Intermediate 20. It was hydrolyzed following general procedure 8 to afford the title compound as an oil. ¹H NMR (DMSO-d₆, 300 MHz) δ 12.22 (brs, 1H), 8.44 (d, J=8.4 Hz, 1H), 8.38 (m, 2H), 7.86 (d, J=8.5 Hz, 1H), 7.58 (m, 2H), 4.60 (s, 2H), 3.71 (t, J=6.3 Hz, 2H), 3.17 (m, 1H), 2.95 (m, 1H), 2.62 (m, 1H), 2.53 (t, J=6.3 Hz, 2H), 2.79 (m, 2H), 1.70-1.20 (m, 4H), 0.78 (d, J=6.0 Hz, 3H). LC/MS (Method B): 490.4 (M+H)+, 488.4 (M−H)−. HPLC (Method A) Rt 5.73 min (Purity: 96.4%).

Example 13

N-methyl-N-(3-{5-[4-(2-methylpiperidin-1-yl)-3-(trifluoromethyl)phenyl]-1,2,4-oxadiazol-3-yl}benzyl)glycine

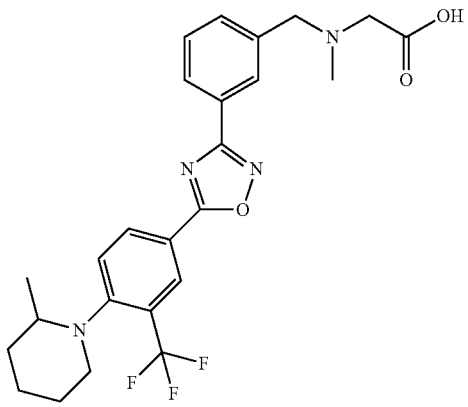 [SMILES: CC1CCCCN1c1ccc(-c2nc(-c3cccc(CN(C)CC(=O)O)c3)no2)cc1C(F)(F)F]

Tert-butyl N-methyl-N-(3-{5-[4-(2-methylpiperidin-1-yl)-3-(trifluoromethyl)phenyl]-1,2,4-oxadiazol-3-yl}benzyl)glycinate was prepared following the general procedure 7 starting from Intermediate 21 and Intermediate 4. It was hydrolyzed following procedure 8, affording the title compound as a white powder. $^1$H NMR (DMSO-d$_6$, 300 MHz) δ 8.50-8.37 (m, 2H), 8.32 (br s, 1H), 8.21 (d, J=7.4 Hz, 1H), 7.88 (d, J=8.6 Hz, 1H), 7.82-7.67 (m, 2H), 4.47 (s, 2H), 4.09 (s, 2H), 3.18 (m, 1H), 3.03-2.91 (m, 1H), 2.80 (s, 3H), 2.69-2.57 (m, 1H). 1.89-1.16 (m, 6H), 0.79 (d, J=6.1 Hz, 3H). LC/MS (Method B): 487.4 (M−H)−, 489.4 (M+H)+. HPLC (Method A) Rt 5.10 min (Purity: 100%).

Example 15

N-(2-chloro-4-{5-[2-(methoxymethyl)-2'-methylbiphenyl-4-yl]-1,2,4-oxadiazol-3-yl}benzoyl)-beta-alanine

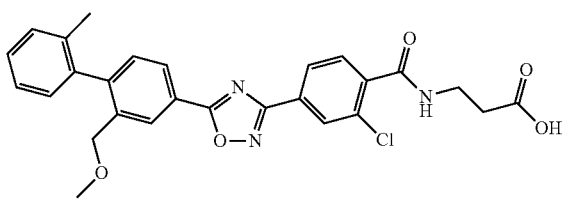 [SMILES: COCc1cc(-c2nc(-c3ccc(C(=O)NCCC(=O)O)c(Cl)c3)no2)ccc1-c1ccccc1C]

Step 1: 2-chloro-4-{5-[2-(methoxymethyl)-2'-methylbiphenyl-4-yl]-1,2,4-oxadiazol-3-yl}benzoic acid Methyl 2-chloro-4-{5-[2-(methoxymethyl)-2'-methylbiphenyl-4-yl]-1,2,4-oxadiazol-3-yl}benzoate was prepared following the general procedure 7 starting from Intermediate 3 and Intermediate 34. It was then hydrolysed following procedure 9, affording the title compound as a white powder. $^1$H NMR (DMSO-d$_6$, 300 MHz) δ 13.77 (br s, 1H), 8.34 (d, J=1.5 Hz, 1H), 8.20-8.15 (m, 3H), 8.02 (d, J=7.9 Hz, 1H), 7.43 (d, J=7.9 Hz, 1H), 7.37-7.27 (m, 3H), 7.15 (d, J=7.2 Hz, 1H), 4.25-4.14 (m, 2H), 3.25 (s, 3H), 2.04 (s, 3H). LC/MS (Method B): 433.2 (M−H)−, 435.2 (M+H)+. HPLC (Method A) Rt 5.35 min (Purity: 98.5%). CHN analysis: [C$_{24}$H$_{19}$N$_2$O$_4$Cl] Calculated: C, 66.29%; H, 4.40%; N, 6.44%; Cl, 8.15%. Found: C, 66.04%; H, 4.52%; N, 6.49%; Cl, 8.23%.

Step 2: N-(2-chloro-4-{5-[2-(methoxymethyl)-2'-methylbiphenyl-4-yl]-1,2,4-oxadiazol-3-yl}benzoyl)-beta-alanine Methyl N-(2-chloro-4-{5-[2-(methoxymethyl)-2'-methylbiphenyl-4-yl]-1,2,4-oxadiazol-3-yl}benzoyl)-beta-alaninate was prepared following the general procedure 14, starting from 2-chloro-4-{5-[2-(methoxymethyl)-2'-methylbiphenyl-4-yl]-1,2,4-oxadiazol-3-yl}benzoic acid and beta-alanine methyl ester hydrochloride. It was hydrolyzed following general procedure 9, to afford the title compound as a white foam. $^1$H NMR (DMSO-d$_6$, 300 MHz) δ 12.25 (brs, 1H), 8.71 (m, 1H), 8.34 (m, 1H), 8.22-8.08 (m, 3H), 7.64 (d, J=7.8 Hz, 1H), 7.44 (d, 7.9 Hz, 1H), 7.40-7.25 (m, 3H), 7.15 (m, 1H), 4.19 (m, 2H), 3.44 (m, 2H), 3.25 (s, 3H), 2.53 (m, 2H), 2.04 (s, 3H). LC/MS (Method B): 506.4 (M+H)+, 504.4 (M−H)−. HPLC (Method B) Rt 5.16 min (Purity: 97.9%).

Example 16

N-(4-{5-[2'-ethyl-2-(methoxymethyl)biphenyl-4-yl]-1,2,4-oxadiazol-3-yl}-2-fluorobenzoyl)-beta-alanine

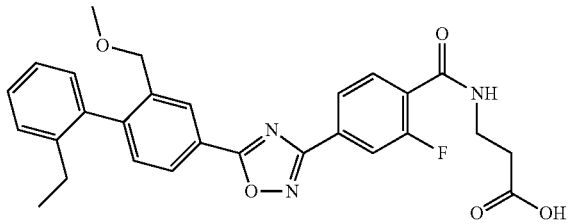 [SMILES: CCc1ccccc1-c1ccc(-c2nc(-c3ccc(C(=O)NCCC(=O)O)c(F)c3)no2)cc1COC]

Ethyl N-(4-{5-[2'-ethyl-2-(methoxymethyl)biphenyl-4-yl]-1,2,4-oxadiazol-3-yl}-2-fluorobenzoyl)-beta-alaninate was prepared following the general procedure 3 starting from Intermediate 7 and Intermediate 6. It was hydrolysed following the general procedure 9 affording the title compound as a white powder. $^1$H NMR (DMSO-d$_6$, 300 MHz) δ 12.31 (s, 1H), 8.61-8.55 (m, 1H), 8.33 (d, J=1.8 Hz, 1H), 8.17 (dd, J=7.9, 1.8 Hz, 1H), 8.03 (dd, J=8.0, 1.5 Hz, 1H), 7.95 (dd, J=10.7, 1.5 Hz, 1H), 7.84 (t, J=7.6 Hz, 1H), 7.45 (d, J=8.0 Hz, 1H), 7.41 (s, 1H), 7.39 (s, 1H), 7.34-7.26 (m, 1H), 7.12 (d, J=7.5 Hz, 1H), 4.23 (d, J=12.8 Hz, 1H), 4.14 (d, J=12.8 Hz, 1H), 3.49 (m, 2H), 3.25 (s, 3H), 2.53 (t, J=6.8 Hz, 2H), 2.47-2.19 (m, 2H), 0.99 (t, J=7.5 Hz, 3H). LC/MS (Method B): 502.4 (M−H)−, 504.4 (M+H)+. HPLC (Method A) Rt 5.03 min (Purity: 97.4%).

Example 17

N-(3-{5-[4-(2-ethylpiperidin-1-yl)-3-(methoxymethyl)phenyl]-1,2,4-oxadiazol-3-yl}benzyl)-N-methylglycine, hydrochloride salt

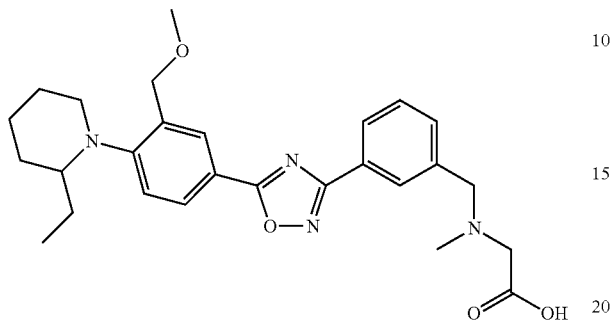

Tert-butyl N-(3-{5-[4-(2-ethylpiperidin-1-yl)-3-(methoxymethyl)phenyl]-1,2,4-oxadiazol-3-yl}benzyl)-N-methylglycinate was prepared following the general procedure 3 starting from Intermediate 9 and Intermediate 21. It was hydrolyzed following general procedure 8 to afford the title compound as a white powder. LC/MS (Method B): 479.4 (M+H)$^+$, 477.4 (M−H)$^−$. HPLC (Method A) Rt 2.74 min (Purity: 98.5%).

Example 18

N-(3-{5-[2'-ethyl-2-(methoxymethyl)biphenyl-4-yl]-1,2,4-oxadiazol-3-yl}benzyl)-beta-alanine, hydrochloride salt

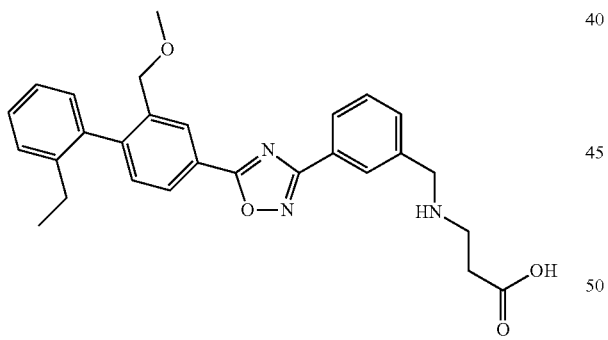

Tert-butyl N-(tert-butoxycarbonyl)-N-(3-{5-[2'-ethyl-2-(methoxymethyl) biphenyl-4-yl]-1,2,4-oxadiazol-3-yl}benzyl)-beta-alaninate was prepared following the general procedure 3 starting from Intermediate 7 and Intermediate 22. It was hydrolyzed following the general procedure 8 affording the title compound as a white solid. $^1$H NMR (DMSO-d$_6$, 300 MHz) δ 9.24 (s, 1H), 8.34 (s, 2H), 8.21-8.15 (m, 2H), 7.81 (d, J=7.7 Hz, 1H), 7.70 (t, J=7.7 Hz, 1H), 7.46 (d, J=8.0 Hz, 1H), 7.44-7.37 (m, 2H), 7.34-7.25 (m, 1H), 7.12 (d, J=7.5 Hz, 1H), 4.33 (s, 2H), 4.24 (d, J=12.9 Hz, 1H), 4.14 (d, J=12.9 Hz, 1H), 3.27 (s, 3H), 3.18 (t, J=7.3 Hz, 2H), 2.74 (t, J=7.2 Hz, 2H), 2.48-2.19 (m, 2H), 0.99 (t, J=7.5 Hz, 3H). LC/MS (Method B): 470.4 (M−H)$^−$, 472.4 (M+H)$^+$. HPLC (Method A) Rt 4.26 min (Purity: 99.1%).

Example 19

N-(2-fluoro-5-{5-[3-(methoxymethyl)-4-(2-methylpiperidin-1-yl)phenyl]-1,2,4-oxadiazol-3-yl}benzyl)-N-methyl-beta-alanine, dihydrochloride salt

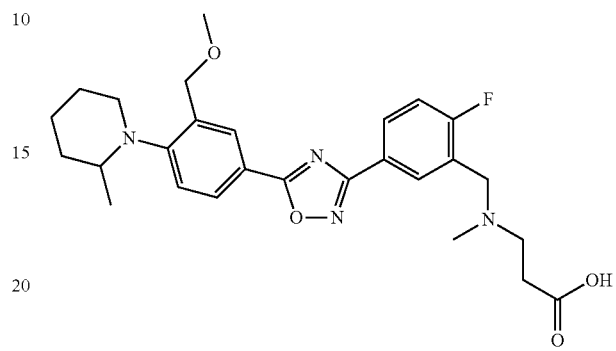

Tert-butyl N-(2-fluoro-5-{5-[3-(methoxymethyl)-4-(2-methylpiperidin-1-yl)phenyl]-1,2,4-oxadiazol-3-yl}benzyl)-N-methyl-beta-alaninate was prepared following the general procedure 3 starting from Intermediate 2 and Intermediate 23. It was hydrolyzed following the general procedure 8 affording the title compound as a pink solid. $^1$H NMR (DMSO-d$_6$, 300 MHz) δ 10.20 (s, 1H), 8.47 (dd, J=6.9, 2.2 Hz, 1H), 8.30-8.21 (m, 1H), 8.20 (d, J=2.2 Hz, 1H), 8.07 (dd, J=8.4, 2.2 Hz, 1H), 7.59 (t, J=9.1 Hz, 1H), 7.40 (d, J=8.7 Hz, 1H), 4.63-4.48 (m, 4H), 3.23 (s, 1H), 3.03 (s, 1H), 2.86 (t, J=7.4 Hz, 2H), 2.76 (s, 3H), 2.63 (s, 1H), 1.92-1.57 (m, 4H), 1.44 (s, 2H), 0.86 (d, J=6.1 Hz, 3H). LC/MS (Method B): 553.6 (M+H)$^+$. HPLC (Method A) Rt 2.55 min (Purity: 96.5%).

Example 20

N-(3-fluoro-5-{5-[2-(methoxymethyl)-2'-methylbiphenyl-4-yl]-1,2,4-oxadiazol-3-yl}benzyl)-N-methylglycine, hydrochloride salt

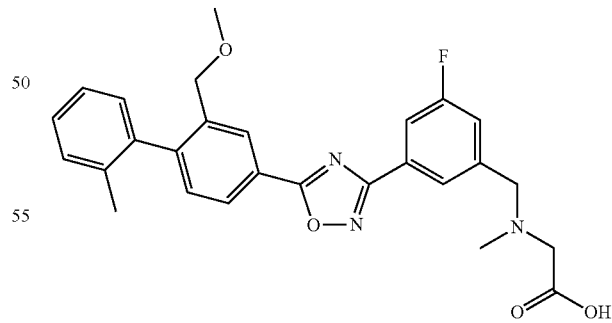

Tert-butyl N-(3-fluoro-5-{5-[2-(methoxymethyl)-2'-methylbiphenyl-4-yl]-1,2,4-oxadiazol-3-yl}benzyl)-N-methylglycinate was prepared following the general procedure 3 starting from Intermediate 3 and Intermediate 24. It was hydrolyzed following the general procedure 8 affording the title compound as a white powder. $^1$H NMR (DMSO-d$_6$, 300 MHz) δ 8.34 (d, J=1.8 Hz, 1H), 8.21-8.12 (m, 2H), 8.03-7.93

(m, 1H), 7.78-7.68 (m, 1H), 7.44 (d, J=8.0 Hz, 1H), 7.38-7.25 (m, 3H), 7.14 (d, J=7.3 Hz, 1H), 4.48 (s, 2H), 4.31-4.08 (m, 2H), 4.10 (s, 2H), 3.25 (s, 3H), 2.81 (s, 3H), 2.04 (s, 3H). LC/MS (Method B): 474.3 (M−H)⁻, 476.2 (M+H)⁺. HPLC (Method A) Rt 4.16 min (Purity: 99.5%). [C$_{27}$H$_{26}$N$_3$O$_4$F— HCl] Corrected: C, 63.34%; H, 5.32%; N, 8.21%; Cl, 6.92%. Found: C, 62.95%; H, 5.24%; N, 8.23%; Cl, 6.67%.

Example 21

N-(3-fluoro-5-{5-[2-(methoxymethyl)-2'-methylbiphenyl-4-yl]-1,2,4-oxadiazol-3-yl}benzyl)-N-methyl-beta-alanine, hydrochloride salt

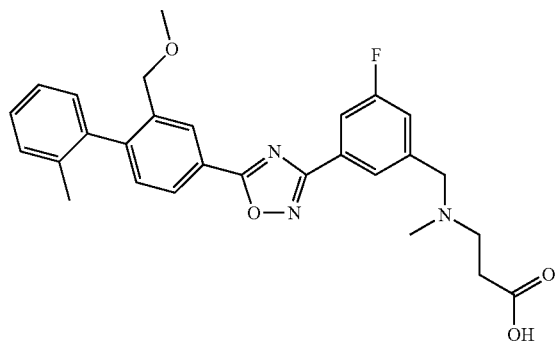 [SMILES: COCc1cc(-c2nc(-c3cc(F)cc(CN(C)CCC(=O)O)c3)no2)ccc1-c1ccccc1C]

Tert-butyl N-(3-fluoro-5-{5-[2-(methoxymethyl)-2'-methylbiphenyl-4-yl]-1,2,4-oxadiazol-3-yl}benzyl)-N-methyl-beta-alaninate was prepared following the general procedure 3 starting from Intermediate 3 and Intermediate 25. It was hydrolyzed following the general procedure 8 affording the title compound as a white powder. ¹H NMR (DMSO-d$_6$/D$_2$O, 300 MHz) δ 8.32 (d, J=1.5 Hz, 1H), 8.21-8.15 (m, 2H), 7.99 (ddd, J=9.1, 2.4, 1.3 Hz, 1H), 7.74-7.69 (m, 1H), 7.43 (d, 1H), 7.37-7.26 (m, 3H), 7.13 (d, J=7.0 Hz, 1H), 4.49 (s, 2H), 4.24-4.12 (m, 2H), 3.38-3.31 (m, 2H), 3.24 (s, 3H), 2.82 (t, J=7.3 Hz, 2H), 2.73 (s, 3H), 2.02 (s, 3H). LC/MS (Method B): 488.3 (M−H)⁻, 490.2 (M+H)⁺. HPLC (Method A) Rt 4.21 min (Purity: 99.4%).

Example 22

3-[(3-{5-[2-(methoxymethyl)-2'-methylbiphenyl-4-yl]-1,2,4-oxadiazol-3-yl}phenyl)amino]propane-1,2-diol

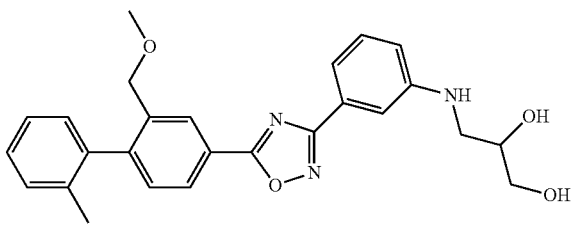 [SMILES: COCc1cc(-c2nc(-c3cccc(NCC(O)CO)c3)no2)ccc1-c1ccccc1C]

The title compound was prepared following the general procedure 4 starting from Intermediate 3 and Intermediate 26. It was purified by preparative HPLC affording the product as a brown powder. LC/MS (Method B): 444.4 (M−H)⁻, 446.3 (M+H)⁺. HPLC (Method A) Rt 4.71 min (Purity: 99.4%).

Example 23

2-(4-{5-[2-(methoxymethyl)-2'-methylbiphenyl-4-yl]-1,2,4-oxadiazol-3-yl}phenoxy)ethanol

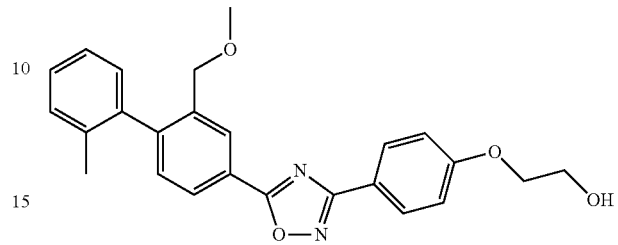

The title compound was prepared following the general procedure 4 starting from Intermediate 3 and Intermediate 27 affording the product as colorless oil. LC/MS (Method B): 417.3 (M+H)⁺. HPLC (Method A) Rt 5.43 min (Purity: 96.4%).

Example 24 methyl N-[(3-{5-[2-(methoxymethyl)-2'-methylbiphenyl-4-yl]-1,2,4-oxadiazol-3-yl}phenyl)acetyl]glycinate

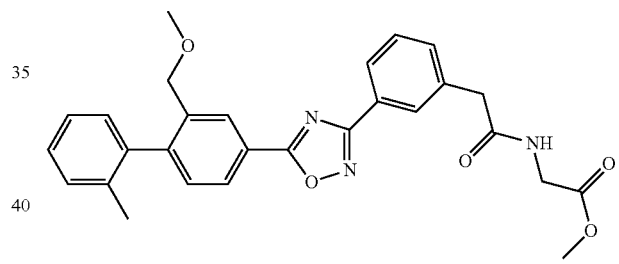

Step 1: (3-{5-[2-(methoxymethyl)-2'-methylbiphenyl-4-yl]-1,2,4-oxadiazol-3-yl}phenyl)acetic acid {3-[amino(hydroxyimino)methyl]phenyl}acetic acid was prepared following the general procedure 1 starting from 3-cyanophenylacetic acid. It was isolated as a colorless oil (1.2 g, quantitative). It was used without further purification in the synthesis of the title compound, following the general procedure 4, together with intermediate 3. The title compound was isolated and used in the next step without further purification (1.5 g, quantitative). LC/MS (Method B): 415.1 (M+H)⁺.

Step 2: methyl N-[(3-{5-[2-(methoxymethyl)-2'-methylbiphenyl-4-yl]-1,2,4-oxadiazol-3-yl}phenyl)acetyl]glycinate To a solution of crude (3-{5-[2-(methoxymethyl)-2'-methylbiphenyl-4-yl]-1,2,4-oxadiazol-3-yl}phenyl)acetic acid (308 mg; 0.74 mmol) in DMF (6 mL) at 0° C. was added DIEA (267 4, 1.5 mmol) and HATU (282 mg; 0.74 mmol). After 10 min, a solution of glycine methyl ester hydrochloride (93 mg; 0.74 mmol) in DMF (2 mL) was added and the reaction mixture stirred at RT overnight. Et₂O was added and the mixture was washed with water. The organic phase was then dried over MgSO₄, filtered and concentrated in vacuo. The crude was purified by preparative HPLC affording the title compound as a white solid. LC/MS (Method B): 484.4 (M−H)⁻, 486.3 (M+H)⁺. HPLC (Method A) Rt 5.40 min (Purity: 99.1%).

Example 25

N-[2-(acetylamino)ethyl]-2-(3-{5-[2-(methoxymethyl)-2'-methylbiphenyl-4-yl]-1,2,4-oxadiazol-3-yl}phenyl)acetamide

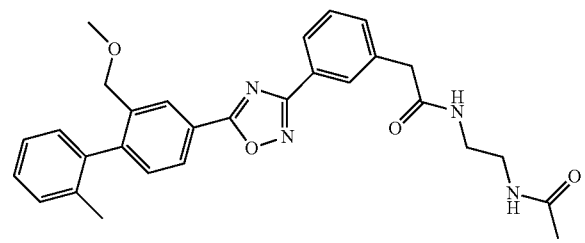 [SMILES: COCc1cc(-c2nc(-c3cccc(CC(=O)NCCNC(C)=O)c3)no2)ccc1-c1ccccc1C]

To a solution of crude (3-{5-[2-(methoxymethyl)-2'-methylbiphenyl-4-yl]-1,2,4-oxadiazol-3-yl}phenyl)acetic acid (preparation described in Example 24, Step 1, 308 mg; 0.74 mmol) in DMF (6 mL) at 0° C. was added DIEA (267 4, 1.5 mmol) and HATU (282 mg; 0.74 mmol). After 10 min, a solution of N-acetylethylenediamine (75 mg, 0.74 mmol) in DMF (2 mL) was added and the reaction mixture was stirred at RT overnight. Et₂O was added and the mixture was washed with water. The organic phase was dried over MgSO₄, filtered and concentrated in vacuo. The crude was purified by preparative HPLC affording the title compound as a white fluffy solid. LC/MS (Method B): 499.3 (M+H)⁺. HPLC (Method A) Rt 4.89 min (Purity: 100.0%).

Example 26

N-[(3-{5-[2-(methoxymethyl)-2'-methylbiphenyl-4-yl]-1,2,4-oxadiazol-3-yl}phenyl)acetyl]glycine

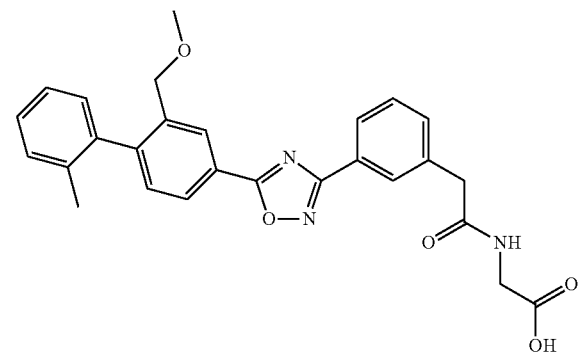 [SMILES: COCc1cc(-c2nc(-c3cccc(CC(=O)NCC(=O)O)c3)no2)ccc1-c1ccccc1C]

The title compound was prepared following the general procedure 9 starting from Example 24. It was isolated as a colorless foam. LC/MS (Method B): 470.3 (M−H)⁻, 472.3 (M+H)⁺. HPLC (Method A) Rt 3.99 min (Purity: 89.0%).

Example 27

N-(2,3-dihydroxypropyl)-2-fluoro-4-{5-[2-(methoxymethyl)-2'-methylbiphenyl-4-yl]-1,2,4-oxadiazol-3-yl}benzamide

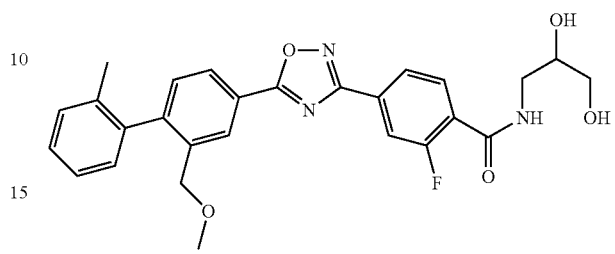

Step 1: 2-fluoro-4-{5-[2-(methoxymethyl)-2'-methylbiphenyl-4-yl]-1,2,4-oxadiazol-3-yl}benzoic acid Methyl 2-fluoro-4-{5-[2-(methoxymethyl)-2'-methylbiphenyl-4-yl]-1,2,4-oxadiazol-3-yl}benzoate was prepared following the general procedure 7 starting from Intermediate 3 and Intermediate 35. It was then hydrolysed following procedure 9, affording the title compound as as a beige solid. ¹H NMR (DMSO, 300 MHz) δ 13.64 (br s, 1H), 8.33 (d, J=1.4 Hz, 1H), 8.17 (dd, J=7.9, 1.4 Hz, 1H), 8.13-8.03 (m, 2H), 7.96 (dd, J=11.1, 1.2 Hz, 1H), 7.43 (d, J=7.9 Hz, 1H), 7.37-7.27 (m, 3H), 7.15 (d, J=7.0 Hz, 1H), 4.25-4.14 (m, 2H), 3.25 (s, 3H), 2.04 (s, 3H). LC/MS (Method B): 419.1 (M+H)⁺; 417.2 (M−H)⁻. HPLC: Rt 5.19 min (Purity: 99.2%).

Step 2: N-(2,3-dihydroxypropyl)-2-fluoro-4-{5-[2-(methoxymethyl)-2'-methylbiphenyl-4-yl]-1,2,4-oxadiazol-3-yl}benzamide 2-Fluoro-4-{5-[2-(methoxymethyl)-2'-methylbiphenyl-4-yl]-1,2,4-oxadiazol-3-yl}benzoic acid (75 mg, 0.18 mmol) was dissolved in anhydrous DMF (1 mL). N-ethyldiisopropylamine (65 µl, 0.38 mmol) was added followed by HATU (72 mg, 0.19 mmol) and the reaction was stirred at RT for 15 minutes. 3-Amino-1,2-propanediol (17 mg, 0.19 mmol) was added and the reaction stirred at RT overnight. EtOAc was added and the organic phase was washed three times with a 1N aqueous solution of HCl and brine. It was dried on MgSO₄, filtered and concentrated. It was purified on preparative HPLC to afford the title compound as a brown solid. LC/MS (Method B): 492.2 (M+H)⁺, 490.3 (M−H)⁻. HPLC (Method A) Rt 4.82 min (Purity: 95.9%).

Example 28

2-(2-fluoro-4-{5-[2-(methoxymethyl)-2'-methylbiphenyl-4-yl]-1,2,4-oxadiazol-3-yl}phenoxy)ethanol

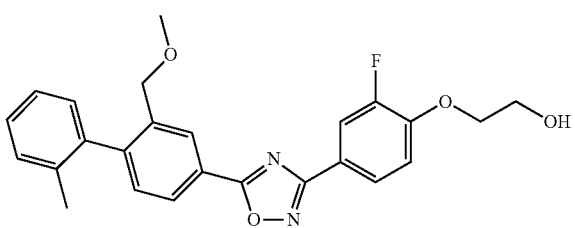 [SMILES: COCc1cc(-c2nc(-c3ccc(OCCO)c(F)c3)no2)ccc1-c1ccccc1C]

3-[4-(2-{[Tert-butyl(dimethyl)silyl]oxy}ethoxy)-3-fluorophenyl]-5-[2-(methoxymethyl)-2'-methylbiphenyl-4-yl]-1,2,4-oxadiazole was prepared following the general procedure 3 starting from intermediate 3 and intermediate 28. It was solubilised in THF (5 mL) and a 1M solution of tetrabutylammonium fluoride in THF (900 μL, 0.90 mmol) was added. The reaction was stirred at RT overnight. The solution was concentrated. EtOAc was added and the organic phase was washed with a saturated aqueous solution of $NH_4Cl$, a saturated aqueous solution of $NaHCO_3$ and brine, dried ($MgSO_4$) and concentrated under vacuum. The crude was purified by preparative HPLC affording the title compound as a colorless solid. $^1$H NMR (DMSO-$d_6$, 300 MHz) δ 8.31 (d, J=1.4 Hz, 1H), 8.16 (dd, J=8.0, 1.8 Hz, 1H), 7.94-7.85 (m, 2H), 7.46-7.26 (m, 5H), 7.15 (d, J=7.0 Hz, 1H), 4.99 (t, J=5.4 Hz, 1H), 4.25-4.14 (m, 4H), 3.79 (q, J=5.0 Hz, 2H), 3.25 (s, 3H), 2.04 (s, 3H). LC/MS (Method B): 435.0 (M+H)$^+$. HPLC (Method A) Rt 5.24 min (Purity: 100.0%).

Example 30

N-{3-[5-(2-ethoxy-2'-methylbiphenyl-4-yl)-1,2,4-oxadiazol-3-yl]benzyl}-N-methylglycine, hydrochloride salt

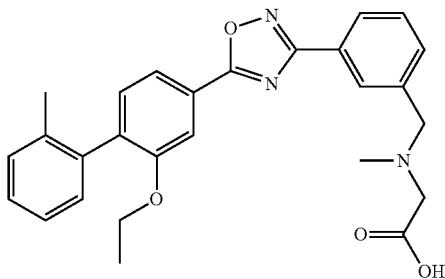 [SMILES: CCOc1cc(-c2nc(-c3cccc(CN(C)CC(=O)O)c3)no2)ccc1-c1ccccc1C]

Tert-butyl N-{3-[5-(2-ethoxy-2'-methylbiphenyl-4-yl)-1,2,4-oxadiazol-3-yl]benzyl}-N-methylglycinate was prepared following the general procedure 4, starting from Intermediate 48 and Intermediate 21. It was hydrolyzed following the general procedure 8 affording the title compound as a white powder. $^1$H NMR (DMSO-$d_6$, 300 MHz) δ 8.34 (s, 1H), 8.22 (d, J=7.8 Hz, 1H), 7.91-7.67 (m, 4H), 7.42 (d, J=7.8 Hz, 1H), 7.36-7.22 (m, 3H), 7.17 (d, J=6.9 Hz, 1H), 4.51 (s, 2H), 4.19 (q, J=6.9 Hz, 2H), 4.13 (s, 2H), 2.81 (s, 3H), 2.12 (s, 3H), 1.25 (t, J=6.9 Hz, 3H). LC/MS (Method B): 456.2 (M−H)$^−$, 458.0 (M+H)$^+$. HPLC (Method A) Rt 4.16 min (Purity: 99.8%). Elemental analysis: [$C_{27}H_{27}N_3O_4$—HCl-0.2$H_2O$] Corrected: C, 65.17%; H, 5.75%; N, 8.44%; Cl, 7.12%. Found: C, 65.24%; H, 5.55%; N, 8.38%; Cl, 7.10%.

Example 34

N-(3-{5-[3-(methoxymethyl)-4-(2-methylpyrrolidin-1-yl)phenyl]-1,2,4-oxadiazol-3-yl}benzyl)-N-methylglycine

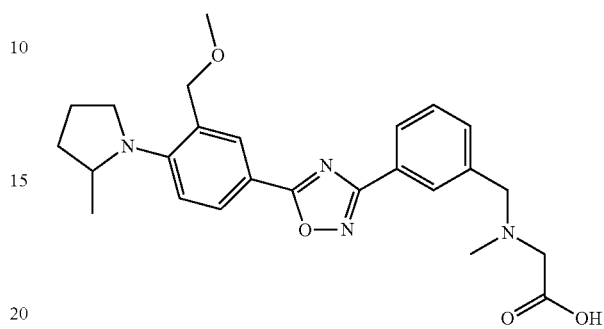

Tert-butyl N-(3-{5-[3-(methoxymethyl)-4-(2-methylpyrrolidin-1-yl)phenyl]-1,2,4-oxadiazol-3-yl}benzyl)-N-methylglycinate was prepared following the general procedure 3 starting from intermediate 14 and intermediate 21. It was hydrolyzed following the general procedure 8 affording the title compound as a white powder. $^1$H NMR (DMSO-$d_6$, 300 MHz) δ 8.07 (m, 2H), 8.01-7.92 (m, 2H), 7.55 (m, 2H), 7.00 (d, J=8.8 Hz, 1H), 4.53-4.41 (m, 2H), 4.00-3.93 (m, 1H), 3.82 (s, 3H), 3.70-3.61 (m, 1H), 3.37 (s, 3H), 3.32-3.25 (m, 1H), 3.28 (s, 2H), 3.33 (s, 3H), 2.23-2.13 (m, 1H), 1.99-1.88 (m, 1H), 1.84-1.70 (m, 1H), 1.67-1.53 (m, 1H), 1.08 (d, J=5.9 Hz, 3H). LC/MS (Method B): 449.2 (M−H)$^−$, 451.1 (M+H)$^+$. HPLC (Method A) Rt 2.97 min (Purity: 97.7%).

Example 35

N-(3-{5-[3'-fluoro-2-(methoxymethyl)-2'-methylbiphenyl-4-yl]-1,2,4-oxadiazol-3-yl}benzyl)-N-methylglycine, hydrochloride salt

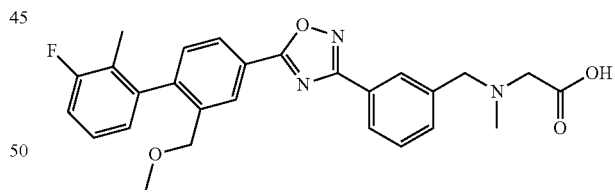

Tert-butyl N-(3-{5-[3'-fluoro-2-(methoxymethyl)-2'-methylbiphenyl-4-yl]-1,2,4-oxadiazol-3-yl}benzyl)-N-methylglycinate was prepared following the general procedure 11 starting from Intermediate 41 and 3-fluoro-2-methylphenylboronic acid (Combiblocks BB-3475). After purification by flash chromatography (silica, cHex/EtOAc), the ester derivative was hydrolyzed following the general procedure 8. After purification by precipitation from ACN, the title compound was obtained as a white powder. HPLC (Method A), Rt 4.1 min (purity: 93.4%). LC/MS (Method B): 474.1 (M−H)$^−$, 476.0 (M+H)$^+$. Melting point: 216-218° C. $^1$H NMR (DMSO-$d_6$, 300 MHz) δ 8.35 (m, 2H), 8.21 (m, 2H), 7.81 (d, J=7.8 Hz, 1H), 7.72 (m, 1H), 7.47 (d, J=7.9 Hz, 1H), 7.38-7.23 (m, 2H), 7.03 (d, J=7.3 Hz, 1H), 4.51 (s, 2H), 4.24 (d, J=12.8 Hz, 1H), 4.19 (d, J=12.8 Hz, 1H), 4.12 (s, 2H), 3.26 (s, 3H), 2.82 (s, 3H), 1.95 (d, J=2.1 Hz, 3H).

Example 36

N-(3-{5-[4'-fluoro-2-(methoxymethyl)-2'-methylbiphenyl-4-yl]-1,2,4-oxadiazol-3-yl}benzyl)-N-methylglycine, hydrochloride salt

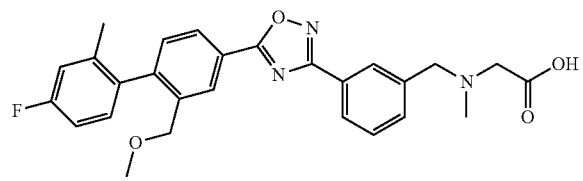 [SMILES: COCc1cc(-c2nc(-c3cccc(CN(C)CC(=O)O)c3)no2)ccc1-c1ccc(F)cc1C]

Tert-butyl N-(3-{5-[4'-fluoro-2-(methoxymethyl)-2'-methylbiphenyl-4-yl]-1,2,4-oxadiazol-3-yl}benzyl)-N-methylglycinate was prepared following the general procedure 11 starting from Intermediate 41 and 4-fluoro-2-methylbenzeneboronic acid. After purification by flash chromatography (silica, cHex/EtOAc), the ester derivative was hydrolyzed following the general procedure 8. After purification by precipitation from ACN, the title compound was obtained as a white powder. HPLC (Method A), Rt 3.9 min (purity: 98.4%). LC/MS (Method B): 474.2 (M−H)⁻, 476.0 (M+H)⁺. Melting point: 214-216° C. ¹H NMR (DMSO-$d_6$, 300 MHz) δ 8.34 (m, 2H), 8.22 (d, J=7.7 Hz, 1H), 8.17 (dd, J=8.0, 1.9 Hz, 1H), 7.81 (d, J=7.8 Hz, 1H), 7.72 (m, 1H), 7.44 (d, J=8.0 Hz, 1H), 7.26-7.10 (m, 3H), 4.51 (s, 2H), 4.23 (d, J=12.8 Hz, 1H), 4.17 (d, J=12.8 Hz, 1H), 4.12 (s, 2H), 3.26 (s, 3H), 2.82 (s, 3H), 2.04 (s, 3H).

Example 37

N-(3-{5-[5'-fluoro-2-(methoxymethyl)-2'-methylbiphenyl-4-yl]-1,2,4-oxadiazol-3-yl}benzyl)-N-methylglycine, hydrochloride salt

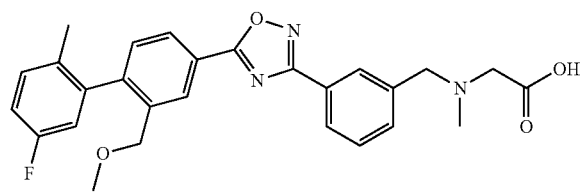 [SMILES: COCc1cc(-c2nc(-c3cccc(CN(C)CC(=O)O)c3)no2)ccc1-c1cc(F)ccc1C]

Tert-butyl N-(3-{5-[5'-fluoro-2-(methoxymethyl)-2'-methylbiphenyl-4-yl]-1,2,4-oxadiazol-3-yl}benzyl)-N-methylglycinate was prepared following the general procedure 11 starting from Intermediate 41 and 5-fluoro-2-methylphenylboronic acid. After purification by flash chromatography (silica, cHex/EtOAc), the ester derivative was hydrolyzed following the general procedure 8. After purification by precipitation from ACN, the title compound was obtained as a white powder. HPLC (Method A), Rt 4 min (purity: 96.1%). LC/MS (Method B): 474.1 (M−H)⁻, 476.0 (M+H)⁺. Melting point: 177-183° C. Elemental analysis: [$C_{27}H_{26}N_3O_4F$—HCl-0.9$H_2O$] Corrected: C, 61.40%; H, 5.50%; N, 7.96%. Found: C, 61.39%; H, 5.13%; N, 8.03%. ¹H NMR (DMSO-$d_6$, 300 MHz) δ 8.34 (m, 2H), 8.20 (m, 2H), 7.81 (d, J=7.7 Hz, 1H), 7.72 (m, 1H), 7.46 (d, J=8.0 Hz, 1H), 7.40 (dd, J=8.3, 6.1 Hz, 1H), 7.20 (m, 1H), 7.04 (dd, J=9.3, 2.7 Hz, 1H), 4.51 (s, 2H), 4.26 (d, J=12.8 Hz, 1H), 4.18 (d, J=12.8 Hz, 1H), 4.12 (s, 2H), 3.27 (s, 3H), 2.82 (s, 3H), 2.00 (s, 3H).

Example 38

[(3-{5-[4-(2-methylpiperidin-1-yl)-3-(trifluoromethyl)phenyl]-1,2,4-oxadiazol-3-yl}benzyl)oxy]acetic acid, hydrochloride salt

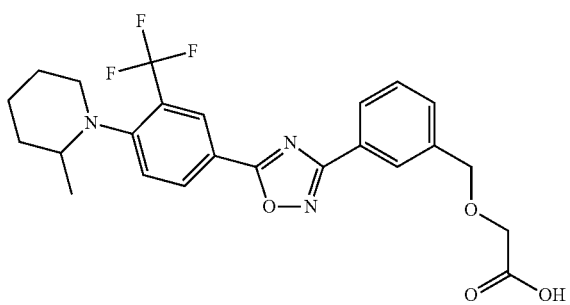 [SMILES: CC1CCCCN1c1ccc(-c2nc(-c3cccc(COCC(=O)O)c3)no2)cc1C(F)(F)F]

Tert-butyl [(3-{5-[4-(2-methylpiperidin-1-yl)-3-(trifluoromethyl)phenyl]-1,2,4-oxadiazol-3-yl}benzyl)oxy]acetate was prepared following the general procedure 3 starting from intermediate 4 and intermediate 17. It was hydrolyzed following the general procedure 8 affording the title compound as an orange oil. ¹H NMR (DMSO-$d_6$, 300 MHz) δ 12.73 (br s, 1H), 8.45 (dd, J=8.3, 2.0 Hz, 1H), 8.38 (d, J=2.0 Hz, 1H), 8.11 (s, 1H), 8.08-8.02 (m, 1H), 7.86 (d, J=8.5 Hz, 1H), 7.61 (s, 1H), 7.59 (s, 1H), 4.67 (s, 2H), 4.15 (s, 2H), 3.22-3.12 (m, 1H), 2.99-2.92 (m, 1H), 2.67-2.54 (m, 1H), 1.83-1.74 (m, 2H), 1.68-1.23 (m, 4H), 0.79 (d, J=6.2 Hz, 3H). LC/MS (Method B): 474.1 (M−H)⁻, 476.0 (M+H)⁺. HPLC (Method A) Rt 5.89 min (Purity: 96.2%).

Example 39

3-[(3-{5-[2-(methoxymethyl)-2'-methylbiphenyl-4-yl]-1,2,4-oxadiazol-3-yl}benzyl)(methyl)amino]propane-1,2-diol

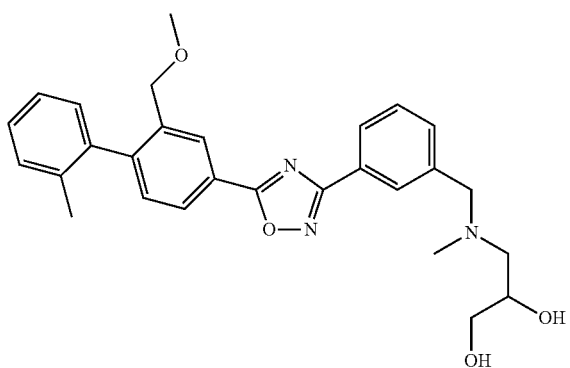 [SMILES: COCc1cc(-c2nc(-c3cccc(CN(C)CC(O)CO)c3)no2)ccc1-c1ccccc1C]

The title compound was prepared following the general procedure 3 starting from intermediate 3 and intermediate 29. It was isolated as a colorless oil. LC/MS (Method B): 474.1 (M+H)⁺. HPLC (Method A) Rt 4.36 min (Purity: 98.0%).

Example 40

2,2'-[(3-{5-[2-(methoxymethyl)-2'-methylbiphenyl-4-yl]-1,2,4-oxadiazol-3-yl}benzyl)imino]diethanol

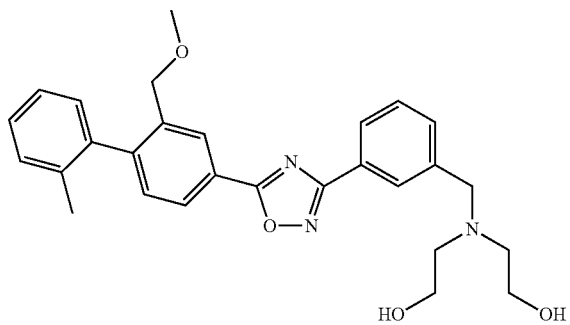 [SMILES: COCc1cc(-c2nc(-c3cccc(CN(CCO)CCO)c3)no2)ccc1-c1ccccc1C]

The title compound was prepared following the general procedure 3 starting from intermediate 3 and intermediate 30. It was isolated as a brown solid. LC/MS (Method B): 474.1 (M+H)+. HPLC (Method A) Rt 4.37 min (Purity: 98.5%).

Example 41

N-[2-(dimethylamino)ethyl]-2-(3-{5-[2-(methoxymethyl)-2'-methylbiphenyl-4-yl]-1,2,4-oxadiazol-3-yl}phenyl)acetamide

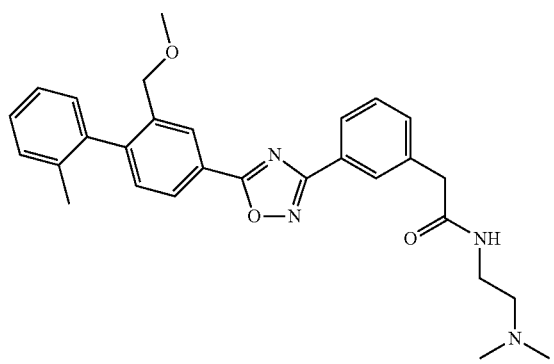 [SMILES: COCc1cc(-c2nc(-c3cccc(CC(=O)NCCN(C)C)c3)no2)ccc1-c1ccccc1C]

To a solution (3-{5-[2-(methoxymethyl)-2'-methylbiphenyl-4-yl]-1,2,4-oxadiazol-3-yl}phenyl)acetic acid (preparation described in Example 24 Step 1, 100 mg, 0.24 mmol) in DMF (2 mL) at 0° C., was added DIEA (126 4, 0.72 mmol) and HATU (92 mg, 0.24 mmol). After 10 min, a solution of 2-dimethylaminoethylamine (21 mg, 0.24 mmol) in DMF (2 mL) was added and the reaction mixture stirred at RT overnight. Et2O was added and the mixture was washed with water. The organic phase was then dried over MgSO4, filtered and concentrated in vacuo. The crude was purified by preparative HPLC affording the title compound as a colorless oil. LC/MS (Method B): 485.0 (M+H)+. HPLC (Method A) Rt 4.59 min (Purity: 91.3%).

Example 42

N-(3-{5-[3',4'-difluoro-2-(methoxymethyl)-2'-methylbiphenyl-4-yl]-1,2,4-oxadiazol-3-yl}benzyl)-N-methylglycine, hydrochloride salt

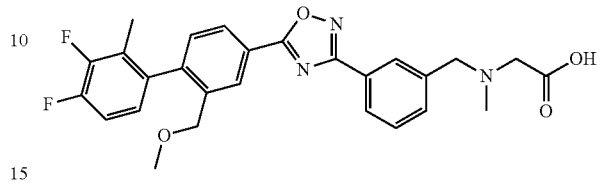

Tert-butyl N-(3-{5-[3',4'-difluoro-2-(methoxymethyl)-2% methylbiphenyl-4-yl]-1,2,4-oxadiazol-3-yl}benzyl)-N-methylglycinate was prepared following the general procedure 11 starting from Intermediate 41 and 3,4-difluoro-2-methylphenylboronic acid pinacol ester (Frontier D1970). After purification by flash chromatography (silica, cHex/EtOAc), the ester derivative was hydrolyzed following the general procedure 8. After purification by precipitation from a mixture of ACN and water, the title compound was obtained as a white powder. HPLC (Method A), Rt 4.1 min (purity: 98.3%). LC/MS (Method B): 492.1 (M−H)−, 494.0 (M+H)+. 1H NMR (DMSO-d6, 300 MHz) δ 8.35 (m, 2H), 8.20 (m, 2H), 7.81 (d, J=7.7 Hz, 1H), 7.72 (m, 1H), 7.47 (d, J=7.9 Hz, 1H), 7.38 (m, 1H), 7.06 (m, 1H), 4.50 (s, 2H), 4.24 (d, J=12.9 Hz, 1H), 4.19 (d, J=12.9 Hz, 1H), 4.12 (s, 2H), 3.26 (s, 3H), 2.81 (s, 3H), 1.99 (d, J=2.4 Hz, 3H).

Example 43

N-[(3-{5-[2-(methoxymethyl)-2% methylbiphenyl-4-yl]-1,2,4-oxadiazol-3-yl}-phenyl)acetyl]-beta-alanine

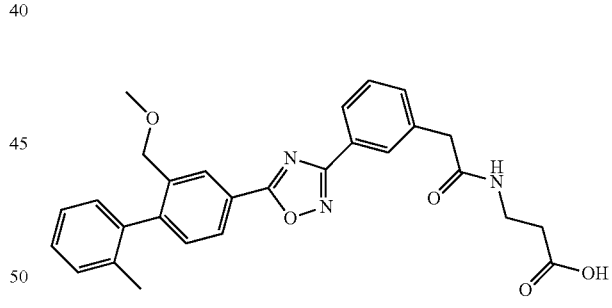

Step 1: Ethyl N-[(3-{5-[2-(methoxymethyl)-2'-methylbiphenyl-4-yl]-1,2,4-oxadiazol-3-yl}phenyl)acetyl]-beta-alaninate To a solution (3-{5-[2-(methoxymethyl)-2'-methylbiphenyl-4-yl]-1,2,4-oxadiazol-3-yl}phenyl)acetic acid (preparation described in Example 24 Step 1, 209 mg, 0.48 mmol) in DMF (2 mL) at 0° C. was added DIEA (252 µL, 1.5 mmol) and HATU (183 mg, 0.48 mmol). After 10 min, a solution of beta-alanine ethyl ester hydrochloride (82 mg, 0.53 mmol) in DMF (1 mL) was added and the reaction mixture stirred at RT overnight. EtOAc was added and the mixture was washed with water. The organic phase was then dried over MgSO4, filtered and concentrated in vacuo affording the title compound (100 mg, 40%). LC/MS (Method B): 514.1 (M+H)+. HPLC (Method A) Rt 4.73 min (Purity: 99.5%).

Step 2: N-[(3-{5-[2-(methoxymethyl)-2'-methylbiphenyl-4-yl]-1,2,4-oxadiazol-3-yl}phenyl)acetyl]-beta-alanine The title compound was prepared following the general procedure 9 starting from ethyl N-[(3-{5-[2-(methoxymethyl)-2'-methylbiphenyl-4-yl]-1,2,4-oxadiazol-3-yl}phenyl)acetyl]-beta-alaninate affording 54 mg (57%) as a white powder. LC/MS (Method B): 484.2 (M−H)−, 486.0 (M+H)+. HPLC (Method A) Rt 5.09 min (Purity: 97.4%).

Example 44

N-[(3-{5-[2-(methoxymethyl)-2'-methylbiphenyl-4-yl]-1,2,4-oxadiazol-3-yl}phenyl)acetyl]-N-methylglycine

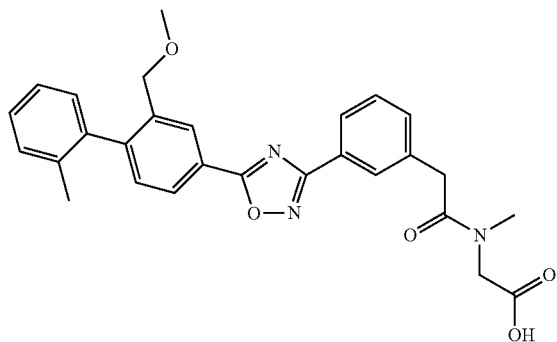 [SMILES: COCc1cc(-c2nc(-c3cccc(CC(=O)N(C)CC(=O)O)c3)no2)ccc1-c1ccccc1C]

Step 1: methyl N-[(3-{5-[2-(methoxymethyl)-2'-methylbiphenyl-4-yl]-1,2,4-oxadiazol-3-yl}phenyl)acetyl]-N-methylglycinate To a solution (3-{5-[2-(methoxymethyl)-2'-methylbiphenyl-4-yl]-1,2,4-oxadiazol-3-yl}phenyl)acetic acid (preparation described in Example 24 Step 1, 209 mg, 0.48 mmol) in DMF (2 mL) at 0° C. was added DIEA (252 µL, 1.5 mmol) and HATU (183 mg, 0.48 mmol). After 10 min, a solution of sarcosine methyl ester hydrochloride (74 mg, 0.53 mmol) in DMF (1 mL) was added and the reaction mixture stirred at RT overnight. EtOAc was added and the mixture was washed with water. The organic phase was then dried over MgSO4, filtered and concentrated in vacuo affording the title compound. LC/MS (Method B): 500.2 (M+H)+. HPLC (Method A) Rt 5.73 min (Purity: 98.9%).

Step 2: N-[(3-{5-[2-(methoxymethyl)-2'-methylbiphenyl-4-yl]-1,2,4-oxadiazol-3-yl}phenyl)acetyl]-N-methylglycine The title compound was prepared following the general procedure 9 starting from methyl N-[(3-{5-[2-(methoxymethyl)-2'-methylbiphenyl-4-yl]-1,2,4-oxadiazol-3-yl}phenyl)acetyl]-N-methylglycinate affording 35 mg (72%) as a white powder. LC/MS (Method B): 484.2 (M−H)−, 486.0 (M+H)+. HPLC (Method A) Rt 5.26 min (Purity: 98.9%).

Example 45

N-methyl-N-(3-{5-[4-[(2R)-2-methylpiperidin-1-yl]-3-(trifluoromethyl)phenyl]-1,2,4-oxadiazol-3-yl}benzyl)glycine, hydrochloride salt

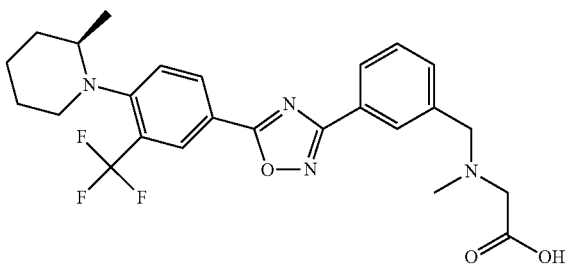 [SMILES: C[C@@H]1CCCCN1c1ccc(-c2nc(-c3cccc(CN(C)CC(=O)O)c3)no2)cc1C(F)(F)F]

Tert-butyl N-methyl-N-(3-{5-[4-[(2R)-2-methylpiperidin-1-yl]-3-(trifluoromethyl)phenyl]-1,2,4-oxadiazol-3-yl}benzyl)glycinate was prepared following the general procedure 4 starting from Intermediate 10 and Intermediate 21. It was hydrolyzed following the general procedure 8 affording the title compound as a white powder. LC/MS (Method B): 487.3 (M−H)−, 489.3 (M+H)+. HPLC (Method A) Rt 5.09 min (Purity: 99.8%).

Example 46

N-methyl-N-(3-{5-[4-[(2S)-2-methylpiperidin-1-yl]-3-(trifluoromethyl)phenyl]-1,2,4-oxadiazol-3-yl}benzyl)glycine, hydrochloride salt

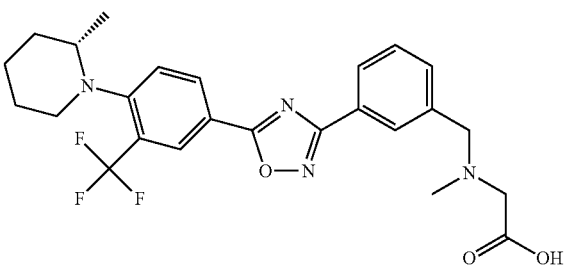 [SMILES: C[C@H]1CCCCN1c1ccc(-c2nc(-c3cccc(CN(C)CC(=O)O)c3)no2)cc1C(F)(F)F]

Tert-butyl N-methyl-N-(3-{5-[4-[(2S)-2-methylpiperidin-1-yl]-3-(trifluoromethyl)phenyl]-1,2,4-oxadiazol-3-yl}benzyl)glycinate was prepared following the general procedure 4 starting from Intermediate 11 and Intermediate 21. It was hydrolyzed following the general procedure 8 affording the title compound as a white powder. LC/MS (Method B): 487.3 (M−H)−, 489.3 (M+H)+. HPLC (Method A) Rt 5.10 min (Purity: 100.0%).

Example 47

N-(2,5-difluoro-4-{5-[2-(methoxymethyl)-2'-methyl-biphenyl-4-yl]-1,2,4-oxadiazol-3-yl}benzoyl)-beta-alanine

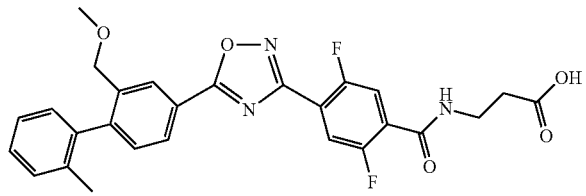 [SMILES: COCc1cc(-c2nc(-c3cc(F)c(C(=O)NCCC(=O)O)cc3F)no2)ccc1-c1ccccc1C]

Step 1: methyl 2,5-difluoro-4-{5-[2-(methoxymethyl)-2'-methylbiphenyl-4-yl]-1,2,4-oxadiazol-3-yl}benzoate Oxalyl chloride (190 mg, 1.50 mmol) was added to a suspension of Intermediate 3 (143 mg, 0.50 mmol) and DMF (catalytic amount) in anhydrous DCM (2 mL) and the resulting mixture was stirred at RT for 1 hour. After evaporation to dryness, the residue was taken up in anhydrous THF (2 mL) and added into a solution of Intermediate 42 (108 mg, 0.50 mmol) and DIEA (193 mg, 1.50 mmol) in anhydrous THF (1 mL). The resulting mixture was heated at 150° C. for 30 minutes under microwave irradiation. It was then filtered through a SPE-NH$_2$ column, which was further washed with THF. After evaporation, the residue was purified by flash chromatography (silica, cHex/EtOAc), affording the title product as an off-white solid. LC/MS (Method B): 451.2 (M+H)$^+$. HPLC (Method A) Rt 6.0 min (Purity: 89.6%).

Step 2: 2,5-difluoro-4-{5-[2-(methoxymethyl)-2'-methylbiphenyl-4-yl]-1,2,4-oxadiazol-3-yl}benzoic acid The title compound was obtained following the general procedure 9, starting from methyl 2,5-difluoro-4-{5-[2-(methoxymethyl)-2'-methylbiphenyl-4-yl]-1,2,4-oxadiazol-3-yl}benzoate. It was isolated as a beige powder. $^1$H NMR (DMSO-d$_6$, 300 MHz) δ 13.92 (bs, 1H), 8.34 (m, 1H), 8.17 (d, J=1.8 Hz, 1H), 8.05 (dd, J=5.3, 10.3 Hz, 1H), 7.90 (dd, J=5.8, 10.3 Hz, 1H), 7.44 (d, J=8.0 Hz, 1H), 7.40-7.11 (m, 4H), 4.22 (d, J=12.8 Hz, 1H), 4.17 (d, J=12.8 Hz, 1H), 3.25 (s, 3H), 2.04 (s, 3H). LC/MS (Method B): 435.2 (M−H)$^-$; 437.1 (M+H)$^+$. HPLC (Method A) Rt 5.05 min (purity: 99.8%).

Step 3: N-(2,5-difluoro-4-{5-[2-(methoxymethyl)-2'-methylbiphenyl-4-yl]-1,2,4-oxadiazol-3-yl}benzoyl)-beta-alanine Methyl N-(2,5-difluoro-4-{5-[2-(methoxymethyl)-2'-methylbiphenyl-4-yl]-1,2,4-oxadiazol-3-yl}benzoyl)-beta-alaninate was prepared following the general procedure 14, starting from 2,5-difluoro-4-{5-[2-(methoxymethyl)-2'-methylbiphenyl-4-yl]-1,2,4-oxadiazol-3-yl}benzoic acid and beta-alanine methyl ester. It was hydrolyzed following general procedure 9 to afford the title compound as a white powder. $^1$H NMR (DMSO-d$_6$, 300 MHz) δ 12.32 (brs, 1H), 8.68 (m, 1H), 8.33 (m, 1H), 8.18 (d, J=7.8 Hz, 1H), 8.03 (m, 1H), 7.70 (m, 1H), 7.44 (d, J=7.9 Hz, 1H), 7.39-7.25 (m, 3H), 7.15 (m, 1H), 4.20 (m, 2H), 3.48 (m, 2H), 3.25 (s, 3H), 2.53 (m, 2H), 2.03 (s, 3H). LC/MS (Method B): 508.0 (M+H)$^+$, 506.1 (M−H)$^-$. HPLC (Method B) Rt 4.83 min (Purity: 98%).

Example 48

[(3-{5-[2'-methyl-2-(trifluoromethyl)biphenyl-4-yl]-1,2,4-oxadiazol-3-yl}benzyl)oxy]acetic acid

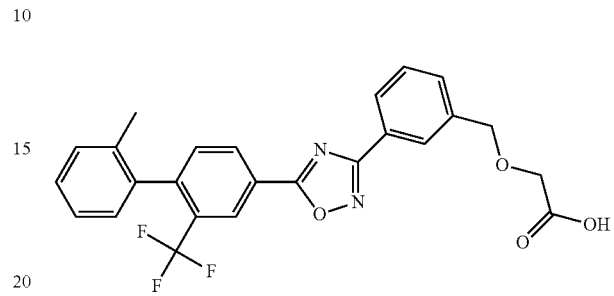

Tert-butyl [(3-{5-[2'-methyl-2-(trifluoromethyl)biphenyl-4-yl]-1,2,4-oxadiazol-3-yl}benzyl)oxy]acetate was prepared following the general procedure 3 starting from intermediate 5 and intermediate 17. It was deprotected following the general procedure 8 affording the title compound as a white powder. $^1$H NMR (DMSO-d$_6$, 300 MHz) δ 12.78 (brs, 1H), 8.55 (d, J=1.4 Hz, 1H), 8.51 (dd, J=7.8, 1.6 Hz, 1H), 8.14 (s, 1H), 8.11-8.05 (m, 1H), 7.66 (d, J=7.9 Hz, 1H), 7.63 (s, 1H), 7.61 (s, 1H), 7.42-7.26 (m, 3H), 7.18 (d, J=7.5 Hz, 1H), 4.69 (s, 2H), 4.15 (s, 2H), 2.03 (s, 3H). LC/MS (Method B): 467.1 (M−H)$^-$, 468.9 (M+H)$^+$. HPLC (Method A) Rt 5.24 min (Purity 100.0%).

Example 51

N-(4-{5-[2-(methoxymethyl)-2'-methylbiphenyl-4-yl]-1,2,4-oxadiazol-3-yl}benzyl)-N-methylglycine, hydrochloride salt

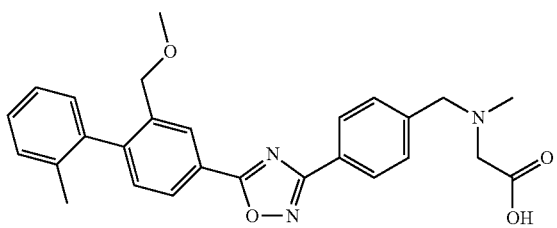 [SMILES: COCc1cc(-c2nc(-c3ccc(CN(C)CC(=O)O)cc3)no2)ccc1-c1ccccc1C]

Tert-butyl N-(4-{5-[2-(methoxymethyl)-2'-methylbiphenyl-4-yl]-1,2,4-oxadiazol-3-yl}benzyl)-N-methylglycinate was prepared following the general procedure 4 starting from intermediate 3 and intermediate 31. It was hydrolyzed following the general procedure 8 affording the title compound as a white powder. $^1$H NMR (DMSO-d$_6$, 300 MHz) δ 8.33 (d, J=1.4 Hz, 1H), 8.24-8.15 (m, 3H), 7.79 (s, 1H), 7.77 (s, 1H), 7.44 (d, J=7.9 Hz, 1H), 7.38-7.27 (m, 3H), 7.15 (d, J=7.0 Hz, 1H), 4.43 (s, 2H), 4.26-4.14 (m, 2H), 4.06 (s, 2H), 3.26 (s, 3H), 2.78 (s, 3H), 2.04 (s, 3H). LC/MS (Method B): 456.1 (M−H)$^-$, 458.0 (M+H)$^+$. HPLC (Method A) Rt 4.01 min (Purity: 99.5%).

Example 52

N-(2-fluoro-4-{5-[2-(methoxymethyl)-2'-methylbiphenyl-4-yl]-1,2,4-oxadiazol-3-yl}benzyl)-N-methylglycine, hydrochloride salt

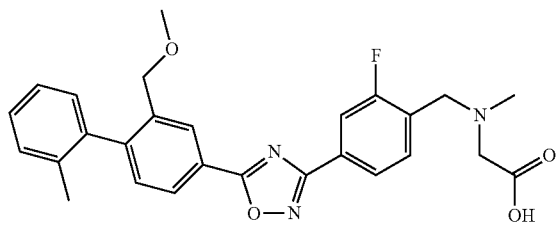 [SMILES: COCc1cc(-c2nc(-c3ccc(CN(C)CC(=O)O)c(F)c3)no2)ccc1-c1ccccc1C]

Tert-butyl N-(2-fluoro-4-{5-[2-(methoxymethyl)-2'-methylbiphenyl-4-yl]-1,2,4-oxadiazol-3-yl}benzyl)-N-methylglycinate was prepared following the general procedure 4 starting from Intermediate 3 and Intermediate 32. It was hydrolyzed following the general procedure 8 affording the title compound as a white powder. $^1$H NMR (DMSO-$d_6$, 300 MHz) δ 8.34 (d, J=1.4 Hz, 1H), 8.18 (dd, J=7.9, 1.7 Hz, 1H), 8.08 (dd, J=7.9, 1.3 Hz, 1H), 7.99 (dd, J=10.2, 1.3 Hz, 1H), 7.91 (t, J=7.7 Hz, 1H), 7.44 (d, J=7.9 Hz, 1H), 7.39-7.27 (m, 3H), 7.15 (d, J=7.0 Hz, 1H), 4.50 (s, 2H), 4.26-4.11 (m, 4H), 3.26 (s, 3H), 2.81 (s, 3H), 2.04 (s, 3H). LC/MS (Method B): 474.2 (M−H)$^−$, 476.0 (M+H)$^+$. HPLC (Method A) Rt 4.06 min (Purity: 99.6%).

Example 53

N-(2-bromo-4-{5-[2-(methoxymethyl)-2'-methylbiphenyl-4-yl]-1,2,4-oxadiazol-3-yl}benzyl)-N-methylglycine, hydrochloride salt

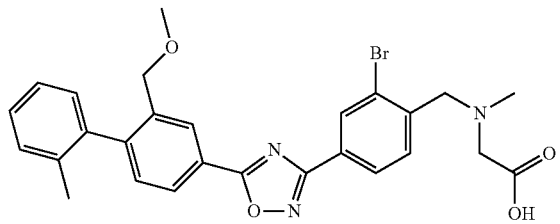 [SMILES: COCc1cc(-c2nc(-c3ccc(CN(C)CC(=O)O)c(Br)c3)no2)ccc1-c1ccccc1C]

Tert-butyl N-(2-bromo-4-{5-[2-(methoxymethyl)-2'-methylbiphenyl-4-yl]-1,2,4-oxadiazol-3-yl}benzyl)-N-methylglycinate was prepared following the general procedure 4 starting from Intermediate 3 and Intermediate 33. It was hydrolyzed following the general procedure 8 affording the title compound as a white powder. $^1$H NMR (DMSO-$d_6$, 300 MHz) δ 8.36 (d, J=1.6 Hz, 1H), 8.34 (d, J=1.6 Hz, 1H), 8.23 (dd, J=7.9, 1.6 Hz, 1H), 8.19 (dd, J=7.9, 1.8 Hz, 1H), 7.95 (d, J=8.1 Hz, 1H), 7.44 (d, J=7.9 Hz, 1H), 7.39-7.27 (m, 3H), 7.15 (d, J=7.0 Hz, 1H), 4.47 (br s, 2H), 4.26-4.15 (m, 2H), 4.05 (br s, 2H), 3.26 (s, 3H), 2.76 (s, 3H), 2.04 (s, 3H). LC/MS (Method B): 534.0, 536.0 (M−H)$^−$, 535.9, 537.9 (M+H)$^+$. HPLC (Method A) Rt 4.22 min (Purity: 98.2%).

Example 54

N-(4-{5-[2'-fluoro-2-(methoxymethyl)biphenyl-4-yl]-1,2,4-oxadiazol-3-yl}benzyl)-N-methylglycine, hydrochloride salt

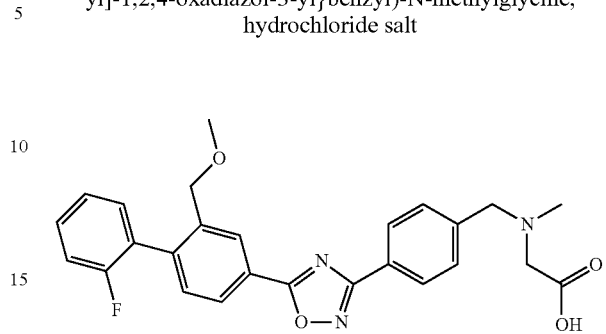

Tert-butyl N-(4-{5-[2'-fluoro-2-(methoxymethyl)biphenyl-4-yl]-1,2,4-oxadiazol-3-yl}benzyl)-N-methylglycinate was prepared following the general procedure 4 starting from Intermediate 12 and Intermediate 31. It was hydrolyzed following the general procedure 8 affording the title compound as a white powder. $^1$H NMR (DMSO-$d_6$, 300 MHz) δ 8.36 (s, 1H), 8.25-8.18 (m, 3H), 7.79 (d, J=8.1 Hz, 2H), 7.61-7.51 (m, 2H), 7.47-7.33 (m, 3H), 4.46 (s, 2H), 4.37 (s, 2H), 4.10 (s, 2H), 3.27 (s, 3H), 2.81 (s, 3H). LC/MS (Method B): 460.1 (M−H)$^−$, 462.0 (M+H)$^+$. HPLC (Method A) Rt 3.77 min (Purity: 99.7%).

Example 55

N-(2-fluoro-4-{5-[2'-fluoro-2-(methoxymethyl)biphenyl-4-yl]-1,2,4-oxadiazol-3-yl}benzyl)-N-methylglycine, hydrochloride salt

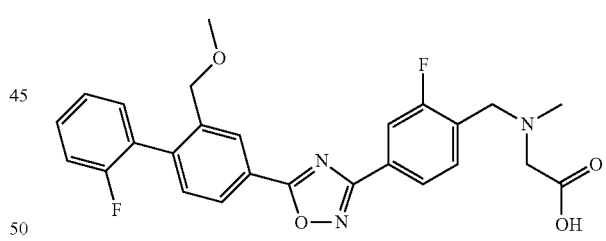

Tert-butyl N-(2-fluoro-4-{5-[2'-fluoro-2-(methoxymethyl)biphenyl-4-yl]-1,2,4-oxadiazol-3-yl}benzyl)-N-methylglycinate was prepared following the general procedure 4 starting from Intermediate 12 and Intermediate 32. It was hydrolyzed following the general procedure 8 affording the title compound as a white powder. $^1$H NMR (DMSO-$d_6$, 300 MHz) δ 8.36 (d, J=1.5 Hz, 1H), 8.21 (dd, J=8.0, 1.8 Hz, 1H), 8.08 (dd, J=8.0, 1.5 Hz, 1H), 8.00 (dd, J=10.3, 1.3 Hz, 1H), 7.91 (t, J=7.7 Hz, 1H), 7.61-7.51 (m, 2H), 7.47-7.33 (m, 3H), 4.50 (s, 2H), 4.37 (s, 2H), 4.14 (s, 2H), 3.27 (s, 3H), 2.81 (s, 3H). LC/MS (Method B): 478.1 (M−H)$^−$, 480.0 (M+H)$^+$. HPLC (Method A) Rt 3.83 min (Purity: 99.6%).

Example 56

N-(3-fluoro-5-{5-[4-(2-methylpiperidin-1-yl)-3-(trifluoromethyl)phenyl]-1,2,4-oxadiazol-3-yl}benzyl)-N-methylglycine, hydrochloride salt

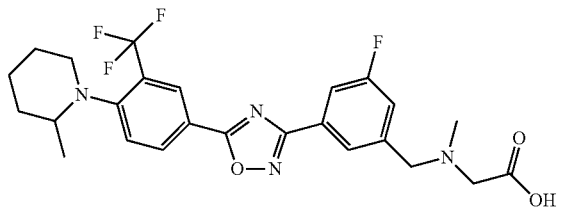 [SMILES: CC1CCCCN1c1ccc(-c2nc(-c3cc(F)cc(CN(C)CC(=O)O)c3)no2)cc1C(F)(F)F]

Tert-butyl N-(3-fluoro-5-{5-[4-(2-methylpiperidin-1-yl)-3-(trifluoromethyl)phenyl]-1,2,4-oxadiazol-3-yl}benzyl)-N-methylglycinate was prepared following the general procedure 3 starting from Intermediate 4 and Intermediate 24. It was hydrolyzed following general procedure 8 to afford the title compound as a pale yellow powder. $^1$H NMR (DMSO-$d_6$, 300 MHz) δ 8.45 (m, 1H), 8.40 (s, 1H), 8.17 (s, 1H), 7.98 (d, J=8.6 Hz, 1H), 7.88 (d, J=8.6 Hz, 1H), 7.73 (d, J=9.0 Hz, 1H), 4.47 (s, 2H), 4.09 (s, 2H), 3.18 (m, 1H), 2.96 (m, 1H), 2.80 (s, 3H), 2.62 (m, 1H), 1.79 (m, 2H), 1.70-1.25 (m, 4H), 0.79 (d, J=6.1 Hz, 3H). LC/MS (Method B): 507.2 (M+H)$^+$, 505.2 (M−H)$^-$. HPLC (Method A) Rt 4.79 min (Purity: 100%).

Example 57

N-(3-fluoro-5-{5-[2'-fluoro-2-(methoxymethyl)biphenyl-4-yl]-1,2,4-oxadiazol-3-yl}benzyl)-N-methylglycine, hydrochloride salt

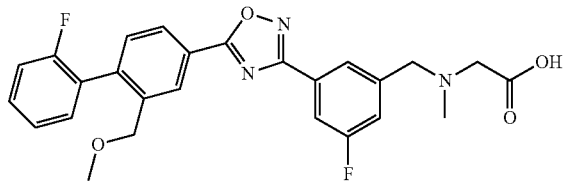 [SMILES: COCc1cc(-c2nc(-c3cc(F)cc(CN(C)CC(=O)O)c3)no2)ccc1-c1ccccc1F]

Tert-butyl N-(3-fluoro-5-{5-[2'-fluoro-2-(methoxymethyl)biphenyl-4-yl]-1,2,4-oxadiazol-3-yl}benzyl)-N-methylglycinate was prepared following the general procedure 3 starting from Intermediate 12 and Intermediate 24. After purification by flash chromatography (silica, heptane/EtOAc), the ester derivative was hydrolyzed following the general procedure 8. After purification by precipitation from ACN, the title compound was obtained as a white powder (873 mg, 70% over 2 steps). HPLC (Method A), Rt 3.9 min (purity: 100%). LC/MS (Method B): 478.1 (M−H)$^-$, 480 (M+H)$^+$. Elemental analysis: [$C_{26}H_{23}N_3O_4F_2$—HCl] Corrected: C, 60.53%; H, 4.69%; N, 8.14%; Cl, 6.87%. Found: C, 60.32%; H, 4.57%; N, 7.93%; Cl, 6.86%. $^1$H NMR (DMSO-$d_6$, 300 MHz) δ 8.36 (d, J=1.5 Hz, 1H), 8.21 (m, 2H), 7.99 (d, J=8.1 Hz, 1H), 7.75 (d, J=9.1 Hz, 1H), 7.59 (d, J=8.0 Hz, 1H), 7.55 (m, 1H), 7.46-7.33 (m, 3H), 4.51 (s, 2H), 4.36 (s, 2H), 4.12 (s, 2H), 3.27 (s, 3H), 2.83 (s, 3H).

Example 58

N-isopropyl-N-(3-{5-[2-(methoxymethyl)-2'-methylbiphenyl-4-yl]-1,2,4-oxadiazol-3-yl}benzyl)glycine, hydrochloride salt

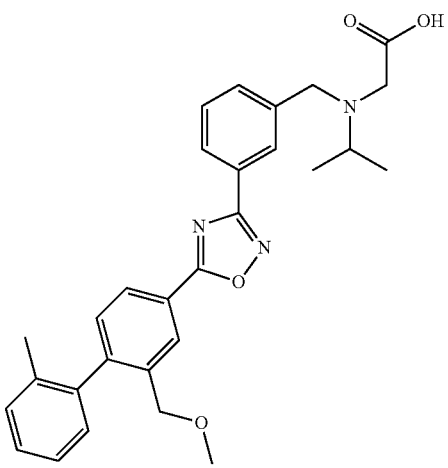 [SMILES: COCc1cc(-c2nc(-c3cccc(CN(CC(=O)O)C(C)C)c3)no2)ccc1-c1ccccc1C]

Step 1: (3-{5-[2-(methoxymethyl)-2'-methylbiphenyl-4-yl]-1,2,4-oxadiazol-3-yl}phenyl)methanol The title compound was prepared following the general procedure 3 starting from Intermediate 3 and Intermediate 70 and was isolated as a yellow oil. HPLC (Method A) Rt 5.16 min (Purity: 97.0%).

Step 2: N-(3-{5-[2-(methoxymethyl)-2'-methylbiphenyl-4-yl]-1,2,4-oxadiazol-3-yl}benzyl)propan-2-amine (3-{5-[2-(methoxymethyl)-2'-methylbiphenyl-4-yl]-1,2,4-oxadiazol-3-yl}phenyl)methanol (100 mg, 0.26 mmol) was dissolved in DCM (2 mL). N-ethyldiisopropylamine (0.090 mL, 0.52 mmol) was added and the mixture was cooled to 0° C. Methanesulfonyl chloride (22 μl, 0.29 mmol) was added and the resulting mixture was stirred at 0° C. for 10 minutes, and then at RT for 2 hours. The reaction mixture was then poured into a solution of isopropylamine (223 μl, 2.60 mmol) in ACN (2 mL) and stirred at RT for 15 hours. It was diluted with EtOAc, washed with water and brine and dried over MgSO$_4$. After concentration under vacuum, the crude product was purified by flash chromatography (silica, cHex/EtOAc containing 1% of TEA) to give the title compound as a colorless oil. HPLC (Method A) Rt 4.25 min (Purity: 97.1%).

Step 3: tert-butyl N-isopropyl-N-(3-{5-[2-(methoxymethyl)-2'-methylbiphenyl-4-yl]-1,2,4-oxadiazol-3-yl}benzyl)glycinate N-(3-{5-[2-(methoxymethyl)-2'-methylbiphenyl-4-yl]-1,2,4-oxadiazol-3-yl}benzyl)propan-2-amine (64 mg, 0.15 mmol) was dissolved in ACN (2 mL). K$_2$CO$_3$ (83 mg, 0.60 mmol) and tert-butyl bromoacetate (48 μl, 0.32 mmol) were added and the mixture was stirred at RT overnight. The reaction mixture was diluted with EtOAc, washed with water and brine, and then dried over MgSO$_4$. After concentration under vacuum, the crude product was purified by flash chromatography (silica, cHex/EtOAc) to give the title compound as a colorless oil (58 mg, 72%). HPLC (Method A) Rt 5.54 min (Purity: 97.7%).

Step 4: N-isopropyl-N-(3-{5-[2-(methoxymethyl)-2'-methylbiphenyl-4-yl]-1,2,4-oxadiazol-3-yl}benzyl)glycine, hydrochloride salt Tert-butyl N-isopropyl-N-(3-{5-[2-(methoxymethyl)-2'-methylbiphenyl-4-yl]-1,2,4-oxadiazol-3-yl}benzyl)glycinate (58 mg, 0.11 mmol) was dissolved in a 4N solution of HCl in dioxane (1.34 ml, 5.35 mmol). The reaction mixture was stirred at RT for 36 hours, and then concentrated under vacuum. The crude product was suspended in ACN and the precipitate was filtered off to give the title compound as a white powder. $^1$H NMR (DMSO-$d_6$, 300 MHz) δ 9.60 (br s, 1H), 8.45 (m, 1H), 8.34 (m, 1H), 8.23-8.15 (m, 2H), 7.92-7.85 (m, 1H), 7.38 (t, J=8.0 Hz, 1H), 7.45 (d, J=8.0 Hz, 1H), 7.40-7.26 (m, 3H), 7.18-7.12 (m, 1H), 4.46 (s, 2H); 4.23 (d, J=12.8 Hz, 1H), 4.17 (d, J=12.8 Hz, 1H), 4.18-3.85 (m, 2H), 3.81-3.58 (m, 1H), 3.26 (s, 3H), 2.04 (s, 3H), 1.34 (d, J=6.4 Hz, 6H). LC/MS (Method B): 484.3 (M−H)$^-$, 486.3 (M+H)$^+$. HPLC (Method A) Rt 4.67 min (Purity: 100%).

Example 59

N-isobutyl-N-(3-{5-[2-(methoxymethyl)-2'-methylbiphenyl-4-yl]-1,2,4-oxadiazol-3-yl}benzyl)glycine, hydrochloride salt

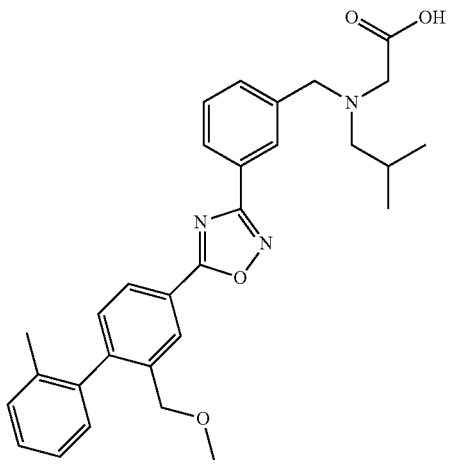 [SMILES: COCc1cc(-c2nc(-c3cccc(CN(CC(=O)O)CC(C)C)c3)no2)ccc1-c1ccccc1C]

The title compound was prepared following the procedure described for Example 58 Steps 1 to 4, but using isobutylamine in Step 2. It was isolated as a white powder. $^1$H NMR (DMSO-$d_6$, 300 MHz) δ 8.34 (m, 2H), 8.23-8.15 (m, 2H), 7.85-7.64 (m, 2H), 7.44 (d, J=7.9 Hz, 1H), 7.40-7.26 (m, 3H), 7.18-7.12 (m, 1H), 4.46 (s, 2H); 4.23 (d, J=12.8 Hz, 1H), 4.17 (d, J=12.8 Hz, 1H), 4.09-3.81 (m, 2H), 3.26 (s, 3H), 3.07-2.80 (m, 1H), 2.22-1.93 (m, 2H), 2.04 (s, 3H), 0.96 (d, J=6.4 Hz, 6H). LC/MS (Method B): 498.3 (M−H)$^-$, 500.3 (M+H)$^+$. HPLC (Method A) Rt 4.91 min (Purity: 97.0%).

Example 60

N-(4-{5-[2-(methoxymethyl)-2'-methylbiphenyl-4-yl]-1,2,4-oxadiazol-3-yl}benzyl)glycine, hydrochloride salt

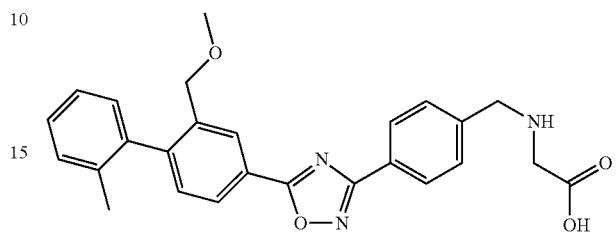

Tert-butyl N-(tert-butoxycarbonyl)-N-(4-{5-[2-(methoxymethyl)-2'-methylbiphenyl-4-yl]-1,2,4-oxadiazol-3-yl}benzyl)glycinate was prepared following the general procedure 4 starting from intermediate 3 and intermediate 36. It was hydrolyzed following the general procedure 8 affording the title compound as a white powder. $^1$H NMR (DMSO-$d_6$, 300 MHz) δ 8.33 (d, J=1.5 Hz, 1H), 8.21-8.15 (m, 3H), 7.77 (d, J=8.5 Hz, 2H), 7.44 (d, J=8.1 Hz, 1H), 7.39-7.27 (m, 3H), 7.15 (d, J=7.0 Hz, 1H), 4.28 (s, 2H), 4.26-4.14 (m, 2H), 3.90 (s, 2H), 3.26 (s, 3H), 2.04 (s, 3H). LC/MS (Method B): 442.1 (M−H)$^-$, 444.0 (M+H)$^+$. HPLC (Method A) Rt 3.96 min (Purity: 99.7%).

Example 61

N-(4-{5-[2'-fluoro-2-(methoxymethyl)biphenyl-4-yl]-1,2,4-oxadiazol-3-yl}benzyl)glycine, hydrochloride salt

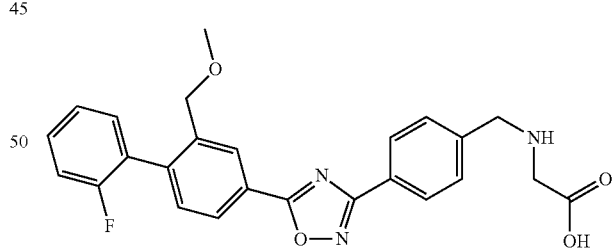

Tert-butyl N-(tert-butoxycarbonyl)-N-(4-{5-[2'-fluoro-2-(methoxymethyl)biphenyl-4-yl]-1,2,4-oxadiazol-3-yl}benzyl)glycinate was prepared following the general procedure 4 starting from intermediate 12 and intermediate 36. It was hydrolyzed following the general procedure 8 affording the title compound as a white powder. $^1$H NMR (DMSO-$d_6$, 300 MHz) δ 8.36 (d, J=1.6 Hz, 1H), 8.22-8.17 (m, 3H), 7.76 (d, J=8.5 Hz, 2H), 7.60-7.51 (m, 2H), 7.47-7.33 (m, 3H), 4.37 (s, 2H), 4.28 (s, 2H), 3.91 (s, 2H), 3.28 (s, 3H). LC/MS (Method B): 446.0 (M−H)$^-$, 448.0 (M+H)$^+$. HPLC (Method A) Rt 3.74 min (Purity: 98.4%).

Example 62

N-ethyl-N-(3-{5-[2'-fluoro-2-(methoxymethyl)biphenyl-4-yl]-1,2,4-oxadiazol-3-yl}benzyl)-beta-alanine, hydrochloride salt

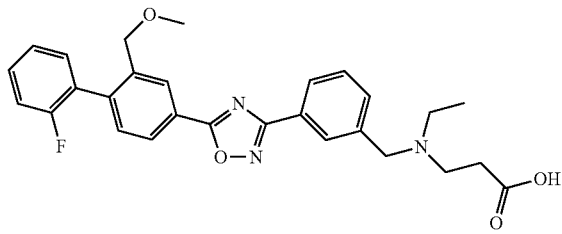 [SMILES: CCN(CCC(=O)O)Cc1cccc(-c2noc(-c3ccc(-c4ccccc4F)c(COC)c3)n2)c1]

Tert-butyl N-ethyl-N-(3-{5-[2'-fluoro-2-(methoxymethyl) biphenyl-4-yl]-1,2,4-oxadiazol-3-yl}benzyl)-beta-alaninate was prepared following the general procedure 3 starting from Intermediate 12 and Intermediate 37. It was hydrolyzed following general procedure 8 to afford the title compound as a white powder. $^1$H NMR (DMSO-$d_6$, 300 MHz) δ 12.73 (brs, 1H), 10.22 (brs, 1H), 8.37 (m, 2H), 8.21 (m, 2H), 7.88 (m, 1H), 7.72 (m, 1H), 7.62-7.50 (m, 1H) 7.48-7.33 (m, 3H), 4.51 (brs, 2H), 4.37 (brs, 2H), 3.40-3.25 (m, 7H), 3.14 (m, 2H), 2.83 (m, 2H), 1.28 (t, J=7.2 Hz, 3H). LC/MS (Method B): 490.2 (M+H)$^+$, 488.2 (M−H)$^−$. HPLC (Method A) Rt 3.91 min (Purity: 99.2%).

Example 63

N-ethyl-N-(3-{5-[2-(methoxymethyl)-2'-methylbiphenyl-4-yl]-1,2,4-oxadiazol-3-yl}benzyl)-beta-alanine, hydrochloride salt

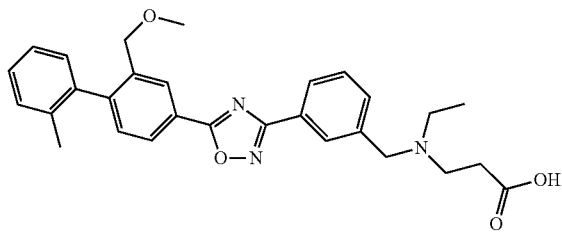 [SMILES: CCN(CCC(=O)O)Cc1cccc(-c2noc(-c3ccc(-c4ccccc4C)c(COC)c3)n2)c1]

Tert-butyl N-ethyl-N-(3-{5-[2-(methoxymethyl)-2'-methylbiphenyl-4-yl]-1,2,4-oxadiazol-3-yl}benzyl)-beta-alaninate was prepared following the general procedure 3 starting from Intermediate 3 and Intermediate 21. It was deprotected following general procedure 8 to afford the title compound as a white powder. $^1$H NMR (DMSO-$d_6$, 300 MHz) δ 12.75 (brs, 1H), 10.20 (brs, 1H), 8.36 (m, 2H), 8.20 (m, 2H), 7.87 (m, 1H), 7.73 (m, 1H), 7.44 (d, J=7.9 Hz, 1H) 7.40-7.26 (m, 3H), 7.15 (m, 1H), 4.50 (brs, 2H), 4.20 (m, 2H), 3.39-3.23 (m, 7H), 3.14 (m, 2H), 2.82 (m, 2H), 2.04 (s, 3H), 1.27 (t, J=7.1 Hz, 3H). LC/MS (Method B): 486.2 (M+H)$^+$, 484.3 (M−H)$^−$. HPLC (Method A) Rt 4.15 min (Purity: 99.3%).

Example 65

N-(3-{5-[2'-chloro-5'-fluoro-2-(methoxymethyl)biphenyl-4-yl]-1,2,4-oxadiazol-3-yl}benzyl)-N-methylglycine, hydrochloride salt

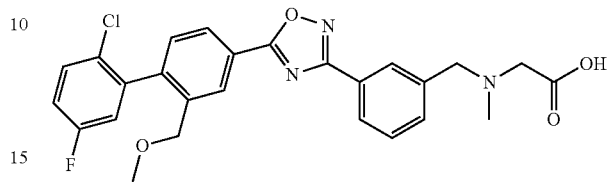

Tert-butyl N-(3-{5-[2'-chloro-5'-fluoro-2-(methoxymethyl)biphenyl-4-yl]-1,2,4-oxadiazol-3-yl}benzyl)-N-methylglycinate was prepared following the general procedure 11 starting from Intermediate 41 and 2-chloro-5-fluorophenylboronic acid (Combiblocks BB-2251). After purification by flash chromatography (silica, cHex/EtOAc), the ester derivative was deprotected following the general procedure 8. After purification by precipitation from ACN, the title compound was obtained as a white powder. HPLC (Method A), Rt 4 min (purity: 97.1%). LC/MS (Method B): 494.1 (M−H)$^−$, 495.9 (M+H)$^+$. Elemental analysis: [$C_{26}H_{23}N_3O_4ClF$—HCl-0.25$H_2O$] Corrected: C, 58.16%; H, 4.60%; N, 7.83%; Cl, 13.21%. Found: C, 58.18%; H, 4.61%; N, 7.77%; Cl, 13.23%. $^1$H NMR (DMSO-$d_6$, 300 MHz) δ 8.35 (m, 2H), 8.22 (m, 2H), 7.81 (d, J=7.8 Hz, 1H), 7.75-7.67 (m, 2H), 7.52 (d, J=8.0 Hz, 1H), 7.43-7.33 (m, 2H), 4.50 (s, 2H), 4.32 (d, J=13.1 Hz, 1H), 4.27 (d, J=13.1 Hz, 1H), 4.11 (s, 2H), 3.27 (s, 3H), 2.81 (s, 3H).

Example 66

N-(2-hydroxyethyl)-N-(3-{5-[2-(methoxymethyl)-2'-methylbiphenyl-4-yl]-1,2,4-oxadiazol-3-yl}benzyl)-beta-alanine, hydrochloride salt

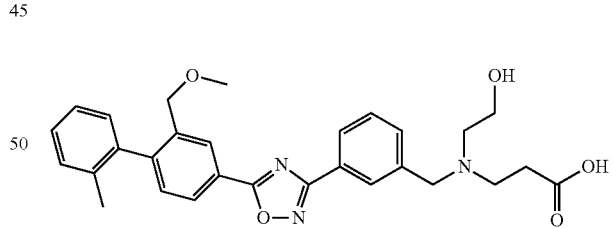

Tert-butyl N-(2-hydroxyethyl)-N-(3-{5-[2-(methoxymethyl)-2'-methylbiphenyl-4-yl]-1,2,4-oxadiazol-3-yl}benzyl)-beta-alaninate was prepared following the general procedure 3 starting from intermediate 3 and Intermediate 38. It was deprotected following general procedure 8 to afford the title compound as a white foam. $^1$H NMR (DMSO-$d_6$, 300 MHz) δ 8.33 (m, 1H), 8.17 (m, 2H), 8.07 (m, 1H), 7.64 (m, 2H), 7.43 (d, J=7.9 Hz, 1H), 7.39-7.26 (m, 3H), 7.15 (m, 1H), 4.20 (m, 2H), 3.98 (m, 2H), 3.57 (m, 2H), 3.25 (s, 3H), 2.97 (m, 2H), 2.73 (m, 2H), 2.56 (m, 2H), 2.04 (s, 3H). LC/MS (Method B): 502.2 (M+H)$^+$, 500.3 (M−H)$^−$. HPLC (Method A) Rt 3.69 min (Purity: 93.9%).

Example 73

N-(2-fluoro-4-{5-[2-(methoxymethyl)-2'-methylbiphenyl-4-yl]-1,2,4-oxadiazol-3-yl}benzyl)-N-methyl-beta-alanine, hydrochloride salt

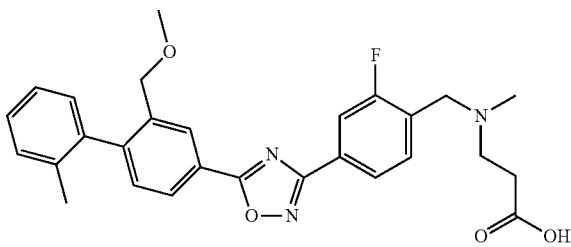 [SMILES: COCc1cc(-c2nc(-c3ccc(CN(C)CCC(=O)O)c(F)c3)no2)ccc1-c1ccccc1C]

Tert-butyl N-(2-fluoro-4-{5-[2-(methoxymethyl)-2'-methylbiphenyl-4-yl]-1,2,4-oxadiazol-3-yl}benzyl)-N-methyl-beta-alaninate was prepared following the general procedure 4 starting from Intermediate 3 and Intermediate 39. It was hydrolyzed following the general procedure 8 affording the title compound as a white powder. $^1$H NMR (DMSO-$d_6$, 300 MHz) δ 8.33 (d, J=1.5 Hz, 1H), 8.18 (dd, J=7.9, 1.8 Hz, 1H), 8.07 (dd, J=8.1, 1.4 Hz, 1H), 8.03-7.97 (m, 2H), 7.44 (d, J=8.0 Hz, 1H), 7.39-7.27 (m, 3H), 7.15 (d, J=7.2 Hz, 1H), 4.49 (s, 2H), 4.25-4.14 (m, 2H), 3.36 (br s, 2H), 3.25 (s, 3H), 2.90 (t, J=7.5 Hz, 2H), 2.74 (s, 3H), 2.04 (s, 3H). LC/MS (Method A): 488.1 (M−H)$^-$, 490.0 (M+H)$^+$. HPLC (Method A) Rt 4.09 min (Purity: 99.1%).

Example 74

N-(4-{5-[2-(methoxymethyl)-2'-methylbiphenyl-4-yl]-1,2,4-oxadiazol-3-yl}benzyl)-N-methyl-beta-alanine, hydrochloride salt

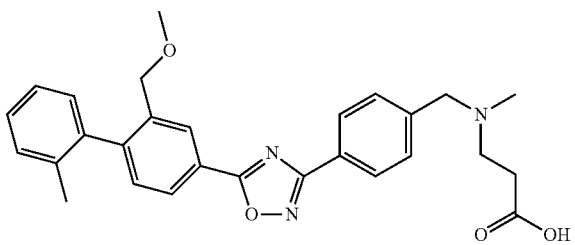 [SMILES: COCc1cc(-c2nc(-c3ccc(CN(C)CCC(=O)O)cc3)no2)ccc1-c1ccccc1C]

Tert-butyl N-(4-{5-[2-(methoxymethyl)-2'-methylbiphenyl-4-yl]-1,2,4-oxadiazol-3-yl}benzyl)-N-methyl-beta-alaninate was prepared following the general procedure 4 starting from Intermediate 3 and Intermediate 40. It was hydrolyzed following the general procedure 8 affording the title compound as a white powder. $^1$H NMR (DMSO-$d_6$, 300 MHz) δ 8.33 (s, 1H), 8.25-8.15 (m, 3H), 7.84 (d, J=8.0 Hz, 2H), 7.47-7.27 (m, 4H), 7.15 (d, J=7.1 Hz, 1H), 4.45 (s, 2H), 4.26-4.14 (m, 2H), 3.41-3.23 (m, 5H), 2.88 (t, J=7.2 Hz, 2H), 2.69 (s, 3H), 2.04 (s, 3H). LC/MS (Method A): 470.2 (M−H)$^-$, 472.1 (M+H)$^+$. HPLC (Method A) Rt 4.03 min (Purity: 99.1%).

Example 77

N-(3-{5-[2-(methoxymethyl)-2'-methylbiphenyl-4-yl]-1,2,4-oxadiazol-3-yl}benzyl)-N-propylglycine, hydrochloride salt

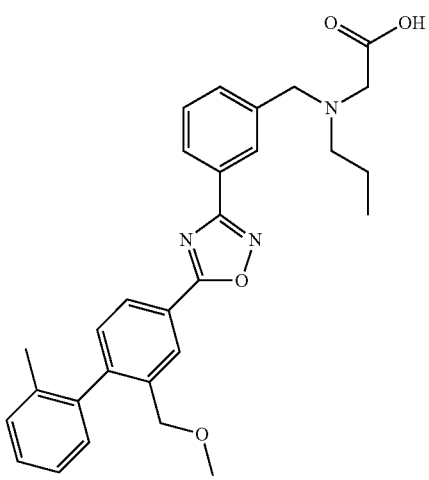 [SMILES: CCCN(CC(=O)O)Cc1cccc(-c2noc(-c3ccc(-c4ccccc4C)c(COC)c3)n2)c1]

The title compound was prepared following the procedure described for example 58 Steps 1 to 4, but using propylamine in Step 2. It was isolated as a white powder. $^1$H NMR (DMSO-$d_6$, 300 MHz) δ 12.18 (br s, 1H), 8.32 (d, J=1.9 Hz, 1H), 8.17 (dd, J=1.9, 7.9 Hz, 1H), 8.12 (m, 1H), 8.06-7.97 (m, 1H), 7.63-7.52 (m, 2H), 7.43 (d, J=7.9 Hz, 1H), 7.39-7.25 (m, 3H), 7.12-7.18 (m, 1H), 4.23 (d, J=12.8 Hz, 1H), 4.17 (d, J=12.8 Hz, 1H), 3.88 (br s, 2H), 3.29 (s, 2H), 3.25 (s, 3H), 2.58 (t, J=6.9 Hz, 2H), 2.04 (s, 3H), 1.47 (m, 2H), 0.84 (t, J=6.9 Hz, 3H). LC/MS (Method B): 484.3 (M−H)$^-$, 486.3 (M+H)$^+$. HPLC (Method A) Rt 4.75 min (97.9%).

Example 78

N-ethyl-N-(3-{5-[2-(methoxymethyl)-2'-methylbiphenyl-4-yl]-1,2,4-oxadiazol-3-yl}benzyl)glycine, hydrochloride salt

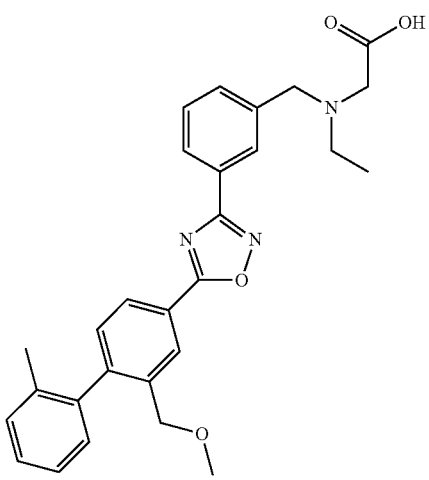 [SMILES: CCN(CC(=O)O)Cc1cccc(-c2noc(-c3ccc(-c4ccccc4C)c(COC)c3)n2)c1]

The title compound was prepared following the procedure described for example 58 Steps 1 to 4, but using ethylamine in Step 2. It was isolated as a white powder. $^1$H NMR (DMSO-$d_6$, 300 MHz) δ 10.23 (br s, 1H), 8.40-8.32 (m, 2H), 8.25-8.14 (m, 2H), 7.86-7.78 (m, 1H), 7.75-7.67 (m, 1H), 7.45 (d, J=8.0 Hz, 1H), 7.41-7.25 (m, 3H), 7.22-7.10 (m, 1H), 4.50 (s, 2H), 4.23 (d, J=12.8 Hz, 1H), 4.17 (d, J=12.8 Hz, 1H), 4.06 (br s, 2H), 3.29-3.17 (m, 2H), 3.26 (s, 3H), 2.04 (s, 3H), 1.29 (t, J=7.1 Hz, 3H). LC/MS (Method B): 470.2 (M−H)$^-$, 472.2 (M+H)$^+$. HPLC (Method A) Rt 4.57 min (97.1%).

Example 79

2-((2-methoxy-4-(5-(2-(methoxymethyl)-2'-methyl-biphenyl-4-yl)-1,2,4-oxadiazol-3-yl)benzyl)(methyl)amino)acetic acid, hydrochloride salt

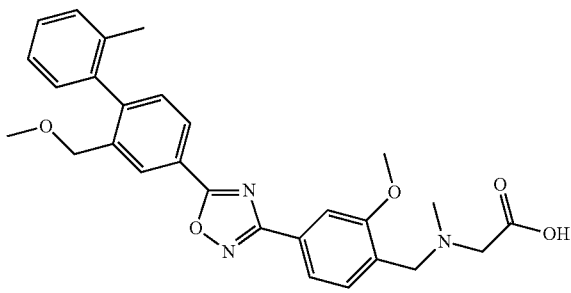 [SMILES: COCc1cc(-c2nc(-c3ccc(CN(C)CC(=O)O)c(OC)c3)no2)ccc1-c1ccccc1C]

Step 1: tert-butyl 2-((2-methoxy-4-(5-(2-(methoxymethyl)-2'-methylbiphenyl-4-yl)-1,2,4-oxadiazol-3-yl)benzyl)(methyl)amino)acetate The title compound was prepared following the procedure 7, starting from Intermediate 44 and Intermediate 3. It was isolated as a colorless gum. $^1$H NMR (CDCl$_3$, 400 MHz) δ 8.43 (1H, s), 8.18 (1H, dd, J=7.9, 1.9 Hz), 7.80 (1H, dd, J=7.7, 1.5 Hz), 7.68 (1H, d, J=1.5 Hz), 7.55 (1H, d, J=7.8 Hz), 7.35-7.24 (4H, m), 7.13 (1H, d, J=7.4 Hz), 4.23 (2H, s), 3.95 (3H, s), 3.81 (2H, s), 3.33 (3H, s), 3.24 (2H, s), 2.44 (3H, s), 2.08 (3H, s), 1.49 (9H, s).

Step 2: 2-((2-methoxy-4-(5-(2-(methoxymethyl)-2'-methylbiphenyl-4-yl)-1,2,4-oxadiazol-3-yl)benzyl)(methyl)amino)acetic acid, hydrochloride salt To tert-butyl 2-((2-methoxy-4-(5-(2-(methoxymethyl)-2'-methylbiphenyl-4-yl)-1,2,4-oxadiazol-3-yl)benzyl)(methyl)amino)acetate (52 mg, 0.09 mmol) was added a 4N solution of HCl in dioxane (3 mL) and the mixture was heated in a tube at 70° C. for 3 hours. The solvent was then removed in vacuo to give the title compound as a white solid (36 mg, 78%). $^1$H NMR (DMSO-$d_6$, 400 MHz) δ 8.28 (1H, s), 8.16 (1, dd, J=7.9, 1.9 Hz), 7.72 (1H, dd, J=7.8, 1.5 Hz), 7.65-7.58 (2H, m), 7.40 (1H, d, J=7.9 Hz), 7.33 (2H, d, J=4.4 Hz), 7.30-7.25 (1H, m), 7.11 (1H, d, J=7.4 Hz), 4.20-4.11 (2H, m), 3.97 (2H, s), 3.91 (3H, s), 3.25-3.20 (5H, m), 2.48 (3H, s), 2.00 (3H, s). LC/MS (Method B): 488 (M+H)$^+$. HPLC (Method F) Rt 3.15 min (Purity: 97.2%).

Example 80

2-((2-methoxy-4-(5-(4-(2-methylpiperidin-1-yl)-3-(trifluoromethyl)phenyl)-1,2,4-oxadiazol-3-yl)benzyl)(methyl)amino)acetic acid, hydrochloride salt

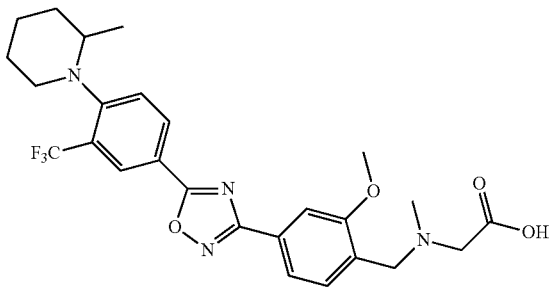 [SMILES: COc1cc(-c2noc(-c3ccc(N4CCCCC4C)c(C(F)(F)F)c3)n2)ccc1CN(C)CC(=O)O]

The title compound was prepared following the procedure described in Example 79 Steps 1 and 2, but starting from Intermediate 4 to give the title compound as a beige solid (41 mg, 73%). $^1$H NMR (DMSO-$d_6$, 400 MHz) δ 8.41 (1H, d, J=8.5 Hz), 8.35 (1H, s), 7.82 (1H, d, J=8.5 Hz), 7.70 (1H, d, J=7.8 Hz), 7.64-7.54 (2H, m), 3.95-3.90 (5H, m), 3.25 (2H, s), 3.20-3.10 (1H, m), 2.92 (1H, d, J=11.0 Hz), 2.59 (1H, t, J=10.0 Hz), 2.42 (3H, s), 1.81-1.70 (2H, m), 1.65-1.51 (2H, m), 1.50-1.39 (1H, m), 1.39-1.20 (1H, m), 0.75 (3H, d, J=6.0 Hz). LC/MS (Method B): 519.0 (M+H)$^+$. HPLC (Method G) Rt 3.67 min (Purity: 97.9%).

Example 82

N-(2-fluoro-4-{5-[2'-fluoro-2-(methoxymethyl)biphenyl-4-yl]-1,2,4-oxadiazol-3-yl}benzyl)glycine, hydrochloride salt

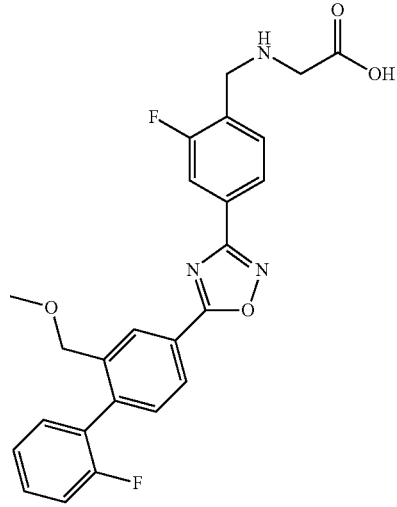 [SMILES: COCc1cc(-c2nc(-c3ccc(CNCC(=O)O)c(F)c3)no2)ccc1-c1ccccc1F]

Tert-butyl N-(tert-butoxycarbonyl)-N-(2-fluoro-4-{5-[2'-fluoro-2-(methoxymethyl)biphenyl-4-yl]-1,2,4-oxadiazol-3-yl}benzyl)glycinate was prepared following the general procedure 4 starting from intermediate 12 and intermediate 45. It was hydrolyzed following the general procedure 8 affording the title compound as a white powder. $^1$H NMR (DMSO-$d_6$, 300 MHz) δ 8.35 (d, J=1.2 Hz, 1H), 8.21 (dd, J=8.2, 1.7 Hz, 1H), 8.06 (dd, J=8.0, 1.4 Hz, 1H), 7.96 (dd, J=10.2, 1.3 Hz, 1H), 7.88 (t, J=7.7 Hz, 1H), 7.62-7.51 (m, 2H), 7.47-7.33 (m, 3H), 4.37 (s, 2H), 4.31 (s, 2H), 3.93 (s, 2H), 3.27 (s, 3H). LC/MS (Method B): 464.1 (M−H)$^-$, 466.0 (M+H)$^+$. HPLC (Method A) Rt 4.26 min (Purity: 100.0%).

Example 83

N-(2-fluoro-4-{5-[2-(methoxymethyl)-2'-methylbiphenyl-4-yl]-1,2,4-oxadiazol-3-yl}benzyl)glycine, hydrochloride salt

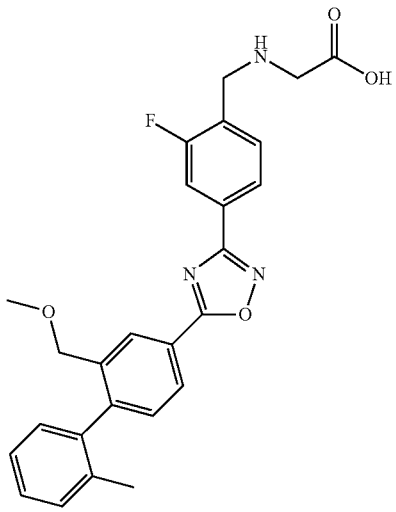 [SMILES: COCc1cc(-c2nc(-c3ccc(CNCC(=O)O)c(F)c3)no2)ccc1-c1ccccc1C]

Tert-butyl N-(tert-butoxycarbonyl)-N-(2-fluoro-4-{5-[2-(methoxymethyl)-2'-methylbiphenyl-4-yl]-1,2,4-oxadiazol-3-yl}benzyl)glycinate was prepared following the general procedure 4 starting from intermediate 3 and intermediate 45. It was hydrolyzed following the general procedure 8 affording the title compound as a white powder. $^1$H NMR (DMSO-d$_6$, 300 MHz) δ 10.90 (br s, 2H), 8.33 (d, J=1.5 Hz, 1H), 8.18 (dd, J=7.8, 1.9 Hz, 1H), 8.05 (dd, J=7.9, 1.6 Hz, 1H), 7.95 (dd, J=10.2, 1.5 Hz, 1H), 7.89 (t, J=7.8 Hz, 1H), 7.44 (d, J=8.0 Hz, 1H), 7.39-7.27 (m, 3H), 7.15 (d, J=7.1 Hz, 1H), 4.32 (s, 2H), 4.26-4.14 (m, 2H), 3.93 (s, 2H), 3.26 (s, 3H), 2.04 (s, 3H). LC/MS (Method B): 460.2 (M−H)$^-$, 462.0 (M+H)$^+$. HPLC (Method A) Rt 4.49 min (Purity: 99.9%).

Example 85

N-(2-fluoro-4-{5-[4-(2-methylpiperidin-1-yl)-3-(trifluoromethyl)phenyl]-1,2,4-oxadiazol-3-yl}benzyl)-N-methylglycine, dihydrochloride salt

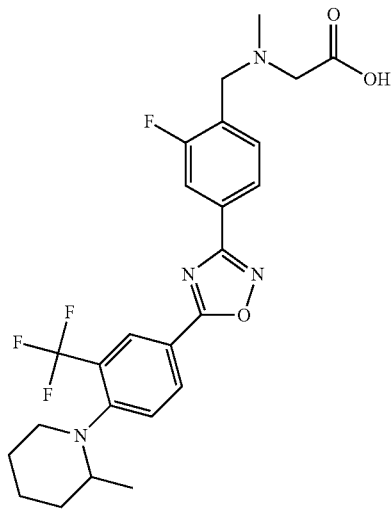 [SMILES: CC1CCCCN1c1ccc(-c2nc(-c3ccc(CN(C)CC(=O)O)c(F)c3)no2)cc1C(F)(F)F]

Tert-butyl N-(2-fluoro-4-{5-[4-(2-methylpiperidin-1-yl)-3-(trifluoromethyl)phenyl]-1,2,4-oxadiazol-3-yl}benzyl)-N-methylglycinate was prepared following the general procedure 4 starting from intermediate 4 and intermediate 32. It was hydrolyzed following the general procedure 8 affording the title compound as a white powder. $^1$H NMR (DMSO-d$_6$, 300 MHz) δ 8.46 (dd, J=8.4, 2.0 Hz, 1H), 8.40 (d, J=1.8 Hz, 1H), 8.06 (dd, J=7.9, 1.7 Hz, 1H), 7.98 (dd, J=10.2, 1.4 Hz, 1H), 7.91-7.84 (m, 2H), 4.47 (s, 2H), 4.10 (s, 2H), 3.23-3.14 (m, 1H), 3.00-2.93 (m, 1H), 2.79 (s, 3H), 2.68-2.58 (m, 1H), 1.84-1.74 (m, 2H), 1.68-1.27 (m, 4H), 0.79 (d, J=6.1 Hz, 3H). LC/MS (Method B): 505.2 (M−H)$^-$, 507.0 (M+H)$^+$. HPLC (Method A) Rt 5.24 min (Purity: 100.0%).

Example 86

[(2-{3-[5-(2-Methoxymethyl-2'-methyl-biphenyl-4-yl)-[1,2,4]oxadiazol-3-yl]-phenyl}-ethyl)-methyl-amino]-acetic acid

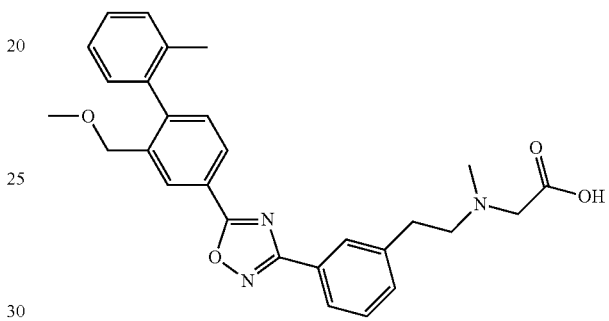

Step 1: 2-(3-{5-[2-(methoxymethyl)-2'-methylbiphenyl-4-yl]-1,2,4-oxadiazol-3-yl}phenyl)ethanol The title compound was prepared according the general procedure 3, starting from Intermediate 3 and Intermediate 68. It was isolated as a colorless oil (2.2 g, 98%). LC/MS (Method B): 401.2 (M+H)$^+$. HPLC (Method A) Rt 5.70 min (Purity: 91.8%).

Step 2: 2-(3-{5-[2-(methoxymethyl)-2'-methylbiphenyl-4-yl]-1,2,4-oxadiazol-3-yl}phenethyl methanesulfonate To a solution of 2-(3-{5-[2-(methoxymethyl)-2'-methylbiphenyl-4-yl]-1,2,4-oxadiazol-3-yl}phenyl)ethanol (0.2 mmol) in DCM (2 mL) at 0° C. was added DIEA (71 μL, 0.4 mmol) and mesyl chloride (17 μL, 0.22 mmol). The resulting mixture was stirred at 0° C. for 10 minutes, allowed to warm to RT and stirred for 2 hours. The mixture was diluted with DCM (20 mL) and washed with a saturated aqueous solution of NaHCO$_3$. The aqueous layer was extracted with DCM (3×20 mL). The combined organic fractions were dried (MgSO$_4$), filtered and the solvent removed in vacuo. The crude residue was all used in the next step without further purification.

Step 3: tert-butyl N-[2-(3-{5-[2-(methoxymethyl)-2'-methylbiphenyl-4-yl]-1,2,4-oxadiazol-3-yl}phenyl)ethyl]-N-methylglycinate To a solution of 2-(3-{5-[2-(methoxymethyl)-2'-methylbiphenyl-4-yl]-1,2,4-oxadiazol-3-yl}phenethyl methanesulfonate (0.2 mmol) in dioxane (2 mL) was added potassium carbonate (165 mg, 1.2 mmol) and tert-butyl N-methylglycinate, hydrochloride salt (0.60 mmol). The mixture was heated at 130° C. for 72 hours, diluted with DCM (5 mL) and water (5 mL). The aqueous layer was extracted with DCM (3×20 mL), the combined organic fractions were dried (MgSO₄), filtered and the solvent removed in vacuo. The residue was purified by flash chromatography (silica, Pet Ether/EtOAc) to give the title compound as a colorless oil (86 mg, 72%).

Step 4: [(2-{3-[5-(2-Methoxymethyl-2'-methyl-biphenyl-4-yl)-[1,2,4]oxadiazol-3-yl]-phenyl}-ethyl)-methyl-amino]-acetic acid To tert-butyl N-[2-(3-{5-[2-(methoxymethyl)-2'-methylbiphenyl-4-yl]-1,2,4-oxadiazol-3-yl}phenyl)ethyl]-N-methylglycinate (86 mg, 0.15 mmol) was added a 4N solution of HCl in dioxane and the mixture was heated in a tube at 70° C. for 3 hours. The solvent was then removed in vacuo and the residue was purified by preparative HPLC to give the title compound as a pale yellow oil. LC/MS (Method A): 472 (M+H)⁺, 470 (M−H)⁻. HPLC (Method K) Rt=18.0 min (Purity: 92.2%).

Example 87

[(2-{4-[5-(2-Methoxymethyl-2'-methyl-biphenyl-4-yl)-[1,2,4]oxadiazol-3-yl]-phenyl}-ethyl)-methyl-amino]-acetic acid

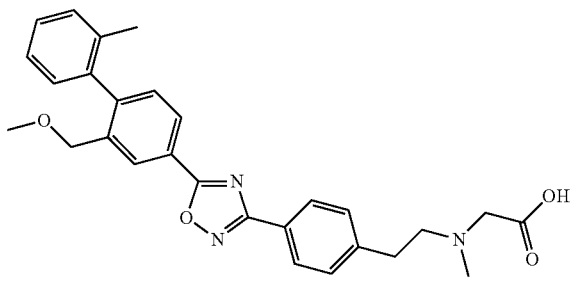 [SMILES: COCc1cc(-c2nc(-c3ccc(CCN(C)CC(=O)O)cc3)no2)ccc1-c1ccccc1C]

Step 1: 2-(4-(5-(2-(methoxymethyl)-2'-methylbiphenyl-4-yl)-1,2,4-oxadiazol-3-yl)phenyl)ethanol The title compound was prepared following the procedure described for Example 113, but starting from Intermediate 69 and Intermediate 3, to give the title compound as a white solid. ¹H NMR (CDCl₃, 400 MHz) δ 8.42 (1H, s), 8.20-8.10 (3H, m), 7.38 (2H, d, J=7.8 Hz), 7.35-7.24 (4H, m), 7.12 (1H, d, J=7.2 Hz), 4.13 (2H, s), 3.90 (2H, t, J=6.5 Hz), 3.33 (3H, s), 2.96 (2H, t, J=6.5 Hz), 2.10 (3H, s). LC/MS (Method A): 401 (M+H)⁺. HPLC (Method H)Rt 21.0 min (Purity: 93.4%).

Step 2: [(2-{4-[5-(2-Methoxymethyl-2'-methyl-biphenyl-4-yl)-[1,2,4]oxadiazol-3-yl]-phenyl}-ethyl)-methyl-amino]-acetic acid The title compound was prepared following the procedure described for Example 86 Steps 2 to 4, but starting from 2-(4-(5-(2-(methoxymethyl)-2'-methylbiphenyl-4-yl)-1,2,4-oxadiazol-3-yl)phenyl)ethanol and tert-butyl N-methylglycinate hydrochloride to give the title compound as a white solid. LC/MS (Method B): 470.0 (M−H)⁻; 472.0 (M+H)⁺. HPLC (Method F) Rt 3.22 min (Purity: 96.8%).

Example 88

N-(3-fluoro-5-{5-[3'-fluoro-2-(methoxymethyl)-2'-methylbiphenyl-4-yl]-1,2,4-oxadiazol-3-yl}benzyl)-N-methylglycine, hydrochloride salt

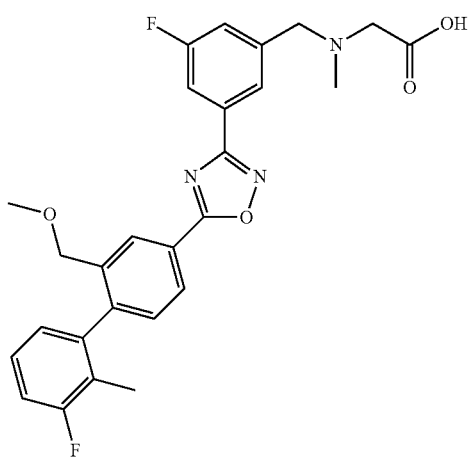 [SMILES: COCc1cc(-c2nc(-c3cc(F)cc(CN(C)CC(=O)O)c3)no2)ccc1-c1cccc(F)c1C]

Tert-butyl N-(3-fluoro-5-{5-[3'-fluoro-2-(methoxymethyl)-2'-methylbiphenyl-4-yl]-1,2,4-oxadiazol-3-yl}benzyl)-N-methylglycinate was prepared following the general procedure 4 starting from Intermediate 1 and Intermediate 24. It was hydrolyzed following the general procedure 8 affording the title compound as a white powder. ¹H NMR (DMSO-d₆, 300 MHz) δ 8.35 (d, J=1.5 Hz, 1H), 8.22-8.18 (m, 2H), 7.98 (d, J=7.9 Hz, 1H), 7.72 (d, J=9.3 Hz, 1H), 7.48 (d, J=8.0 Hz, 1H), 7.39-7.23 (m, 2H), 7.03 (d, J=7.3 Hz, 1H), 4.46 (s, 2H), 4.28-4.17 (m, 2H), 4.08 (s, 2H), 3.26 (s, 3H), 2.80 (s, 3H), 1.95 (d, J=2.1 Hz, 3H). LC/MS (Method B): 492.1 (M−H)⁻, 494.0 (M+H)⁺. HPLC (Method A) Rt 4.19 min (Purity: 100.0%).

Example 90

N-(4-{5-[3'-fluoro-2-(methoxymethyl)-2'-methylbiphenyl-4-yl]-1,2,4-oxadiazol-3-yl}benzyl)-N-methylglycine, hydrochloride salt

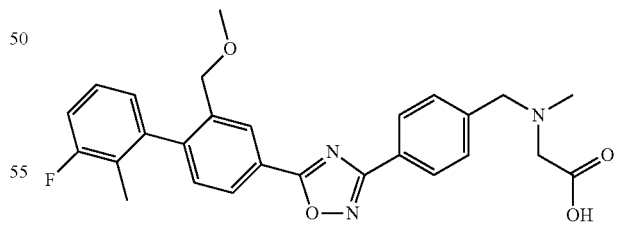

Tert-butyl N-(4-{5-[3'-fluoro-2-(methoxymethyl)-2'-methylbiphenyl-4-yl]-1,2,4-oxadiazol-3-yl}benzyl)-N-methylglycinate was prepared following the general procedure 4 starting from intermediate 1 and intermediate 31. It was hydrolyzed following the general procedure 8 affording the title compound as a white powder. ¹H NMR (DMSO-d₆, 300 MHz) δ 8.35 (d, J=1.7 Hz, 1H), 8.25-8.18 (m, 3H), 7.78 (d, J=8.2 Hz, 2H), 7.47 (d, J=8.0 Hz, 1H), 7.39-7.23 (m, 2H), 7.03 (d, J=7.3 Hz, 1H), 4.44 (s, 2H), 4.28-4.17 (m, 2H), 4.08

(s, 2H), 3.26 (s, 3H), 2.80 (s, 3H), 1.95 (d, J=2.1 Hz, 3H). LC/MS (Method B): 474.1 (M−H)⁻, 476.0 (M+H)⁺. HPLC (Method A) Rt 4.06 min (Purity: 100.0%).

Example 91

N-(2-fluoro-4-{5-[3'-fluoro-2-(methoxymethyl)-2'-methylbiphenyl-4-yl]-1,2,4-oxadiazol-3-yl}benzyl)-N-methylglycine, hydrochloride salt

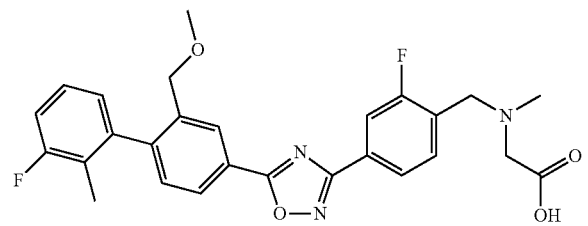 [SMILES: COCc1cc(-c2nc(-c3ccc(CN(C)CC(=O)O)c(F)c3)no2)ccc1-c1cccc(F)c1C]

Tert-butyl N-(2-fluoro-4-{5-[3'-fluoro-2-(methoxymethyl)-2'-methylbiphenyl-4-yl]-1,2,4-oxadiazol-3-yl}benzyl)-N-methylglycinate was prepared following the general procedure 4 starting from Intermediate 1 and Intermediate 32. It was hydrolyzed following the general procedure 8 affording the title compound as a white powder. $^1$H NMR (DMSO-$d_6$, 300 MHz) δ 8.35 (d, J=1.6 Hz, 1H), 8.20 (dd, J=8.0, 1.9 Hz, 1H), 8.08 (dd, J=8.0, 1.6 Hz, 1H), 7.99 (dd, J=10.3, 1.5 Hz, 1H), 7.90 (t, J=7.7 Hz, 1H), 7.47 (d, J=8.0 Hz, 1H), 7.39-7.23 (m, 2H), 7.03 (d, J=7.6 Hz, 1H), 4.49 (s, 2H), 4.28-4.09 (m, 4H), 3.26 (s, 3H), 2.81 (s, 3H), 1.95 (d, J=2.2 Hz, 3H). LC/MS (Method B): 492.1 (M−H)⁻, 494.0 (M+H)⁺. HPLC (Method A) Rt 4.12 min (Purity: 100.0%).

Example 92

N-{4-[5-(2-ethoxy-2'-methylbiphenyl-4-yl)-1,2,4-oxadiazol-3-yl]-2-fluorobenzyl}-N-methylglycine, hydrochloride salt

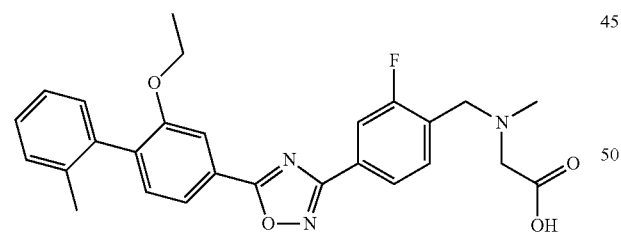

Tert-butyl N-{4-[5-(2-ethoxy-2'-methylbiphenyl-4-yl)-1,2,4-oxadiazol-3-yl]-2-fluorobenzyl}-N-methylglycinate was prepared following the general procedure 4 starting from Intermediate 48 and Intermediate 32. It was hydrolyzed following the general procedure 8 affording the title compound as a white powder. $^1$H NMR (DMSO-$d_6$, 300 MHz) δ 8.07 (dd, J=7.8, 1.5 Hz, 1H), 7.98 (dd, J=10.2, 1.2 Hz, 1H), 7.91 (d, J=7.7 Hz, 1H), 7.86 (dd, J=7.7, 1.5 Hz, 1H), 7.79 (d, J=1.3 Hz, 1H), 7.42 (d, J=7.8 Hz, 1H), 7.33-7.23 (m, 3H), 7.17 (d, J=6.6 Hz, 1H), 4.47 (s, 2H), 4.19 (q, J=7.0 Hz, 2H), 4.09 (s, 2H), 2.79 (s, 3H), 2.12 (s, 3H), 1.24 (t, J=6.9 Hz, 3H). LC/MS (Method B): 474.2 (M−H)⁻, 476.0 (M+H)⁺. HPLC (Method A) Rt 4.25 min (Purity: 99.6%).

Example 93

N-(3-chloro-5-{5-[2-(methoxymethyl)-2'-methylbiphenyl-4-yl]-1,2,4-oxadiazol-3-yl}benzyl)-N-methylglycine, hydrochloride salt

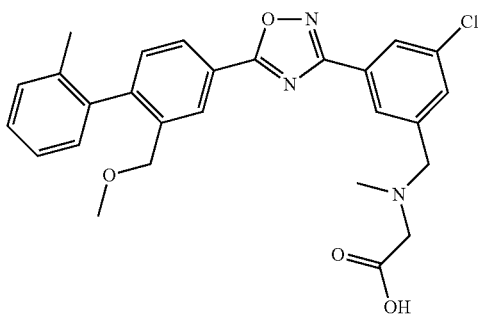 [SMILES: COCc1cc(-c2nc(-c3cc(Cl)cc(CN(C)CC(=O)O)c3)no2)ccc1-c1ccccc1C]

Tert-butyl N-(3-chloro-5-{5-[2-(methoxymethyl)-2'-methylbiphenyl-4-yl]-1,2,4-oxadiazol-3-yl}benzyl)-N-methylglycinate was prepared following the general procedure 3 starting from Intermediate 3 and Intermediate 43. It was hydrolyzed following general procedure 8 to afford the title compound as a white powder. $^1$H NMR (DMSO-$d_6$, 400 MHz) δ 8.34 (m, 1H), 8.30 (m, 1H), 8.17 (m, 2H), 8.07 (m, 1H), 7.91 (m, 1H), 7.44 (d, J=7.8 Hz, 1H), 4.46 (m, 1H), 4.20 (m, 2H), 4.09 (m, 2H), 3.25 (s, 3H), 2.80 (s, 3H), 2.03 (s, 3H). LC/MS (Method B): 492.0 (M+H)⁺, 490.1 (M−H)⁻. HPLC (Method A) Rt 4.31 min (Purity: 99%).

Example 94

(2-{3-[5-(2-Methoxymethyl-2'-methyl-biphenyl-4-yl)-[1,2,4]oxadiazol-3-yl]-phenyl}-ethylamino)-acetic acid

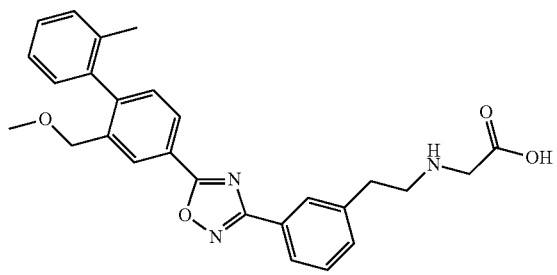 [SMILES: COCc1cc(-c2nc(-c3cccc(CCNCC(=O)O)c3)no2)ccc1-c1ccccc1C]

The title compound was prepared following the procedure described for Example 86, but using tert-butyl glycinate in Step 3, to give the title compound as a white solid. LC/MS (Method B): 458 (M+H)⁺. HPLC (Method G) Rt 3.12 min (Purity: 90.5%).

Example 99

N-{4-[5-(2-ethoxy-2'-ethylbiphenyl-4-yl)-1,2,4-oxadiazol-3-yl]benzyl}-N-methylglycine, hydrochloride salt

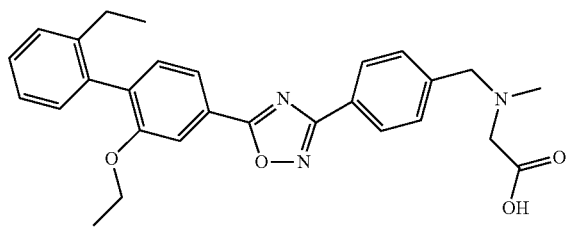 [SMILES: CCOc1cc(-c2nc(-c3ccc(CN(C)CC(=O)O)cc3)no2)ccc1-c1ccccc1CC]

Tert-butyl N-{4-[5-(2-ethoxy-2'-ethylbiphenyl-4-yl)-1,2,4-oxadiazol-3-yl]benzyl}-N-methylglycinate was prepared following the general procedure 3 starting from Intermediate 49 and Intermediate 31. It was hydrolyzed following general procedure 8 to afford the title compound as a white powder (225 mg, 75%). $^1$H NMR (DMSO-$d_6$, 300 MHz) δ 8.21 (m, 2H), 7.86 (d, J=7.8 Hz, 1H), 7.78 (m, 3H), 7.41 (d, J=7.8 Hz, 1H), 7.37-7.21 (m, 3H), 7.12 (m, 1H), 4.45 (m, 2H), 4.17 (m, 2H), 4.09 (m, 2H), 2.80 (s, 3H), 2.44 (m, 2H), 1.22 (t, J=6.9 Hz, 3H), 1.02 (t, J=7.5 Hz, 3H). LC/MS (Method B): 472.2 (M+H)$^+$, 470.3 (M−H)$^−$. HPLC (Method A) Rt 4.87 min (Purity: 100%).

Example 102

2-((4-(5-(2-(methoxymethyl)-2'-methylbiphenyl-4-yl)-1,2,4-oxadiazol-3-yl)-3-methylbenzyl)(methyl)amino)acetic acid

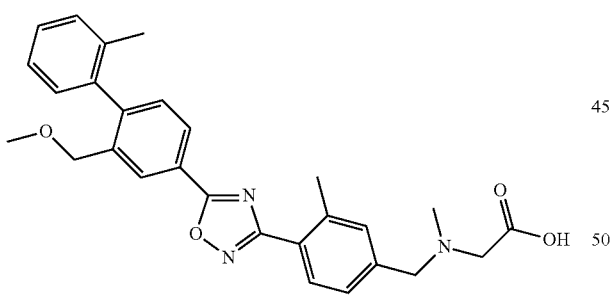

Step 1: (4-(5-(2-(methoxymethyl)-2'-methylbiphenyl-4-yl)-1,2,4-oxadiazol-3-yl)-3-methylphenyl)methanol The title compound was prepared following the procedure described in Example 113, but using Intermediate 73 and Intermediate 3. It was isolated as a colourless gum. $^1$H NMR (CDCl$_3$, 400 MHz) δ 8.43 (1H, s), 8.21-8.11 (2H, m), 7.38-7.22 (6H, m), 7.14 (1H, d, J=7.4 Hz), 4.77 (2H, s), 4.25-4.17 (2H, m), 3.32 (3H, s), 2.72 (3H, s), 2.11-2.02 (3H, m). LC/MS (Method A): 401 (M+H)$^+$. HPLC (Method G) Rt 4.25 min (Purity: 95.9%).

Step 2: 4-(5-(2-(methoxymethyl)-2'-methylbiphenyl-4-yl)-1,2,4-oxadiazol-3-yl)-3-methylbenzaldehyde (4-(5-(2-(methoxymethyl)-2'-methylbiphenyl-4-yl)-1,2,4-oxadiazol-3-yl)-3-methylphenyl)methanol (401 mg, 1.0 mmol) was dissolved in dioxane (10 mL) and manganese dioxide (1.0 g, 11.6 mmol) was added. The mixture was heated at 70° C. overnight and then the solvent was removed in vacuo. The residue was triturated with a mixture of petrol and diethyl ether to give the title compound as a white solid (361 mg, 90%). $^1$H NMR (CDCl$_3$, 400 MHz) δ 10.10 (1H, s), 8.45 (1H, s), 8.33 (1H, d, J=8.3 Hz), 8.19 (1H, dd, J=7.8, 1.9 Hz), 7.87 (2H, d, J=6.9 Hz), 7.38-7.24 (4H, m), 7.14 (1H, d, J=7.4 Hz), 4.24-4.21 (2H, m), 3.34 (3H, s), 2.81 (3H, s), 2.09 (3H, s).

Step 3: 2-((4-(5-(2-(methoxymethyl)-2'-methylbiphenyl-4-yl)-1,2,4-oxadiazol-3-yl)-3-methylbenzyl)(methyl)amino)acetic acid Sodium cyanoborohydride (29.7 mg; 0.47 mmol) was added into a solution of 4-(5-(2-(methoxymethyl)-2'-methylbiphenyl-4-yl)-1,2,4-oxadiazol-3-yl)-3-methylbenzaldehyde (185 mg, 0.43 mmol) and 2-(methylamino)acetic acid (65 mg, 0.87 mmol) in a mixture of methanol (3 mL), DCM (3 mL) and acetic acid (75 µl). The mixture was stirred at room temperature overnight and the solvent was then removed in vacuo. The residue was purified by preparative HPLC to give the title compound as a pale yellow gum. $^1$H NMR (DMSO-$d_6$, 400 MHz) δ 8.37-8.32 (1H, m), 8.20 (1H, dd, J=7.8, 1.9 Hz), 8.06 (1H, d, J=7.7 Hz), 7.47-7.37 (5H, m), 7.38-7.29 (1H, m), 7.18 (1H, d, J=7.3 Hz), 4.23 (2H, m), 3.78 (2H, s), 3.28 (3H, s), 3.25 (2H, s), 2.67 (3H, s), 2.34 (3H, s), 2.07 (3H, s). LC/MS (Method A): 472 (M+H)$^+$. HPLC (Method F) Rt 3.19 min (Purity: 99.2%).

Example 105

2-((4-(5-(2-(methoxymethyl)-2'-methylbiphenyl-4-yl)-1,2,4-oxadiazol-3-yl)-2-(trifluoromethyl)benzyl)(methyl)amino)acetic acid

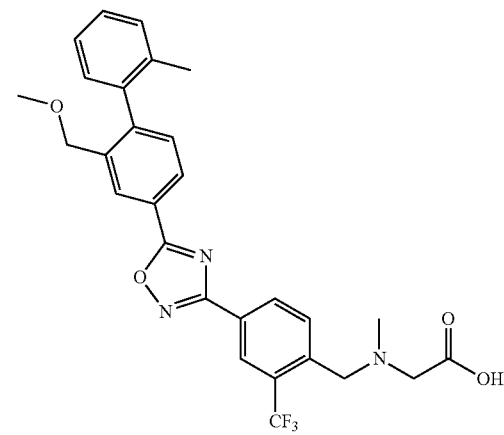 [SMILES: COCc1cc(-c2nc(-c3ccc(CN(C)CC(=O)O)c(C(F)(F)F)c3)no2)ccc1-c1ccccc1C]

To a solution of Intermediate 74 (0.112 g, 0.31 mmol) and Intermediate 3 (0.067 mg, 0.26 mmol) in MeCN (2 mL) was added EDC (0.069 g, 0.36 mmol). The reaction mixture was stirred at room temperature for 18 hours. The reaction mixture was diluted with pyridine (2 mL) and heated at 150° C. in the microwave for 30 minutes. The reaction was repeated and combined to work up. The solvent was removed in vacuo and the residue dissolved in DCM. The mixture was washed with water and the organic phase passed through a hydrophobic frit. The solvent was evaporated in vacuo. The residue was purified by SCX chromatography. The material was treated with a 4N solution of HCl in dioxane (4 mL) and the resulting mixture was stirred at 70° C. for 18 hours. The solvent was evaporated in vacuo and the residue purified by preparative HPLC, affording the title compound as an orange oil. $^1$H NMR (CDCl$_3$, 400 MHz) δ 8.98 (1H, br s), 8.50 (1H, s), 8.43-8.34 (2H, m), 8.14 (2H, d, J=8.0 Hz), 7.34-7.21 (4H, m), 7.12 (1H, d, J=7.4 Hz), 4.26-4.18 (4H, m), 3.56 (2H, s), 3.32 (3H, s), 2.62 (3H, s), 2.07 (3H, s). LC/MS (Method A): 526 (M+H)$^+$. HPLC (Method F) Rt 3.74 min (Purity: 99.4%).

Example 106

2-(4-(5-(2-(methoxymethyl)-2'-methylbiphenyl-4-yl)-1,2,4-oxadiazol-3-yl)-3-methylbenzylamino)acetic acid

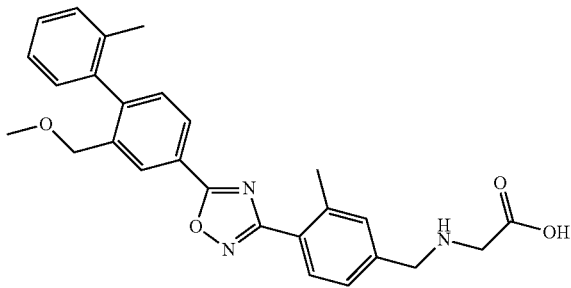 [SMILES: COCc1cc(-c2nc(-c3ccc(CNCC(=O)O)cc3C)no2)ccc1-c1ccccc1C]

The title compound was prepared following the procedure described in Example 102, but using aminoacetic acid in Step 3. It was isolated as a white solid (16 mg, 5%). $^1$H NMR (DMSO-d$_6$, 400 MHz) δ 8.35 (1H, s), 8.22-8.17 (1H, m), 8.11 (1H, d, J=7.9 Hz), 7.57-7.48 (2H, m), 7.46 (1H, d, J=7.9 Hz), 7.41-7.36 (2H, m), 7.38-7.30 (1H, m), 7.18 (1H, d, J=7.4 Hz), 4.23 (2H, m), 4.09 (2H, s), 3.44 (2H, s), 3.28 (3H, s), 2.68 (3H, s), 2.07 (3H, s). LC/MS (Method A): 458 (M+H)$^+$. HPLC (Method F) Rt 3.05 min (Purity: 99.1%).

Example 107

2-(3-methyl-4-(5-(2'-methyl-2-(trifluoromethyl)biphenyl-4-yl)-1,2,4-oxadiazol-3-yl)benzylamino)acetic acid

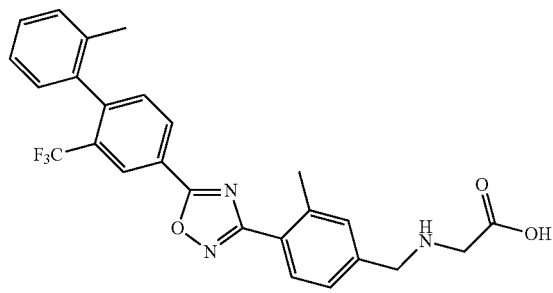 [SMILES: Cc1cc(CNCC(=O)O)ccc1-c1noc(-c2ccc(-c3ccccc3C)c(C(F)(F)F)c2)n1]

The title compound was prepared following the procedure described in Example 102, but using Intermediate 5 in Step 1 and aminoacetic acid in step 3, to give the title compound as a white solid (13 mg, 7%). $^1$H NMR (DMSO-d$_6$, 400 MHz) δ 8.60-8.55 (1H, m), 8.57-8.50 (1H, m), 8.10 (1H, d, J=7.8 Hz), 7.70 (1H, d, J=7.9 Hz), 7.53-7.46 (2H, m), 7.42-7.37 (2H, m), 7.35-7.29 (1H, m), 7.21 (1H, d, J=7.5 Hz), 3.99 (2H, s), 3.21 (2H, s), 2.73-2.65 (3H, m), 2.06 (3H, s). LC/MS (Method A): 482 (M+H)$^+$. HPLC (Method H) Rt 16.24 min (Purity: 94.1%).

Example 108

N-isopropyl-N-(3-{5-[2-(methoxymethyl)-2'-methylbiphenyl-4-yl]-1,2,4-oxadiazol-3-yl}benzyl)-beta-alanine, hydrochloride salt

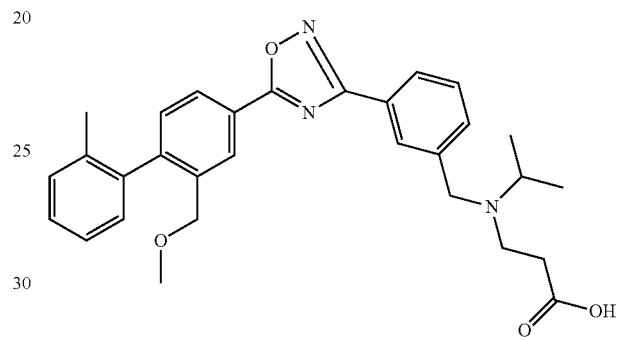

Tert-butyl N-isopropyl-N-(3-{5-[2-(methoxymethyl)-2'-methylbiphenyl-4-yl]-1,2,4-oxadiazol-3-yl}benzyl)-beta-alaninate was prepared following the general procedure 3 starting from Intermediate 3 and Intermediate 59. It was hydrolyzed following general procedure 8 to afford the title compound as a white powder (104 mg, 17%). $^1$H NMR (DMSO-d$_6$, 300 MHz) δ 12.70 (brs, 1H), 9.84 (brs, 1H), 8.38 (m, 1H), 8.34 (m, 1H), 8.25-8.15 (m, 2H), 7.90 (d, J=7.7 Hz, 1H), 7.72 (t, J=7.7 Hz, 1H), 7.44 (d, J=7.9 Hz, 1H), 7.40-7.25 (m, 3H), 7.14 (d, J=7.2 Hz, 1H), 4.47 (brs, 2H), 4.20 (m, 2H), 3.56 (m, 1H), 3.26 (s, 3H), 2.74 (m, 2H), 2.04 (s, 3H), 1.35 (m, 6H). LC/MS (Method B): 500.1 (M+H)$^+$, 498.2 (M−H)$^-$. HPLC (Method A) Rt 4.21 min (Purity: 98.6%).

Example 118

N-(4-{5-[2'-chloro-2-(methoxymethyl)biphenyl-4-yl]-1,2,4-oxadiazol-3-yl}benzyl)-N-methylglycine, hydrochloride salt

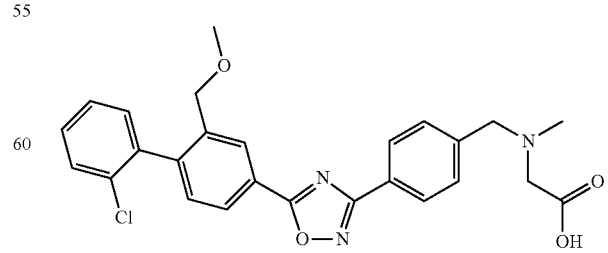

Tert-butyl N-(4-{5-[2'-chloro-2-(methoxymethyl)biphenyl-4-yl]-1,2,4-oxadiazol-3-yl}benzyl)-N-methylglycinate was prepared following the general procedure 3 starting from Intermediate 13 and Intermediate 31. It was deprotected following the general procedure 8 affording the title compound as a white powder. LC/MS (Method B): 476.2 (M–H)⁻, 478.1 (M+H)⁺. HPLC (Method A) Rt 3.95 min (Purity: 99.5%). Melting point: 194-200° C.

Example 119

N-(4-{5-[2'-chloro-2-(methoxymethyl)biphenyl-4-yl]-1,2,4-oxadiazol-3-yl}-2-fluorobenzyl)-N-methylglycine, hydrochloride salt

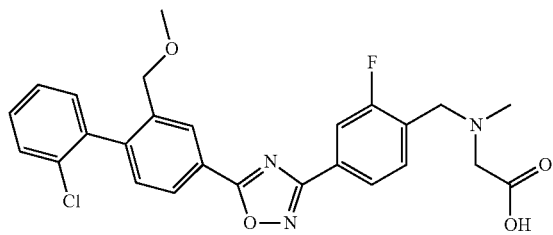 [SMILES: COCc1cc(-c2nc(-c3ccc(CN(C)CC(=O)O)c(F)c3)no2)ccc1-c1ccccc1Cl]

Tert-butyl N-(4-{5-[2'-chloro-2-(methoxymethyl)biphenyl-4-yl]-1,2,4-oxadiazol-3-yl}-2-fluorobenzyl)-N-methylglycinate was prepared following the general procedure 3 starting from intermediate 13 and intermediate 32. It was deprotected following the general procedure 8 affording the title compound as a white powder. LC/MS (Method B): 494.2 (M–H)⁻, 496.1 (M+H)⁺. HPLC (Method A) Rt 4.01 min (Purity: 98.0%). Melting point: 181-188° C.

Example 121

N-(4-{5-[2'-chloro-3'-fluoro-2-(methoxymethyl)biphenyl-4-yl]-1,2,4-oxadiazol-3-yl}-2-fluorobenzyl)-N-methylglycine, hydrochloride salt

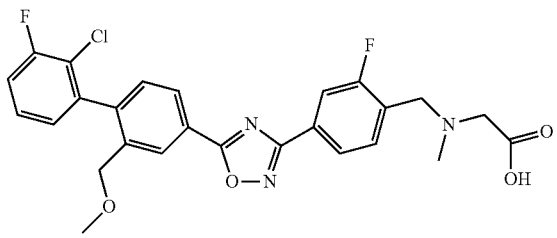 [SMILES: COCc1cc(-c2nc(-c3ccc(CN(C)CC(=O)O)c(F)c3)no2)ccc1-c1cccc(F)c1Cl]

Tert-butyl N-(4-{5-[2'-chloro-3'-fluoro-2-(methoxymethyl)biphenyl-4-yl]-1,2,4-oxadiazol-3-yl}-2-fluorobenzyl)-N-methylglycinate was prepared following the general procedure 3 starting from Intermediate 62 and Intermediate 32. It was hydrolyzed following general procedure 8 to afford the title compound as a white powder. ¹H NMR (DMSO-d₆, 300 MHz) δ 8.36 (brs, 1H), 8.23 (m, 1H), 8.08 (m, 1H), 8.00 (m, 1H), 7.89 (m, 1H), 7.54 (m, 3H), 7.26 (m, 1H), 4.48 (brs, 2H), 4.28 (m, 2H), 4.12 (brs, 2H), 3.25 (s, 3H), 2.80 (s, 3H). LC/MS (Method B): 514.1 (M+H)⁺, 512.2 (M–H)⁻. HPLC (Method A) Rt 3.90 min (Purity: 100%).

Example 122

N-(4-{5-[2'-chloro-3'-fluoro-2-(methoxymethyl)biphenyl-4-yl]-1,2,4-oxadiazol-3-yl}benzyl)-N-methylglycine, hydrochloride salt

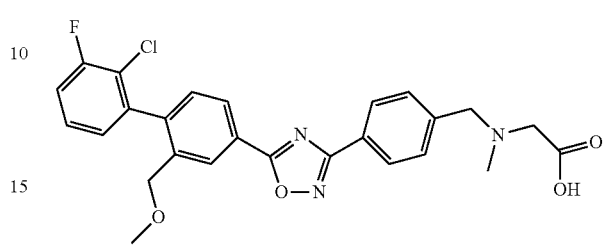

Tert-butyl N-(4-{5-[2'-chloro-3'-fluoro-2-(methoxymethyl)biphenyl-4-yl]-1,2,4-oxadiazol-3-yl}benzyl)-N-methylglycinate was prepared following the general procedure 3 starting from Intermediate 62 and Intermediate 31. It was hydrolyzed following general procedure 8 to afford the title compound as a white powder (326 mg, 80%). ¹H NMR (DMSO-d₆, 300 MHz) δ 8.35 (brs, 1H), 8.22 (m, 3H), 7.81 (d, J=8.4 Hz, 2H), 7.59-7.48 (m, 3H), 7.26 (m, 1H), 4.48 (brs, 2H), 4.28 (m, 2H), 4.11 (brs, 2H), 3.25 (s, 3H), 2.81 (s, 3H). LC/MS (Method B): 496.1 (M+H)⁺, 494.2 (M–H)⁻. HPLC (Method A) Rt 3.96 min (Purity: 100%).

Example 124

2-((2-ethyl-4-(5-(2-(methoxymethyl)-2'-methylbiphenyl-4-yl)-1,2,4-oxadiazol-3-yl)benzyl)(methyl)amino)acetic acid

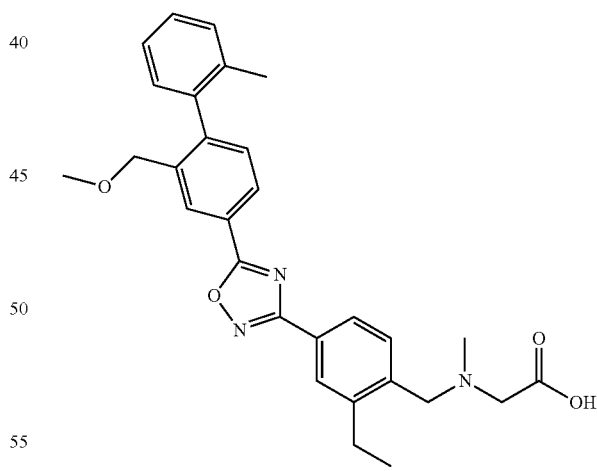

Step 1: tert-butyl N-(2-ethyl-4-{5-[2-(methoxymethyl)-2'-methylbiphenyl-4-yl]-1,2,4-oxadiazol-3-yl}phenyl)-N-methylglycinate To a solution of Intermediate 67 (0.385 g, 1.20 mmol) and Intermediate 3 (0.308 g, 1.20 mmol) in MeCN (3 mL) was added EDC (0.231 g, 1.20 mmol). The reaction mixture was stirred at room temperature for 18 hours. The reaction mixture was diluted with pyridine (2 mL) and heated at 150° C.

under microwave irradiations for 30 minutes. The solvent was removed in vacuo and the residue dissolved in DCM. The mixture was washed with water and the organic phase passed through a hydrophobic frit. The solvent was evaporated in vacuo. The residue was purified by flash chromatography (silica, iso-hexane/EtOAc) to afford the title compound. $^1$H NMR (CDCl$_3$, 40 MHz) δ 8.43 (1H, d, J=1.6 Hz), 8.20-8.17 (1H, m), 8.03 (1H, d, J=1.6 Hz), 7.99-7.97 (1H, m), 7.53-7.51 (1H, d, J=8.0 Hz), 7.34-7.25 (4H, m), 7.14 (1H, d, J=7.2 Hz), 4.23 (2H, s), 3.77 (2H, s), 3.33 (3H, s), 3.20 (2H, s), 2.85 (2H, q, J=7.2 Hz), 2.41 (3H, s), 2.08 (3H, s), 1.47 (9H, s), 1.30 (3H, t, J=7.2 Hz).

Step 2: 2-((2-ethyl-4-(5-(2-(methoxymethyl)-2'-methylbiphenyl-4-yl)-1,2,4-oxadiazol-3-yl)benzyl)(methyl)amino)acetic acid To tert-butyl N-(2-ethyl-4-{5-[2-(methoxymethyl)-2'-methylbiphenyl-4-yl]-1,2,4-oxadiazol-3-yl}phenyl)-N-methylglycinate (0.210 g; 0.39 mmol) was added a 4N solution of HCl in dioxane (10 mL) and the reaction mixture stirred at room temperature for 18 hours. The solvent was evaporated in vacuo and the residue triturated with hot EtOAc to afford the title compound as an off-white solid (0.142 g, 75%). $^1$H NMR (DMSO-d$_6$, 400 MHz) δ 8.34 (1H, d, J=1.6 Hz), 8.20-8.17 (1H, m), 8.06-8.03 (2H, m), 7.78 (1H, d, J=8 Hz), 7.45 (1H, d, J=8 Hz), 7.39-7.28 (3H, m), 7.16 (1H, d, J=7.2 Hz), 4.45 (2H, br s), 4.25-4.14 (4H, m), 3.26 (3H, s), 2.95-2.89 (2H, q, J=7.2 Hz), 2.82 (3H, s), 2.05 (3H, s), 1.24 (3H, t, J=7.2 Hz). LC/MS (Method A): 486 (M+H)$^+$. HPLC (Method F) Rt 3.31 min (Purity: 95.9%).

Example 125

2-((4-(5-(2-(methoxymethyl)-2'-methylbiphenyl-4-yl)-1,2,4-oxadiazol-3-yl)-2-methylbenzyl)(methyl)amino)acetic acid

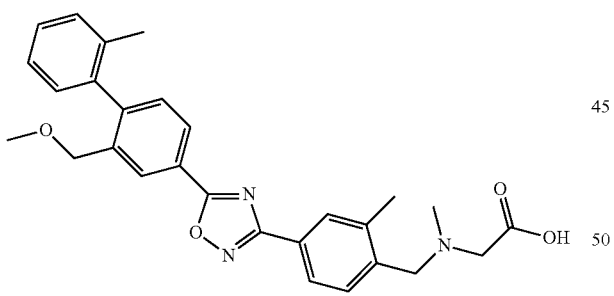

Step 1: (4-(5-(2-(methoxymethyl)-2'-methylbiphenyl-4-yl)-1,2,4-oxadiazol-3-yl)-2-methylphenyl)methanol The oxadiazole was prepared following the procedure described in Example 113, but using Intermediate 66 and Intermediate 3, to give the title compound as a white solid. $^1$H NMR (CDCl$_3$, 400 MHz) δ 8.45 (1H, d, J=1.7 Hz), 8.20 (1H, dd, J=7.9, 1.8 Hz), 8.09-8.03 (2H, m), 7.57 (1H, d, J=7.8 Hz), 7.38-7.25 (4H, m), 7.19-7.13 (1H, m), 4.81 (2H, s), 4.28-4.22 (2H, m), 3.35 (3H, s), 2.46 (3H, s), 2.10 (3H, s). LC/MS (Method A): 401 (M+H)$^+$. HPLC (Method H) Rt 11.0 min (Purity: 95.8%).

Step 2: 4-(5-(2-(methoxymethyl)-2'-methylbiphenyl-4-yl)-1,2,4-oxadiazol-3-yl)-2-methylbenzaldehyde The aldehyde was prepared following the procedure described for Example 102 Step 2, but starting from (4-(5-(2-(methoxymethyl)-2'-methylbiphenyl-4-yl)-1,2,4-oxadiazol-3-yl)-2-methylphenyl)methanol to give the title compound as a white solid (191 mg, 95%). $^1$H NMR (CDCl$_3$, 400 MHz) δ 10.36 (1H, s), 8.44 (1H, s), 8.22-8.15 (2H, m), 8.14 (1H, s), 7.96 (1H, d, J=7.9 Hz), 7.37-7.23 (4H, m), 7.13 (1H, d, J=7.4 Hz), 4.27-4.18 (2H, m), 3.34 (3H, s), 2.79 (3H, s), 2.08 (3H, s).

Step 3: 2-((4-(5-(2-(methoxymethyl)-2'-methylbiphenyl-4-yl)-1,2,4-oxadiazol-3-yl)-2-methylbenzyl)(methyl)amino)acetic acid Sodium cyanoborohydride (35 mg, 0.55 mmol) was added into a solution of 4-(5-(2-(methoxymethyl)-2'-methylbiphenyl-4-yl)-1,2,4-oxadiazol-3-yl)-2-methylbenzaldehyde (194 mg, 0.49 mmol) and 2-(methylamino)acetic acid (86 mg, 0.97 mmol) in a mixture of methanol (3 mL), DCM (3 mL) and acetic acid (75 μl). The mixture was stirred at room temperature overnight and the solvent was then removed in vacuo. The residue was purified by preparative HPLC to give the title compound as a white solid. $^1$H NMR (DMSO-d$_6$, 400 MHz) δ 8.47-8.31 (1H, m), 8.15-8.09 (1H, m), 8.06-7.99 (2H, m), 7.69 (1H, d, J=7.9 Hz), 7.33-7.20 (4H, m), 7.11 (1H, d, J=7.4 Hz), 4.33 (2H, s), 4.21 (2H, m), 3.67 (2H, s), 3.30 (3H, s), 2.78 (3H, s), 2.54 (3H, s), 2.07 (3H, s). LC/MS (Method A): 472 (M+H)$^+$. HPLC (Method F) Rt 3.19 min (Purity: 98.5%).

Example 126

N-(3,4-difluoro-5-{5-[2-(methoxymethyl)-2'-methylbiphenyl-4-yl]-1,2,4-oxadiazol-3-yl}benzyl)-N-methylglycine, hydrochloride salt

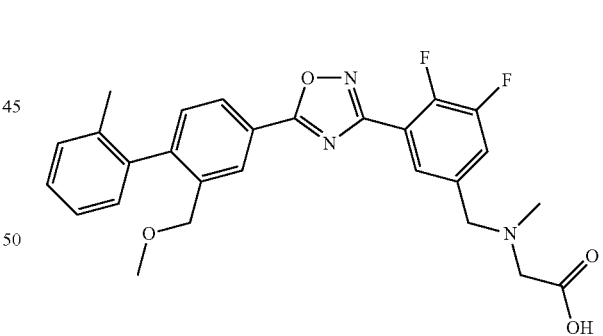

Tert-butyl N-(3,4-difluoro-5-{5-[2-(methoxymethyl)-2'-methylbiphenyl-4-yl]-1,2,4-oxadiazol-3-yl}benzyl)-N-methylglycinate was prepared following the general procedure 3 starting from Intermediate 3 and Intermediate 63. It was hydrolyzed following general procedure 8 to afford the title compound as a white powder. $^1$H NMR (DMSO-d$_6$, 300 MHz) δ 8.33 (brs, 1H), 8.19 (m, 2H), 7.94 (m, 1H), 7.46 (d, J=7.9 Hz, 1H), 7.39-7.25 (m, 3H), 7.15 (d, J=7.2 Hz, 1H), 4.45 (brs, 2H), 4.20 (m, 2H), 4.07 (brs, 2H), 3.25 (s, 3H), 2.80 (s, 3H), 2.04 (s, 3H). LC/MS (Method B): 494.3 (M+H)$^+$, 492.3 (M−H)$^−$. HPLC (Method A) Rt 4.13 min (Purity: 99.2%).

Example 127

N-(4-{5-[5'-fluoro-2-(methoxymethyl)-2'-methylbiphenyl-4-yl]-1,2,4-oxadiazol-3-yl}benzyl)-N-methylglycine, hydrochloride salt

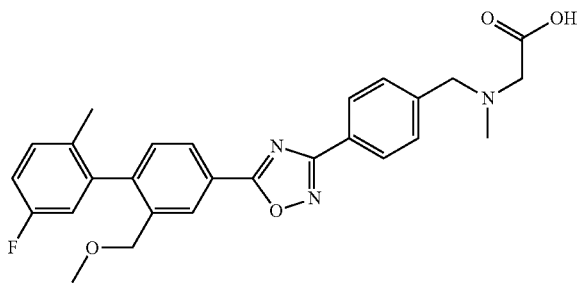 [SMILES: COCc1cc(-c2nc(-c3ccc(CN(C)CC(=O)O)cc3)no2)ccc1-c1cc(F)ccc1C]

Tert-butyl N-(4-{5-[5'-fluoro-2-(methoxymethyl)-2'-methylbiphenyl-4-yl]-1,2,4-oxadiazol-3-yl}benzyl)-N-methylglycinate was prepared following the general procedure 3 starting from Intermediate 46 and Intermediate 31. It was hydrolyzed following general procedure 8 to afford the title compound as a white powder. $^1$H NMR (DMSO-d$_6$, 300 MHz) δ 8.33 (brs, 1H), 8.20 (m, 3H), 7.80 (d, J=8.4 Hz, 2H), 7.46 (d, J=8.0 Hz, 1H), 7.40 (m, 1H), 7.20 (m, 1H), 7.05 (dd, J=9.3 Hz, 1H), 4.48 (brs, 2H), 4.22 (m, 2H), 4.11 (brs, 2H), 3.26 (s, 3H), 2.82 (s, 3H), 2.00 (s, 3H). LC/MS (Method B): 476.4 (M+H)$^+$, 474.4 (M−H)$^−$. HPLC (Method A) Rt 4.03 min (Purity: 100%).

Example 128

2-((4-(5-(2-(methoxymethyl)-2'-methylbiphenyl-4-yl)-1,2,4-oxadiazol-3-yl)-2-chlorobenzyl)(methyl)amino)acetic acid

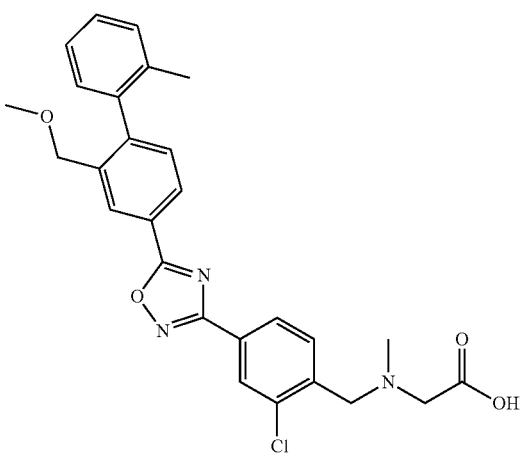 [SMILES: COCc1cc(-c2nc(-c3ccc(CN(C)CC(=O)O)c(Cl)c3)no2)ccc1-c1ccccc1C]

Step 1: tert-butyl 2-((2-chloro-4-(5-(2-(methoxymethyl)-2'-methylbiphenyl-4-yl)-1,2,4-oxadiazol-3-yl)benzyl)(methyl)amino)acetate To a solution of Intermediate 75 (0.270 g, 0.83 mmol) and Intermediate 3 (0.192 g, 0.75 mmol) in ACN (2 mL) was added EDC (0.201 g, 1.05 mmol). The reaction mixture was stirred at room temperature for 18 hours. The reaction mixture was diluted with pyridine (2 mL) and heated at 150° C. under microwave irradiations for 45 minutes. The solvent was removed in vacuo and the residue dissolved in DCM. The mixture was washed with water and the organic phase passed through a hydrophobic frit. The solvent was evaporated in vacuo. The residue was purified by flash chromatography (silica, iso-hexane/EtOAc) to afford the title compound. $^1$H NMR (CDCl$_3$, 400 MHz) δ 8.43 (1H, d, J=1.8 Hz), 8.21 (1H, d, J=1.7 Hz), 8.17 (1H, dd, J=7.9, 1.9 Hz), 8.08 (1H, dd, J=8.0, 1.7 Hz), 7.72 (1H, d, J=8.0 Hz), 7.35-7.21 (4H, m), 7.13 (1H, d, J=7.4 Hz), 4.29-4.17 (2H, m), 3.90 (2H, s), 3.33 (3H, s), 3.29 (2H, s), 2.46 (3H, s), 2.08 (3H, s), 1.50 (9H, s).

Step 2: 2-((4-(5-(2-(methoxymethyl)-2'-methylbiphenyl-4-yl)-1,2,4-oxadiazol-3-yl)-2-chlorobenzyl)(methyl)amino)acetic acid To tert-butyl 2-((2-chloro-4-(5-(2-(methoxymethyl)-2'-methylbiphenyl-4-yl)-1,2,4-oxadiazol-3-yl)benzyl)(methyl)amino)acetate (0.192 g, 0.35 mmol) was added a 4N solution of HCl in dioxane (2 mL) and the reaction mixture stirred at 80° C. for 2 hours. The reaction mixture was concentrated in vacuo. The residue was purified by SCX-2 chromatography eluting with methanol followed by DCM and ammoniacal MeOH (7M) to afford the title compound as a white solid. $^1$H NMR (DMSO-d$_6$, 400 MHz) δ 8.32 (1H, d, J=1.8 Hz), 8.17 (1H, dd, J=7.9, 1.9 Hz), 8.08-8.01 (2H, m), 7.84 (1H, d, J=7.9 Hz), 7.42 (1H, d, J=7.9 Hz), 7.38-7.33 (2H, m), 7.33-7.26 (1H, m), 7.15 (1H, d, J=7.4 Hz), 4.26-4.13 (2H, m), 3.84 (2H, s), 3.25 (3H, s), 2.94 (2H, s), 2.30 (3H, s), 2.04 (3H, s). LC/MS (Method A): 492 (M+H)$^+$. HPLC (Method F) Rt 3.29 min (Purity: 98.0%).

Example 130

N-{4-[5-(2,2'-dimethylbiphenyl-4-yl)-1,2,4-oxadiazol-3-yl]benzyl}-N-methylglycine, hydrochloride salt

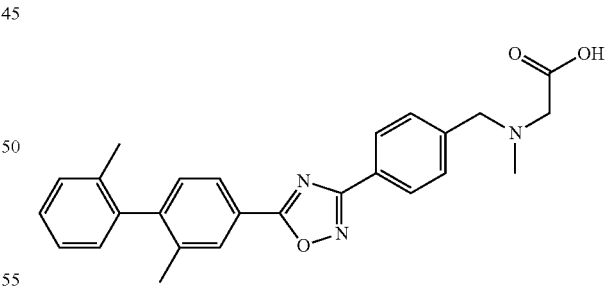

Tert-butyl N-{4-[5-(2,2'-dimethylbiphenyl-4-yl)-1,2,4-oxadiazol-3-yl]benzyl}-N-methylglycinate was prepared following the general procedure 3 starting from Intermediate 53 and Intermediate 31. It was hydrolyzed following general procedure 8 to afford the title compound as a white powder. $^1$H NMR (DMSO-d$_6$, 300 MHz) δ 8.20 (m, 3H), 8.07 (m, 1H), 7.80 (d, J=7.8 Hz, 2H), 7.41-7.26 (m, 4H), 7.13 (m, 1H), 4.48 (brs, 2H), 4.11 (brs, 2H), 2.81 (s, 3H), 2.14 (s, 3H), 2.04 (s, 3H). LC/MS (Method B): 428.3 (M+H)$^+$, 426.4 (M−H)$^−$. HPLC (Method A) Rt 4.14 min (Purity: 100%).

Example 131

N-{4-[5-(2,2'-dimethylbiphenyl-4-yl)-1,2,4-oxadiazol-3-yl]-2-fluorobenzyl}-N-methylglycine, hydrochloride salt

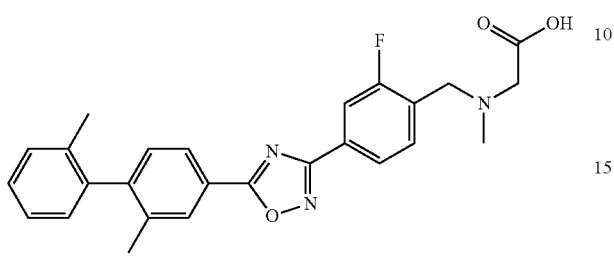

Tert-butyl N-{4-[5-(2,2'-dimethylbiphenyl-4-yl)-1,2,4-oxadiazol-3-yl]-2-fluorobenzyl}-N-methylglycinate was prepared following the general procedure 3 starting from Intermediate 53 and Intermediate 32. It was hydrolyzed following general procedure 8 to afford the title compound as a white powder. $^1$H NMR (DMSO-$d_6$, 300 MHz) δ 8.17 (m, 1H), 8.07 (m, 2H), 7.96 (m, 2H), 7.41-7.26 (m, 4H), 7.12 (m, 1H), 4.52 (brs, 2H), 4.15 (brs, 2H), 2.82 (s, 3H), 2.14 (s, 3H), 2.04 (s, 3H). LC/MS (Method B): 446.2 (M+H)$^+$, 444.2 (M–H)$^-$. HPLC (Method A) Rt 4.24 min (Purity: 100%).

Example 132

N-{3-[5-(2,2'-dimethylbiphenyl-4-yl)-1,2,4-oxadiazol-3-yl]benzyl}-N-methylglycine, hydrochloride salt

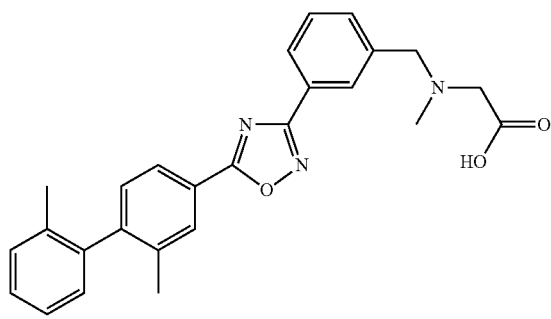 [SMILES: Cc1ccccc1-c1ccc(-c2nc(-c3cccc(CN(C)CC(=O)O)c3)no2)cc1C]

Tert-butyl N-{3-[5-(2,2'-dimethylbiphenyl-4-yl)-1,2,4-oxadiazol-3-yl]benzyl}-N-methylglycinate was prepared following the general procedure 3 starting from Intermediate 53 and Intermediate 21. It was hydrolyzed following general procedure 8 to afford the title compound as a white powder. $^1$H NMR (DMSO-$d_6$, 300 MHz) δ 8.33 (brs, 1H), 8.21 (m, 1H), 8.17 (brs, 1H), 8.08 (m, 1H), 7.82 (m, 1H), 7.72 (m, 1H), 7.40 (d, J=7.9 Hz, 1H), 7.38-7.26 (m, 3H), 7.13 (m, 1H), 4.50 (brs, 2H), 4.12 (brs, 2H), 2.82 (s, 3H), 2.14 (s, 3H), 2.04 (s, 3H). LC/MS (Method B): 428.2 (M+H)$^+$, 426.3 (M–H)$^-$. HPLC (Method A) Rt 4.16 min (Purity: 100%).

Example 133

N-{3-[5-(2,2'-dimethylbiphenyl-4-yl)-1,2,4-oxadiazol-3-yl]-5-fluorobenzyl}-N-methylglycine, hydrochloride salt

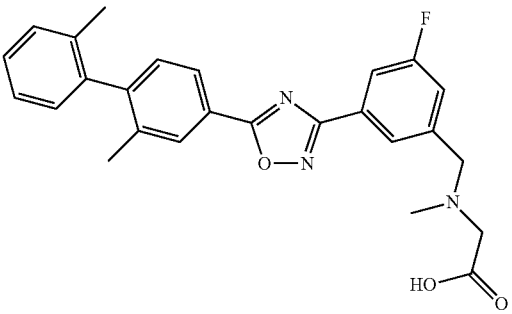 [SMILES: Cc1ccccc1-c1ccc(-c2nc(-c3cc(F)cc(CN(C)CC(=O)O)c3)no2)cc1C]

Tert-butyl N-{3-[5-(2,2'-dimethylbiphenyl-4-yl)-1,2,4-oxadiazol-3-yl]-5-fluorobenzyl}-N-methylglycinate was prepared following the general procedure 3 starting from Intermediate 53 and Intermediate 24. It was hydrolyzed following general procedure 8 to afford the title compound as a white powder. $^1$H NMR (DMSO-$d_6$, 400 MHz) δ 8.19 (brs, 1H), 8.17 (brs, 1H), 8.07 (m, 1H), 7.97 (m, 1H), 7.78 (m, 1H), 7.40 (d, J=7.9 Hz, 1H), 7.37-7.26 (m, 3H), 7.12 (m, 1H), 4.53 (brs, 2H), 4.13 (brs, 2H), 2.83 (s, 3H), 2.14 (s, 3H), 2.04 (s, 3H). LC/MS (Method B): 446.2 (M+H)$^+$, 444.3 (M–H)$^-$. HPLC (Method A) Rt 4.30 min (Purity: 99.9%).

Example 137

N-(4-{5-[2'-(difluoromethyl)-2-methylbiphenyl-4-yl]-1,2,4-oxadiazol-3-yl}benzyl)-N-methylglycine, hydrochloride salt

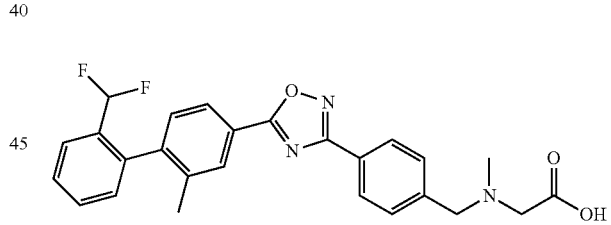

Tert-butyl N-(4-{5-[2'-(difluoromethyl)-2-methylbiphenyl-4-yl]-1,2,4-oxadiazol-3-yl}benzyl)-N-methylglycinate was prepared following the general procedure 6 starting from Intermediate 31 and Intermediate 55. After purification by flash chromatography (silica, cHex/EtOAc), the ester derivative was deprotected following the general procedure 8. After purification by precipitation from a mixture of ACN and a few drops of a 5N aqueous solution of HCl, the title compound was obtained as a white powder. HPLC (Method A), Rt 4.0 min (purity: 98.9%). LC/MS (Method B): 462.3 (M–H)$^-$, 464.2 (M+H)$^+$. Melting point: 229-234° C. Elemental analysis: [$C_{26}H_{23}N_3O_3F_2$—HCl] Corrected: C, 62.46%; H, 4.84%; N, 8.40%; Cl, 7.09%. Found: C, 62.29%; H, 4.99%; N, 8.43%; Cl, 7.18%. $^1$H NMR (DMSO-$d_6$, 300 MHz) δ 8.21 (d, J=8.4 Hz, 2H), 8.19 (d, J=1.6 Hz, 1H), 8.09 (dd, J=7.9, 1.6 Hz, 1H), 7.79 (m, 3H), 7.70-7.59 (m, 2H), 7.44 (d, J=7.9 Hz, 1H), 7.33 (d, J=6.5 Hz, 1H), 6.64 (t, J=54.7 Hz, 1H), 4.46 (s, 2H), 4.10 (s, 2H), 2.80 (s, 3H), 2.14 (s, 3H).

Example 140

N-(4-{5-[2-(1-methoxyethyl)-2'-methylbiphenyl-4-yl]-1,2,4-oxadiazol-3-yl}benzyl)-N-methylglycine, hydrochloride salt

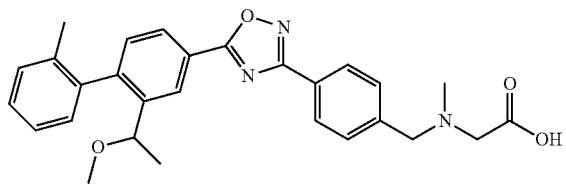 [SMILES: COC(C)c1cc(-c2nc(-c3ccc(CN(C)CC(=O)O)cc3)no2)ccc1-c1ccccc1C]

Tert-butyl N-(4-{5-[2-(1-methoxyethyl)-2'-methylbiphenyl-4-yl]-1,2,4-oxadiazol-3-yl}benzyl)-N-methylglycinate was prepared following the general procedure 6 starting from Intermediate 31 and Intermediate 77. After purification by flash chromatography (silica, heptane/MTBE), the ester derivative was deprotected following the general procedure 8. After purification by precipitation from a mixture of ACN and a 1N aqueous solution of HCl, the title compound was obtained as a white powder. HPLC (Method A), Rt 4.1 min (purity: 96.9%). LC/MS (Method B): 469.9 (M−H)⁻, 471.9 (M+H)⁺. Melting point: 179-181° C. Elemental analysis: [$C_{28}H_{29}N_3O_4$—HCl-0.4$H_2O$] Corrected: C, 65.27%; H, 6.03%; N, 8.16%; Cl, 6.88%. Found: C, 65.31%; H, 6.06%; N, 8.33%; Cl, 6.85%. ¹H NMR (DMSO-$d_6$, 300 MHz) δ 8.32 (d, J=1.9 Hz, 0.4H), 8.30 (d, J=1.9 Hz, 0.6H), 8.23 (d, J=8.4 Hz, 2H), 8.16 (m, 1H), 7.79 (d, J=8.4 Hz, 2H), 7.44-7.27 (m, 4H), 7.19 (d, J=7.1 Hz, 0.4H), 7.12 (d, J=7.1 Hz, 0.6H), 4.46 (s, 2H), 4.22 (q, J=6.4 Hz, 0.4H), 4.09 (s, 2H), 3.99 (q, J=6.4 Hz, 0.6H), 3.13 (s, 1.2H), 3.11 (s, 1.8H), 2.80 (s, 3H), 2.08 (s, 1.8H), 2.04 (s, 1.2H), 1.26 (d, J=6.4 Hz, 1.8H), 1.19 (d, J=6.4 Hz, 1.2H).

Example 142

4-[(4-{5-[2'-methyl-2-(trifluoromethyl)biphenyl-4-yl]-1,2,4-oxadiazol-3-yl}benzyl)amino]butanoic acid

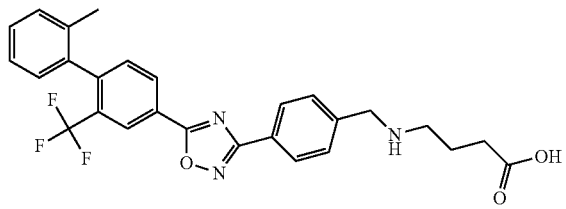 [SMILES: Cc1ccccc1-c1ccc(-c2nc(-c3ccc(CNCCCC(=O)O)cc3)no2)cc1C(F)(F)F]

Sodium cyanoborohydride (18 mg, 0.28 mmol) was added to a solution of 4-(5-(2'-methyl-2-(trifluoromethyl)biphenyl-4-yl)-1,2,4-oxadiazol-3-yl)benzaldehyde (0.25 mmol) and 4-aminobutanoic acid (0.25 mmol) in a mixture of methanol (3 mL), DCM (3 mL) and acetic acid (38 µl). The mixture was stirred at room temperature overnight and was filtered through a frit under positive pressure. The solvent was removed in vacuo and the residue purified by reverse phase HPLC to give the title compound as a off-white solid. LC/MS (Method A): 494 (M−H)⁻, 496 (M+H)⁺. HPLC (Method K) Rt=17.93 min (Purity: 93.64%).

Example 143

2-((4-(5-(2-(methoxymethyl)-2'-methylbiphenyl-4-yl)-1,2,4-oxadiazol-3-yl)-3-(trifluoromethyl)benzyl)(methyl)amino)acetic acid

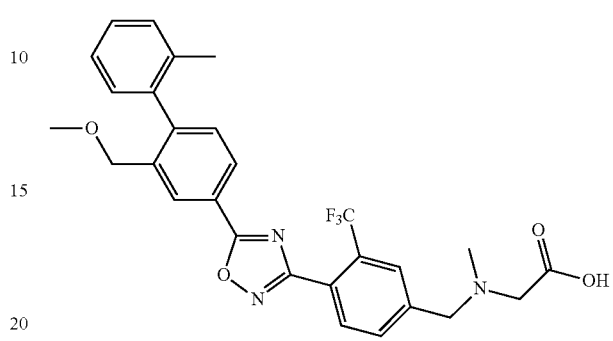

The title compound was prepared following the procedures described for Example 105 and Intermediate 74, but starting from 4-methyl-2-(trifluoromethyl)benzonitrile to give the title compound as a pale yellow gum. ¹H NMR (DMSO-$d_6$, 400 MHz) δ 8.31 (1H, d, J=1.8 Hz), 8.14 (1H, dd, J=7.9, 1.9 Hz), 8.00 (1H, s), 7.95 (1H, d, J=7.9 Hz), 7.85 (1H, d, J=8.0 Hz), 7.39 (1H, d, J=7.9 Hz), 7.35-7.25 (3H, m), 7.12 (1H, d, J=7.4 Hz), 4.27-4.11 (2H, m), 3.90 (2H, s), 3.34 (2H, s), 3.23 (3H, s), 2.35 (3H, s), 2.03 (3H, s). LC/MS (Method A): 526 (M+H)⁺. HPLC (Method F) Rt 3.28 min (Purity: 99.8%).

Example 144

2-((4-(5-(2-(methoxymethyl)-2'-methylbiphenyl-4-yl)-1,2,4-oxadiazol-3-yl)-3-chlorobenzyl)(methyl)amino)acetic acid

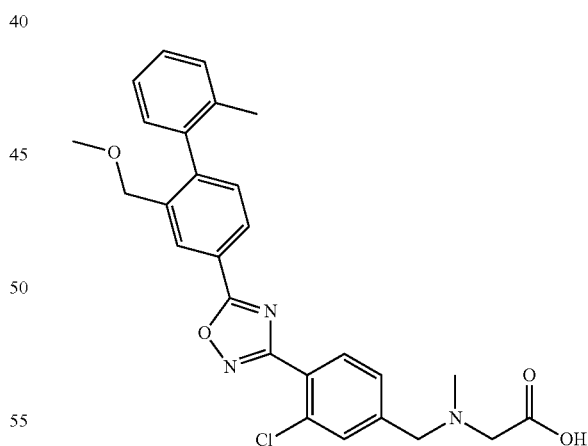

Step 1: tert-butyl 2-((3-chloro-4-(5-(2-(methoxymethyl)-2'-methylbiphenyl-4-yl)-1,2,4-oxadiazol-3-yl)benzyl)(methyl)amino)acetate To a solution of Intermediate 65 (0.298 g, 0.91 mmol) and Intermediate 3 (0.79 g, 0.70 mmol) in MeCN (2 mL) was added EDC (0.188 g, 0.98 mmol). The reaction mixture was stirred at room temperature for 18 hours. The reaction mixture was diluted with pyridine (2 mL) and heated at 150° C.

under microwave irradiation for 20 minutes. The solvent was removed in vacuo and the residue dissolved in DCM. The mixture was washed with water and the organic phase passed through a hydrophobic frit. The solvent was evaporated in vacuo. The residue was purified by flash chromatography (silica, iso-hexane/EtOAc) to afford the title compound. $^1$H NMR (CDCl$_3$, 400 MHz) δ 8.43 (1H, d, J=1.8 Hz), 8.17 (1H, dd, J=7.9, 1.9 Hz), 7.99 (1H, d, J=7.9 Hz), 7.59 (1H, s), 7.42 (1H, dd, J=8.0, 1.6 Hz), 7.37-7.21 (4H, m), 7.13 (1H, d, J=7.4 Hz), 4.22 (2H, m), 3.75 (2H, s), 3.31 (3H, s), 3.22 (2H, s), 2.41 (3H, s), 2.08 (3H, s), 1.50 (9H, s).

Step 2: 2-((4-(5-(2-(methoxymethyl)-2'-methylbiphenyl-4-yl)-1,2,4-oxadiazol-3-yl)-3-chlorobenzyl)(methyl)amino)acetic acid To tert-butyl 2-((2-chloro-4-(5-(2-(methoxymethyl)-2'-methylbiphenyl-4-yl)-1,2,4-oxadiazol-3-yl)benzyl)(methyl)amino)acetate (0.192 g, 0.35 mmol) was added a 4N solution of HCl in dioxane (2 mL) and the reaction mixture stirred at 80° C. for 2 hours. The reaction mixture was allowed to cool and the solvent evaporated in vacuo. The residue was purified by SCX-2 chromatography eluting with methanol followed by DCM and ammoniacal MeOH (7M) to afford the title compound as a colorless gum. $^1$H NMR (CDCl$_3$, 400 MHz) δ 8.38 (1H, s), 8.12 (1H, d, J=7.9 Hz), 8.07 (1H, d, J=8.0 Hz), 7.72 (1H, s), 7.55 (1H, d, J=8.1 Hz), 7.32-7.19 (4H, m), 7.10 (1H, d, J=7.4 Hz), 4.19 (4H, m), 3.57 (2H, s), 3.28 (3H, s), 2.72 (3H, s), 2.05 (3H, s). LC/MS (Method A): 492 (M+H)$^+$. HPLC (Method F) Rt 3.19 min (Purity: 98.8%).

Example 146

2-((3-fluoro-4-(5-(2-(methoxymethyl)-2'-methylbiphenyl-4-yl)-1,2,4-oxadiazol-3-yl)benzyl)(methyl)amino)acetic acid, hydrochloride salt

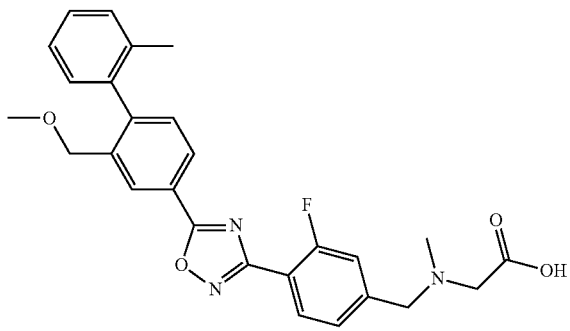 [SMILES: COCc1cc(-c2nc(-c3ccc(CN(C)CC(=O)O)cc3F)no2)ccc1-c1ccccc1C]

Step 1: (3-fluoro-4-(5-(2-(methoxymethyl)-2'-methylbiphenyl-4-yl)-1,2,4-oxadiazol-3-yl)phenyl)methanol The title compound was prepared following the procedures described for Example 125 and Intermediate 66, but starting from 4-bromo-3-fluorobenzoic acid to give the title compound as a white solid. $^1$H NMR (CDCl$_3$, 400 MHz) δ 8.43 (1H, d, J=1.8 Hz), 8.24-8.14 (2H, m), 7.36-7.21 (6H, m), 7.13 (1H, d, J=7.5 Hz), 4.81 (2H, d, J=5.7 Hz), 4.23 (2H, t, J=13.4 Hz), 3.32 (3H, s), 2.08 (3H, s), 1.90 (1H, t, J=6.0 Hz). LC/MS (Method A): 405 (M+H)$^+$. HPLC (Method F) Rt 4.25 min (Purity: 99.1%).

Step 2: 2-((3-fluoro-4-(5-(2-(methoxymethyl)-2'-methylbiphenyl-4-yl)-1,2,4-oxadiazol-3-yl)benzyl)(methyl)amino)acetic acid, hydrochloride salt The title compound was prepared following the procedure described for Example 125 Steps 2 and 3, but starting from (3-fluoro-4-(5-(2-(methoxymethyl)-2'-methylbiphenyl-4-yl)-1,2,4-oxadiazol-3-yl)phenyl)methanol to give the title compound as a white solid. $^1$H NMR (DMSO-d$_6$, 400 MHz) δ 8.31 (1H, d, J=1.8 Hz), 8.24 (1H, t, J=7.7 Hz), 8.18 (1H, dd, J=7.9, 1.9 Hz), 7.66 (1H, d, J=11.3 Hz), 7.60 (1H, dd, J=8.1, 1.6 Hz), 7.43 (1H, d, J=7.9 Hz), 7.37-7.26 (3H, m), 7.13 (1H, d, J=7.4 Hz), 4.42 (2H, s), 4.24-4.12 (2H, m), 4.08 (2H, s), 3.23 (3H, s), 2.81 (3H, s), 2.02 (3H, s). LC/MS (Method A): 476 (M+H)$^+$. HPLC (Method F) Rt 3.08 min (Purity: 99.4%).

Example 147

2-(2,6-difluoro-4-(5-(2-(methoxymethyl)-2'-methylbiphenyl-4-yl)-1,2,4-oxadiazol-3-yl)benzylamino)acetic acid, hydrochloride salt

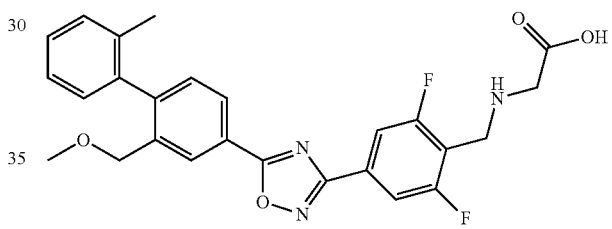

Step 1: (2,6-difluoro-4-(5-(2-(methoxymethyl)-2'-methylbiphenyl-4-yl)-1,2,4-oxadiazol-3-yl)phenyl)methanol To a solution of Intermediate 64 (0.091 g; 0.45 mmol) and Intermediate 3 (0.096 mg; 0.375 mmol) in MeCN (2.5 mL) was added EDC (0.101 g; 0.53 mmol). The reaction mixture was stirred at ambient temperature for 18 h. The reaction mixture was diluted with pyridine (2.5 mL) and heated at 150° C. in the microwave for 30 minutes. The reaction was repeated three times and combined for the work up. The solvent was removed in vacuo and the residue dissolved in DCM. The mixture was washed with water and the organic phase passed through a hydrophobic frit. The solvent was evaporated in vacuo. The residue was purified by flash chromatography on silica, eluting with iso-hexane/EtOAc (100% iso-hexane to 100% EtOAc) to afford the title compound (0.276 g, 58%). $^1$H NMR: (CDCl$_3$, 400 MHz) δ 8.42 (1H, d, J=1.8 Hz), 8.16 (1H, dd, J=7.9, 1.9 Hz), 7.82-7.73 (2H, m), 7.37-7.21 (4H, m), 7.13 (1H, d, J=7.4 Hz), 4.86 (2H, m), 4.23 (2H, m), 3.34 (3H, s), 2.08 (3H, s), 1.96 (1H, t, J=6.7 Hz). LC/MS (Method B): 423 (M+H)$^+$. HPLC (Method F) Rt 4.89 min (Purity: 99.1%).

Step 2: 2-(2,6-difluoro-4-(5-(2-(methoxymethyl)-2'-methylbiphenyl-4-yl)-1,2,4-oxadiazol-3-yl)benzylamino)acetic acid, hydrochloride salt The title compound was prepared following the procedure described in Example 125, but using (2,6-difluoro-4-(5-(2-(methoxymethyl)-2'-methylbiphenyl-4-yl)-1,2,4-oxadiazol-3-yl)phenyl)methanol in Step 2 and 2-aminoacetic acid in step 3, to give the title compound as a white solid. $^1$H NMR (DMSO-$d_6$, 400 MHz) δ 8.33 (1H, s), 8.21 (1H, d, J=8.0 Hz), 7.90 (2H, d, J=7.5 Hz), 7.45 (1H, d, J=7.9 Hz), 7.38 (2H, d, J=4.4 Hz), 7.35-7.29 (1H, m), 7.15 (1H, d, J=7.4 Hz), 4.37 (2H, s), 4.26-4.15 (2H, m), 3.97 (2H, s), 3.25 (3H, s), 2.04 (3H, s). LC/MS (Method A): 480 (M+H)$^+$. HPLC (Method I) Rt 8.77 min (Purity: 97.6%).

Example 149

2-((2,3-difluoro-4-(5-(2-(methoxymethyl)-2'-methylbiphenyl-4-yl)-1,2,4-oxadiazol-3-yl)benzyl)(methyl)amino)acetic acid, hydrochloride salt

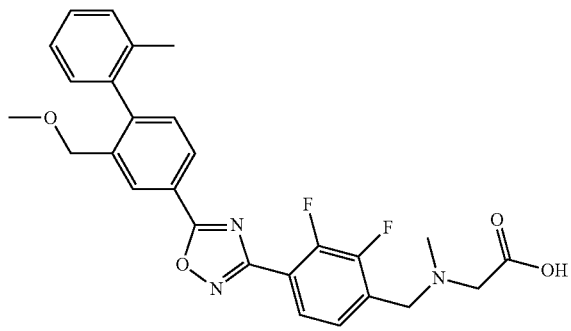 [SMILES: COCc1cc(-c2nc(-c3ccc(CN(C)CC(=O)O)c(F)c3F)no2)ccc1-c1ccccc1C]

The title compound was prepared according to the protocol described for Example 148, but using Intermediate 3, and the protocol described for Intermediate 76, but using 2,3-difluoro-4-methylbenzonitrile. $^1$H NMR (DMSO-$d_6$, 400 MHz) δ 8.37 (1H, d, J=1.8 Hz), 8.21 (1H, dd, J=7.9, 1.9 Hz), 8.10 (1H, ddd, J=8.3, 6.2, 1.6 Hz), 7.77 (1H, t, J=7.2 Hz), 7.48 (1H, d, J=7.9 Hz), 7.41-7.30 (3H, m), 7.18 (1H, d, J=7.4 Hz), 4.57 (2H, s), 4.23 (2H, m), 4.17 (2H, s), 3.29 (3H, s), 2.86 (3H, s), 2.07 (3H, s). LC/MS (Method A): 494 (M+H)$^+$. HPLC (Method F) Rt 3.19 min (Purity: 99.2%).

Example 151

2-((2,6-difluoro-4-(5-(2-(methoxymethyl)-2'-methylbiphenyl-4-yl)-1,2,4-oxadiazol-3-yl)benzyl)(methyl)amino)acetic acid, hydrochloride salt

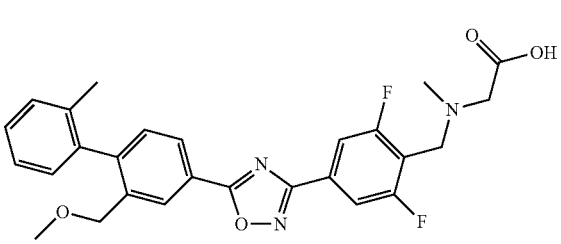 [SMILES: COCc1cc(-c2nc(-c3cc(F)c(CN(C)CC(=O)O)c(F)c3)no2)ccc1-c1ccccc1C]

The title compound was prepared according to the protocol described for Example 148, but using Intermediate 3, to give the title compound as a white solid. $^1$H NMR (DMSO-$d_6$, 400 MHz) δ 8.34 (1H, s), 8.21 (1H, dd, J=7.9, 1.9 Hz), 7.91 (2H, d, J=7.7 Hz), 7.45 (1H, d, J=7.9 Hz), 7.38 (2H, d, J=4.4 Hz), 7.36-7.28 (1H, m), 7.15 (1H, d, J=7.4 Hz), 4.44 (2H, s), 4.27-4.15 (2H, m), 4.03 (2H, s), 3.25 (3H, s), 2.76 (3H, s), 2.04 (3H, s). LC/MS (Method A): 494 (M+H)$^+$. HPLC (Method F) Rt 3.22 min (Purity: 97.1%).

Example 156

In Vitro Assays

Membranes Preparation:

Membranes were prepared from CHO cells expressing S1P1 or S1P3 for use in ligand and 355-GTPγS binding studies. Cells were suspended in 50 mM TRIS, pH 7.4, 2 mM EDTA, 250 mM Sucrose (buffer A) and 1× Complete protease inhibitor cocktail (Roche), and disrupted at 4° C. by N2 decompression using a cell disruption bomb (Parr Instrument). Following centrifugation at 1000 RPM for 10 min at 4° C., the supernatant was diluted (2×) in buffer A and centrifuged again at 19000 RPM for 75 min at 4° C. The pellet was then suspended in 10 mM HEPES, pH 7.4, 1 mM EDTA, 250 mM Sucrose (Buffer B), and 1× Complete EDTA-free protease inhibitor cocktail and homogenized using a potter. Membranes were flash frozen in liquid $N_2$ and stored at −80° C.

Receptor binding assay: [33P]sphingosine 1-phosphate (3000 Ci/mmol; American Radiolabeled Chemicals, Inc.) was added to test compounds in 20% DMSO by competition. Membranes and WGA SPA beads (GE Healthcare) were added to give a final volume of 100 μl in 96-well plates or 50 μl in 384-well plates with assay concentrations of 30 μM or 15 μM [33P]sphingosine 1-phosphate (respectively for S1P1 or S1P3), 50 mM HEPES, pH 7.5, 5 mM MgCl2, 100 mM NaCl, 0.4% fatty acid-free BSA, 1-5 μg/well of proteins in 96-well plates vs 0.6-1 μg/well of proteins in 384-well plates and 100 μg/well of WGA SPA beads in 96-well plates vs 75 μg/well of WGA SPA beads in 384-well plates. Binding was performed for 60 min at RT on a shaker and bound radioactivity was measured on a PerkinElmer 1450 MicroBeta counter. Triplicate samples were averaged and normalized as percentage of inhibition relative to total binding (only DMSO in well) and nonspecific binding (1000-fold excess of unlabeled S1P). Binding data were analyzed using the GraphPad Prism program or Genedata software.

Measurements of 35S-GTPγS Binding:

Membranes (1 to 10 μg protein) prepared as described above, were incubated in 96-well Scintiplates (PerkinElmer) with test compounds diluted in DMSO, in 140 μl of 20 mM HEPES, pH 7.4, 10 mM MgCl2, 2 μg/well Saponin, 0.2% fatty acid free BSA (Assay buffer), 125 mM NaCl and 1.5 μM GDP. The assay was initiated with the addition of 60 μl of 1.5 nM [35S]-GTPγS (1100 Ci/mmol; GE Healthcare) in assay buffer. After 60 min incubation at 30° C. on a shaker, plates were centrifuged for 10 min at 2000 RPM. Supernatant was discarded and membrane bound radioactivity was measured on a PerkinElmer 1450 MicroBeta counter. Triplicate samples were averaged and expressed as % response relative to S1P activation in absence of compound (n=2).

Cellular functional assays: Internalization of Sphingosine-1-phosphate receptor 1 ($S1P_1$) in a human Cell line (U2OS) in a 384-well format using a Cell Imaging analysis.

Jo, E.; Sanna, M. G.; Gonzalez-Cabrera, P. J.; Thangada, S.; Tigyi, S.; Osborne, D. A.; Hla, T.; Parrill, A. L.; Rosen, H. Chem. Biol. 2005, 12, 703

The $S1P_1$ internalization assay was performed in 384 well plates (Corning® 384 black with clear bottom 3712) using $S1P_1$-U2OS cells from Biolmage (C039A), a human epithelial cell line (Human Bone Osteosarcoma Epithelial Cells). These cells expressed the human $S1P_1$ Receptor fused to the green fluorescent protein (EGFP). A standard CMV promoter (cytomegalovirus promoter) controls the expression of S1P1-EGFP and continuous expression was maintained by addition of geneticin to the culture medium.

$S1P_1$ Receptor desensitization induced the internalization of the membrane-localized $S1P_1$-EGFP fusion protein to endosomes, which can be monitored by cell imaging analysis. The cells are plated in low serum medium (Dulbecco's Modified Eagle Medium (DMEM) with Glutamax-1 and high glucose, 1% Penicillin/Streptomycin, 1% Fetal Calf Serum (FCS), 0.5 mg/ml Geneticin) overnight.

The next day, $S1P_1$-U2OS cells are incubated in 20 μl serum free medium (DMEM with Glutamax-1 and high glucose, 0.1% of fatty-acid free Bovin Serum Albumin (BSA), 10 mM, N'-2-Hydroxyethylpiperazine-N'-2 ethanesulphonic acid (HEPES) 1M) for 2 hours at 37° C./5% $CO_2$. The cells are then treated with 4 μl compounds/agonists (6×/3% DMSO) for a total volume of 24 μl, and plates are incubated for 1 hour at 37° C./5% $CO_2$.

$S1P_1$-U2OS cells are fixed with 25 μl Paraformaldehyde 8% and stained with Hoechst 33345 dye (1:1000) for 20 minutes.

They were then washed 3 times with Phosphate Buffered Saline (PBS) and plates are sealed. The internalization of the receptor $S1P_1$-EGFP is measured on Cellomics by calculating the "spot count per object" ("object" corresponds to nuclear and "spot" corresponds to $S1P_1$-EGFP receptor). Internalization data were observed thanks to vHCS View and analyzed using Genedata® software.

The compounds of formula (I) have utility as immunoregulatory agents as demonstrated by their activity as potent agonists of the $S_1P_1$ receptor, as measured in the assays described above. $EC_{50}$ of the compounds of formula (I) and subformulae for $S_1P_1$ is below 0.1 μM. Preferred compounds of formula (I) exhibit an $EC_{50}$ for S1P1 receptor below 0.01 μM. More preferred compounds of Formula (I) exhibit $EC_{50}$ for $S_1P_1$ below 0.001 μM. Compounds of formula (I) exhibit a selectivity for the $S_1P_1$ receptor over the $S_1P_3$ receptor as measured by the ratio of $EC_{50}$ for the $S_1P_1$ receptor to the $EC_{50}$ for the $S_1P_3$ receptor as evaluated in the $^{35}$S-GTPγS binding assay described above. The ratio of EC50 $S_1P_1$ to EC50 $S_1P_3$ is more than 20, preferably more than 50, more preferably more than 100 and even more preferably more than 1000.

The "potency" or the "activity" of the compounds is determined by the EC50 values as evaluated in the above described 35S-GTPγS binding assay. The lowest EC50 values characterize the most potent or active compounds, according to the present invention.

The following results have been obtained:

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 1 | 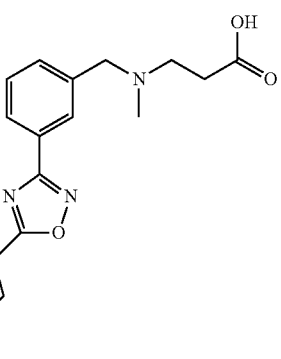 | 8.93E−10 | 3.17E−07 | 4.20E−10 | — | — | — | 3.13E−09 |

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 2 | (structure) | 2.87E−10 | 4.48E−08 | 1.36E−10 | — | — | — | — |
| 3 | (structure) | 8.43E−09 | — | 8.32E−10 | — | — | — | 7.76E−09 |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 4 | 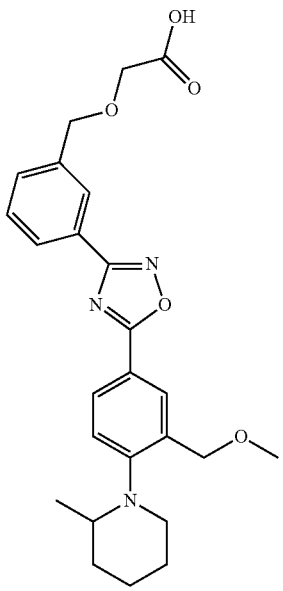 [SMILES: COCc1cc(-c2nc(-c3cccc(COCC(=O)O)c3)no2)ccc1N1CCCCC1C] | 1.05E−09 | 3.13E−07 | 4.76E−10 | — | — | 7.53E−07 | — |
| 5 | 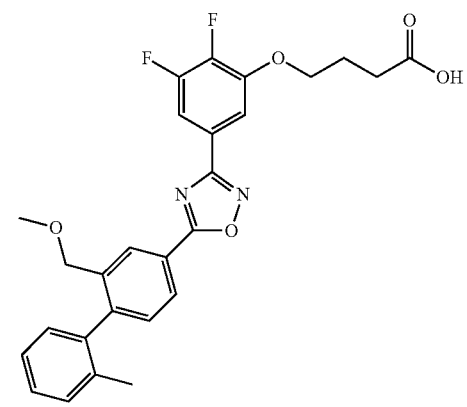 [SMILES: COCc1cc(-c2nc(-c3cc(F)c(F)c(OCCCC(=O)O)c3)no2)ccc1-c1ccccc1C] | 2.27E−08 | — | 4.09E−09 | — | 1.45E−08 | — | 1.57E−07 |
| 6 | 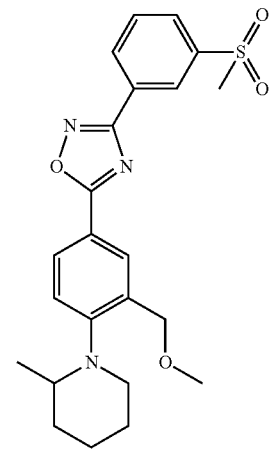 [SMILES: COCc1cc(-c2nc(-c3cccc(S(C)(=O)=O)c3)no2)ccc1N1CCCCC1C] | 1.90E−09 | 2.28E−06 | 1.24E−09 | — | — | — | 4.39E−09 |

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 7 | 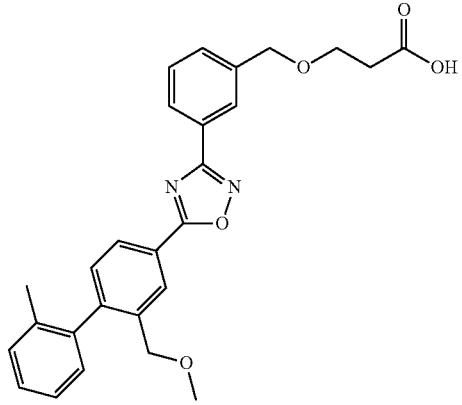 [SMILES: COCc1cc(-c2nc(-c3cccc(COCCC(=O)O)c3)no2)ccc1-c1ccccc1C] | 8.05E−09 | 2.01E−06 | 3.29E−09 | — | — | — | 2.55E−08 |
| 8 | 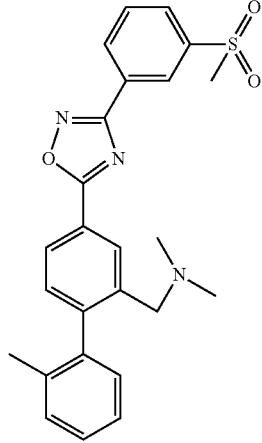 [SMILES: Cc1ccccc1-c1ccc(-c2nc(-c3cccc(S(C)(=O)=O)c3)no2)cc1CN(C)C] | 1.17E−08 | — | — | — | — | — | — |
| 9 | 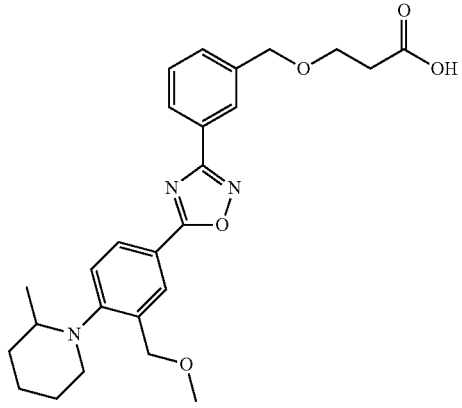 [SMILES: COCc1cc(-c2nc(-c3cccc(COCCC(=O)O)c3)no2)ccc1N1CCCCC1C] | 3.85E−09 | — | 8.04E−10 | — | — | — | — |

-continued

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 10 | 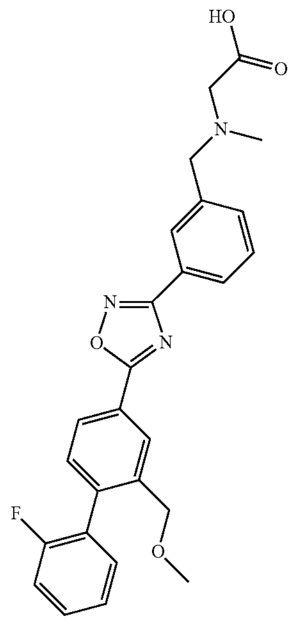 [SMILES: COCc1cc(-c2nc(-c3cccc(CN(C)CC(=O)O)c3)no2)ccc1-c1ccccc1F] | 9.07E−10 | 1.30E−07 | 1.79E−10 | 2.33E−08 | — | 1.22E−07 | 3.31E−09 |
| 11 | 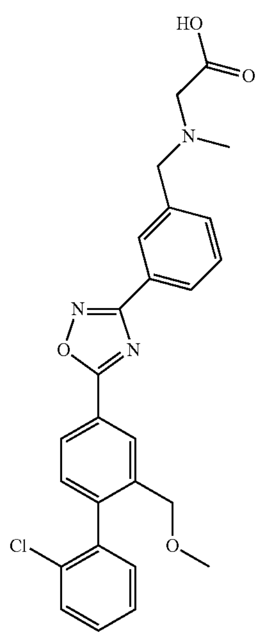 [SMILES: COCc1cc(-c2nc(-c3cccc(CN(C)CC(=O)O)c3)no2)ccc1-c1ccccc1Cl] | 2.74E−09 | 6.73E−07 | 6.21E−10 | — | — | — | 1.06E−08 |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 12 | 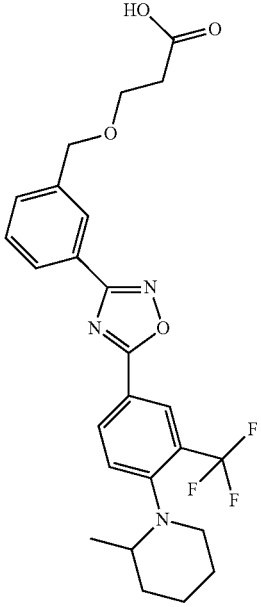 [SMILES: CC1CCCCN1c1ccc(-c2nc(-c3cccc(COCCC(=O)O)c3)no2)cc1C(F)(F)F] | 4.61E−09 | 6.92E−07 | 3.08E−09 | — | — | — | 9.84E−09 |
| 13 | 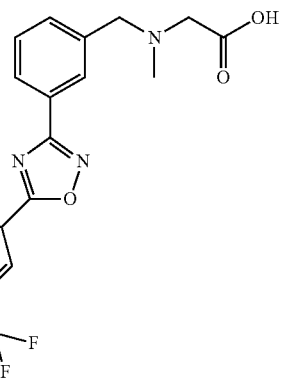 | 9.60E−10 | 4.70E−07 | 4.58E−10 | 8.95E−08 | — | 2.75E−07 | 7.38E−09 |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 15 | 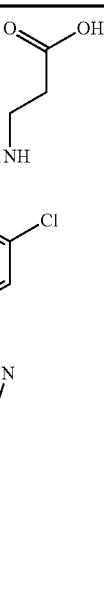 | 2.09E−08 | 5.53E−07 | 1.06E−09 | — | — | — | — |
| 16 | 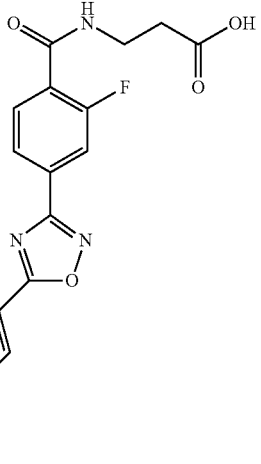 | 6.07E−09 | 5.31E−07 | 2.22E−09 | — | — | — | — |
| 17 | 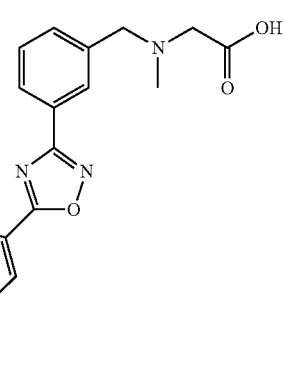 | 1.41E−09 | 2.55E−07 | 4.46E−10 | — | — | — | — |

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 18 | 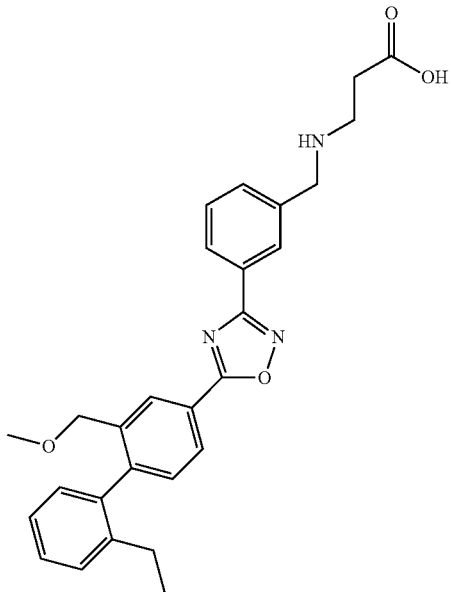 [SMILES: CCc1ccccc1-c1ccc(-c2nc(-c3cccc(CNCCC(=O)O)c3)no2)cc1COC] | 4.70E−10 | 4.96E−09 | 1.68E−10 | — | — | — | — |
| 19 | 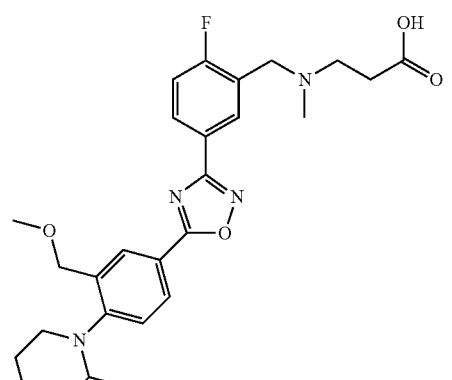 | 5.45E−10 | 3.44E−08 | 1.94E−10 | — | — | — | — |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 20 | 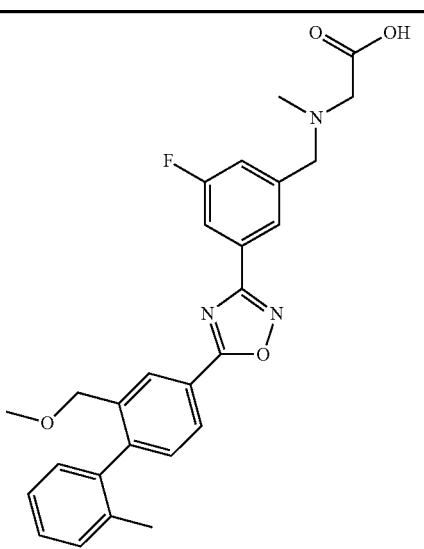 | 7.17E−10 | 5.99E−08 | 1.69E−10 | 1.73E−08 | 1.33E−09 | 7.78E−08 | 5.33E−09 |
| 21 | 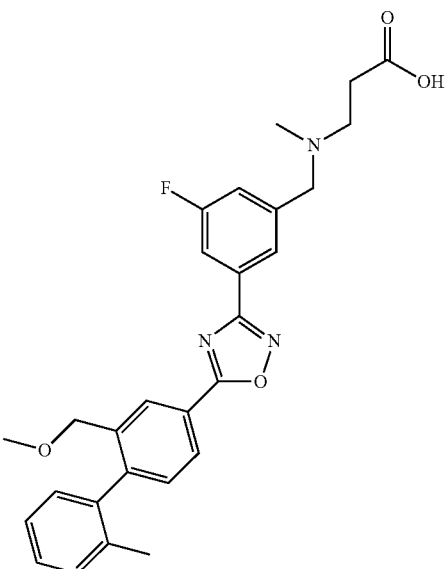 | 3.32E−10 | 1.50E−08 | 1.17E−10 | 1.13E−08 | 9.99E−10 | 1.56E−08 | 4.52E−09 |

-continued

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 22 | 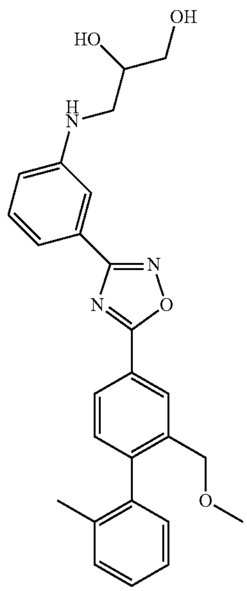 [SMILES: COCc1cc(-c2nc(-c3cccc(NCC(O)CO)c3)no2)ccc1-c1ccccc1C] | 1.36E−0.9 | 2.93E−07 | 7.11E−10 | — | — | — | — |
| 23 | 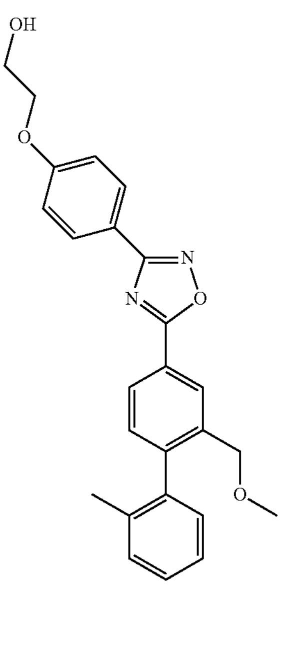 [SMILES: COCc1cc(-c2nc(-c3ccc(OCCO)cc3)no2)ccc1-c1ccccc1C] | 7.07E−09 | 1.99E−07 | 2.17E−09 | — | — | — | — |

-continued

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 24 | 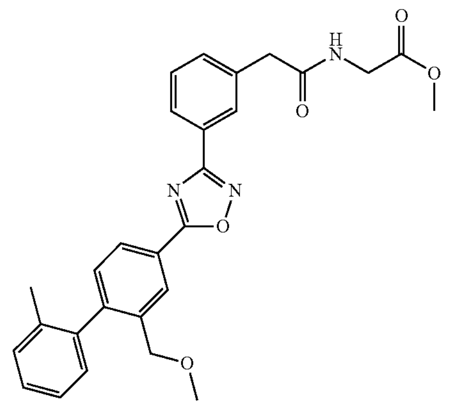 [SMILES: COCc1cc(-c2nc(-c3cccc(CC(=O)NCC(=O)OC)c3)no2)ccc1-c1ccccc1C] | 2.11E−09 | — | 9.12E−10 | — | — | — | — |
| 25 | 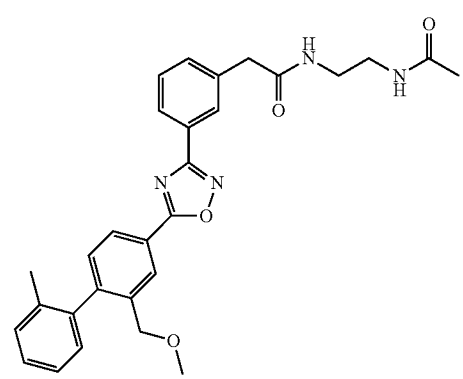 [SMILES: COCc1cc(-c2nc(-c3cccc(CC(=O)NCCNC(C)=O)c3)no2)ccc1-c1ccccc1C] | 7.08E−09 | 6.35E−07 | 8.51E−10 | — | — | — | — |
| 26 | 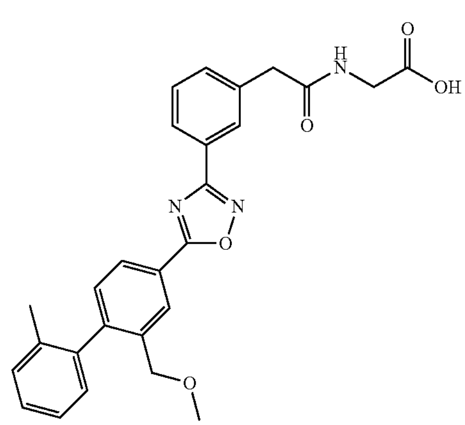 [SMILES: COCc1cc(-c2nc(-c3cccc(CC(=O)NCC(=O)O)c3)no2)ccc1-c1ccccc1C] | 1.07E−08 | — | — | — | — | — | — |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 27 | 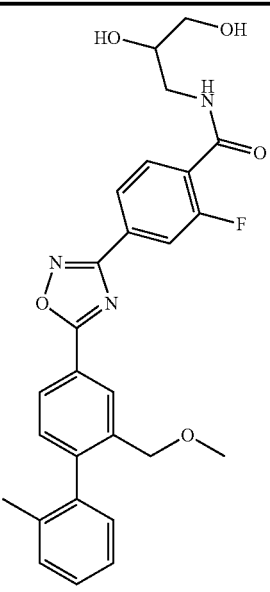 | 1.78E−08 | — | — | — | — | — | — |
| 28 | 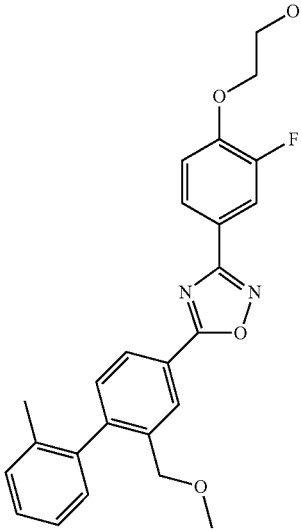 | — | — | 8.88E−10 | 2.14E−07 | — | — | 1.19E−08 |
| 29 | 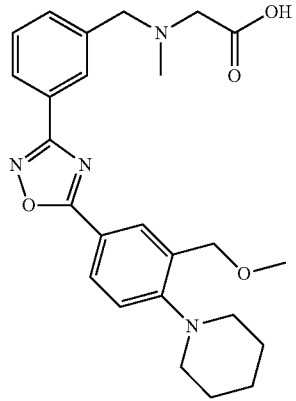 [SMILES: COCc1cc(-c2nc(-c3cccc(CN(C)CC(=O)O)c3)no2)ccc1N1CCCCC1] | — | — | 1.47E−10 | — | — | 2.38E−07 | 7.33E−09 |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 30 | 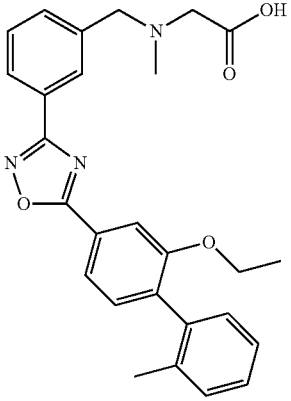 [SMILES: CCOc1cc(-c2nc(-c3cccc(CN(C)CC(=O)O)c3)no2)ccc1-c1ccccc1C] | — | — | 2.01E−10 | 3.00E−08 | — | — | 8.92E−09 |
| 33 | 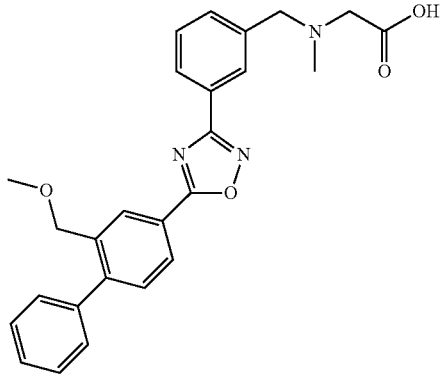 [SMILES: COCc1cc(-c2nc(-c3cccc(CN(C)CC(=O)O)c3)no2)ccc1-c1ccccc1] | — | — | 1.83E−10 | 6.24E−08 | — | — | 6.96E−09 |
| 34 | 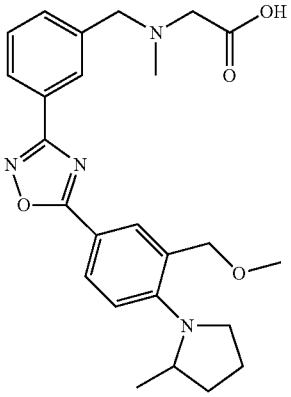 [SMILES: COCc1cc(-c2nc(-c3cccc(CN(C)CC(=O)O)c3)no2)ccc1N1CCCC1C] | — | — | 1.18E−10 | 3.03E−07 | — | — | 1.35E−08 |

-continued

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 35 | 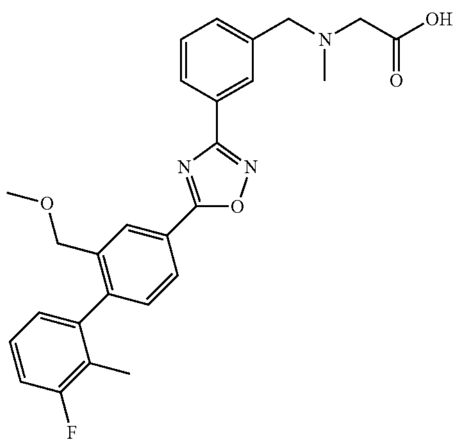 [SMILES: COCc1cc(-c2nc(-c3cccc(CN(C)CC(=O)O)c3)no2)ccc1-c1cccc(F)c1C] | — | — | 1.98E−10 | 9.40E−08 | — | — | 5.88E−09 |
| 36 | 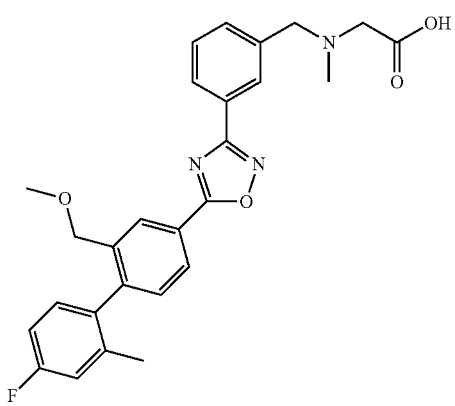 [SMILES: COCc1cc(-c2nc(-c3cccc(CN(C)CC(=O)O)c3)no2)ccc1-c1ccc(F)cc1C] | — | — | 5.59E−10 | — | 1.97E−09 | 2.71E−07 | 1.48E−08 |
| 37 | 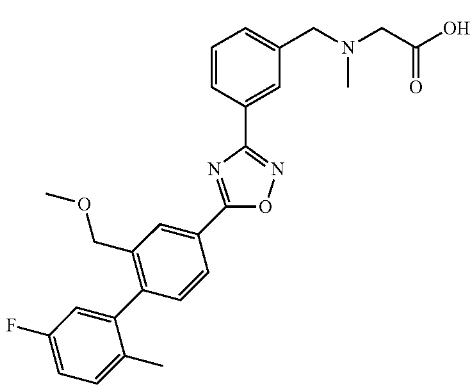 [SMILES: COCc1cc(-c2nc(-c3cccc(CN(C)CC(=O)O)c3)no2)ccc1-c1cc(F)ccc1C] | — | — | 3.33E−10 | 6.34E−08 | — | — | 6.56E−09 |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 38 | 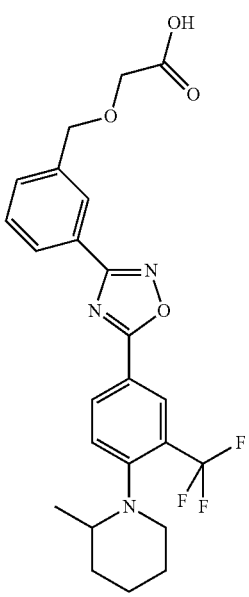 [SMILES: CC1CCCCN1c1ccc(-c2nc(-c3cccc(COCC(=O)O)c3)no2)cc1C(F)(F)F] | — | — | 6.22E−10 | 6.74E−07 | — | — | 1.54E−08 |
| 39 | 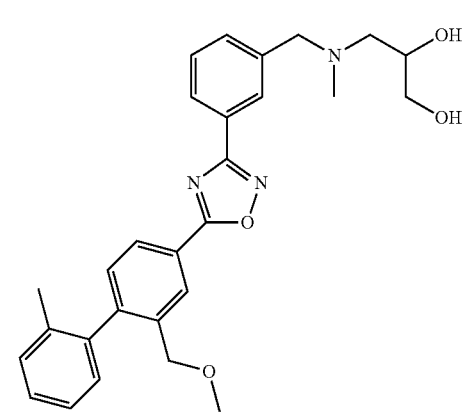 [SMILES: COCc1cc(-c2nc(-c3cccc(CN(C)CC(O)CO)c3)no2)ccc1-c1ccccc1C] | — | — | 3.71E−10 | 8.48E−07 | 2.08E−09 | 1.18E−06 | 1.35E−08 |
| 40 | 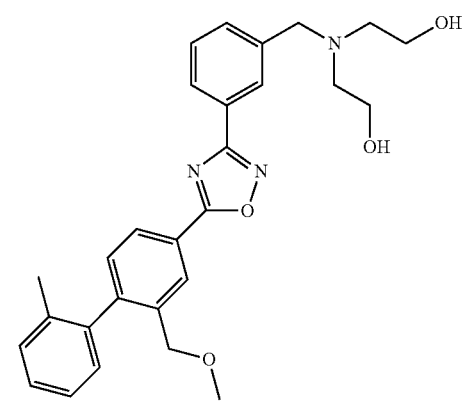 [SMILES: COCc1cc(-c2nc(-c3cccc(CN(CCO)CCO)c3)no2)ccc1-c1ccccc1C] | — | — | 4.52E−10 | 5.35E−07 | — | 9.69E−07 | 1.82E−08 |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 41 | 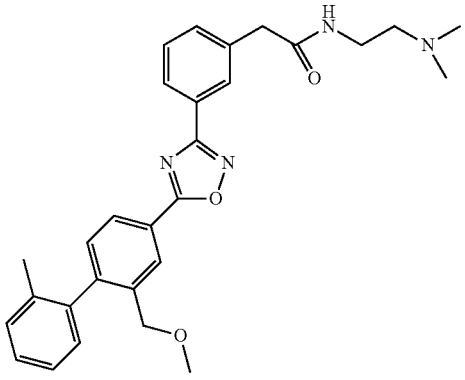 [SMILES: COCc1cc(-c2nc(-c3cccc(CC(=O)NCCN(C)C)c3)no2)ccc1-c1ccccc1C] | — | — | 1.27E−09 | 8.34E−09 | 4.30E−06 | 7.69E−08 | |
| 42 | 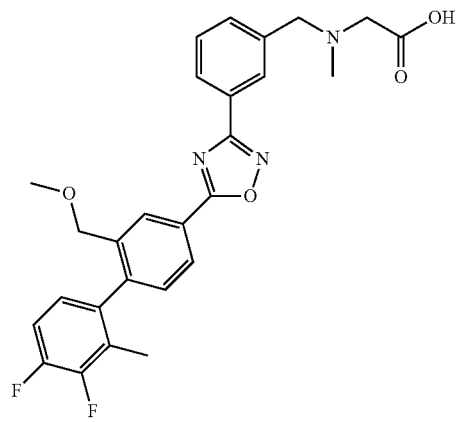 [SMILES: COCc1cc(-c2nc(-c3cccc(CN(C)CC(=O)O)c3)no2)ccc1-c1ccc(F)c(F)c1C] | — | — | 1.82E−10 | — | 1.70E−09 | 2.75E−07 | 1.83E−08 |
| 43 | 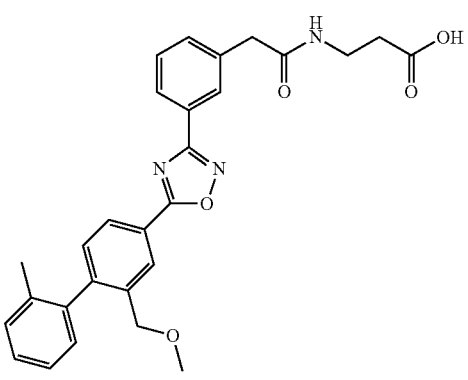 [SMILES: COCc1cc(-c2nc(-c3cccc(CC(=O)NCCC(=O)O)c3)no2)ccc1-c1ccccc1C] | — | — | 2.16E−09 | — | 6.60E−09 | 2.00E−07 | 3.45E−08 |

| Nb | structure | S1P1/GTPG EC50 (M) | S1P3/GTPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 44 | 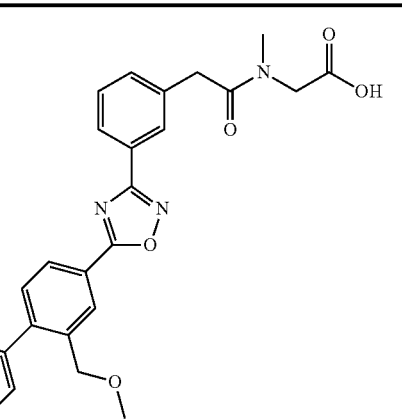 | — | — | 1.71E−09 | — | 1.02E−08 | 1.31E−07 | 1.15E−07 |
| 45 | 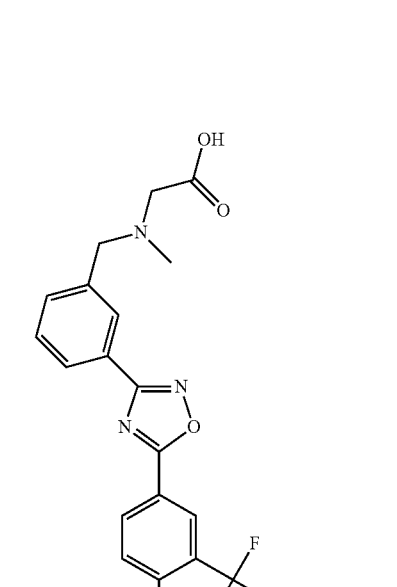 | — | — | 5.20E−10 | 1.82E−07 | — | — | 1.21E−08 |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 46 | 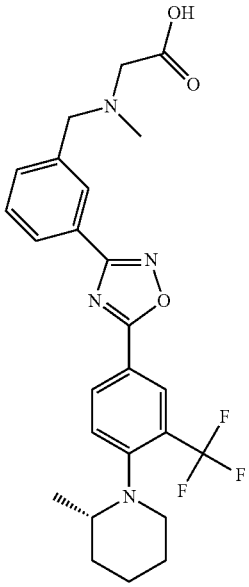 [SMILES: C[C@H]1CCCCN1c1ccc(-c2nc(-c3cccc(CN(C)CC(=O)O)c3)no2)cc1C(F)(F)F] | — | — | 1.07E−10 | 1.31E−07 | — | — | 5.19E−09 |
| 47 | 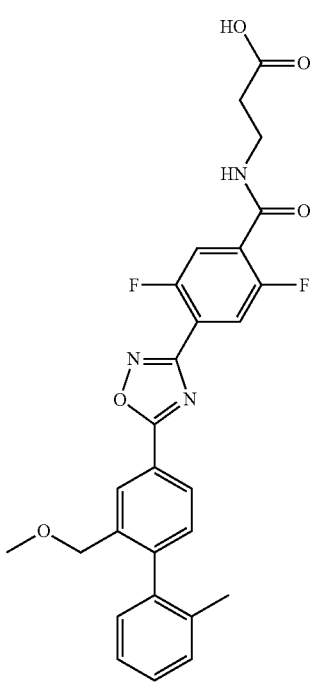 [SMILES: COCc1cc(-c2nc(-c3cc(F)c(C(=O)NCCC(=O)O)cc3F)no2)ccc1-c1ccccc1C] | — | — | 8.50E−10 | 4.03E−07 | — | 5.20E−07 | 2.02E−08 |

-continued

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 48 | 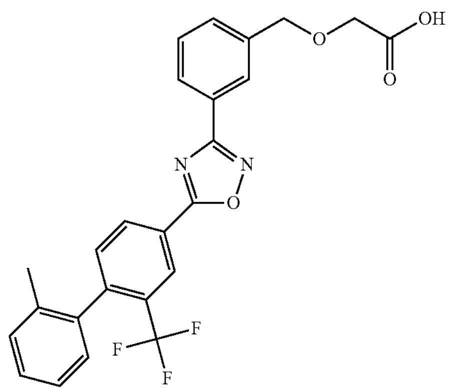 [SMILES: Cc1ccccc1-c1ccc(-c2nc(-c3cccc(COCC(=O)O)c3)no2)cc1C(F)(F)F] | — | — | 9.79E−10 | 6.03E−07 | 1.97E−09 | 1.08E−06 | 7.12E−09 |
| 51 | 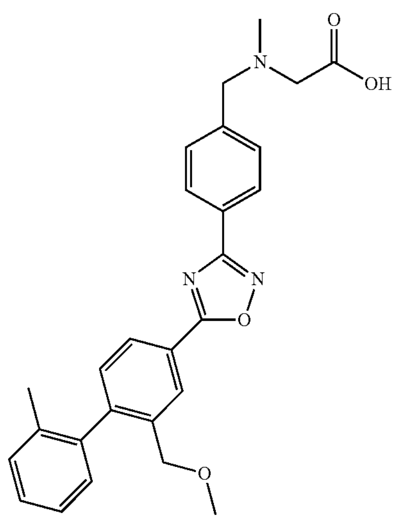 [SMILES: COCc1cc(-c2nc(-c3ccc(CN(C)CC(=O)O)cc3)no2)ccc1-c1ccccc1C] | — | — | 3.38E−10 | 7.32E−07 | 2.10E−09 | 9.17E−07 | 4.92E−09 |
| 52 | 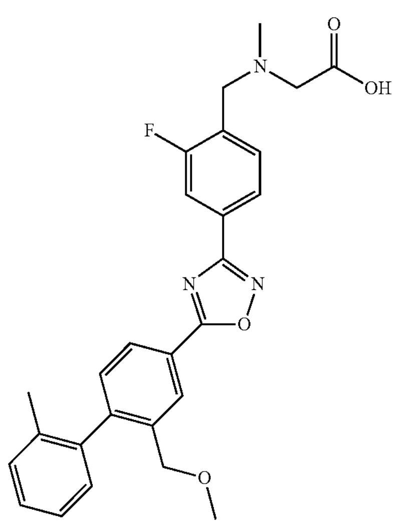 [SMILES: COCc1cc(-c2nc(-c3ccc(CN(C)CC(=O)O)c(F)c3)no2)ccc1-c1ccccc1C] | — | — | 1.96E−10 | 1.27E−07 | — | — | 2.52E−09 |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 53 | 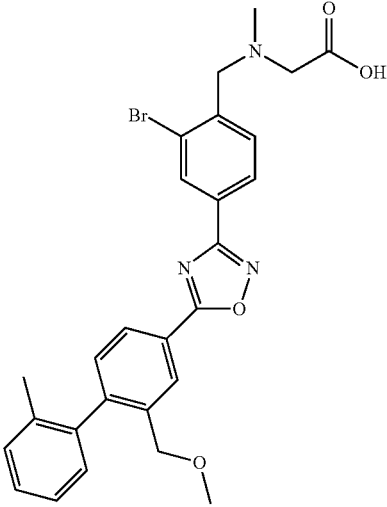 [SMILES: COCc1cc(-c2nc(-c3ccc(CN(C)CC(=O)O)c(Br)c3)no2)ccc1-c1ccccc1C] | — | — | 2.14E−10 | 7.00E−07 | — | — | 7.61E−09 |
| 54 | 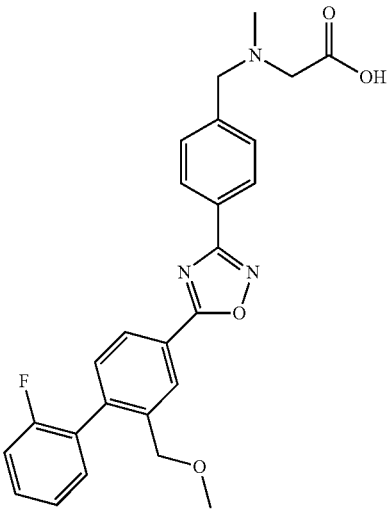 [SMILES: COCc1cc(-c2nc(-c3ccc(CN(C)CC(=O)O)cc3)no2)ccc1-c1ccccc1F] | — | — | 3.04E−10 | 3.21E−07 | 9.76E−10 | 2.59E−07 | 6.36E−09 |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 55 | 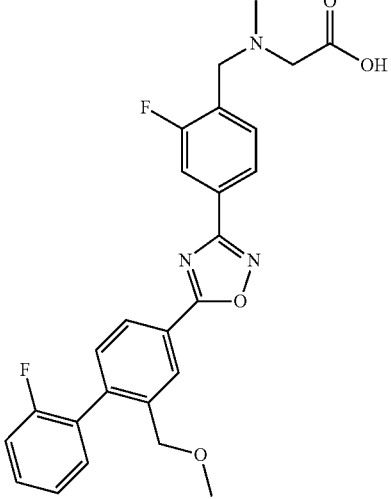 | — | — | 1.59E−10 | 7.12E−08 | 5.23E−10 | 9.20E−08 | 8.46E−09 |
| 56 | 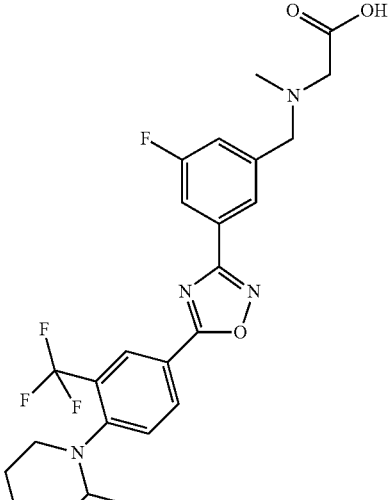 | — | — | 3.25E−10 | 3.79E−08 | — | — | 2.02E−08 |

-continued

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 57 | 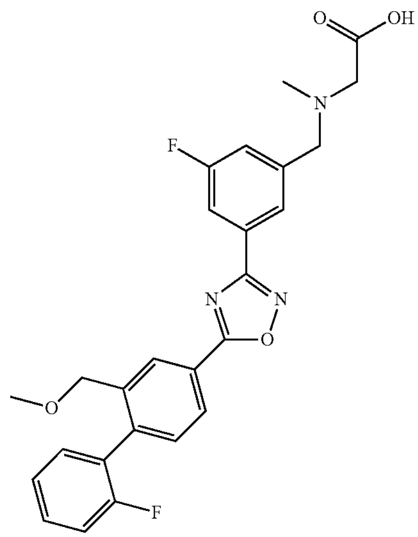 | — | — | 1.14E−10 | 7.22E−09 | — | — | 8.46E−09 |
| 58 | 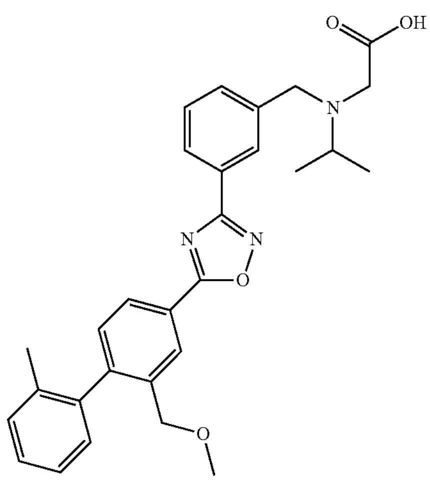 [SMILES: COCc1cc(-c2nc(-c3cccc(CN(CC(=O)O)C(C)C)c3)no2)ccc1-c1ccccc1C] | — | — | 3.91E−10 | 2.02E−07 | — | — | 7.87E−09 |
| 59 | 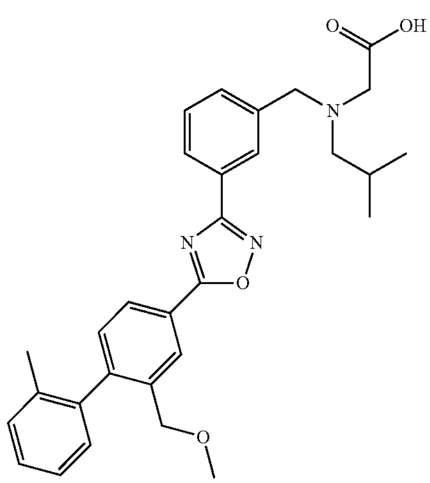 [SMILES: COCc1cc(-c2nc(-c3cccc(CN(CC(=O)O)CC(C)C)c3)no2)ccc1-c1ccccc1C] | — | — | 1.10E−09 | — | 7.94E−09 | 8.49E−07 | 7.45E−08 |

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 60 | 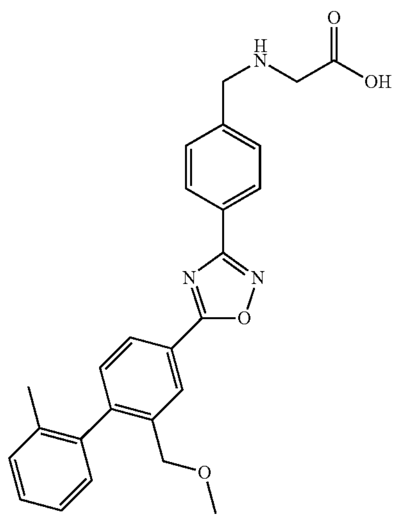 [SMILES: COCc1cc(-c2nc(-c3ccc(CNCC(=O)O)cc3)no2)ccc1-c1ccccc1C] | — | — | 3.09E−10 | 1.93E−07 | — | — | 1.78E−09 |
| 61 | 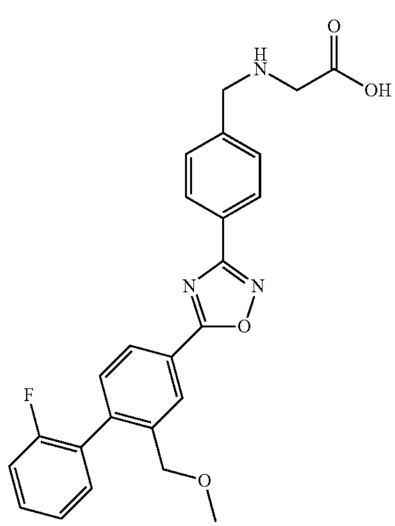 [SMILES: COCc1cc(-c2nc(-c3ccc(CNCC(=O)O)cc3)no2)ccc1-c1ccccc1F] | — | — | 2.26E−10 | 1.91E−07 | — | — | 3.36E−09 |

-continued

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 62 | 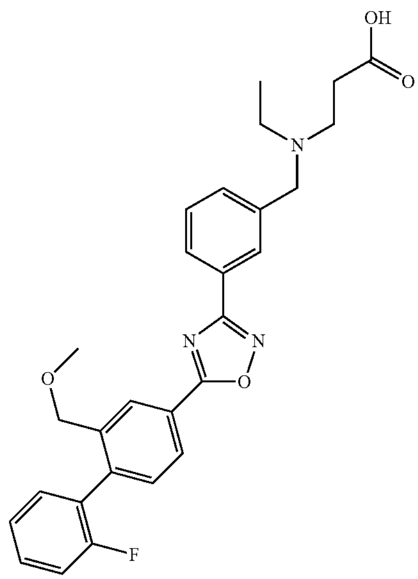 | — | — | 1.68E−10 | 1.72E−08 | — | — | 2.91E−09 |
| 63 | 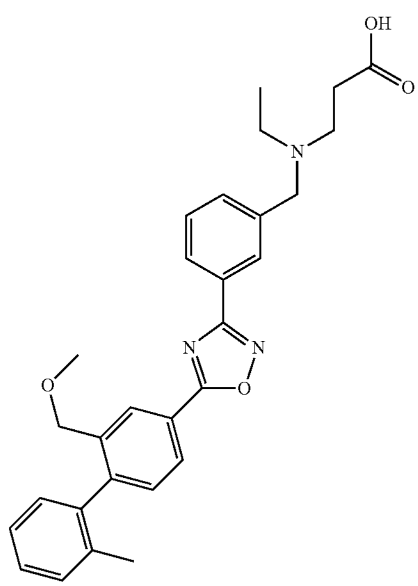 | — | — | 1.61E−10 | 3.98E−08 | — | 1.25E−07 | 3.38E−09 |
| 65 | 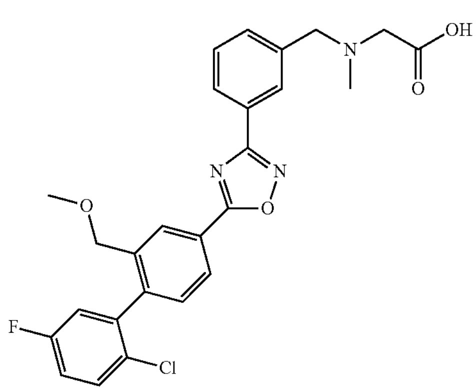 | — | — | 5.31E−10 | 2.31E−07 | — | 3.68E−07 | 2.18E−08 |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 66 | 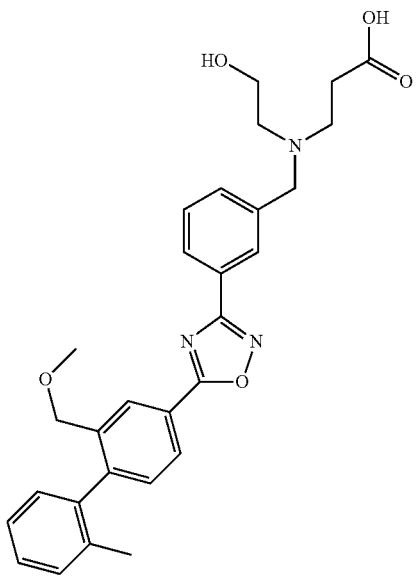 [SMILES: COCc1cc(-c2nc(-c3cccc(CN(CCO)CCC(=O)O)c3)no2)ccc1-c1ccccc1C] | — | — | 5.36E−10 | — | 2.42E−09 | 1.40E−06 | 4.49E−08 |
| 73 | 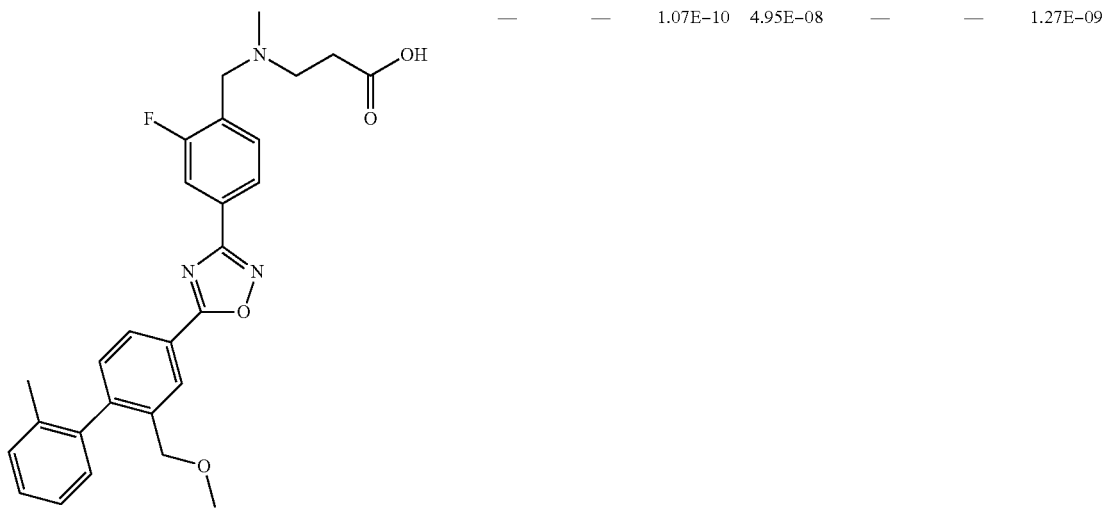 | — | — | 1.07E−10 | 4.95E−08 | — | — | 1.27E−09 |

-continued

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 74 | 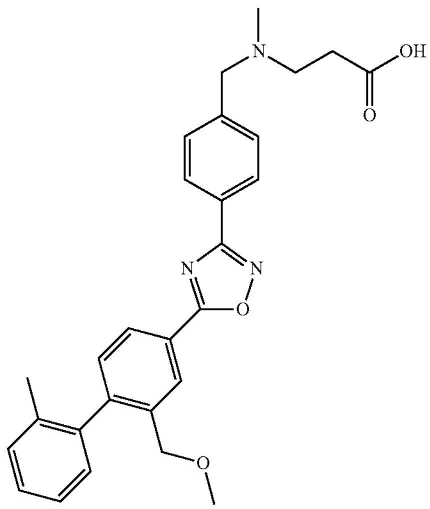 [SMILES: COCc1cc(-c2nc(-c3ccc(CN(C)CCC(=O)O)cc3)no2)ccc1-c1ccccc1C] | — | — | 2.01E−10 | 1.08E−07 | — | — | 1.46E−09 |
| 75 | 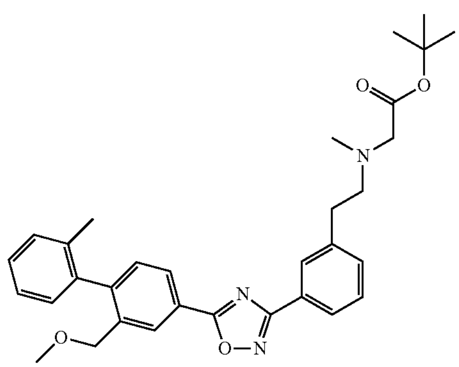 [SMILES: COCc1cc(-c2nc(-c3cccc(CCN(C)CC(=O)OC(C)(C)C)c3)no2)ccc1-c1ccccc1C] | — | — | 3.04E−09 | — | — | — | 1.95E−07 |
| 76 | 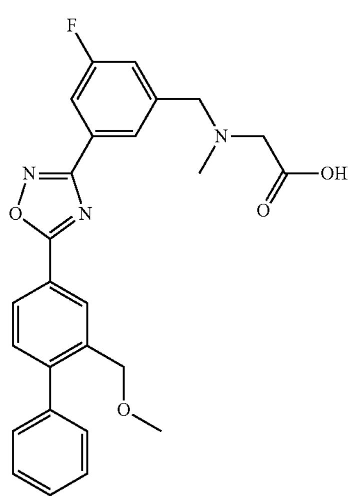 [SMILES: COCc1cc(-c2nc(-c3cc(F)cc(CN(C)CC(=O)O)c3)no2)ccc1-c1ccccc1] | — | — | 1.81E−10 | 1.09E−08 | — | — | 5.36E−09 |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 77 | 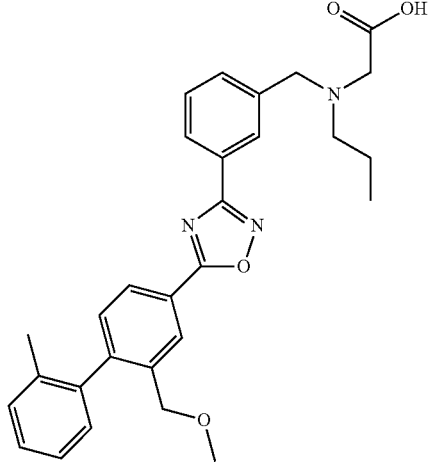 | — | — | 1.58E−09 | 6.05E−07 | 9.83E−10 | — | 5.26E−08 |
| 78 | 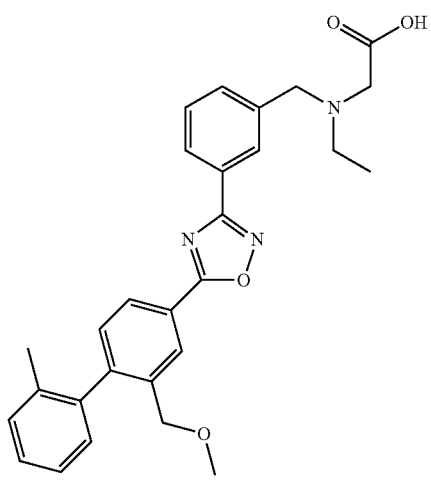 [SMILES: CCN(CC(=O)O)Cc1cccc(-c2noc(-c3ccc(-c4ccccc4C)c(COC)c3)n2)c1] | — | — | 4.41E−10 | 1.50E−07 | 2.47E−09 | 3.54E−07 | 3.43E−08 |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 79 | 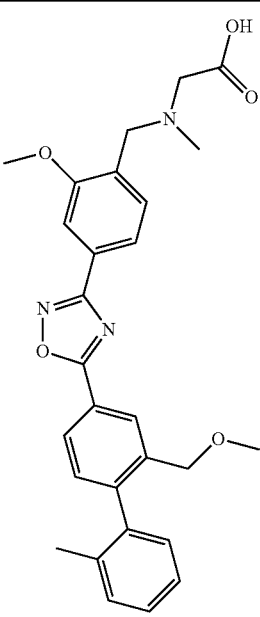 | — | — | 2.69E−09 | 4.84E−06 | 5.33E−09 | — | 4.77E−08 |
| 80 | 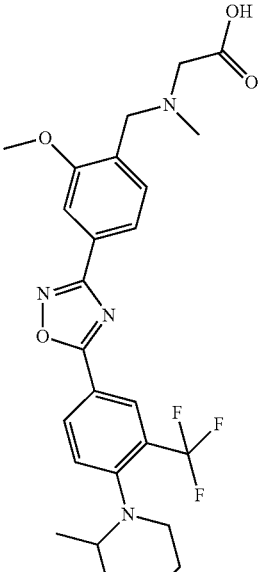 | — | — | 1.60E−09 | 2.79E−06 | 3.12E−09 | — | 4.70E−08 |

-continued

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 82 | 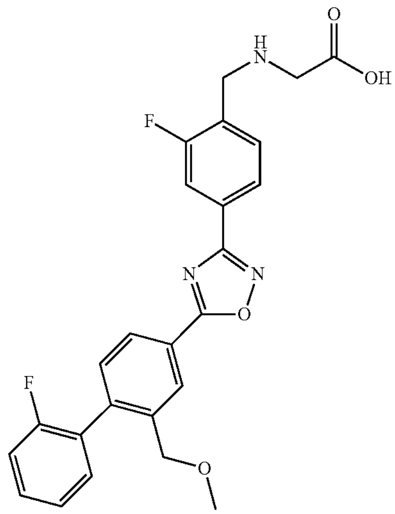 [SMILES: COCc1cc(-c2nc(-c3ccc(CNCC(=O)O)c(F)c3)no2)ccc1-c1ccccc1F] | — | — | 5.42E−11 | 4.66E−08 | 3.74E−10 | 5.24E−08 | 1.73E−09 |
| 83 | 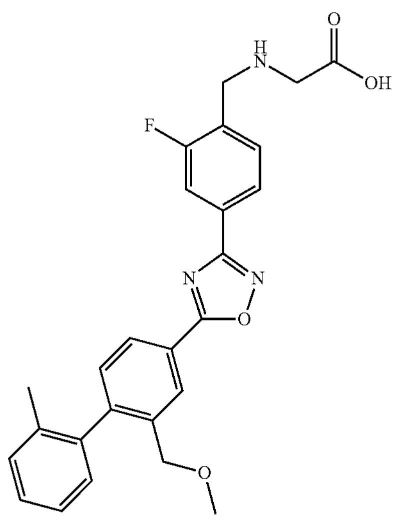 [SMILES: COCc1cc(-c2nc(-c3ccc(CNCC(=O)O)c(F)c3)no2)ccc1-c1ccccc1C] | — | — | 7.39E−11 | 1.01E−07 | 1.80E−10 | 2.75E−07 | 1.20E−09 |
| 84 | 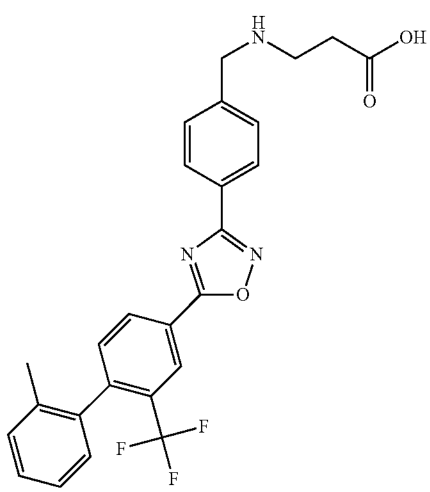 [SMILES: Cc1ccccc1-c1ccc(-c2nc(-c3ccc(CNCCC(=O)O)cc3)no2)cc1C(F)(F)F] | — | — | 1.43E−10 | 1.56E−07 | 3.77E−10 | 1.73E−07 | 1.55E−09 |

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 85 | 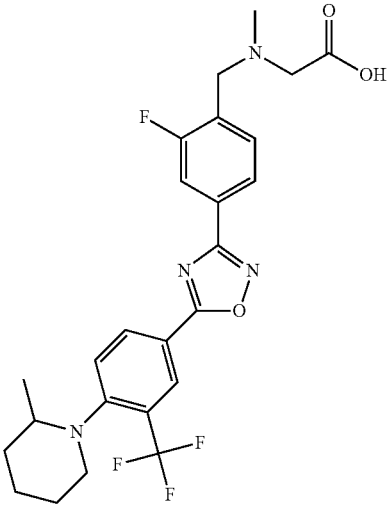 [SMILES: CC1CCCCN1c1ccc(-c2nc(-c3ccc(CN(C)CC(=O)O)c(F)c3)no2)cc1C(F)(F)F] | — | — | 3.16E−10 | 1.77E−07 | 9.74E−10 | — | 1.36E−08 |
| 86 | 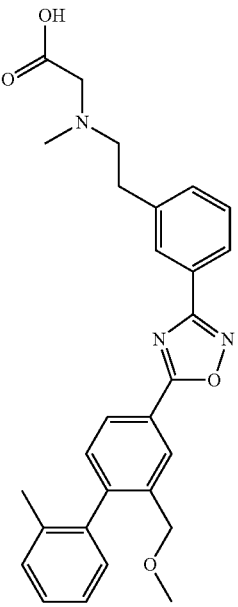 [SMILES: COCc1cc(-c2nc(-c3cccc(CCN(C)CC(=O)O)c3)no2)ccc1-c1ccccc1C] | — | — | 1.46E−10 | 3.18E−08 | 4.97E−10 | — | 4.98E−09 |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 87 | 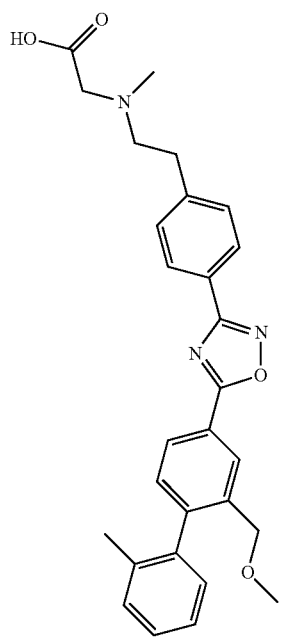 [SMILES: COCc1cc(-c2nc(-c3ccc(CCN(C)CC(=O)O)cc3)no2)ccc1-c1ccccc1C] | — | — | 4.23E−10 | 4.20E−07 | 9.45E−10 | 3.85E−07 | 1.36E−08 |
| 88 | 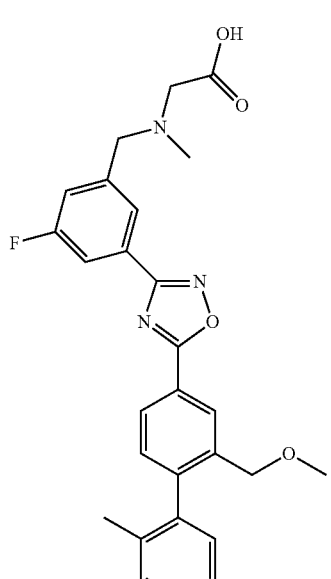 | — | — | 1.57E−10 | 3.37E−08 | — | — | 6.63E−09 |

-continued

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 90 | 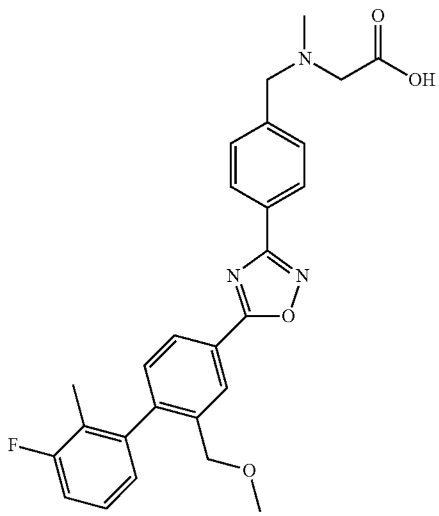 [SMILES: COCc1cc(-c2nc(-c3ccc(CN(C)CC(=O)O)cc3)no2)ccc1-c1cccc(F)c1C] | — | — | 2.78E−10 | 5.45E−07 | 8.65E−10 | 8.49E−07 | 4.46E−09 |
| 91 | 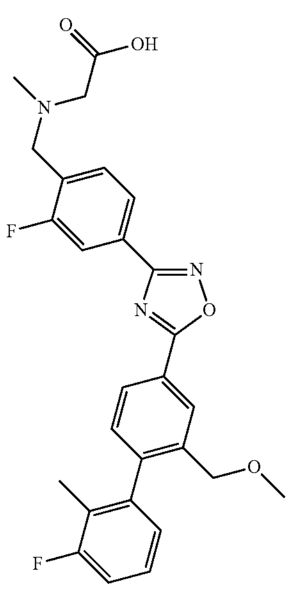 [SMILES: COCc1cc(-c2nc(-c3ccc(CN(C)CC(=O)O)c(F)c3)no2)ccc1-c1cccc(F)c1C] | — | — | 1.63E−10 | 2.00E−07 | 1.13E−09 | 3.35E−07 | 5.53E−09 |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 92 | 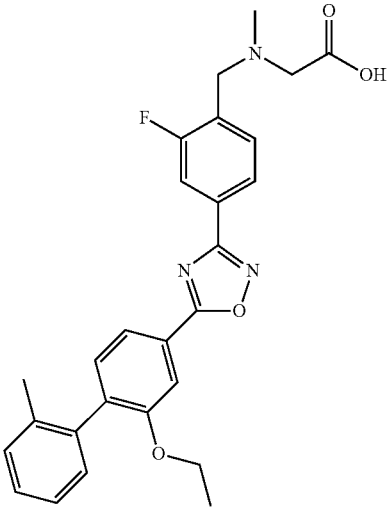 [SMILES: CCOc1cc(-c2nc(-c3ccc(CN(C)CC(=O)O)c(F)c3)no2)ccc1-c1ccccc1C] | — | — | 1.72E−10 | 9.91E−08 | — | — | 7.91E−09 |
| 93 | 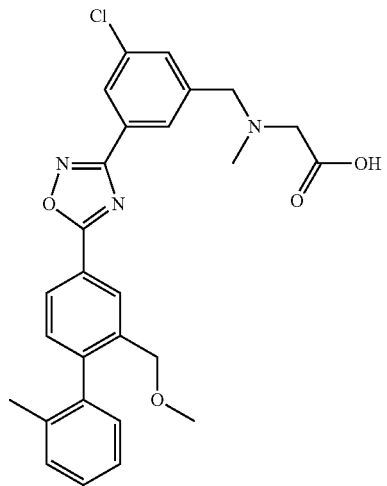 [SMILES: COCc1cc(-c2nc(-c3cc(Cl)cc(CN(C)CC(=O)O)c3)no2)ccc1-c1ccccc1C] | — | — | 3.96E−10 | 9.40E−08 | — | — | 2.65E−08 |

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 102 | 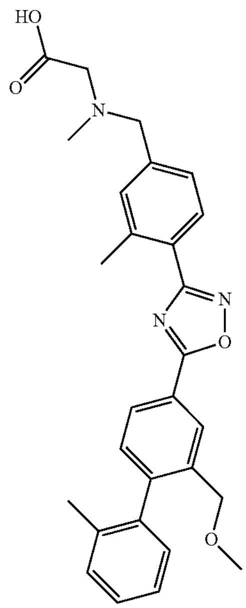 [SMILES: COCc1cc(-c2nc(-c3ccc(CN(C)CC(=O)O)cc3C)no2)ccc1-c1ccccc1C] | — | — | — | 2.90E−07 | 1.44E−09 | 6.99E−07 | 1.37E−08 |
| 105 | 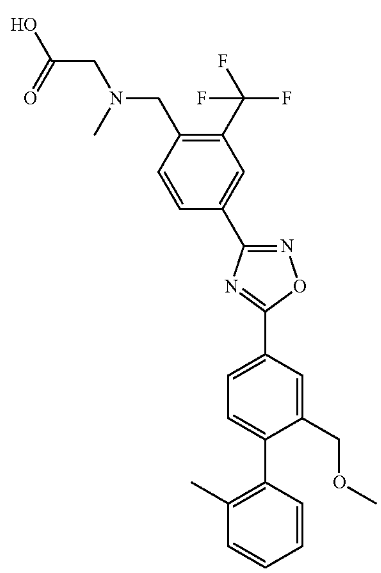 [SMILES: COCc1cc(-c2nc(-c3ccc(CN(C)CC(=O)O)c(C(F)(F)F)c3)no2)ccc1-c1ccccc1C] | — | — | — | 1.83E−06 | 3.30E−09 | 1.88E−06 | 7.49E−08 |

-continued

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 106 | 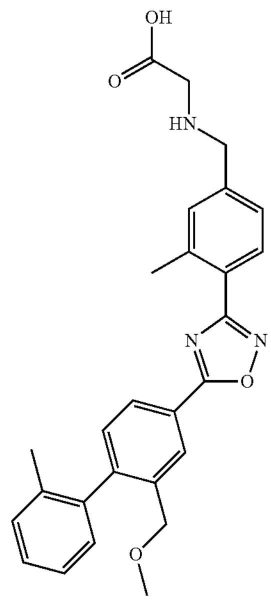 [SMILES: COCc1cc(-c2nc(-c3ccc(CNCC(=O)O)cc3C)no2)ccc1-c1ccccc1C] | — | — | — | 1.59E−07 | 4.66E−10 | 2.96E−07 | 4.12E−09 |
| 107 | 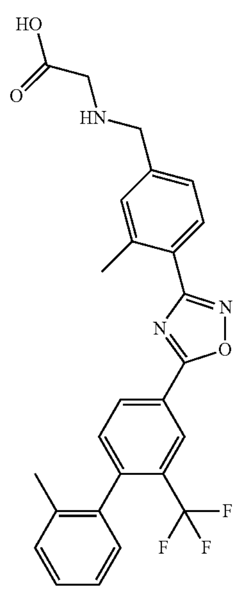 [SMILES: Cc1cc(CNCC(=O)O)ccc1-c1noc(-c2ccc(-c3ccccc3C)c(C(F)(F)F)c2)n1] | | | | | 4.79E−10 | 2.12E−07 | 2.84E−09 |

-continued

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 108 | 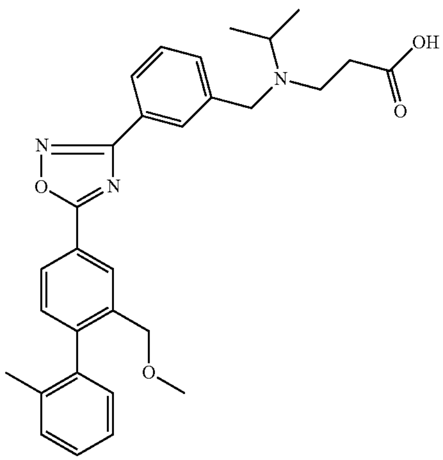 [SMILES: COCc1cc(-c2nc(-c3cccc(CN(CCC(=O)O)C(C)C)c3)no2)ccc1-c1ccccc1C] | | | | | 5.06E−10 | 1.10E−06 | 1.40E−08 |
| 118 | 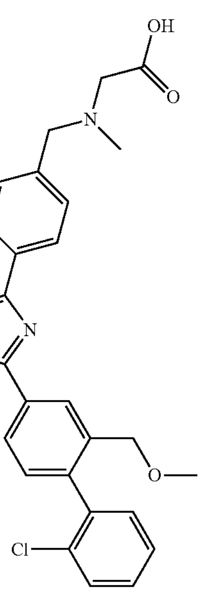 | — | — | — | — | 1.10E−09 | 5.67E−07 | 9.94E−09 |

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 119 | 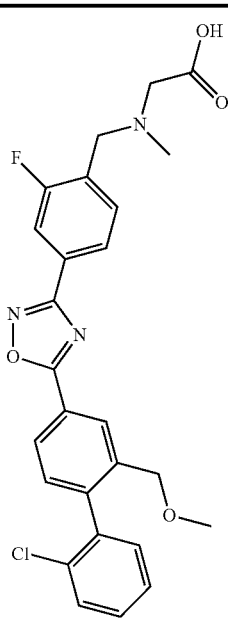 | — | — | — | — | 9.55E−10 | 3.83E−07 | 1.15E−08 |
| 121 | 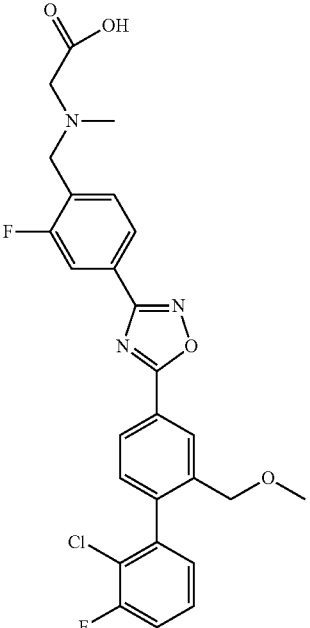 | — | — | — | — | 1.54E−09 | 5.26E−07 | 6.56E−09 |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 122 | 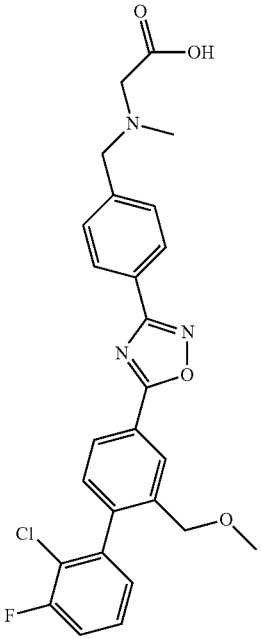 [SMILES: COCc1cc(-c2nc(-c3ccc(CN(C)CC(=O)O)cc3)no2)ccc1-c1cccc(F)c1Cl] | — | — | — | — | 1.31E−09 | 2.50E−06 | 5.10E−09 |
| 124 | 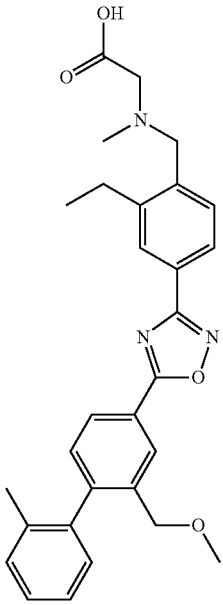 [SMILES: CCc1cc(-c2noc(-c3ccc(-c4ccccc4C)c(COC)c3)n2)ccc1CN(C)CC(=O)O] | — | — | — | — | 1.98E−09 | 4.10E−06 | 2.32E−08 |

-continued

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 125 | 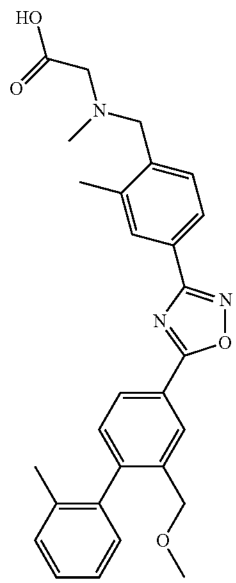 [SMILES: COCc1cc(-c2nc(-c3ccc(CN(C)CC(=O)O)c(C)c3)no2)ccc1-c1ccccc1C] | — | — | — | — | 2.31E−09 | 1.92E−06 | 7.65E−09 |
| 126 | 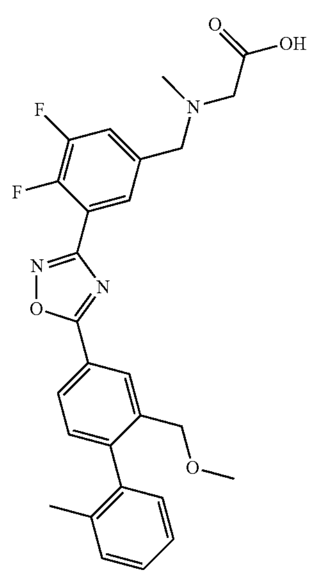 [SMILES: COCc1cc(-c2nc(-c3cc(CN(C)CC(=O)O)cc(F)c3F)no2)ccc1-c1ccccc1C] | — | — | — | — | 2.88E−09 | 6.55E−07 | 4.70E−08 |

-continued

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 127 | 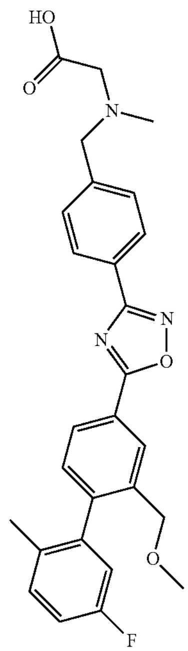 | — | — | — | — | 1.12E−09 | 7.60E−07 | 8.68E−09 |
| 128 | 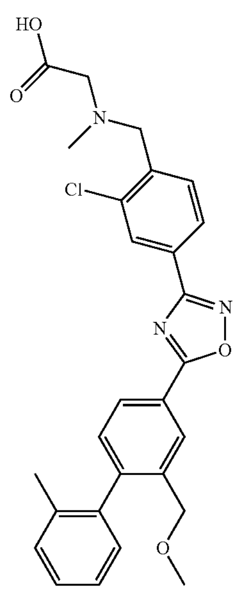 [SMILES: COCc1cc(-c2nc(-c3ccc(CN(C)CC(=O)O)c(Cl)c3)no2)ccc1-c1ccccc1C] | — | — | — | — | 1.45E−09 | 5.66E−07 | 1.33E−08 |

-continued

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 130 | 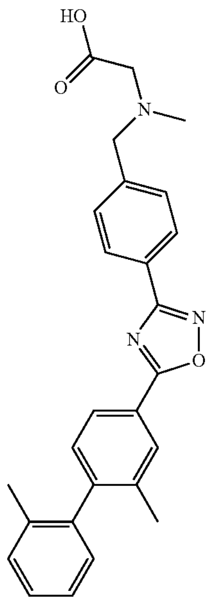 [SMILES: Cc1ccccc1-c1ccc(-c2nc(-c3ccc(CN(C)CC(=O)O)cc3)no2)cc1C] | — | — | 8.34E−10 | — | 2.53E−09 | 5.38E−06 | 2.33E−08 |
| 131 | 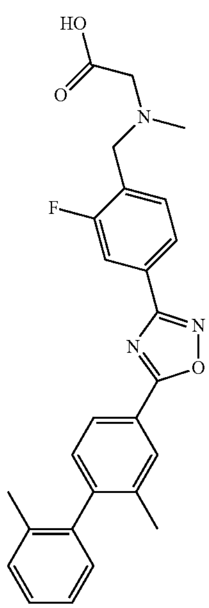 [SMILES: Cc1ccccc1-c1ccc(-c2nc(-c3ccc(CN(C)CC(=O)O)c(F)c3)no2)cc1C] | — | — | — | — | 1.68E−09 | 1.98E−06 | 1.62E−08 |

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 132 | 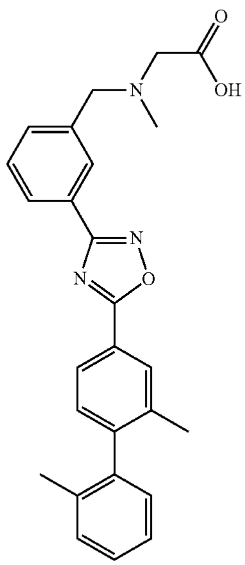 [SMILES: Cc1ccccc1-c1ccc(-c2nc(-c3cccc(CN(C)CC(=O)O)c3)no2)cc1C] | — | — | — | — | 3.65E−09 | 1.64E−06 | 2.35E−07 |
| 133 | 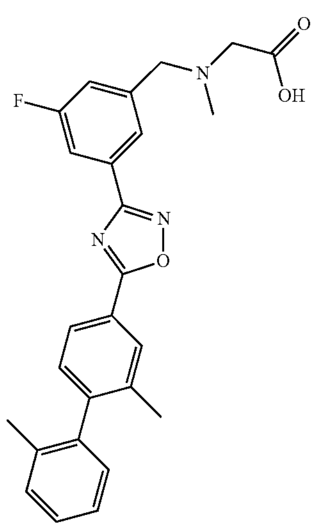 [SMILES: Cc1ccccc1-c1ccc(-c2nc(-c3cc(F)cc(CN(C)CC(=O)O)c3)no2)cc1C] | — | — | — | — | 2.81E−09 | 4.72E−07 | 4.22E−08 |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 137 | 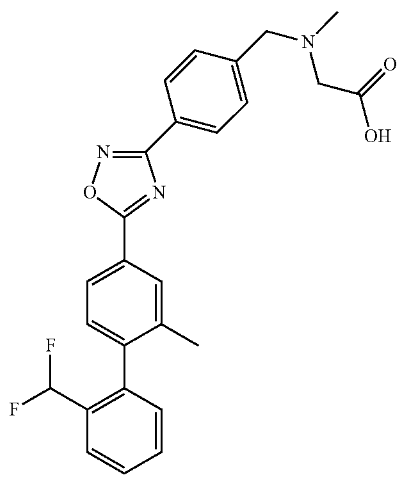 [SMILES: Cc1cc(-c2nc(-c3ccc(CN(C)CC(=O)O)cc3)no2)ccc1-c1ccccc1C(F)F] | — | — | 8.55E−10 | — | 2.37E−09 | — | 2.89E−08 |
| 140 | 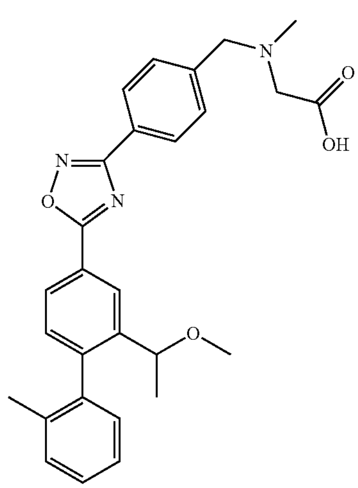 [SMILES: COC(C)c1cc(-c2nc(-c3ccc(CN(C)CC(=O)O)cc3)no2)ccc1-c1ccccc1C] | — | — | 1.89E−10 | 1.64E−07 | 9.81E−10 | 3.89E−07 | 3.75E−09 |
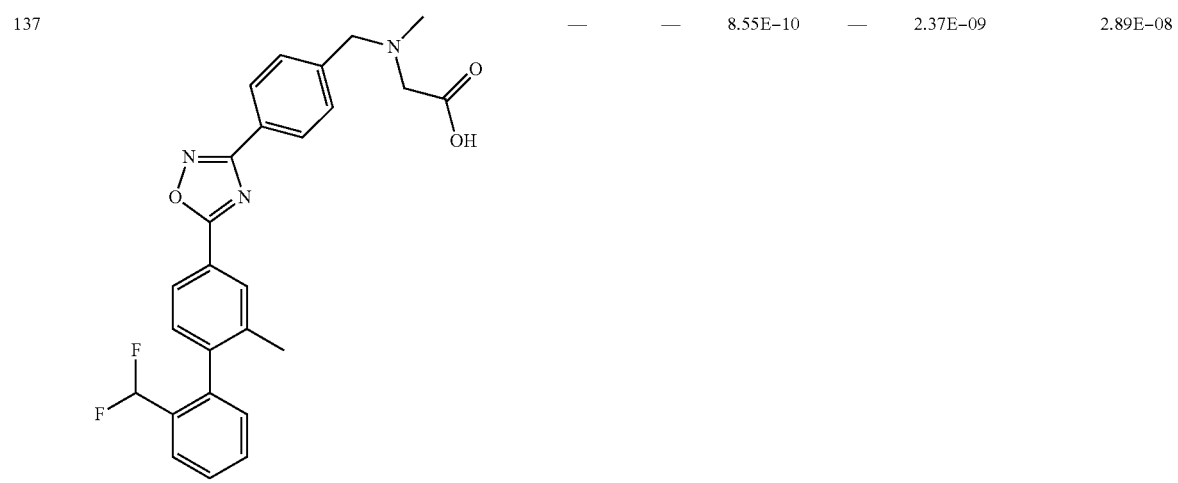

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 142 | 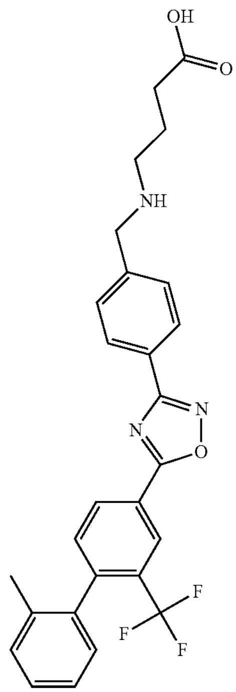 [SMILES: Cc1ccccc1-c1ccc(-c2nc(-c3ccc(CNCCCC(=O)O)cc3)no2)cc1C(F)(F)F] | — | — | — | — | 5.49E−10 | 3.73E−07 | 8.02E−10 |
| 143 | 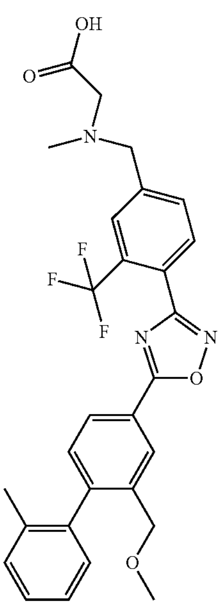 [SMILES: COCc1cc(-c2nc(-c3ccc(CN(C)CC(=O)O)cc3C(F)(F)F)no2)ccc1-c1ccccc1C] | — | — | — | — | 2.32E−09 | 1.83E−06 | 8.55E−08 |

-continued
| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 144 | 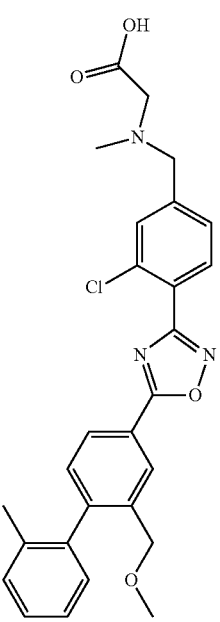 [SMILES: COCc1cc(-c2nc(-c3ccc(CN(C)CC(=O)O)cc3Cl)no2)ccc1-c1ccccc1C] | — | — | — | — | 1.73E−09 | 3.55E−07 | 2.57E−08 |
| 146 | 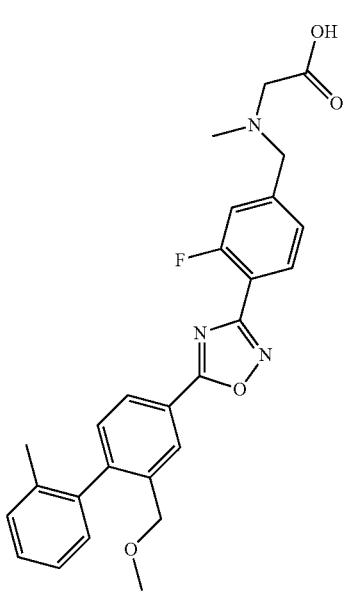 [SMILES: COCc1cc(-c2nc(-c3ccc(CN(C)CC(=O)O)cc3F)no2)ccc1-c1ccccc1C] | — | — | — | — | 9.36E−10 | 3.68E−07 | 3.36E−08 |

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 147 | 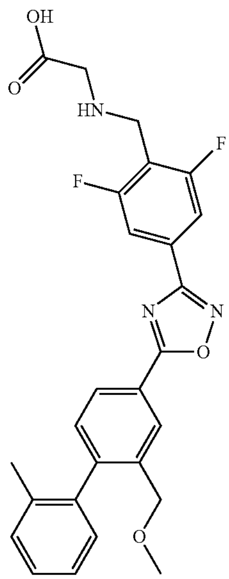 [SMILES: COCc1cc(-c2nc(-c3cc(F)c(CNCC(=O)O)c(F)c3)no2)ccc1-c1ccccc1C] | — | — | — | — | 6.95E−10 | 1.35E−07 | 1.54E−09 |
| 149 | 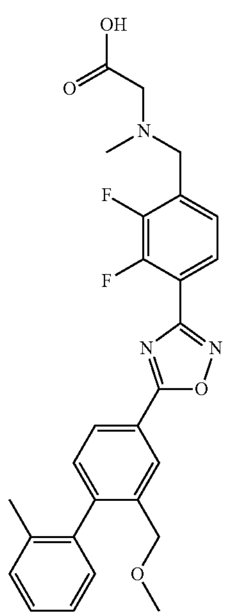 [SMILES: COCc1cc(-c2nc(-c3ccc(CN(C)CC(=O)O)c(F)c3F)no2)ccc1-c1ccccc1C] | — | — | — | — | 1.26E−09 | 1.48E−07 | 9.54E−09 |

| Nb | structure | S1P1/G TPG EC50 (M) | S1P3/G TPG EC50 (M) | S1P1 binding Ki (M) (96 well-plate) | S1P3 binding Ki (M) (96 well-plate) | S1P1 binding Ki (M) (384 well-plate) | S1P3 binding Ki (M) (384 well-plate) | S1P1 Internalization EC50 (M) |
|---|---|---|---|---|---|---|---|---|
| 151 | (structure) | — | — | — | — | 3.53E−09 | 3.90E−07 | 2.16E−08 |

Example 157

Animal Models Evaluating the In Vivo Efficacy of S1P Agonists Model of S1P Agonists-Induced Lymphopenia in Mice Female C57BL/6 mice (Elevage Janvier) (8 week old) receive S1P agonists by oral route. Blood is sampled in heparinized (100 IU/kg, ip) mice by intracardiac or retroorbital puncture under isoflurane anesthesia 2 to 120 hrs after drug treatment. The white blood cells (lymphocytes and neutrophils) are counted using a Beckman/Coulter counter. The quality of blood sampling is assessed by counting erythocytes and platelets.

Model of MOG-Induced Experimental Autoimmune Encephalomyelytis (EAE) in Mice

EAE was induced in 9 weeks old female mice (C57BL/6, Elevage Janvier) by an immunization against MOG. The mice received Pertussis toxin (Alexis, 300 ng/mouse in 200 μl of PBS) by ip route and 100 μl of an emulsion containing MOG35-55 peptide (NeoMPS, 200 μg/mouse), *Mycobacterium Tuberculosis* (0.25 mg/mouse) in Complete Freund's Adjuvant (DIFCO) by subcutaneous injection into the back. Two days later an additional injection of Pertussis toxin (Alexis, 300 ng/mouse in 200 μl of PBS) was done by ip route. After EAE induction, mice were weighed daily and the neurological impairment was quantified using a 15-points clinical scale assessing the paralysis (tail, hind limbs and fore limbs), the incontinency and the death.

Pharmacokinetics Data:

The pharmacoinetic properties of compound of example 20, N-(3-fluoro-5-{5-[2-(methoxymethyl)-2'-methylbiphenyl-4-yl]-1,2,4-oxadiazol-3-yl}benzyl)-N-methylglycine, hydrochloride salt, are the following:

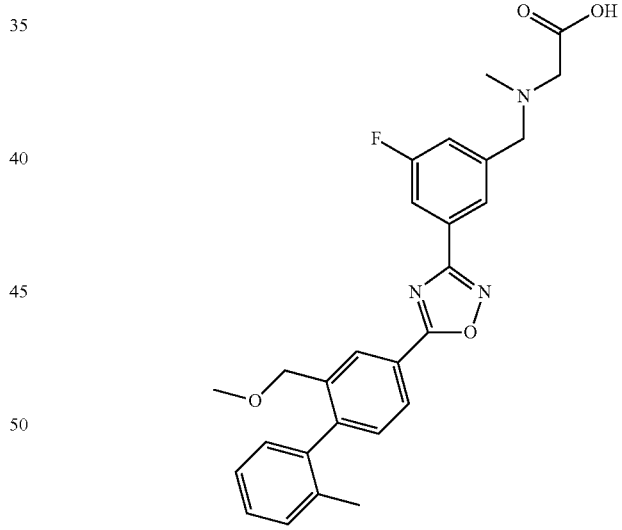

Example 20

| | |
|---|---|
| % Lymphopenia in mouse at 48 h | 72 ± 5 |
| PK Parameters from lymphopenia (mouse) | PK (30 mpk) + PK-PD |
| Plasma AUD? (h*ng/ml) | 202751 |
| $C_{max}$ (ng/ml) | 10293 |
| $T_{max}$ (h) | 4 |
| $T_{1/2}$ (h) | 5.3 |
| Cl/F (L/kg/h) (Fz%) | 0.15 |

| | |
|---|---|
| Brain/Plasma-Ratio: | 0.15 |
| AUC$_Z$ (h*ng/ml) Lymph node/ plasma ratio:24 h/ 48 h | 0.8/0.7 |

Clinical Score
1—Tail
Score=0 A normal mouse holds its tail erect when moving.
Score=1 If the extremity of the tail is flaccid with a tendency to fall.
Score=2 If the tail is completely flaccid and drags on the table.
2—Hind limbs
Score=0 A normal mouse has an energetic walk and doesn't drag his paws.
Score=1 Either one of the following tests is positive:
a—Flip test: while holding the tail between thumb and index finger, flip the animal on his back and observe the time it takes to right itself. A healthy mouse will turn itself immediately. A delay suggests hind-limb weakness.
b—Place the mouse on the wire cage top and observe as it crosses from one side to the other. If one or both limbs frequently slip between the bars we consider that there is a partial paralysis.
Score=2 Both previous tests are positive.
Score=3 One or both hind limbs show signs of paralysis but some movements are preserved; for example: the animal can grasp and hold on to the underside of the wire cage top for a short moment before letting go
Score=4 When both hind legs are paralyzed and the mouse drags them when moving.
3—Fore limbs:
Score=0 A normal mouse uses his front paws actively for grasping and walking and holds his head erect.
Score=1 Walking is possible but difficult due to a weakness in one or both of the paws, for example, the front paws are considered weak when the mouse has difficulty grasping the underside of the wire top cage. Another sign of weakness is head drooping.
Score=2 When one forelimb is paralyzed (impossibility to grasp and the mouse turns around the paralyzed limb). At this time the head has also lost much of its muscle tone.
Score=3 Mouse cannot move, and food and water are unattainable.
4—Bladder:
Score=0 A normal mouse has full control of his bladder.
Score=1 A mouse is considered incontinent when his lower body is soaked with urine.
5—Death:
Score=15
The final score for each animal is determined by the addition of all the above-mentioned categories. The maximum score for live animals is 10.
At day 12 (first signs of paralysis) the mice were stratified in experimental groups (n=10) according to the clinical score and the body weight loss. The semi-curative treatment started at day 14.

Example 158

Preparation of a Pharmaceutical Formulation

Formulation 1—Tablets
A compound of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules
A compound of formula (I) is admixed as a dry powder with a starch diluent in an approximate 1:1 weight ratio. The mixture is filled into 250 mg capsules (125 mg of active compound according to the invention per capsule).

Formulation 3—Liquid
A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets
A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection
A compound of formula (I) is dissolved in a buffered sterile saline injectable aqueous medium to a concentration of approximately 5 mg/mL.

The invention claimed is:
1. An oxadiazole derivative of Formula (AC)

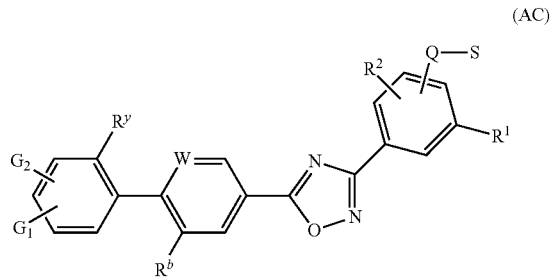

(AC)

wherein
$R^1$, $R^2$ independently denote H, Hal, $CF_3$, $OCF_3$, CN, $NO_2$, OH, A, or OA,
W is CH,
$R^y$ is $CH_3$, F, Br, or Cl,
$G_1$, $G_2$ independently from one another denote H, F, Br, Cl or $CH_3$, with the proviso that one of $G_1$ and $G_2$ is other than H and that one of $R^y$, $G_1$ and $G_2$ is F, Br, or Cl,
$R^b$ is $CH_2OCH_3$,
A is branched or linear alkyl having 1 to 12 C-atoms, wherein one or more 1 to 7 H-atoms may be replaced by Hal, $OR^3$, $COOR^3$, CN, $N(R^3)_2$ and wherein one or more 1 to 7 non-adjacent $CH_2$-groups may be replaced by O, —$NR^3CO$—, —CO— or S and/or by —CH=CH— or —C≡C— groups or cycloalkylene groups having 3 to 7 carbon atoms, or denotes cycloalkyl or cycloalkylalkylen having 3-7 ring C atoms,
Hal is F, Cl, or Br,
$R^3$ is H or A; two geminal groups $R^3$ together may form a ring with the atom they are attached to, Q-S denotes the following group:

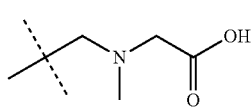

and pharmaceutically acceptable salts and stereoisomers thereof.

2. A pharmaceutical composition comprising at least one compound according to claim 1 and a pharmaceutically acceptable excipient.

3. A pharmaceutical composition comprising at least one compound according to claim 1 and at least one further active ingredient.

4. A kit consisting of separate packs of:
  (a) an effective amount of a compound according to claim 1; and
  (b) an effective amount of a second active ingredient.

5. The oxadiazole derivative according to claim 1, wherein said oxadiazole derivative is selected from:

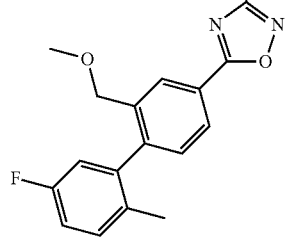

35

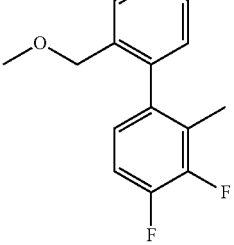

36

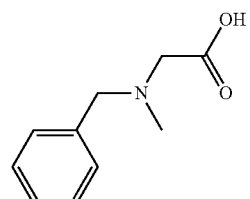

37

42

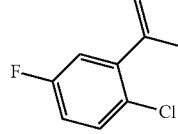

65

88 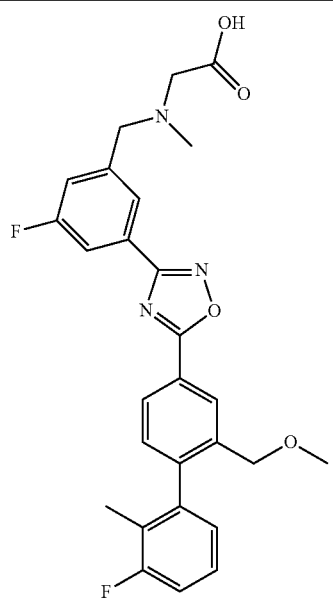
91 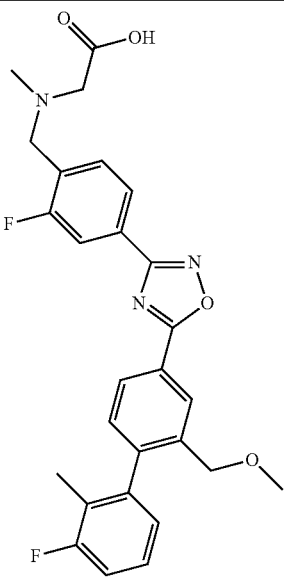
90 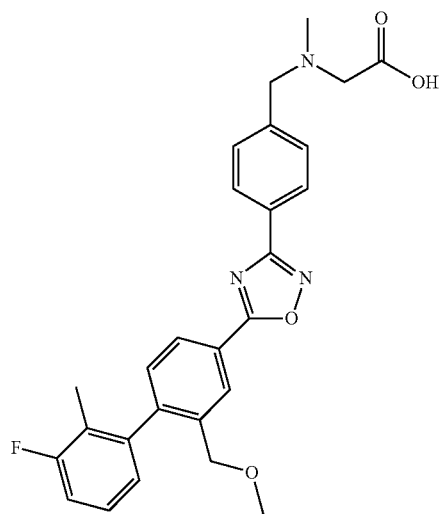 [SMILES: COCc1cc(-c2nc(-c3ccc(CN(C)CC(=O)O)cc3)no2)ccc1-c1cccc(F)c1C]
121 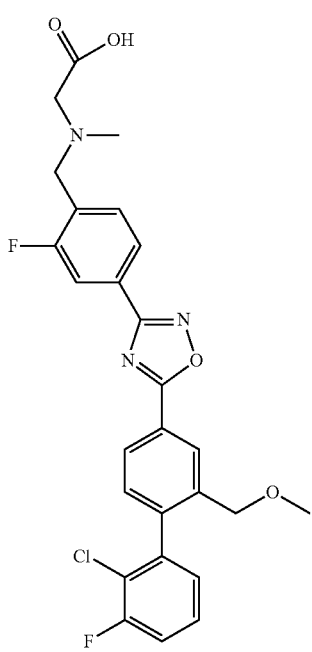 [SMILES: COCc1cc(-c2nc(-c3ccc(CN(C)CC(=O)O)c(F)c3)no2)ccc1-c1cccc(F)c1Cl]

| 307 -continued | 308 -continued |
|---|---|
| 122 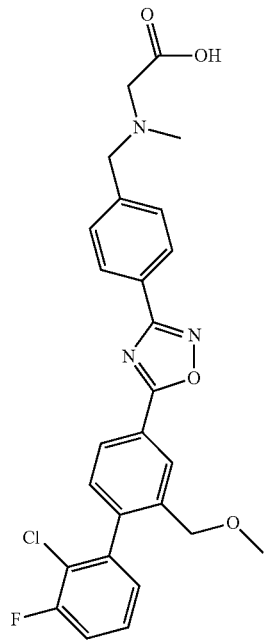 [SMILES: COCc1cc(-c2nc(-c3ccc(CN(C)CC(=O)O)cc3)no2)ccc1-c1cccc(F)c1Cl] | 127 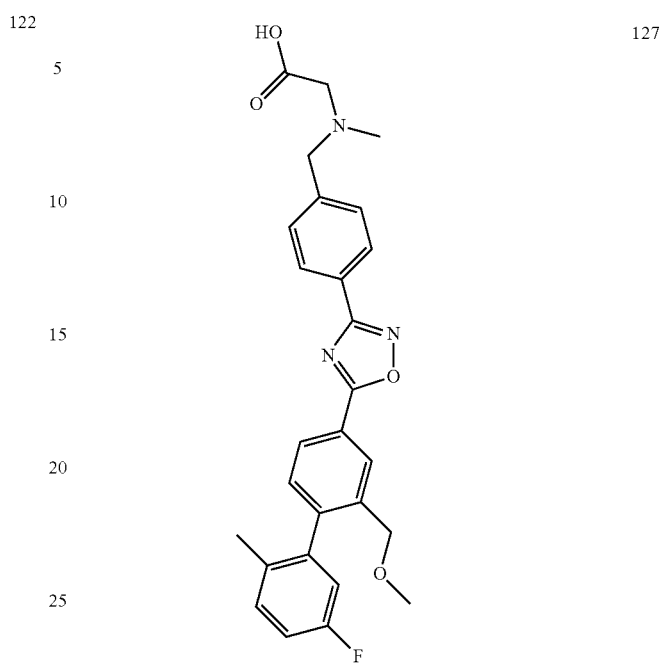 |
and pharmaceutically acceptable salts and stereoisomers thereof.
* * * * *

UNITED STATES PATENT AND TRADEMARK OFFICE
CERTIFICATE OF CORRECTION

PATENT NO. : 8,815,919 B2
APPLICATION NO. : 13/260779
DATED : August 26, 2014
INVENTOR(S) : Anna Quattropani et al.

Page 1 of 4

It is certified that error appears in the above-identified patent and that said Letters Patent is hereby corrected as shown below:

In the specification

Column 7,
Line 21, "N($R^3$), and" should read --N($R^3$)$_2$ and--.

Column 10,
Line 21, "51P$_3$/Edg3" should read --S1P$_3$/Edg3--.

Column 33,
Lines 45-46, "tert-butyl N-{4-[amino(hydroxyimino) methyl]-2-chlorobenzyl}-N-methylglycinate" should read
--tert-butyl N-{5-[amino(hydroxyimino) methyl]-2-chlorobenzyl}-N-methylglycinate--.

Column 44,
Lines 63-64, "-(CH$_2$)$_n$—O—(CH$_2$)$_n$CO$_2$R$^3$" should read -- -(CH$_2$)$_n$O(CH$_2$)$_n$CO$_2$R$^3$--.

Column 45,
Lines 2-3, "-(CH$_2$)$_n$—O—(CH$_2$)$_n$CO$_2$R$^3$" should read -- -(CH$_2$)$_n$O(CH$_2$)$_n$CO$_2$R$^3$--.

Signed and Sealed this
Tenth Day of November, 2015

Michelle K. Lee
*Director of the United States Patent and Trademark Office*

CERTIFICATE OF CORRECTION (continued)
U.S. Pat. No. 8,815,919 B2

In the specification

Column 60,
Lines 5-30, " 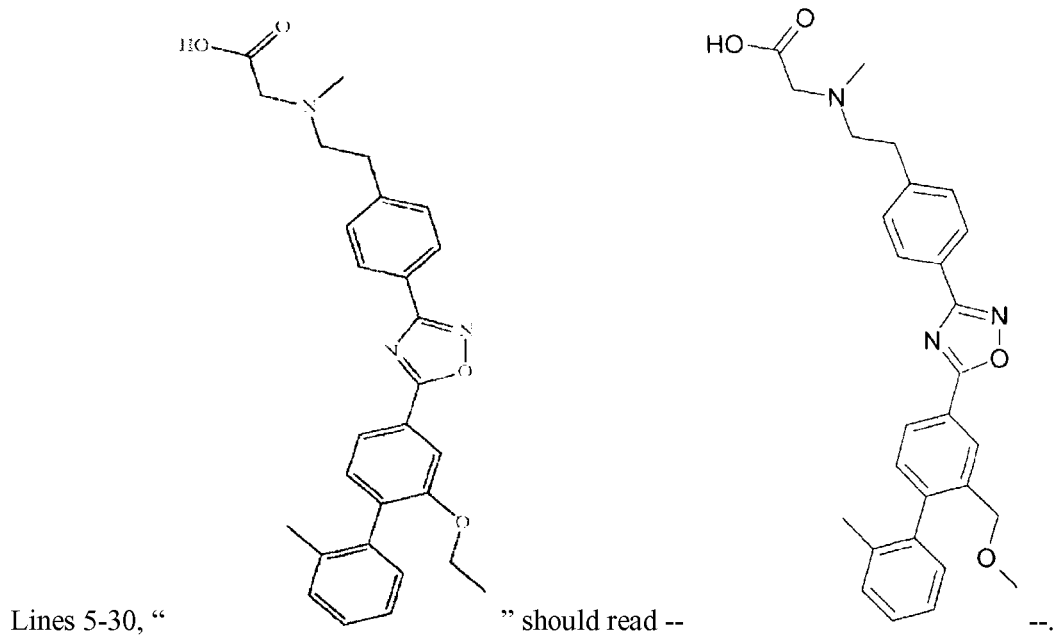 " should read -- --.

Column 77,
Lines 31-32, "—CH$_2$—O—(CH$_2$)$_n$COOH" should read -- -CH$_2$O(CH$_2$)$_n$COOH--.

Column 81,
Lines 28-29, "—CH$_2$ O—(CH$_2$)$_n$CO$_2$R$^3$" should read -- -CH$_2$O(CH$_2$)$_n$CO$_2$R$^3$--.

Column 90,
Line 41, "018," should read --C18,--.
Line 54, "HPLC/MS:" should read --UPLC/MS:--.
Line 55, "HPLC BEH" should read --UPLC BEH--.

Column 96,
Line 32, "HPLC/MS," should read --UPLC/MS,--.
Lines 52-53, "HPLC/MS," should read --UPLC/MS,--.

Column 97,
Line 11, "HPLC/MS," should read --UPLC/MS,--.
Line 37, "HPLC/MS," should read --UPLC/MS,--.

Column 127,
Line 66, "229.0 (M-H)$^+$," should read --229.0 (M-H)$^-$,--.

CERTIFICATE OF CORRECTION (continued)
U.S. Pat. No. 8,815,919 B2

In the specification

Column 134,
Lines 55-56, "methyl 2% (difluoromethyl)-2-methylbiphenyl-4-carboxylate" should read
--methyl 2'-(difluoromethyl)-2-methylbiphenyl-4-carboxylate--.

Column 151,
Lines 8-10, "3-[4(3-{5-[3-(methoxymethyl)-4-(2-methylpiperidin-1-yl)phenyl]-1,2,4-
oxadiazol-3-yl}benzyl)oxy]propanoic acid, hydrochloride salt"
should read
--3-[(3-{5-[3-(methoxymethyl)-4-(2-methylpiperidin-1-yl)phenyl]-1,2,4-
oxadiazol-3-yl}benzyl)oxy]propanoic acid, hydrochloride salt--.

Column 158,
Line 65, "(267 4," should read --(267 µL,--.

Column 159,
Line 31, "(267 4," should read --(267 µL,--.

Column 160,
Line 26, "compound as as a" should read --compound as a--.

Column 165,
Line 57, "(126 4," should read --(126 µL,--.

Column 166,
Lines 17-18, "N-(3-{5-[3',4'-difluoro-2-(methoxymethyl)-2% methylbiphenyl-4-yl]-
1,2,4-oxadiazol-3-yl}benzyl)-N-methylglycinate" should read
--N-(3-{5-[3',4'-difluoro-2-(methoxymethyl)-2'-methylbiphenyl-4-yl]-
1,2,4-oxadiazol-3-yl}benzyl)-N-methylglycinate--.
Lines 37-39, "N-[(3-{5-[2-(methoxymethyl)-2% methylbiphenyl-4-yl]-1,2,4-oxadiazol-3-
yl}phenyl)acetyl]-beta-alanine" should read
--N-[(3-{5-[2-(methoxymethyl)-2'-methylbiphenyl-4-yl]-1,2,4-oxadiazol-3-
yl}phenyl)acetyl]-beta-alanine--.

Column 186,
Lines 3-5, "N-(3-fluoro-5-{5-[3% fluoro-2-(methoxymethyl)-2'-methylbiphenyl-4-yl]-
1,2,4-oxadiazol-3-yl}benzyl)-N-methylglycine, hydrochloride salt"
should read
--N-(3-fluoro-5-{5-[3'-fluoro-2-(methoxymethyl)-2'-methylbiphenyl-4-yl]-
1,2,4-oxadiazol-3-yl}benzyl)-N-methylglycine, hydrochloride salt--.

Column 206,
Line 35, "355-GTPγS" should read --35S-GTPγS--.
Lines 54-55, "30 µM or 15 µM" should read --30 pM or 15 pM--.

CERTIFICATE OF CORRECTION (continued)

In the specification

Column 207,
Nb structure 1,

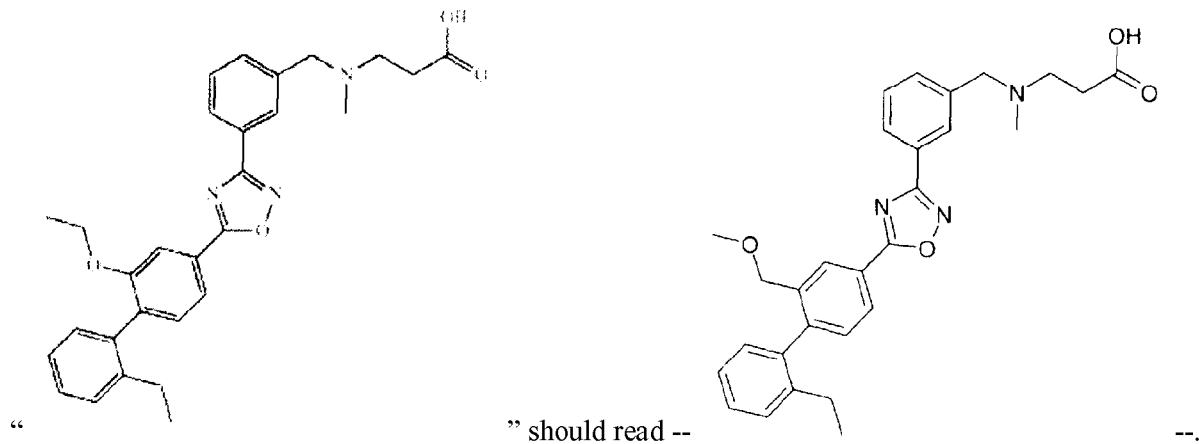

Column 300,
Line 62, "Plasma AUD?" should read --Plasma AUC?--.